US012753229B2

(12) United States Patent
Flies et al.

(10) Patent No.: US 12,753,229 B2
(45) Date of Patent: Oct. 6, 2026

(54) COMPOSITIONS AND METHODS FOR MODULATING FLRT3 MEDIATED SIGNAL TRANSDUCTION

(71) Applicant: NEXTCURE, INC., Beltsville, MD (US)

(72) Inventors: Dallas Benjamin Flies, Rockville, MD (US); Kushal Prajapati, Rockville, MD (US); Adem Can Koksal, Gaithersburg, MD (US); Linda Liu, Clarksville, MD (US); Solomon Langermann, Baltimore, MD (US)

(73) Assignee: NEXTCURE, INC., Beltsville, MD (US)

( * ) Notice: Subject to any disclaimer, the term of this patent is extended or adjusted under 35 U.S.C. 154(b) by 786 days.

(21) Appl. No.: 18/010,974

(22) PCT Filed: Jun. 21, 2021

(86) PCT No.: PCT/US2021/038201
§ 371 (c)(1),
(2) Date: Dec. 16, 2022

(87) PCT Pub. No.: WO2021/258040
PCT Pub. Date: Dec. 23, 2021

(65) Prior Publication Data

US 2023/0357384 A1 Nov. 9, 2023

Related U.S. Application Data

(60) Provisional application No. 63/107,975, filed on Oct. 30, 2020, provisional application No. 63/040,654, filed on Jun. 18, 2020.

(51) Int. Cl.
*C07K 16/28* (2006.01)
*A61K 39/00* (2006.01)
*A61P 35/00* (2006.01)

(52) U.S. Cl.
CPC .............. *C07K 16/28* (2013.01); *A61P 35/00* (2018.01); *A61K 2039/505* (2013.01); *C07K 2317/14* (2013.01); *C07K 2317/24* (2013.01); *C07K 2317/52* (2013.01); *C07K 2317/56* (2013.01); *C07K 2317/92* (2013.01); *C07K 2319/30* (2013.01)

(58) Field of Classification Search
None
See application file for complete search history.

(56) References Cited

U.S. PATENT DOCUMENTS 5,013,556 A 5/1991 Woodle et al.
5,120,727 A 6/1992 Kao et al.
5,162,333 A 11/1992 Failli et al.
5,190,929 A 3/1993 Borch et al.
5,202,332 A 4/1993 Hughes et al.
5,385,908 A 1/1995 Nelson et al.
5,484,790 A 1/1996 Failli et al.
5,530,006 A 6/1996 Waranis et al.
5,559,112 A 9/1996 Skotnicki et al.
5,567,709 A 10/1996 Skotnicki et al.
5,624,821 A 4/1997 Winter et al.
5,780,462 A 7/1998 Lee et al.
5,989,591 A 11/1999 Nagi
6,005,079 A 12/1999 Casterman et al.
6,015,809 A 1/2000 Zhu et al.
6,194,551 B1 2/2001 Idusogie et al.
7,052,694 B2 5/2006 Pease et al.
7,332,582 B2 2/2008 Hardy et al.
7,390,888 B2 6/2008 Pease et al.
7,411,051 B2 8/2008 Rosen et al.
7,488,802 B2 2/2009 Collins et al.
7,521,051 B2 4/2009 Collins et al.
7,524,498 B2 4/2009 Hardy et al.
7,563,869 B2 7/2009 Honjo et al.
7,981,416 B2 7/2011 Hardy et al.
8,088,905 B2 1/2012 Collins et al.
8,114,845 B2 2/2012 Langermann et al.
(Continued)

FOREIGN PATENT DOCUMENTS

CN 101489589 A 7/2009
CN 110431150 A 11/2019
(Continued)

OTHER PUBLICATIONS

Yamagishi et al. FLRT2 and FLRT3 act as repulsive guidance cues for Unc5-positive neurons. The EMBO Journal (2011) 30, 2920-2933. (Year: 2011).*
Sela-Culang et al. The structural basis of antibody-antigen recognition. Fron. Immuno., vol. 4, Article 302, Oct. 2013. (Year: 2013).*
Herold et al. Determinants of the assembly and function of antibody variable domains. Nature Scientific Reports, 7:12276, Sep. 25, 2017. (Year: 2017).*
Angal, S., et al., "A single amino acid substitution abolishes the heterogeneity of chimeric mouse/human (IgG4) antibody," Immunol., vol. 30, No. 1, 1993, pp. 105-108.
Bass, K.K., et al., "Immunopotentiation with low-dose cyclophosphamide in the active specific immunotherapy of cancer," Cancer Immunol. Immunother., vol. 47, No. 1, 1998, pp. 1-2.
(Continued)

*Primary Examiner* — Julie Wu
*Assistant Examiner* — Amy M. Chattin
(74) *Attorney, Agent, or Firm* — Judy Jarecki-Black; Sharon Ngwenya

(57) ABSTRACT

Compositions and methods of use thereof for modulating FLRT3 mediated signaling are provided. For example, immunomodulatory agents are provided that reduce FLRT3 expression, ligand binding, crosslinking, FLRT3 mediated signaling, or a combination thereof. In another embodiment, immunomodulatory agents are provided that enhance or promote FLRT3 expression, ligand binding, crosslinking, FLRT3 mediated signaling, or a combination thereof. Such agents can be used to modulate an immune response in a subject in need thereof.

9 Claims, 61 Drawing Sheets

Specification includes a Sequence Listing.

(56) References Cited

U.S. PATENT DOCUMENTS

| | | | |
|---|---|---|---|
| 8,188,238 B2 | 5/2012 | Pease et al. | |
| 8,287,856 B2 | 10/2012 | Li et al. | |
| 8,383,796 B2 | 2/2013 | Korman et al. | |
| 8,580,247 B2 | 11/2013 | Li et al. | |
| 8,609,089 B2 | 12/2013 | Langermann et al. | |
| 8,709,416 B2 | 4/2014 | Langermann et al. | |
| 8,728,474 B2 | 5/2014 | Honjo et al. | |
| 8,779,105 B2 | 7/2014 | Korman et al. | |
| 9,067,999 B1 | 6/2015 | Honjo et al. | |
| 9,073,994 B2 | 7/2015 | Honjo et al. | |
| 9,084,776 B2 | 7/2015 | Korman et al. | |
| 9,102,725 B2 | 8/2015 | Korman et al. | |
| 9,205,148 B2 | 12/2015 | Langermann et al. | |
| 9,255,147 B2 | 2/2016 | Pease et al. | |
| 9,273,135 B2 | 3/2016 | Korman et al. | |
| 9,358,289 B2 | 6/2016 | Korman et al. | |
| 9,387,247 B2 | 7/2016 | Korman et al. | |
| 9,393,301 B2 | 7/2016 | Honjo et al. | |
| 9,492,539 B2 | 11/2016 | Korman et al. | |
| 9,492,540 B2 | 11/2016 | Korman et al. | |
| 9,580,507 B2 | 2/2017 | Korman et al. | |
| 2004/0141964 A1 | 7/2004 | Abdel-Meguid et al. | |
| 2017/0129942 A1 | 5/2017 | Plante et al. | |
| 2018/0002419 A1* | 1/2018 | Yamashita | C12Q 1/6883 |
| 2018/0036441 A1 | 2/2018 | Kufe et al. | |

FOREIGN PATENT DOCUMENTS

| | | | | |
|---|---|---|---|---|
| EP | 4168046 A4 | 10/2024 | | |
| JP | WO2016129627 A1 | 1/2018 | | |
| WO | 94/04678 A1 | 3/1994 | | |
| WO | 94/25591 A1 | 11/1994 | | |
| WO | 99/58572 A1 | 11/1999 | | |
| WO | 2004/084933 A1 | 10/2004 | | |
| WO | 2007/056539 A2 | 5/2007 | | |
| WO | 2008/147482 A2 | 12/2008 | | |
| WO | WO-2019232503 A1 * | 12/2019 | A61K 40/31 | |
| WO | WO-2021173307 A1 * | 9/2021 | C07K 16/2878 | |
| WO | 2021/258040 A2 | 12/2021 | | |
| WO | WO-2021246413 A1 * | 12/2021 | C07K 16/28 | |
| WO | WO-2025167991 A1 * | 8/2025 | G01N 33/68 | |

OTHER PUBLICATIONS

Berger, R., et al., "Phase I safety and pharmacokinetic study of CT-011, a humanized antibody interacting with PD-1, in with advanced hematologic malignancies," Clin. Cancer Res., vol. 14, No. 10, 2008, 30443051.
Butte, M.J., et al., "PD-L1 interacts specifically with B7-1 to inhibit T cell proliferation," Immunity, vol. 27, No. 1, 2007, pp. 111-122.
Chapoval, A.I., et al., "Immunoglobulin Fusion Proteins as a Tool for Evaluation of T-Cell Costimulatory Molecules," Methods Mol. Med., vol. 45, 2000, pp. 247-255.
Chothia, C., et al., "Canonical structures for the hypervariable regions of immunoglobulins," J. Mol. Biol., vol. 196, 1987 pp. 901-917.
Cubillos-Ruiz, J.R., et al., "Polyethylenimine-based siRNA nanocomplexes reprogram tumor-associated dendritic cells via to elicit therapeutic antitumor immunity," J. Clin. Invest., vol. 119, No. 8, 2009, pp. 2231-2244.
Erbe, D.V., et al., "Small Molecule Ligands Define a Binding Site on the Immune Regulatory Protein B7.1," J. Biol. Chem., vol. 277, No. 9, 2002, pp. 7363-7368.
Freeman, G.J., "Structures of PD-1 with its ligands: Sideways and dancing cheek to cheek," Proc. Natl. Acad. Sci. U. S. A, vol. 105, No. 30, 2008, pp. 10275-10276.
Guatelli, J.C., et al. "Isothermal, in vitro amplification of nucleic acids by a multienzyme reaction modeled after retroviral," Proc. Natl. Acad. Sci. USA, vol. 87, 1990, pp. 1874-1878.
Hengst, J.C., et al. "Cooperation between Cyclophosphamide Tumoricidal Activity and Host Antitumor Immunity in the Cure Mice Bearing Large MOPC-315 Tumors," Cancer Res., vol. 41, 1981, pp. 2163-2167.
Hengst, J.C., et al., "Importance of Timing of Cyclophosphamide Therapy of MOPC-315 Tumor-bearing Mice," Cancer vol. 40, 1980, pp. 2135-2141.
Hyrup, B., et al. "Peptide nucleic acids (PNA): synthesis, properties and potential applications," Bioorgan. Med. Chem., vol. 4, No. 1, 1996, pp. 5-23.
International Preliminary Report on Patentability received for PCT Patent Application No. PCT/US21/038201, mailed on Dec. 29, 2022, 10 pages.
International Search Report and Written Opinion received for PCT Patent Application No. PCT/US21/038201, mailed on Dec. 20, 2021, 16 pages.
Iwai, Y., et al., "Cancer immunotherapies targeting the PD-1 signaling pathway," Journal of Biomedical Science, vol. 24, No. 26, 2017, pp. 1-11.
Li, B., et al., "Vascular Endothelial Growth Factor Blockade Reduces Intratumoral Regulatory T Cells and Enhances the Efficacy of a GM-CSF—Secreting Cancer Immunotherapy," Clin Cancer Res., vol. 12, No. 22, 2006, pp. 6808-6816.
Liang, J., et al., "Design of new oxazaphosphorine anticancer drugs," Curr. Pharm. Des., vol. 13 No. 9, 2007, pp. 963-978.
Machiels, J.P.H., et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice," Cancer Res., vol. 61, 2001, pp. 3689-3697.
Mathiowitz, E., et al., "Novel microcapsules for delivery systems", Reactive Polymers, vol. 6, 1987, pp. 275-283.
Mathiowitz, E., et al., "Polyanhydride microspheres as drug carriers I. Hot-melt microencapsulation", Controlled Release, vol. 5, 1987, pp. 13-22.
Mathiowitz, E., et al., "Polyanhydride microspheres as drug carriers. II. Microencapsulation by solvent removal", J. Appl. Polymer Sci., 35: 755-774 (1988).
Mediero et al., "Netrin-1 and its receptor Unc5b are novel targets for the treatment of inflammatory arthritis", FASEB J., vol. 30, No. 11, 2016, pp. 3835-3844.
Molnar, E.L., et al., "Crystal structure of the complex between programmed death-1 (PD-1_ and its ligand PD-L2", PNAS, vol. 105, No. 30, 2008, pp. 10483-10488.
Muyldermans, S., et al., Recognition of antigens by single-domain antibody fragments:the superfluous luxury of paried Trends Biochem. Sci. vol. 26, No. 4, 2001, pp. 226-230.
NCBI Accession FLRT3_HUMAN, Full=Leucine-rich repeat transmembrane protein FLRT3; AltName: Full=Fibronectin-like domain-containing leucine-rich transmembrane protein 3, Apr. 22, 2020 (online]. [Retrieved on Nov. 7, 2021]. Retrieved from the Internet <URL:https://www.ncbi .nlm .nih.gov/protein/20138400?sat=48&satkey=90143068>.
Newmark, J., et al., "Preparation and Properties of Adducts of Streptokinase and Streptokinase-Plasmin Complex with Polyethylene Glycol and Pluronic Polyol F38," J. Appl. Biochem., vol. 4, 1982, pp. 185-189.
Nuttall, S.D., et al., "Immunoglobulin VH Domains and Beyond: Design and Selection of Single-Domain Binding and Reagents," Curr. Pharm. Biotech., vol. 1, 2000, pp. 253-263.
Pluckthun in The Pharmacology of Monoclonal Antibodies, Rosenburg and Moore eds. Springer-Verlag, New York, vol. 113, 1994, pp. 269-315.
Riechmann, L., et al., "Single domain aintibodies: comparison of camel VH and camelised human VH domainsx," J. Immunol. Meth., 231: 25 (1999).
Summerton, J., et al., "Morpholino antisense oligomers: design, preparation, and properties," Antisense Nucleic Acid Drug Dev., vol. 7, No. 3, 1997, pp. 187-195.
Taieb, J., et al., "Chemoimmunotherapy of tumors: cyclophosphamide synergizes with exosome based vaccines," J Immunol, vol. 176, 2006, pp. 2722-2729.
Van der Most et al., "Cyclophosphamide Chemotherapy Sensitizes Tumor Cells to TRAIL-Dependent CD8 T Cell-Mediated Immune Attack Resulting in Suppression of Tumor Growth," Cancer Immunol. Immunother., vol. 58, 2009, pp. 1219-1228.

(56) References Cited

OTHER PUBLICATIONS

Weiss, R., "Hot Prospect for New Gene Amplifier," Science, vol. 254, 1991, pp. 1292-1293.
Wong, G.G., et al. "Human GM-CSF: Molecular Cloning of the Complementary DNA and Purification of the Natural and Recombinant Proteins," Science, vol. 228, 810-815 (1985).
Yasinska et al., "The Tim-3-Galectin-9 Pathway and Its Regulatory Mechanisms in Human Breast Cancer", Front Immunol., vol. 10, article ID 1594, 2019, pp. 1-13.
Japanese Office Action cited in connection with JP application No. JP2022-578562 and machine translation thereof, dated Aug. 4, 2025, 09 pages.
Extended European Search Report and Search Opinion received for EP Application No. 21827024.7, mailed on Sep. 16, 2024, 16 pages.
European Search Report and Search Opinion received for European Application No. 21827024.7, mailed on Jun. 25, 2024, 19 pages.
Robinson M et al., "FLRT3 is expressed in sensory neurons after peripheral nerve injury and regulates neurite outgrowth", Molecular And Cellular Neurosciences, vol. 27, No. 2, Oct. 1, 2004, pp. 202-214.
Silva I. G. et al., "The Tim-3-galectin-9 Secretory Pathway is Involved in the Immune Escape of Human Acute Myeloid Leukemia Cells", Ebiomedicine, vol. 22, Jul. 19, 2017, pp. 44-57.
Svetlana Sakhnevych: "Tim-3-galectin-9 immunosuppressive pathway in human acute myeloid leukaemia and solid tumour cells and biochemical functions of its crucial components", Mar. 9, 2020, pp. 1-245.
Yamada, M., "Increased Expression of Fibronectin Leucine-Rich Transmembrane Protein 3 in the Dorsal Root Ganglion Induces Neuropathic Pain in Rats", The Journal Of Neuroscience, vol. 39, No. 38, Sep. 18, 2019, pp. 7615-7627.
Chu Xiangjian et al., "Expression and clinical significances of FLRT3 in liver cell cancer tissues." Jiangsu Medical Journal 45(10):1033-1037 (2019). English abstract.
Rudikoff, et al., "Single amino acid substitution altering antigen-binding specificity." PNAS, 79(6):1979-1983 (1982).
Examination Report Article 94(3) EPC received for European Application No. 21827024.7, mailed on Nov. 24, 2025. 8 pages.
First Office Action received for Chinese Application No. 202180050412.4, mailed on Nov. 8, 2025. 16 pages.

* cited by examiner

COMPOSITIONS AND METHODS FOR MODULATING FLRT3 MEDIATED SIGNAL TRANSDUCTION

CROSS-REFERENCE TO RELATED APPLICATIONS

The present invention is filed under 35 U.S.C. § 371 as the U.S. national phase of International Application No. PCT/US2021/038201, filed Jun. 21, 2020, which designated the U.S. and claims the right of priority of U.S. Provisional Application No. 63/040,654, filed Jun. 18, 2020, and to U.S. Provisional Application No. 63/107,975, filed Oct. 30, 2020. The entire disclosures of the above-identified priority applications are hereby fully incorporated herein by reference.

SEQUENCE LISTING

The instant application contains a Sequence Listing which was submitted in ASCII format via EFS-Web and is hereby incorporated by reference in its entirety. Said ASCII copy, created on Jun. 21, 2021, is 532 kilobytes in size.

FIELD OF THE INVENTION

The invention is generally related to the field of immunomodulation, and more particularly to compositions and methods for modulating immune responses in a subject.

BACKGROUND OF THE INVENTION

Immunotherapies have made significant advances in the treatment of diseases such as cancer (Iwai, Y., et al., Journal of Biomedical Science, 24:26 (2017). Early immunotherapies accelerated T-cell activity. Current immune-checkpoint inhibitors take the brakes off the anti-tumor immune responses. Successful clinical trials with programmed cell death protein 1 (PD-1) monoclonal antibodies and other immune-checkpoint inhibitors have opened new avenues in cancer immunology. The failure of a large subset of cancer patients to respond to these new immunotherapies has led to intensified research to find new therapies.

FLRT3 (fibronectin and leucine-rich transmembrane protein-3) is a member of the fibronectin leucine-rich repeat transmembrane protein family and has a FN (fibronectin) type III domain and leucine-rich repeats. FLRT3 is expressed in various tissues including kidney, skeletal muscle, brain and lung. FLRT3 has been reported to have crucial functions during early embryonic development. Most of the literature describe functions in neurons: neuronal development, migration, axonal guidance, neurite outgrowth. Expression of FLRT3 has been shown to have prognostic value in certain cancers. In renal clear cell carcinoma, higher expression level of FLRT3 was associated with a better survival of the patients during a 5-years follow-up time (The Human Protein Atlas, 2018a), while in one of the less vascularized cancers, pancreatic cancer (Longo et al., 2016), a lower expression level of FLRT3 associates with better prognosis (The Human Protein Atlas, 2018b).

LPHN3, UNC5B and UNC5D have been reported binding partners of FLRT3. FLRTs, LPHNs, and UNC5s are families of interacting neuronal cell-surface receptors that mediate brain development. The LPHN3/FLRT3 structure reveals that LPHN3 binds to FLRT3 at a site distinct from UNC5. FLRT3 simultaneously binds to LPHN3 and UNC5, and forms a trimeric complex. UNC5B mediates apoptosis in tumors in the absence of netrin through the activation of DAP kinase and is involved in leukocyte migration inhibition. UNC5B has been shown to be expressed on thymocytes and T cells. Expression of UNC5B correlates with bladder cancer stage and the receptor is a potential predictor of both bladder and colorectal cancer prognosis and possible disease recurrence.

FLRT3 is positively regulated by both FGF and TGF-β suggesting that it is involved in the regulation of FGF signaling in many tissues during development.

Therefore, it is an object of the invention to provide compositions that modulate leucine-rich repeat transmembrane protein FLRT3 (FLRT3) mediated signal transduction thereby promoting a suppressive immunological response. Such compositions are useful for the treatment of inflammatory diseases and disorders and autoimmune diseases.

It is also an object of the invention to provide compositions that modulate FLRT3 mediated signal transduction by blocking FLRT3 interacting with its ligands. Such compositions are useful for the treatment of cancer.

SUMMARY OF THE INVENTION

Compositions and methods of their use for modulating FLRT3 mediated signal transduction are provided. One embodiment provides compositions and methods that induce, promote, or enhance FLRT3 mediated signal transduction. For example, immunomodulatory agents are provided that induce, promote, or enhance FLRT3 expression, ligand binding, crosslinking, signal transduction, or a combination thereof.

Exemplary anti-FLRT3 antibody or antigen-binding fragment thereof including the following light and heavy chain variable regions are disclosed:

a) a light chain variable region having at least 50%, 60%, 70%, 80%, 85%, 90%, 95%, 99%, or more sequence identity to an amino acid sequence selected from the group consisting of SEQ ID NO:17, 19, 21, 23, 25, 27, and 29, and b) a heavy chain variable region having at least 50%, 60%, 70%, 80%, 85%, 90%, 95%, 99%, or more sequence identity to an amino acid sequence selected from the group consisting of SEQ ID NO:38, 42, 46, 50, 54, 58, 62, 66, 70, 74, 78, 82, 86, 90, 94, and 98, wherein the antibody of antigen-binding fragment thereof binds to FLRT3.

In one embodiment, the antibody or antigen-binding fragment further includes one or more constant domains from an immunoglobulin constant region (Fc). In another embodiment, the antibody or antigen-binding fragment is humanized.

Other embodiments provide exemplary anti-FLRT3 antibody or antigen-binding fragments thereof that have a heavy chain variable region and a light chain variable region selected from the group consisting of:

a) heavy chain variable region having at least 50%, 60%, 70%, 80%, 85%, 90%, 95%, 99%, or more sequence identity to SEQ ID NO:209, and light chain variable region having at least 50%, 60%, 70%, 80%, 85%, 90%, 95%, 99%, or more sequence identity to SEQ ID NO:206;

b) heavy chain variable region having at least 50%, 60%, 70%, 80%, 85%, 90%, 95%, 99%, or more sequence identity to SEQ ID NO:200, and light chain variable region having at least 50%, 60%, 70%, 80%, 85%, 90%, 95%, 99%, or more sequence identity to SEQ ID NO:195;

c) heavy chain variable region having at least 50%, 60%, 70%, 80%, 85%, 90%, 95%, 99%, or more sequence identity to SEQ ID NO:107, and a light chain variable region having at least 50%, 60%, 70%, 80%, 85%, 90%, 95%, 99%, or more sequence identity to SEQ ID NO:102;

d) heavy chain variable region having at least 50%, 60%, 70%, 80%, 85%, 90%, 95%, 99%, or more sequence identity to SEQ ID NO:119, and a light chain variable region having at least 50%, 60%, 70%, 80%, 85%, 90%, 95%, 99%, or more sequence identity to SEQ ID NO:114;

e) heavy chain variable region having at least 50%, 60%, 70%, 80%, 85%, 90%, 95%, 99%, or more sequence identity to SEQ ID NO:128, and a light chain variable region having at least 50%, 60%, 70%, 80%, 85%, 90%, 95%, 99%, or more sequence identity to SEQ ID NO:126;

f) heavy chain variable region having at least 50%, 60%, 70%, 80%, 85%, 90%, 95%, 99%, or more sequence identity to SEQ ID NO:136, and a light chain variable region having at least 50%, 60%, 70%, 80%, 85%, 90%, 95%, 99%, or more sequence identity to SEQ ID NO:134;

g) heavy chain variable region having at least 50%, 60%, 70%, 80%, 85%, 90%, 95%, 99%, or more sequence identity to SEQ ID NO:144, and a light chain variable region having at least 50%, 60%, 70%, 80%, 85%, 90%, 95%, 99%, or more sequence identity to SEQ ID NO:141;

h) heavy chain variable region having at least 50%, 60%, 70%, 80%, 85%, 90%, 95%, 99%, or more sequence identity to SEQ ID NO:149, and a light chain variable region having at least 50%, 60%, 70%, 80%, 85%, 90%, 95%, 99%, or more sequence identity to SEQ ID NO:134;

i) heavy chain variable region having at least 50%, 60%, 70%, 80%, 85%, 90%, 95%, 99%, or more sequence identity to SEQ ID NO:157, and a light chain variable region having at least 50%, 60%, 70%, 80%, 85%, 90%, 95%, 99%, or more sequence identity to SEQ ID NO:153;

j) heavy chain variable region having at least 50%, 60%, 70%, 80%, 85%, 90%, 95%, 99%, or more sequence identity to SEQ ID NO:167, and a light chain variable region having at least 50%, 60%, 70%, 80%, 85%, 90%, 95%, 99%, or more sequence identity to SEQ ID NO:162;

k) heavy chain variable region having at least 50%, 60%, 70%, 80%, 85%, 90%, 95%, 99%, or more sequence identity to SEQ ID NO:177, and a light chain variable region having at least 50%, 60%, 70%, 80%, 85%, 90%, 95%, 99%, or more sequence identity to SEQ ID NO:172; and l) heavy chain variable region having at least 50%, 60%, 70%, 80%, 85%, 90%, 95%, 99%, or more sequence identity to SEQ ID NO:188, and a light chain variable region having at least 50%, 60%, 70%, 80%, 85%, 90%, 95%, 99%, or more sequence identity to SEQ ID NO:183.

In one embodiment, the antibody or antigen-binding fragment thereof has one or more constant domains from an immunoglobulin constant region (Fe). In another embodiment, the antibody or antigen-binding fragment is humanized.

Another embodiment provides an anti-FLRT3 antibody produced by a hybridoma selected from the group consisting of 14B7, 17A1, 15G11, 18A7, 9F3, 1H5, 2F7, 5C2, 7H7, 10C6, 12A4, 13B2, 14D3, and 20C3.

Other embodiments provide a pharmaceutical composition including any one of the disclosed antibodies or antigen-binding fragments, and a pharmaceutically acceptable excipient.

One embodiment provides a fusion protein or an antigen binding fragment thereof having 80%, 85%, 90%, 95%, 99%, or 100% to SEQ ID NO:215, 216, or 217.

Also provided are methods for treating a tumor in a subject in need thereof by administering a therapeutically effective amount of any one of the disclosed antibody or antigen-binding fragments or fusion proteins to the subject to reduce tumor burden in the subject. The tumor can be a colorectal tumor, a lymphoma tumor, or an ovarian tumor.

Another embodiment provides a method for promoting an immune response in a subject in need thereof by administering a therapeutically effective amount of any one of the disclosed antibody or antigen-binding fragments or fusion proteins in an amount effective to promote an immune response in the subject. The promoted immune response retards or prevents tumor growth, inhibits tumor-mediated immune suppression, eliminates tumors, depletes or blocks the activity of tumor-associated macrophages (TAMs), decreases TAM-mediated immune suppression, reduces or reverses T cell suppression, increases T cell priming, activation, proliferation and effector function, or a combination thereof.

Yet another embodiment provides a method of treating an autoimmune disease is a subject in need thereof by administering a therapeutically effective amount of any one of the disclosed antibody or antigen-binding fragments or fusion proteins to treat the autoimmune disease.

BRIEF DESCRIPTION OF THE DRAWINGS

FIG. 1A is an illustration of NFκB activation in human Jurkat T cells. FIG. 1B is a bar graph showing the effect of FLRT3, PD-L1 and CD80 on NFκB activation in human Jurkat GFP reporter cells. FIG. 1C is an illustration of IFNγ production in human primary T cells. FIG. 1D is a bar graph showing the effect of FLRT3, PD-L1 and CD80 on the production of IFNγ.

FIG. 2A is a bar graph showing expression levels of FLRT3 in mouse cancer cells. FIG. 2B is a graph showing FLRT3 expression levels in human cancer cells.

FIG. 3 is a box plot comparing TCGA tumor tissue (red)+TCGA normal and GTEx normal tissues (grey).

FIG. 6A is an illustration of the protocol used to inject the mice and determine tumor measurements. FIGS. 6B-6C are line graphs showing the change in tumor volume after 52 days of inoculating the mice.

FIG. 7A is the illustration showing the mice treatment protocol. FIG. 7B is a line graph showing clinical GvHD scores up to 58 days post tumor challenge with FLRT3 and control.

FIG. 8A is an illustration of the protocol used to treat mice to determine tumor measurements. FIG. 8B is a line graph showing the effect of FLRT3 on tumor growth in the HT-29 mouse tumor model. FIG. 8C-8J are flow cytometry and bar graphs showing the effect of FLRT3 Fc on cytokine production.

FIG. 9A is an illustration of the treatment of NSG mice. FIG. 9B is a line graph showing the effect of FLRT3 on tumor size.

FIGS. 12A-12B are a line graph (12A) and non-linear regression fit graph (12B) showing the maximal response of the top binders.

FIG. 14A is an illustration of the Unc5B-FLRT3 interaction. FIG. 14B shows the fluorescence intensity of Unc5B-Fc binding to FLRT3 Fc relative to control Fc. FIG. 14C is a line graph showing the binding of FLRT3 to Unc5B-FC.

FIGS. 15A-15B are line graphs showing the treatment of 14B7 and 14D3 on FLRT3-Fc (15A) and antibody concentrations (15B).

FIG. 16A is a bar graph showing FLRT3-Fc binding on coated Unc5 proteins. FIGS. 16B-16E show the effect of 14B7 on FLRT3-Fc binding to Unc5 proteins.

FIG. 17A is an illustration of binding of Unc5B-Fc biotin to FLRT3-Fc in presence of increasing of antibodies. FIG. 17B is a bar graph showing the mean fluorescence intensity of Unc5B Fc binding to FLRT3 Fc in comparison to control Fc. FIG. 17C is a line graph showing the effect of 14B7 on Unc5B-FC binding to FLRT3 Fc.

FIG. 20A is a line graph and FIG. 20B is non-linear regression fit graph of normalized data for the top binders.

FIG. 21A is an illustration of the assay. FIG. 21B-21E are bar graphs showing FLRT3 suppresses IFN-γ production, and FIG. 21F-21I are bar graphs showing FLRT3 inhibits T cell proliferation in total PBMCs for donors 46 (21B, 25F), 66 (21C, 21G), 67 (21D, 21H), and 68 (21E, 21I).

FIG. 22A is an illustration of the assay and FIG. 22B is bar graph showing FLRT3 increased Jurkat T cell death and reversal by 14B7 antibody. FIG. 22C is and illustration of the assay and FIG. 22D is a bar graph showing FLRT3 inhibits NF-kB-GFP signaling and reversal by 14B7 antibody.

FIGS. 23A-23B are bar graphs showing total PBMCs from Donor 68 (23A) and Donor 67 (23B) in the presence of empty vector or FLRT3-HMC3-OKT3+/− FLRT3 Abs and reversal of primary T cell inhibition by FLRT3 antibodies.

FIG. 24A is an illustration of the assay. FIGS. 24B-24D are bar graphs showing 14B7 increased IFN-g production in co-culture of 293T-FLRT3 cells with PBMC donors 68, 76 and 1805E. FIGS. 24E-2G are bar graphs showing 14B7 increased IFN-g production in co-culture of A375 melanoma cells with PBMC donors 68, 76 and 1805E. FIGS. 24H-24J are bar graphs showing 14B7 increased IFN-g production in co-culture of SKOV3 cells with PBMC donors 68, 76 and 1805E.

FIG. 25A is an illustration of the assay. FIG. 25B-25D are bar graphs showing 14B7 increased IFN-g production in co-culture of SKOV3 cells with PBMC donors 81, 83 and 97.

FIG. 26A illustrates the treatment protocol of using NSG mice. FIG. 26B is a line graph showing the effect of 14B7 in tumor growth post treatment. FIG. 26C is a survival probability graph showing the effect of 14B7 on survival post treatment.

FIG. 27A is an illustration of the treatment protocol with NSG mice. FIG. 27B is a line graph showing the effect of 14B7 in tumor growth post treatment. FIG. 27C is a dot plot showing the effect of 14B7 on tumor volume.

FIG. 28A is an illustration of the treatment protocol with Balb/c mice. FIG. 28B is a bar graph showing the effect of 14B7 in tumor growth on day 21 after tumor injection.

DETAILED DESCRIPTION OF THE INVENTION

I. Definitions

Figure 1A:
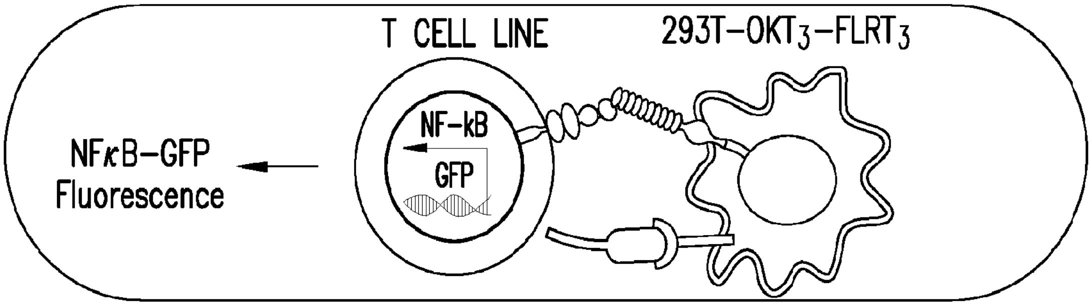
FIGS. 1A-1D show that FLRT3's immunosuppression in vitro is comparable to PD-L1.

As used herein, the terms "immunomodulatory agent" and "binding moiety" are used interchangeably.

As used herein, the term "FLRT3 immunomodulatory agent" refers to leucine-rich repeat transmembrane protein FLRT3 (FLRT3) binding moieties including, but not limited to antibodies and antigen binding fragments thereof, and FLRT3 fusion proteins and binding fragments thereof. In one embodiment, FLRT3 has an amino acid sequence according to UniProtKB—Q9NZU0 (FLRT3_HUMAN) which is incorporated by reference in its entirety. Other names for FLRT3 include fibronectin-like domain-containing leucine-rich transmembrane protein 3.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "activating" or "stimulatory" signals encompass signals that result in enhancing an activity or enhancing signal transduction.

As used herein, "suppressive" signals refer to signals that suppress immune activity.

The term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. In some embodiments, such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, or about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions

A. FLRT3 Polypeptides

Fibronectin leucine-rich repeat transmembrane protein FLRT3 is a member of the FLRT family of proteins which structurally resemble small leucine-rich proteoglycans found in the extracellular matrix. FLRT3 functions in cell-cell adhesion, cell migration, and axon guidance, exerting either an attractive or repulsive role depending on its interaction partner. Interaction with ADGR3 on adjacent cells mediates cell-cell adhesion. FLRT3 interaction with the intracellular domain of ROBO1 mediates axon attraction towards cells expressing NTN1. Interaction with UNC5B mediates axon growth cone collapse and plays a repulsive role in neuron guidance. FLRT3 also plays a role in fibroblast growth factor-mediated signaling cascades.

FLRT3 is expressed in the kidney, brain, pancreas, skeletal muscle, lung, liver, placenta, and heart. Down regulation of FLRT3 has been detected in lung transplant patients with primary graft dysfunction. Mutations in FLRT3 are associated with hypogonadotropic hypogonadism 21 with or without anosmia (HH21).

1. Human FLRT3

Sequences for human FLRT3 are known in the art. For example, the nucleic acid sequence for human FLRT3 transcript variant 1 is as follows:

```
CTTCTTCAGCCACTGCGAGGTGAAGCTTTAAACTTCAGACTTGGAGGTG
GGCTGTGTGCAGTAAACTGGAATGCTCTCCCTCGCTCACTCCTCAGTGT
AGGAGTGATCTGAAGCAGGACAAGCTCAGCCTGCAGCTGCCGTGGGCTT
TGTGTGGACTGGACGCAGAGCTTGGGAGACGGGGGAGGGCTATTACTCC
AATTCACTGTCAATGGAATTACAGCTATAGCGGCAGTGTATATAGGATT
GCTTTTTCTCGTCTTCCTGGGTTCTGAAGTAACGGAAGCTACCTTGTAT
AAAGACCTCAACACTGCTGACCATGATCAGCGCAGCCTGGAGCATCTTC
CTCATCGGGACTAAAATTGGGCTGTTCCTTCAAGTAGCACCTCTATCAG
TTATGGCTAAATCCTGTCCATCTGTGTGTCGCTGCGATGCGGGTTTCAT
TTACTGTAATGATCGCTTTCTGACATCCATTCCAACAGGAATACCAGAG
GATGCTACAACTCTCTACCTTCAGAACAACCAAATAAATAATGCTGGGA
TTCCTTCAGATTTGAAAAACTTGCTGAAAGTAGAAAGAATATACCTATA
CCACAACAGTTTAGATGAATTTCCTACCAACCTCCCAAAGTATGTAAAA
GAGTTACATTTGCAAGAAAATAACATAAGGACTATCACTTATGATTCAC
TTTCAAAAATTCCCTATCTGGAAGAATTACATTTAGATGACAACTCTGT
CTCTGCAGTTAGCATAGAAGAGGGAGCATTCCGAGACAGCAACTATCTC
CGACTGCTTTTCCTGTCCCGTAATCACCTTAGCACAATTCCCTGGGGTT
TGCCCAGGACTATAGAAGAACTACGCTTGGATGATAATCGCATATCCAC
TATTTCATCACCATCTCTTCAAGGTCTCACTAGTCTAAAACGCCTGGTT
CTAGATGGAAACCTGTTGAACAATCATGGTTTAGGTGACAAAGTTTTCT
TCAACCTAGTTAATTTGACAGAGCTGTCCCTGGTGCGGAATTCCCTGAC
TGCTGCACCAGTAAACCTTCCAGGCACAAACCTGAGGAAGCTTTATCTT
CAAGATAACCACATCAATCGGGTGCCCCCAAATGCTTTTTCTTATCTAA
GGCAGCTCTATCGACTGGATATGTCCAATAATAACCTAAGTAATTTACC
```

-continued

```
TCAGGGTATCTTTGATGATTTGGACAATATAACACAACTGATTCTTCGC
AACAATCCCTGGTATTGCGGGTGCAAGATGAAATGGGTACGTGACTGGT
TACAATCACTACCTGTGAAGGTCAACGTGCGTGGGCTCATGTGCCAAGC
CCCAGAAAAGGTTCGTGGGATGGCTATTAAGGATCTCAATGCAGAACTG
TTTGATTGTAAGGACAGTGGGATTGTAAGCACCATTCAGATAACCACTG
CAATACCCAACACAGTGTATCCTGCCCAAGGACAGTGGCCAGCTCCAGT
GACCAAACAGCCAGATATTAAGAACCCCAAGCTCACTAAGGATCACCAA
ACCACAGGGAGTCCCTCAAGAAAAACAATTACAATTACTGTGAAGTCTG
TCACCTCTGATACCATTCATATCTCTTGGAAACTTGCTCTACCTATGAC
TGCTTTGAGACTCAGCTGGCTTAAACTGGGCCATAGCCCGGCATTTGGA
TCTATAACAGAAACAATTGTAACAGGGGAACGCAGTGAGTACTTGGTCA
CAGCCCTGGAGCCTGATTCACCCTATAAAGTATGCATGGTTCCCATGGA
AACCAGCAACCTCTACCTATTTGATGAAACTCCTGTTTGTATTGAGACT
GAAACTGCACCCCTTCGAATGTACAACCCTACAACCACCCTCAATCGAG
AGCAAGAGAAAGAACCTTACAAAAACCCCAATTTACCTTTGGCTGCCAT
CATTGGTGGGGCTGTGGCCCTGGTTACCATTGCCCTTCTTGCTTTAGTG
TGTTGGTATGTTCATAGGAATGGATCGCTCTTCTCAAGGAACTGTGCAT
ATAGCAAAGGGAGGAGAAGAAAGGATGACTATGCAGAAGCTGGCACTAA
GAAGGACAACTCTATCCTGGAAATCAGGGAAACTTCTTTTCAGATGTTA
CCAATAAGCAATGAACCCATCTCGAAGGAGGAGTTTGTAATACACACCA
TATTTCCTCCTAATGGAATGAATCTGTACAAAAACAATCACAGTGAAAG
CAGTAGTAACCGAAGCTACAGAGACAGTGGTATTCCAGACTCAGATCAC
TCACACTCATGATGCTGAAGGACTCACAGCAGACTTGTGTTTTGGGTTT
TTTAAACCTAAGGGAGGTGATGGTAGGAACCCTGTTCTACTGCAAAACA
CTGGAAAAAGAGACTGAAAAAAAGCAATGTACTGTACATTTGCCATATA
ATTTATATTTAAGAACTTTTTATTAAAAGTTTCAAATTTCAGGTTACTG
CTGCGATTGATGTAGTGGAGATGCCTGAACACAATTCTATATTTTAGTA
TTTTTTAGTAATTTGTACTGTATTTTCCTTGCAAATATTGGAGTTATAA
ACCATTTACTTTGTGTTCTACTGAGTAAGATGACTTGTTGACTGTGAAA
GTGAATTTTCTTGCTGTGTCGAACAATCAGGACTGCATTCATATGAGAT
CCTTGTAGTATAAGCACAGGCCATTTTTCACTTTGGTATTAATAAAATG
TAAAAAAAAAAAACTGGCTGAATGGCTGAATGAGATAAAATTTAATTTT
AAAAAATGGTTATGAAATAATGTTCCAATTATTAAATTTGTATTATCCC
AGTGGTATTCAATAAATCAAAATGTGTGAAGTAATGGGCAATATCAAAC
TTCCTGCATATCTCCATTTTTGCTCTAGGCAAATTAATTATCCTTAAAA
AAGTTAAGCATATCTTCTGAACTGAATACATCAGCTGGCATAAAAGGAG
CATGAAGTCTGTTAAAGCCATTGTCAGCAAAGCTTTGAAAATAAAGGAC
TTCACAAAAACGGTAATGTAAATGTGCTTCCAAGTTGGGGGGAAAATGT
GTACTTAGGAAAACATGGAAACTTAGACTTGTATAGTGTAATGAACACA
AATACCAAAACTGCATTTTGGTTTTGCCTATACCATCCTGATTTTTGAA
```

-continued

AAGTGAATTATAAACACAAAATTGTTAGTGTTTATGATGTTTTTATCAT

AAAGGATGTCAGAGAAACTTTATGCATATTAAAAATGTAATGTAATTAT

AAGCGATTCCCCTCAACAATCCAGAGAAAGTAGTTCTTTAAATAAGAGA

TAATTTAAAGAAAAATAAATACTAGACATCAAATTTAGATCTGGTTTAT

GTCAAAGGTTTTAACACTGTACATAAATGTTCAATTTACTTTTACAAAG

ATCAAGAATACTGCCCATTACTGTCACAATTTTCCAGATATTATATAAT

GAACTCGTAATGTAACATTTCCTTCTAGCTTCCTACTGAATTGTGAGCT

GTTACTTGTTGAAAAACCATATCACTTTTCTGTTGCCATGATTTTTTTT

TTTTCAACAAAAAACCAAAGTGCATTGTACGCCCTTTGGCCAGTCTTGT

ATGTGCCTTGATCCAACGCTACATGTATTCAGCTTTTAAAACTCCACAA

ATTTTTCATACTCCTTAAATATGAAAAATTATGGTCTTATTGCTGAATA

AAACTTTTAAAAAGTACAGAATAATTGTGCTTGCTTTTTCAGGATTGTG

TTACTATCACTAAGTAGCAAATTGCCCAGCACATTAGTCCTAAACGTCC

CATGTATTTTTCTAGGCATAAAAATAAAAGTTGGCTAAAAATTTTAAAA

AATCAACA (SEQ ID NO:1, NCBI Reference Sequence: NM_013281.3 which is incorporated by reference in its entirety.)

Sequence: NM_013281.3 which is incorporated by reference in its entirety.)

The consensus amino acid sequence for FLRT3 is:

(SEQ ID NO: 2)

10 20 30 40 50
MISAAWSIFL IGTKIGLFLQ VAPLSVMAKS CPSVCRCDAG FIYCNDRFLT 60 70 80 90 100
SIPTGIPEDA TILYLQNNQI NNAGIPSDLK NLLKVERIYL YHNSLDEFPT 110 120 130 140 150
NLPKYVKELH LQENNIRTIT YDSLSKIPYL EELHLDDNSV SAVSIEEGAF 160 170 180 190 200
RDSNYLRLLF ISRNHLSTIP WGLPRTIEEL RLDDNRISTI SSPSLQGLTS 210 220 230 240 250
LKRLVLDGNL LNNHGLGDKV FENLVNLTEL SLVRNSLTAA PVNLPGTNLR 260 270 280 290 300
KLYLQDNHIN RVPPNAFSYL RQLYRLDMSN NNLSNLPQGI FDDLDNITQL 310 320 330 340 350
ILRNNPWYCG CKMKWVRDWL QSLPVKVNVR GLMCQAPEKV RGMAIKDLNA 360 370 380 390 400
ELFDCKDSGI VSTIQITTAI PNTVYPAQGQ WPAPVTKQPD IKNPKLTKDH 410 420 430 440 450
QTTGSPSRKT ITITVKSVTS DTIHISWKLA LPMTALRLSW LKLGHSPAFG 460 470 480 490 500
SITETIVIGE RSEYLVIALE PDSPYKVCMV PMETSNLYLF DETPVCIETE 510 520 530 540 550
TAPIRMYNPT TILNREQEKE PYKNPNLPLA AIIGGAVALV TIALLALVCW 560 570 580 590 600
YVHRNGSLFS RNCAYSKGRR RKDDYAEAGT KKDNSILEIR ETSFQMLPIS 610 620 630 640
NEPISKEEFV IHTIFPPNGM NLYKNNHSES SSNRSYRDSG IPDSDHSHS

UniProt accession number Q9NZU0-1 which is incorporated by reference in its entirety.

The underlined sequence is the signal sequence. The bolded sequence is the transmembrane sequence, and the double underlined sequence is the intracellular domain. In one embodiment, the FLRT3 protein does not contain the signal sequence.

In one embodiment, the FLRT3 amino acid sequence has 85%, 90%, 95%, 99%, 100% sequence identity to SEQ ID NO:2.

One embodiment provides an immunomodulatory agent that specifically binds to SEQ ID NO:2 or a functional fragment thereof and modulates FLRT3 mediated signal transduction.

Amino acids 29-528 of SEQ ID NO:2 represent the extracellular domain of human FLRT3 and has the following sequence:

(SEQ ID NO: 3)

KSCPSVCRCDAGFIYCNDRFLTSIPTGIPEDATTLYLQNNQINNAGIPS

DLKNLLKVERIYLYHNSLDEFPTNLPKYVKELHLQENNIRTITYDSLS

KIPYLEELHLDDNSVSAVSIEEGAFRDSNYLRLLFLSRNHLSTIPWGL

PRTIEELRLDDNRISTISSPSLQGLTSLKRLVLDGNLLNNHGLGDKVFF

NLVNLTELSLVRNSLTAAPVNLPGTNLRKLYLQDNHINRVPPNAFSY

LRQLYRLDMSNNNLSNLPQGIFDDLDNITQLILRNNPWYCGCKMKW

VRDWLQSLPVKVNVRGLMCQAPEKVRGMAIKDLNAELFDCKDSGI

VSTIQITTAIPNTVYPAQGQWPAPVTKQPDIKNPKLTKDHQTTGSPSR

-continued

KTITITVKSVTSDTIHISWKLALPMTALRLSWLKLGHSPAFGSITETIV

TGERSEYLVTALEPDSPYKVCMVPMETSNLYLFDETPVCIETETAPL

RMYNPTTTLNREQEKEPYKNPNLP

One embodiment provides an immunomodulatory agent that specifically binds to SEQ ID NO:3 or a functional fragment thereof and modulates FLRT3 mediated signal transduction.

2. Murine FLRT3

The amino acid sequence for murine FLRT3 is:

```
                                        (SEQ ID NO: 4)
        10         20         30         40         50
MISPAWSLFL IGTKIGLFFQ VAPLSVVAKS CPSVCRCDAG FIYCNDRSLT

        60         70         80         90        100
SIPVGIPEDA TTLYLQNNQI NNVGIPSDLK NLLKVQRIYL YHNSLDEFPT

       110        120        130        140        150
NLPKYVKELH LQENNIRTIT YDSLSKIPYL EELHLDDNSV SAVSIEEGAF

       160        170        180        190        200
RDSNYLRLLF LSRNHLSTIP GGLPRTIEEL RLDDNRISTI SSPSLHGLTS

       210        220        230        240        250
LKRLVLDGNL INNHGLGDKV FENLVNLTEL SLVRNSLTAA PVNLPGTSLR

       260        270        280        290        300
KLYLQDNHIN RVPPNAFSYL RQLYRLDMSN NNLSNLPQGI EDDLDNITQL

       310        320        330        340        350
ILRNNPWYCG CKMKWVRDWL QSLPVKVNVR GLMCQAPEKV RGMAIKDLSA

       360        370        380        390        400
ELFDCKDSGI VSTIQITTAI PNTAYPAQGQ WPAPVIKQPD IKNPKLIKDQ

       410        420        430        440        450
RTTGSPSRKT ILITVKSVTP DTIHISWRLA LPMTALRLSW LKLGHSPAFG

       460        470        480        490        500
SITETIVIGE RSEYLVTALE PESPYRVCMV PMETSNLYLF DETPVCIETQ

       510        520        530        540        550
TILNREQEKE PYKNPNLPLA AIIGGAVALV SIALLALVCW TAPIRMYNPT

       560        570        580        590        600
YVHRNGSLFS RNCAYSKGRR RKDDYAEAGT KKDNSILEIR ETSFQMLPIS

       610        620        630        640
NEPISKEEFV IHTIFPPNGM NLYKNNLSES SSNRSYRDSG IPDSDHSHS
```

Uniprot accession number Q8BGT1-1 which is incorporated by reference in its entirety.

One embodiment provides an immunomodulatory agent that specifically binds to SEQ ID NO:4 or a functional fragment thereof and modulates FLRT3 mediated signal transduction.

Amino acids 29-528 of SEQ ID NO:2 represent the extracellular domain of murine FLRT3 and has the following sequence:

(SEQ ID NO: 5)

KSCPSVCRCDAGFIYCNDRSLTSIPVGIPEDATTLYLQNNQINNVGIPS

DLKNLLKVQRIYLYHNSLDEFPTNLPKYVKELHLQENNIRTITYDSLS

KIPYLEELHLDDNSVSAVSIEEGAFRDSNYLRLLFLSRNHLSTIPGGLP

RTIEELRLDDNRISTISSPSLHGLTSLKRLVLDGNLLNNHGLGDKVFF

NLVNLTELSLVRNSLTAAPVNLPGTSLRKLYLQDNHINRVPPNAFSY

-continued

LRQLYRLDMSNNNLSNLPQGIFDDLDNITQLILRNNPWYCGCKMKW

VRDWLQSLPVKVNVRGLMCQAPEKVRGMAIKDLSAELFDCKDSGI

VSTIQITTAIPNTAYPAQGQWPAPVTKQPDIKNPKLIKDQRTTGSPSR

KTILITVKSVTPDTIHISWRLALPMTALRLSWLKLGHSPAFGSITETIV

TGERSEYLVTALEPESPYRVCMVPMETSNLYLFDETPVCIETQTAPL

RMYNPTTTLNREQEKEPYKNPNLP

One embodiment provides an immunomodulatory agent that specifically binds to SEQ ID NO:5 or a functional fragment thereof and modulates FLRT3 mediated signal transduction.

B. Binding Partners

One embodiment provides immunomodulatory agents that specifically bind to a binding partner of FLRT3 and modulates FLRT3 mediated signal transduction. Exemplary binding partners of FLRT3 include but are not limited to ROBO1, members of the latrophilin family (such as ADGRL3), and members of the UNC-5 family (such as UNC5B).

Roundabout homolog 1 (ROBO1) interacts with the intracellular domain of FLRT3 to mediate axonal attraction. The consensus amino acid sequence for ROBO1 is as follows:

(SEQ ID NO: 6)

```
        10         20         30         40         50
MKWKHVPFLV MISLLSLSPN HLFLAQLIPD PEDVERGNDH GTPIPTSDND

        60         70         80         90        100
DNSLGYTGSR LRQEDFPPRI VEHPSDLIVS KGEPATINCK AEGRPTPTIE

       110        120        130        140        150
WYKGGERVET DKDDPRSHRM LLPSGSLFFL RIVHGRKSRP DEGVYVCVAR

       160        170        180        190        200
NYLGEAVSHN ASLEVAILRD DFRQNPSDVM VAVGEPAVME CQPPRGHPEP

       210        220        230        240        250
TISWKKDGSP LDDKDERITI RGGKLMITYT RKSDAGKYVC VGTNMVGERE

       260        270        280        290        300
SEVAELTVLE RPSEVKRPSN LAVTVDDSAE FKCEARGDPV PTVRWRKDDG

       310        320        330        340        350
ELPKSRYEIR DDHTLKIRKV TAGDMGSYTC VAENMVGKAE ASATLTVQEP

       360        370        380        390        400
PHFVVKPRDQ VVALGRTVTF QCEATGNPQP AIFWRREGSQ NLLESYQPPQ

       410        420        430        440        450
SSSRFSVSQT GDLTITNVQR SDVGYYICQT LNVAGSIITK AYLEVTDVIA

       460        470        480        490        500
DRPPPVIRQG PVNQTVAVDG TEVLSCVATG SPVPTILWRK DGVLVSTQDS

       510        520        530        540        550
RIKQLENGVI QIRYAKLGDT GRYTCIASTP SGEATWSAYI EVQEFGVPVQ

       560        570        580        590        600
PPRPTDPNLI PSAPSKPEVT DVSRNTVTLS WQPNLNSGAT PTSYIIEAFS

       610        620        630        640        650
HASGSSWQTV AENVKTETSA IKGLKPNAIY LFLVRAANAY GISDPSQISD

       660        670        680        690        700
PVKTQDVLPT SQGVDHKQVQ RELGNAVLHL HNPTVLSSSS IEVHWTVDQQ

       710        720        730        740        750
SQYIQGYKIL YRPSGANHGE SDWLVFEVRI PAKNSVVIPD LRKGVNYEIK

       760        770        780        790        800
ARPFFNEFQG ADSEIKFAKT LEEAPSAPPQ GVTVSKNDGN GTAILVSWQP

       810        820        830        840        850
PPEDTQNGMV QEYKVWCIGN ETRYHINKTV DGSTESVVIP FLVPGIRYSV

       860        870        880        890        900
EVAASTGAGS GVKSEPQFIQ LDAHGNPVSP EDQVSLAQQI SDVVKQPAFI

       910        920        930        940        950
AGIGAACWII LMVFSIWLYR HRKKRNGLTS TYAGIRKVPS FTFTPTVTYQ

       960        970        980        990       1000
RGGEAVSSGG RPGLLNISEP AAQPWLADTW PNTGNNHNDC SISCCTAGNG

      1010       1020       1030       1040       1050
NSDSNLTTYS RPADCIANYN NQLDNKQTNL MLPESTVYGD VDLSNKINEM

      1060       1070       1080       1090       1100
KTFNSPNLKD GRFVNPSGQP TPYATTQLIQ SNLSNNMNNG SGDSGEKHWK

      1110       1120       1130       1140       1150
PLGQQKQEVA PVQYNIVEQN KLNKDYRAND TVPPTIPYNQ SYDQNTGGSY

      1160       1170       1180       1190       1200
NSSDRGSSTS GSQGHKKGAR TPKVPKQGGM NWADLLPPPP AHPPPHSNSE

      1210       1220       1230       1240       1250
EYNISVDESY DQEMPCPVPP ARMYLQQDEL EEEEDERGPT PPVRGAASSP

      1260       1270       1280       1290       1300
AAVSYSHQST ATLTPSPQEE LQPMLQDCPE ETGHMQHQPD RRRQPVSPPP

      1310       1320       1330       1340       1350
PPRPISPPHT YGYISGPLVS DMDTDAPEEE EDEADMEVAK MQTRRLLLRG
```

-continued

```
      1360       1370       1380       1390       1400
LEQTPASSVG DLESSVIGSM INGWGSASEE DNISSGRSSV SSSDGSFFTD

      1410       1420       1430       1440       1450
ADFAQAVAAA AEYAGLKVAR RQMQDAAGRR HFHASQCPRP TSPVSTDSNM

      1460       1470       1480       1490       1500
SAAVMQKTRP AKKLKHQPGH LRRETYTDDL PPPPVPPPAI KSPTAQSKTQ

      1510       1520       1530       1540       1550
LEVRPVVVPK IPSMDARTDR SSDRKGSSYK GREVIDGRQV VDMRTNPGDP

      1560       1570       1580       1590       1600
REAQEQQNDG KGRGNKAAKR DLPPAKTHLI QEDILPYCRP TFPTSNNPRD

      1610       1620       1630       1640       1650
PSSSSSMSSR GSGSRQREQA NVGRRNIAEM QVLGGYERGE DNNEELEETE

S
```

UniProt accession number Q9Y6N7-1 which is incorporated by reference in its entirety.

One embodiment provides an immunomodulatory agent that specifically binds to SEQ ID NO:6 or a functional fragment thereof and modulates FLRT3 mediated signal transduction.

In one embodiment, the functional fragment is an isoform of ROBO1. Several isoforms are recognized in the art including but not limited to isoform 2, isoform 3, isoform 4, isoform 5, and isoform 6.

One embodiment provides an immunomodulatory agent that specifically binds to any one of the isoforms of ROBO1 or a functional fragment thereof and modulates FLRT3 mediated signal transduction.

Adhesion G protein-coupled receptor L3 (ADGRL3) interacts with the extracellular domain of FLRT3 to mediate cell-cell adhesion and neuron guidance. The consensus amino acid sequence for ADGRL3 is as follows:

```
                                             (SEQ ID NO: 7)
        10         20         30         40         50
MWPSQLLIFM MLLAPIIHAF SRAPIPMAVV RRELSCESYP IELRCPGTDV

        60         70         80         90        100
IMIESANYGR TDDKICDSDP AQMENIRCYL PDAYKIMSQR CNNRTQCAVV

       110        120        130        140        150
AGPDVFPDPC PGTYKYLEVQ YECVPYKVEQ KVFLCPGLLK GVYQSEHLFE

       160        170        180        190        200
SDHQSGAWCK DPLQASDKIY YMPWTPYRTD TLTEYSSKDD FIAGRPTTTY

       210        220        230        240        250
KLPHRVDGTG FVVYDGALFF NKERTRNIVK FDLRTRIKSG EAIIANANYH

       260        270        280        290        300
DTSPYRWGGK SDIDLAVDEN GLWVIYATEQ NNGKIVISQL NPYTLRIEGT

       310        320        330        340        350
WDTAYDKRSA SNAFMICGIL YVVKSVYEDD DNEATGNKID YIYNTDQSKD

       360        370        380        390        400
SLVDVPFPNS YQYIAAVDYN PRDNLLYVWN NYHVVKYSLD FGPLDSRSGQ

       410        420        430        440        450
AHHGQVSYIS PPIHLDSELE RPSVKDISTT GPLGMGSTTT STTLRTTTLS

       460        470        480        490        500
PGRSTTPSVS GRRNRSTSTP SPAVEVLDDM TTHLPSASSQ IPALEESCEA

       510        520        530        540        550
VEAREIMWFK TRQGQIAKQP CPAGTIGVST YLCLAPDGIW DPQGPDLSNC

       560        570        580        590        600
SSPWVNHITQ KLKSGETAAN IARELAEQTR NHLNAGDITY SVRAMDQLVG

       610        620        630        640        650
LLDVQLRNLT PGGKDSAARS LNKAMVETVN NILQPQALNA WRDLTTSDQL

       660        670        680        690        700
RAATMLLHTV EESAFVLADN LLKTDIVREN TDNIKLEVAR LSTEGNLEDL

       710        720        730        740        750
KFPENMGHGS TIQLSANTLK QNGRNGEIRV AFVLYNNLGP YLSTENASMK
```

-continued

```
       760        770        780        790        800
LGTEALSTNH SVIVNSPVIT AAINKEFSNK VYLADPVVFT VKHIKQSEEN

       810        820        830        840        850
FNPNCSFWSY SKRTMTGYWS TQGCRLLTTN KTHTTCSCNH LINFAVLMAH

       860        870        880        890        900
VEVKHSDAVH DLLLDVITWV GILLSLVCLL ICIFTFCFFR GLQSDRNTIH

       910        920        930        940        950
KNLCISLEVA ELLFLIGINR TDQPIACAVF AALLHFFFLA AFTWMFLEGV

       960        970        980        990       1000
QLYIMLVEVE ESEHSRRKYF YLVGYGMPAL IVAVSAAVDY RSYGTDKVCW

      1010       1020       1030       1040       1050
LRLDTYFIWS FIGPATLIIM INVIFLGIAL YKMFHHTAIL KPESGCLDNI

      1060       1070       1080       1090       1100
KSWVIGAIAL LCLLGLTWAF GLMYINESTV IMAYLFTIFN SLQGMFIFIF

      1110       1120       1130       1140       1150
HCVLQKKVRK EYGKCLRTHC CSGKSTESSI GSGKTSGSRT PGRYSTGSQS

      1160       1170       1180       1190       1200
RIRRMWNDTV RKQSESSFIT GDINSSASIN REGLINNARD TSVMDTLPLN

      1210       1220       1230       1240       1250
GNHGNSYSIA SGEYLSNCVQ IIDRGYNHNE TALEKKILKE LTSNYIPSYL

      1260       1270       1280       1290       1300
NNHERSSEQN RNLMNKLVNN LGSGREDDAI VIDDATSFNH EESLGLELIH

      1310       1320       1330       1340       1350
EESDAPLLPP RVYSTENHQP HHYTRRRIPQ DHSESFFPLL TNEHTEDLQS

      1360       1370       1380       1390       1400
PHRDSLYTSM PTLAGVAATE SVTISTQTEP PPAKCGDAED VYYKSMPNLG

      1410       1420       1430       1440
SRNHVHQLHT YYQLGRGSSD GFIVPPNKDG TPPEGSSKGP AHLVTSL
```

UniProt accession number Q9HAR2-1 which is incorporated by reference in its entirety.

One embodiment provides an immunomodulatory agent that specifically binds to SEQ ID NO:7 or a functional fragment thereof and modulates FLRT3 mediated signal transduction.

One embodiment provides an immunomodulatory agent that specifically binds to any one of the isoforms of ADGRL1 or a functional fragment thereof and modulates FLRT3 mediated signal transduction.

Netrin receptor UNC5B (UNC5B) interacts with the extracellular domain of FLRT3 to mediate axon growth cone collapse and play a repulsive role in neuron guidance. The consensus amino acid sequence for UNC5B is as follows:

```
                                              (SEQ ID NO: 8)
        10         20         30         40         50
MISPAWSLFL IGTKIGLFFQ VAPLSVVAKS CPSVCRCDAG FIYCNDRSLT

        60         70         80         90        100
SIPVGIPEDA TILYLQNNQI NNVGIPSDLK NLLKVQRIYL YHNSLDEFPT

       110        120        130        140        150
NLPKYVKELH LQENNIRTIT YDSLSKIPYL EELHLDDNSV SAVSIEEGAF

       160        170        180        190        200
RDSNYLRLLF LSRNHLSTIP GGLPRTIEEL RLDDNRISTI SSPSLHGLTS

       210        220        230        240        250
LKRLVLDGNL LNNHGLGDKV FENLVNLTEL SLVRNSLTAA PVNLPGTSLR

       260        270        280        290        300
KLYLQDNHIN RVPPNAFSYL RQLYRLDMSN NNLSNLPQGI FDDLDNITQL

       310        320        330        340        350
ILRNNPWYCG CKMKWVRDWL QSLPVKVNVR GLMCQAPEKV RGMAIKDLSA

       360        370        380        390        400
ELFDCKDSGI VSTIQITTAI PNTAYPAQGQ WPAPVTKQPD IKNPKLIKDQ
```

-continued

```
       410        420        430        440        450
RTTGSPSRKT ILITVKSVTP DTIHISWRLA LPMTALRLSW LKLGHSPAFG

       460        470        480        490        500
SITETIVTGE RSEYLVTALE PESPYRVCMV PMETSNLYLF DETPVCIETQ

       510        520        530        540        550
TAPLRMYNPT TILNREQEKE PYKNPNLPLA AIIGGAVALV SIALLALVCW

       560        570        580        590        600
YVHRNGSLES RNCAYSKGRR RKDDYAEAGT KKDNSILEIR ETSFQMLPIS

       610        620        630        640
NEPISKEEFV IHTIFPPNGM NLYKNNLSES SSNRSYRDSG IPDSDHSHS
```

UniProt accession number Q8BGT1-1 which is incorporated by reference in its entirety.

One embodiment provides an immunomodulatory agent that specifically binds to SEQ ID NO:8 or a functional fragment thereof and modulates FLRT3 mediated signal transduction.

C. Immunomodulatory Agents or Binding Moieties

Immunomodulatory agents or binding moieties including agonists and antagonists of FLRT3 are provided. An agonist of FLRT3 typically induces, promotes, or enhances FLRT3 mediated signaling. An antagonist of FLRT3 typically inhibits, reduces, or blocks FLRT3 mediated signaling. The disclosed compositions and methods can be used to modulate FLRT3 and/or counter-receptor signaling on, for example, immune cells including but not limited to monocytes, Tregs, tumor-associated macrophages (TAMs), Myeloid Derived Suppressor Cells (MDSC), T cells, Th2 cells, myeloid cells including antigen-presenting cells (e.g., monocyte, macrophage, or dendritic cell), T cells, Natural Killer (NK) cells, or a combination thereof. In some embodiments, the compositions are specifically targeted to one or more cell types. In some embodiments, the disclosed compositions can be used on tumor cells.

In some embodiments, the anti-FLRT3 agonists induce, promote, or enhance FLRT3 mediated signaling through a known ligand or unknown counter-receptor through FLRT3 interaction with said known or unknown counter-receptor. For example, in some embodiments, the FLRT3 agonist binds to, induces, promotes or creates a conformational change, or otherwise promotes FLRT3 mediated signal transduction.

In some embodiments, the anti-FLRT3 antagonists inhibit, reduce, block, or otherwise disrupt signaling through a known or unknown counter-receptor through blockade of FLRT3 interaction with said known or unknown counter-receptor. For example, in some embodiments, the FLRT3 antagonist binds to FLRT3 or a ligand thereof and inhibits, blocks, creates a conformational change, or otherwise interferes with FLRT3 mediated signal transduction.

1. Antibodies

The sequences of light and heavy chain variable regions for monoclonal antibodies produced by 14 hybridomas, referred to herein as 14B7, 17A1, 15G11, 18A7, 9F3, 1H5, 2F7, 5C2, 7H7, 10C6, 12A4, 13B2, 14D3, and 20C3 are provided below. CDRs are underlined and bolded in the context of the light and heavy chain sequences.

One embodiment provides an anti-FLRT3 antibody produced by a hybridoma selected from the group consisting of 14B7, 17A1, 15G11, 18A7, 9F3, 1H5, 2F7, 5C2, 7H7, 10C6, 12A4, 13B2, 14D3, and 20C3.

Another embodiment provides an anti-FLRT3 antibody having at least one light chain or at least one heavy chain of the antibody produced by one or more of the hybridomas selected from the group consisting of 14B7, 17A1, 15G11, 18A7, 9F3, 1H5, 2F7, 5C2, 7H7, 10C6, 12A4, 13B2, 14D3, and 20C3.

a. 14B7 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 12)
DIQMNQSPSSLSASLGDTITIACRASQNIDIWLSWYQQKPGSIPKLLIY
KASNLHTGVPSRFSGSGSGTDFTLTISSLQPEDIATYYCLQGQSFPFT
FGSGTKLEIK*

The light chain CDRs of 14B7 are bolded and are as follows:

| | | |
|---|---|---|
| CDR1 | RASQNIDIWLS | SEQ ID NO: 13 |
| CDR2 | KASNLHT | SEQ ID NO: 14 |
| CDR3 | LQGQSFPFT | SEQ ID NO: 15 |

In another embodiment, SEQ ID NO:12 includes the sequence of human kappa constant domain:

(SEQ ID NO: 16)
DIQMTQSPSSVSASLGDRVTITCRASQNIDIWLSWYQQKPGKAPKLL
IYKASNLHTGVPSRFSGSGSGTDFTLTISSLQPEDFATYYCLQGQSFP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC.

Other exemplary light chains produced by hybridoma 14B7 include the following:

VL-1

(SEQ ID NO: 17)
DIQMTQSPSSVSASVGDRVTITCRASQNIDIWLSWYQQKPGKAPKLL
IYKASNLHTGVPSRFSGSGSGTDFTLTISSLQPEDFATYYCLQGQSFP
FTFGSGTKLEIK

SEQ ID NO:17 with human kappa constant domain:

(SEQ ID NO: 18)
DIQMTQSPSSVSASVGDRVTITCRASQNIDIWLSWYQQKPGKAPKLL
IYKASNLHTGVPSRFSGSGSGTDFTLTISSLQPEDFATYYCLQGQSFP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

VL-2
(SEQ ID NO: 19)
DIQMTQSPSSVSASVGDRVTITCRASQNIDTNLSWYQQKPGKAPKLL
IYKASNLHTGVPSRFSGSGSGTDFTLTISSLQPEDFATYYCLQGQSFP
FTFGSGTKLEIK

SEQ ID NO:19 with human kappa constant domain:

(SEQ ID NO: 20)
DIQMTQSPSSVSASVGDRVTITCRASQNIDTNLSWYQQKPGKAPKLL
IYKASNLHTGVPSRFSGSGSGTDFTLTISSLQPEDFATYYCLQGQSFP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

VL-3
(SEQ ID NO: 21)
DIQMTQSPSSVSASVGDRVTITCRASQNIDIWLSWYQQKPGKAPKLL
IYKASNLHTGVPSRFSGSGSGTDFTLTISSLQPEDFATYYCLQGQSTP
FTFGSGTKLEIK

SEQ ID NO:21 with human kappa constant domain:

(SEQ ID NO: 22)
DIQMTQSPSSVSASVGDRVTITCRASQNIDTNLSWYQQKPGKAPKLL
IYKASNLHTGVPSRFSGSGSGTDFTLTISSLQPEDFATYYCLQGQSFP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

VL-4
(SEQ ID NO: 23)
DIQMTQSPSSVSASVGDRVTITCRASQNIDIWLSWYQQKPGKAPKLL
IYKASNLHTGVPSRFSGSGSGTDFTLTISSLQPEDFATYYCLQGQSTP
FTFGSGTKLEIK

SEQ ID NO:23 with human kappa constant domain:

(SEQ ID NO: 24)
DIQMTQSPSSVSASVGDRVTITCRASQNIDIWLSWYQQKPGKAPKLL
IYKASNLHTGVPSRFSGSGSGTDFTLTISSLQPEDFATYYCLQGQSTP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

-continued

VL-5
(SEQ ID NO: 25)
DIQMTQSPSSVSASVGDRVTITCRASQNIDTNLSWYQQKPGKAPKLL
IYKASNLHTGVPSRFSGSGSGTDFTLTISSLQPEDFATYYCLQGQSTP
FTFGSGTKLEIK

SEQ ID NO:25 with human kappa constant domain:

(SEQ ID NO: 26)
DIQMTQSPSSVSASVGDRVTITCRASQNIDTNLSWYQQKPGKAPKLL
IYKASNLHTGVPSRFSGSGSGTDFTLTISSLQPEDFATYYCLQGQSTP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

VL-6
(SEQ ID NO: 27)
DIQMTQSPSSVSASVGDRVTITCRASQNIDSWLSWYQQKPGKAPKLL
IYKASNLHTGVPSRFSGSGSGTDFTLTISSLQPEDFATYYCLQGQSFP
FTFGSGTKLEIK

SEQ ID NO:27 with human kappa constant domain:

(SEQ ID NO: 28)
DIQMTQSPSSVSASVGDRVTITCRASQNIDSWLSWYQQKPGKAPKLL
IYKASNLHTGVPSRFSGSGSGTDFTLTISSLQPEDFATYYCLQGQSFP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC

VL-7
(SEQ ID NO: 29)
DIQMTQSPSSVSASVGDRVTITCRASQNIDSWLSWYQQKPGKAPKLL
IYKASNLHTGVPSRFSGSGSGTDFTLTISSLQPEDFATYYCLQGQSTP
FTFGSGTKLEIK

SEQ ID NO:29 with human kappa constant domain:

(SEQ ID NO: 30)
DIQMTQSPSSVSASVGDRVTITCRASQNIDSWLSWYQQKPGKAPKLL
IYKASNLHTGVPSRFSGSGSGTDFTLTISSLQPEDFATYYCLQGQSTP
FTFGSGTKLEIKRTVAAPSVFIFPPSDEQLKSGTASVVCLLNNFYPREA
KVQWKVDNALQSGNSQESVTEQDSKDSTYSLSSTLTLSKADYEKHK
VYACEVTHQGLSSPVTKSFNRGEC ii. Heavy Chain One embodiment provides a humanized antibody or antigen binding fragment with a heavy chain variable region having at least 60, 65, 70, 75, 80, 85, 90, 95, 99, or 100% sequence identity with the following: QVQLQQSGPEL-VKPGASVNISCKASGYAFGNSWMNWVKQRPGKGL EWIGWIYPGDGNANYNGKFKGKATLTAD-KSSSTAYMQLSSLTSED SAVYFCARALYDYDGW-FAYWGQGTLVTVSA* (SEQ ID NO:31)

The heavy chain CDRs of 14B7 are bolded and are as follows:

| | | |
|---|---|---|
| CDR1 | **NSWMN** | SEQ ID NO: 32 |
| CDR2 | **WIYPGDGNANYNGKFKG** | SEQ ID NO: 33 |
| CDR3 | **ALYDYDGWFAY** | SEQ ID NO: 34 |

In another embodiment, SEQ ID NO:31 includes the sequence of human IgG constant domain:

(SEQ ID NO: 35)
QVQLQQSGPELVKPGASVNISCKASGYAFGNSWMNWVKQRPGKGL
EWIGWIYPGDGNANYNGKFKGKATLTADKSSSTAYMQLSSLTSED
SAVYFCARALYDYDGWFAYWGQGTLVTVSAASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTC
PPCPAPELLGGPSVFLFPPKPKDTLMISRTPEVTCVVVDVSHEDPEVK
FNWYVDGVEVHNAKTKPREEQYNSTYRVVSVLTVLHQDWLNGKE
YKCKVSNKALPAPIEKTISKAKGQPREPQVYTLPPSRDELTKNQVSLT
CLVKGFYPSDIAVEWESNGQPENNYKTTPPVLDSDGSFFLYSKLTVD
KSRWQQGNVFSCSVMHEALHNHYTQKSLSLSPG*

In one embodiment, SEQ ID NO:31 includes the sequence of human IgG constant domain, G1FES:

(SEQ ID NO: 36)
QVQLQQSGPELVKPGASVNISCKASGYAFGNSWMNWVKQRPGKGL
EWIGWIYPGDGNANYNGKFKGKATLTADKSSSTAYMQLSSLTSED
SAVYFCARALYDYDGWFAYWGQGTLVTVSAASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTC
PPCPAPEFEGGPSVFLFPPKPKDTLMISRTPEVTCVVVDVSHEDPEVK
FNWYVDGVEVHNAKTKPREEQYNSTYRVVSVLTVLHQDWLNGKE
YKCKVSNKALPASIEKTISKAKGQPREPQVYTLPPSRDELTKNQVSLT
CLVKGFYPSDIAVEWESNGQPENNYKTTPPVLDSDGSFFLYSKLTVD
KSRWQQGNVFSCSVMHEALHNHYTQKSLSLSPG*

In one embodiment, SEQ ID NO:31 includes the sequence of human IgG4 constant domain, G4P:

(SEQ ID NO: 37)
QVQLQQSGPELVKPGASVNISCKASGYAFGNSWMNWVKQRPGKGL
EWIGWIYPGDGNANYNGKFKGKATLTADKSSSTAYMQLSSLTSEDS
AVYFCARALYDYDGWFAYWGQGTLVTVSAASTKGPSVFPLAPCSRS
TSESTAALGCLVKDYFPEPVTVSWNSGALTSGVHTFPAVLQSSGLYS
LSSVVTVPSSSLGTKTYTCNVDHKPSNTKVDKRVESKYGPPCPPCPA
PEFLGGPSVFLFPPKPKDTLMISRTPEVTCVVVDVSQEDPEVQFNWY
VDGVEVHNAKTKPREEQFNSTYRVVSVLTVLHQDWLNGKEYKCKV

-continued

SNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQ
EGNVFSCSVMHEALHNHYTQKSLSLSLG

Other exemplary heavy chains produced by hybridoma 14B7 include the following:

(SEQ ID NO: 38)
QVQLVQSGAEVKKPGASVKVSCKASGYAFGNSWMNWVRQAPGQG
LEWMGWIYPGDGNANYSQKFQGRVTLTADKSASTAYMELSSLRSE
DTAVYYCARALYDYDGWFAYWGQGTLVTVSS

SEQ ID NO:38 with human IgG1 constant domain:

(SEQ ID NO: 39)
QVQLVQSGAEVKKPGASVKVSCKASGYAFGNSWMNWVRQAPGQG
LEWMGWIYPGDGNANYSQKFQGRVTLTADKSASTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:38 with human IgG1 constant domain, GIFES:

(SEQ ID NO: 40)
QVQLVQSGAEVKKPGASVKVSCKASGYAFGNSWMNWVRQAPGQG
LEWMGWIYPGDGNANYSQKFQGRVTLTADKSASTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:38 with human IgG4 constant domain, G4P:

(SEQ ID NO: 41)
QVQLVQSGAEVKKPGASVKVSCKASGYAFGNSWMNWVRQAPGQG
LEWMGWIYPGDGNANYSQKFQGRVTLTADKSASTAYMELSSLRSE
DTAVYYCARALYDYDGWFAYWGQGTLVTVSSASTKGPSVFPLAPC
SRSTSESTAALGCLVKDYFPEPVTVSWNSGALTSGVHTFPAVLQSSG

-continued

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

VH1:

(SEQ ID NO: 42)

QVQLVQSGAEVKKPGASVKVSCKASGYAFGNSWMNWVRQAPGQG

LEWMGWIYPGDGNANYAQKFQGRVTLTADKSASTAYMELSSLRS

EDTAVYYCARALYDYDGWFAYWGQGTLVTVSS

SEQ ID NO:42 with human IgG1 constant domain:

(SEQ ID NO: 43)

QVQLVQSGAEVKKPGASVKVSCKASGYAFGNSWMNWVRQAPGQG

LEWMGWIYPGDGNANYAQKFQGRVTLTADKSASTAYMELSSLRS

EDTAVYYCARALYDYDGWFAYWGQGTLVTVSSASTKGPSVFPLAP

SSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTH

TCPPCPAPELLGGPSVFLFPPKPKDTLMISRTPEVTCVVVDVSHEDPE

VKFNWYVDGVEVHNAKTKPREEQYNSTYRVVSVLTVLHQDWLNG

KEYKCKVSNKALPAPIEKTISKAKGQPREPQVYTLPPSRDELTKNQVS

LTCLVKGFYPSDIAVEWESNGQPENNYKTTPPVLDSDGSFFLYSKLT

VDKSRWQQGNVFSCSVMHEALHNHYTQKSLSLSPG

SEQ ID NO:42 with human IgG1 constant domain, G1FES:

(SEQ ID NO: 44)

QVQLVQSGAEVKKPGASVKVSCKASGYAFGNSWMNWVRQAPGQG

LEWMGWIYPGDGNANYAQKFQGRVTLTADKSASTAYMELSSLRS

EDTAVYYCARALYDYDGWFAYWGQGTLVTVSSASTKGPSVFPLAP

SSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTH

TCPPCPAPEFEGGPSVFLFPPKPKDTLMISRTPEVTCVVVDVSHEDPE

VKFNWYVDGVEVHNAKTKPREEQYNSTYRVVSVLTVLHQDWLNG

KEYKCKVSNKALPASIEKTISKAKGQPREPQVYTLPPSRDELTKNQVS

LTCLVKGFYPSDIAVEWESNGQPENNYKTTPPVLDSDGSFFLYSKLT

VDKSRWQQGNVFSCSVMHEALHNHYTQKSLSLSPG

SEQ ID NO:42 with human IgG4 constant domain, G4P:

(SEQ ID NO: 45)

QVQLVQSGAEVKKPGASVKVSCKASGYAFGNSWMNWVRQAPGQG

LEWMGWIYPGDGNANYAQKFQGRVTLTADKSASTAYMELSSLRS

EDTAVYYCARALYDYDGWFAYWGQGTLVTVSSASTKGPSVFPLAP

-continued

CSRSTSESTAALGCLVKDYFPEPVTVSWNSGALTSGVHTFPAVLQSS

GLYSLSSVVTVPSSSLGTKTYTCNVDHKPSNTKVDKRVESKYGPPCP

PCPAPEFLGGPSVFLFPPKPKDTLMISRTPEVTCVVVDVSQEDPEVQF

NWYVDGVEVHNAKTKPREEQFNSTYRVVSVLTVLHQDWLNGKEY

KCKVSNKGLPSSIEKTISKAKGQPREPQVYTLPPSQEEMTKNQVSLTC

LVKGFYPSDIAVEWESNGQPENNYKTTPPVLDSDGSFFLYSRLTVDK

SRWQEGNVFSCSVMHEALHNHYTQKSLSLSLG

VH2:

(SEQ ID NO: 46)

QVQLVQSGAEVKKPGASVKVSCKASGYAFGNSWMNWVRQAPGQG

LEWMGWIYPGDGNANYSQKFQGRVTLTADKSASTAYMELSSLRSE

DTATYYCARALYDYDGWFAYWGQGTLVTVSS

SEQ ID NO:46 with human IgG1 constant domain:

(SEQ ID NO: 47)

QVQLVQSGAEVKKPGASVKVSCKASGYAFGNSWMNWVRQAPGQG

LEWMGWIYPGDGNANYSQKFQGRVTLTADKSASTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:46 with human IgG1 constant domain, G1FES:

(SEQ ID NO: 48)

QVQLVQSGAEVKKPGASVKVSCKASGYAFGNSWMNWVRQAPGQC

LEWMGWIYPGDGNANYSQKFQGRVTLTADKSASTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPASIEKTISKAKGQPREPQVYTLPPSRDELTKNQVSI

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:46 with human IgG1 constant domain, G4P:

(SEQ ID NO: 49)

QVQLVQSGAEVKKPGASVKVSCKASGYAFGNSWMNWVRQAPGQG

LEWMGWIYPGDGNANYSQKFQGRVTLTADKSASTAYMELSSLRSE

-continued

DTATYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-2.1

(SEQ ID NO: 50)
QVQLVQSGAEVKKPGASVKVSCKASGYAFGNSWMNWVRQAPGQG
LEWMGWIYPGDGNANYAQKFQGRVTLTADKSASTAYMELSSLRS
EDTATYYCARALYDYDGWFAYWGQGTLVTVSS

SEQ ID NO:50 with human IgG1 constant domain:

(SEQ ID NO: 51)
QVQLVQSGAEVKKPGASVKVSCKASGYAFGNSWMNWVRQAPGQG
LEWMGWIYPGDGNANYAQKFQGRVTLTADKSASTAYMELSSLRS
EDTATYYCARALYDYDGWFAYWGQGTLVTVSSASTKGPSVFPLAP
SSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPE
VKFNWYVDGVEVHNAKTKPREEQYNSTYRVVSVLTVLHQDWLNG
KEYKCKVSNKALPAPIEKTISKAKGQPREPQVYTLPPSRDELTKNQVS
LTCLVKGFYPSDIAVEWESNGQPENNYKTTPPVLDSDGSFFLYSKLT
VDKSRWQQGNVFSCSVMHEALHNHYTQKSLSLSPG

SEQ ID NO:50 with human IgG1 constant domain, G1FES:

(SEQ ID NO: 52)
QVQLVQSGAEVKKPGASVKVSCKASGYAFGNSWMNWVRQAPGQG
LEWMGWIYPGDGNANYAQKFQGRVTLTADKSASTAYMELSSLRS
EDTATYYCARALYDYDGWFAYWGQGTLVTVSSASTKGPSVFPLAP
SSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTH
TCPPCPAPEFEGGPSVFLFPPKPKDTLMISRTPEVTCVVVDVSHEDPE
VKFNWYVDGVEVHNAKTKPREEQYNSTYRVVSVLTVLHQDWLNG
KEYKCKVSNKALPASIEKTISKAKGQPREPQVYTLPPSRDELTKNQVS
LTCLVKGFYPSDIAVEWESNGQPENNYKTTPPVLDSDGSFFLYSKLT
VDKSRWQQGNVFSCSVMHEALHNHYTQKSLSLSPG

SEQ ID NO:50 with human IgG4 constant domain, G4P:

(SEQ ID NO: 53)
QVQLVQSGAEVKKPGASVKVSCKASGYAFGNSWMNWVRQAPGQG
LEWMGWIYPGDGNANYAQKFQGRVTLTADKSASTAYMELSSLRS
EDTATYYCARALYDYDGWFAYWGQGTLVTVSSASTKGPSVFPLAP
CSRSTSESTAALGCLVKDYFPEPVTVSWNSGALTSGVHTFPAVLQSS
GLYSLSSVVTVPSSSLGTKTYTCNVDHKPSNTKVDKRVESKYGPPCP
PCPAPEFLGGPSVFLFPPKPKDTLMISRTPEVTCVVVDVSQEDPEVQF
NWYVDGVEVHNAKTKPREEQFNSTYRVVSVLTVLHQDWLNGKEY
KCKVSNKGLPSSIEKTISKAKGQPREPQVYTLPPSQEEMTKNQVSLTC
LVKGFYPSDIAVEWESNGQPENNYKTTPPVLDSDGSFFLYSRLTVDK
SRWQEGNVFSCSVMHEALHNHYTQKSLSLSLG

VH3

(SEQ ID NO: 54)
QVQLVQSGAEVKKPGASVKVSCKASGYAFGNSWMNWVRQAPGQG
LEWMGWIYPGDGNANYSQKFQGRVTLTADKSTSTAYMELSSLRSE
DTAVYYCARALYDYDGWFAYWGQGTLVTVSS

SEQ ID NO:54 with human IgG1 constant domain:

(SEQ ID NO: 55)
QVQLVQSGAEVKKPGASVKVSCKASGYAFGNSWMNWVRQAPGQC
LEWMGWIYPGDGNANYSQKFQGRVTLTADKSTSTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSI
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:54 with human IgG1 constant domain, GIFES:

(SEQ ID NO: 56)
QVQLVQSGAEVKKPGASVKVSCKASGYAFGNSWMNWVRQAPGQG
LEWMGWIYPGDGNANYSQKFQGRVTLTADKSTSTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:55 with human IgG4 constant domain, G4P:

(SEQ ID NO: 57)

QVQLVQSGAEVKKPGASVKVSCKASGYAFGNSWMNWVRQAPGQG
LEWMGWIYPGDGNANYSQKFQGRVTLTADKSTSTAYMELSSLRSE
DTAVYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH3.1

(SEQ ID NO: 58)

QVQLVQSGAEVKKPGASVKVSCKASGYAFGNSWMNWVRQAPGQG
LEWMGWIYPGDGNANYAQKFQGRVTLTADKSTSTAYMELSSLRSE
DTAVYYCARALYDYDGWFAYWGQGTLVTVSS

SEQ ID NO:58 with human IgG1 constant domain:

(SEQ ID NO: 59)

QVQLVQSGAEVKKPGASVKVSCKASGYAFGNSWMNWVRQAPGQG
LEWMGWIYPGDGNANYAQKFQGRVTLTADKSTSTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:58 with human IgG1 constant domain, G1FES:

(SEQ ID NO: 60)

QVQLVQSGAEVKKPGASVKVSCKASGYAFGNSWMNWVRQAPGQG
LEWMGWIYPGDGNANYAQKFQGRVTLTADKSTSTAYMELSSLRSE
DTAVYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:58 with human IgG4 constant domain, G4P:

(SEQ ID NO: 61)

QVQLVQSGAEVKKPGASVKVSCKASGYAFGNSWMNWVRQAPGQG
LEWMGWIYPGDGNANYAQKFQGRVTLTADKSTSTAYMELSSLRSE
DTAVYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-4

(SEQ ID NO: 62)

QVQLVQSGAEVKKPGASVKVSCKASGYAFGNSWMNWVRQAPGQG
LEWMGWIYPGDGNANYSQKFQGRVTLTADKSTSTAYMELSSLRSE
DTATYYCARALYDYDGWFAYWGQGTLVTVSS

SEQ ID NO:62 with human IgG1 constant domain:

(SEQ ID NO: 63)

QVQLVQSGAEVKKPGASVKVSCKASGYAFGNSWMNWVRQAPGQG
LEWMGWIYPGDGNANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:62 with IgG1 constant domain, GIFES:

(SEQ ID NO: 64)

QVQLVQSGAEVKKPGASVKVSCKASGYAFGNSWMNWVRQAPGQG
LEWMGWIYPGDGNANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:62 with human IgG4 constant domain, G4P:

(SEQ ID NO: 65)
QVQLVQSGAEVKKPGASVKVSCKASGYAFGNSWMNWVRQAPGQG
LEWMGWIYPGDGNANYSQKFQGRVTLTADKSTSTAYMELSSLRSE
DTATYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-4.1

(SEQ ID NO: 66)
QVQLVQSGAEVKKPGASVKVSCKASGYAFGNSWMNWVRQAPGQG
LEWMGWIYPGDGNANYAQKFQGRVTLTADKSTSTAYMELSSLRSE
DTATYYCARALYDYDGWFAYWGQGTLVTVSS

SEQ ID NO:66 with human IgG1 constant domain:

(SEQ ID NO: 67)
QVQLVQSGAEVKKPGASVKVSCKASGYAFGNSWMNWVRQAPGQG
LEWMGWIYPGDGNANYAQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:66 with human IgG1 constant domain, G1FES:

(SEQ ID NO: 68)
QVQLVQSGAEVKKPGASVKVSCKASGYAFGNSWMNWVRQAPGQG
LEWMGWIYPGDGNANYAQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:66 with human IgG4 constant domain, G4P:

(SEQ ID NO: 69)
QVQLVQSGAEVKKPGASVKVSCKASGYAFGNSWMNWVRQAPGQG
LEWMGWIYPGDGNANYAQKFQGRVTLTADKSTSTAYMELSSLRSE
DTATYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-5

(SEQ ID NO: 70)
QVQLVQSGAEVKKPGASVKVSCKASGYAFGSSWMNWVRQAPGQG
LEWMGWIYPGDGNANYSQKFQGRVTLTADKSTSTAYMELSSLRSE
DTATYYCARALYDYDGWFAYWGQGTLVTVSS

SEQ ID NO:70 with human IgG1 constant domain:

(SEQ ID NO: 71)
QVQLVQSGAEVKKPGASVKVSCKASGYAFGSSWMNWVRQAPGQG
LEWMGWIYPGDGNANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:70 with human IgG1 constant domain, G1FES:

(SEQ ID NO: 72)
QVQLVQSGAEVKKPGASVKVSCKASGYAFGSSWMNWVRQAPGQG
LEWMGWIYPGDGNANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:70 with human IgG4 constant domain, G4P:

(SEQ ID NO: 73)

QVQLVQSGAEVKKPGASVKVSCKASGYAFGSSWMNWVRQAPGQG

LEWMGWIYPGDGNANYSQKFQGRVTLTADKSTSTAYMELSSLRSE

DTATYYCARALYDYDGWFAYWGQGTLVTVSSASTKGPSVFPLAPC

SRSTSESTAALGCLVKDYFPEPVTVSWNSGALTSGVHTFPAVLQSSG

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

VH-5.1

(SEQ ID NO: 74)

QVQLVQSGAEVKKPGASVKVSCKASGYAFGSSWMNWVRQAPGQG

LEWMGWIYPGDGNANYAQKFQGRVTLTADKSTSTAYMELSSLRSE

DTATYYCARALYDYDGWFAYWGQGTLVTVSS

SEQ ID NO:74 with human IgG1 constant domain:

(SEQ ID NO: 75)

QVQLVQSGAEVKKPGASVKVSCKASGYAFGSSWMNWVRQAPGQG

LEWMGWIYPGDGNANYAQKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:74 with human IgG1 constant domain, G1FES:

(SEQ ID NO: 76)

QVQLVQSGAEVKKPGASVKVSCKASGYAFGSSWMNWVRQAPGQG

LEWMGWIYPGDGNANYAQKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPASIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:74 with human IgG4 constant domain, G4P:

(SEQ ID NO: 77)

QVQLVQSGAEVKKPGASVKVSCKASGYAFGSSWMNWVRQAPGQG

LEWMGWIYPGDGNANYAQKFQGRVTLTADKSTSTAYMELSSLRSE

DTATYYCARALYDYDGWFAYWGQGTLVTVSSASTKGPSVFPLAPC

SRSTSESTAALGCLVKDYFPEPVTVSWNSGALTSGVHTFPAVLQSSG

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

VH-6

(SEQ ID NO: 78)

QVQLVQSGAEVKKPGASVKVSCKASGYAFGNSWMNWVRQAPGQG

LEWMGWIYPGSGNANYSQKFQGRVTLTADKSTSTAYMELSSLRSE

DTATYYCARALYDYDGWFAYWGQGTLVTVSS

SEQ ID NO:78 with human IgG1 constant domain:

(SEQ ID NO: 79)

QVQLVQSGAEVKKPGASVKVSCKASGYAFGNSWMNWVRQAPGQG

LEWMGWIYPGSGNANYSQKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:78 with human IgG1 constant domain, GIFES:

(SEQ ID NO: 80)

QVQLVQSGAEVKKPGASVKVSCKASGYAFGNSWMNWVRQAPGQG

LEWMGWIYPGSGNANYSQKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPASIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:78 with human IgG4 constant domain, G4P:

(SEQ ID NO: 81)
QVQLVQSGAEVKKPGASVKVSCKASGYAFGNSWMNWVRQAPGQG
LEWMGWIYPGSGNANYSQKFQGRVTLTADKSTSTAYMELSSLRSE
DTATYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-6.1

(SEQ ID NO: 82)
QVQLVQSGAEVKKPGASVKVSCKASGYAFGNSWMNWVRQAPGQG
LEWMGWIYPGSGNANYAQKFQGRVTLTADKSTSTAYMELSSLRSE
DTATYYCARALYDYDGWFAYWGQGTLVTVSS

SEQ ID NO:82 with human IgG1 constant domain:

(SEQ ID NO: 83)
QVQLVQSGAEVKKPGASVKVSCKASGYAFGNSWMNWVRQAPGQG
LEWMGWIYPGSGNANYAQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:82 with human IgG1 constant domain, G1FES:

(SEQ ID NO: 84)
QVQLVQSGAEVKKPGASVKVSCKASGYAFGNSWMNWVRQAPGQG
LEWMGWIYPGSGNANYAQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:82 with human IgG4 constant domain, G4P:

(SEQ ID NO: 85)
QVQLVQSGAEVKKPGASVKVSCKASGYAFGNSWMNWVRQAPGQG
LEWMGWIYPGSGNANYAQKFQGRVTLTADKSTSTAYMELSSLRSE
DTATYYCARALYDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-7

(SEQ ID NO: 86)
QVQLVQSGAEVKKPGASVKVSCKASGYAFGNSWMNWVRQAPGQG
LEWMGWIYPGDGSANYSQKFQGRVTLTADKSTSTAYMELSSLRSE
DTATYYCARALYDYDGWFAYWGQGTLVTVSS

SEQ ID NO:86 with human IgG1 constant domain:

(SEQ ID NO: 87)
QVQLVQSGAEVKKPGASVKVSCKASGYAFGNSWMNWVRQAPGQG
LEWMGWIYPGDGSANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLOSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:86 with human IgG1 constant domain, GIFES:

(SEQ ID NO: 88)
QVQLVQSGAEVKKPGASVKVSCKASGYAFGNSWMNWVRQAPGQG
LEWMGWIYPGDGSANYSQKFQGRVTLTADKSTSTAYMELSSLRSE
DTATYYCARALYDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:86 with human IgG4 constant domain, G4P:

(SEQ ID NO: 89)

QVQLVQSGAEVKKPGASVKVSCKASGYAFGNSWMNWVRQAPGQG

LEWMGWIYPGDGSANYSQKFQGRVTLTADKSTSTAYMELSSLRSE

DTATYYCARALYDYDGWFAYWGQGTLVTVSSASTKGPSVFPLAPC

SRSTSESTAALGCLVKDYFPEPVTVSWNSGALTSGVHTFPAVLQSSG

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

VH-8

(SEQ ID NO: 90)

QVQLVQSGAEVKKPGASVKVSCKASGYAFGSSWMNWVRQAPGQG

LEWMGWIYPGSGSANYSQKFQGRVTLTADKSTSTAYMELSSLRSE

DTATYYCARALYDYDGWFAYWGQGTLVTVSS

SEQ ID NO:90 with human IgG1 constant domain:

(SEQ ID NO: 91)

QVQLVQSGAEVKKPGASVKVSCKASGYAFGSSWMNWVRQAPGQG

LEWMGWIYPGSGSANYSQKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:90 with human IgG1 constant domain, GIFES:

(SEQ ID NO: 92)

QVQLVQSGAEVKKPGASVKVSCKASGYAFGSSWMNWVRQAPGQG

LEWMGWIYPGSGSANYSOKFQGRVTLTADKSTSTAYMELSSLRSE

DTATYYCARALYDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPASIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:90 with human IgG4 constant domain, G4P:

(SEQ ID NO: 93)

QVQLVQSGAEVKKPGASVKVSCKASGYAFGSSWMNWVRQAPGQG

LEWMGWIYPGSGSANYSQKFQGRVTLTADKSTSTAYMELSSLRSE

DTATYYCARALYDYDGWFAYWGQGTLVTVSSASTKGPSVFPLAPC

SRSTSESTAALGCLVKDYFPEPVTVSWNSGALTSGVHTFPAVLQSSG

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

VH-9

(SEQ ID NO: 94)

QVQLVQSGAEVKKPGASVKVSCKASGYAFGNSWMNWVRQAPGQG

LEWMGWIYPGDGNANYSOKFQGRVTLTADKSTSTAYMELSSLRSE

DTATYYCARALQDYDGWFAYWGQGTLVTVSS

SEQ ID NO:94 with human IgG1 constant domain:

(SEQ ID NO: 95)

QVQLVQSGAEVKKPGASVKVSCKASGYAFGNSWMNWVRQAPGQG

LEWMGWIYPGDGNANYSQKFQGRVTLTADKSTSTAYMELSSLRSE

DTATYYCARALQDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:94 with human IgG1 constant domain, GIFES:

(SEQ ID NO: 96)

QVQLVQSGAEVKKPGASVKVSCKASGYAFGNSWMNWVRQAPGQG

LEWMGWIYPGDGNANYSQKFQGRVTLTADKSTSTAYMELSSLRSE

DTATYYCARALQDYDGWFAYWGQGTLVTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPASIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

SEQ ID NO:94 with human IgG4 constant domain, G4P:

(SEQ ID NO: 97)
QVQLVQSGAEVKKPGASVKVSCKASGYAFGNSWMNWVRQAPGQG
LEWMGWIYPGDGNANYSQKFQGRVTLTADKSTSTAYMELSSLRSE
DTATYYCARALQDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

VH-10
(SEQ ID NO: 98)
QVQLVQSGAEVKKPGASVKVSCKASGYAFGSSWMNWVRQAPGQG
LEWMGWIYPGSGSANYSQKFQGRVTLTADKSTSTAYMELSSLRSE
DTATYYCARALQDYDGWFAYWGQGTLVTVSS

SEQ ID NO:98 with human IgG1 constant domain:

(SEQ ID NO: 99)
QVQLVQSGAEVKKPGASVKVSCKASGYAFGSSWMNWVRQAPGQG
LEWMGWIYPGSGSANYSQKFQGRVTLTADKSTSTAYMELSSLRSE
DTATYYCARALQDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPAPIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:98 with human IgG1 constant domain, GIFES:

(SEQ ID NO: 100)
QVQLVQSGAEVKKPGASVKVSCKASGYAFGSSWMNWVRQAPGQG
LEWMGWIYPGSGSANYSQKFQGRVTLTADKSTSTAYMELSSLRSE
DTATYYCARALQDYDGWFAYWGQGTLVTVSSASTKGPSVFPLAPS
SKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT
CPPCPAPEFEGGPSVFLFPPKPKDTLMISRTPEVTCVVVDVSHEDPEV
KFNWYVDGVEVHNAKTKPREEQYNSTYRVVSVLTVLHQDWLNGK
EYKCKVSNKALPASIEKTISKAKGQPREPQVYTLPPSRDELTKNQVSL
TCLVKGFYPSDIAVEWESNGQPENNYKTTPPVLDSDGSFFLYSKLTV
DKSRWQQGNVFSCSVMHEALHNHYTQKSLSLSPG

SEQ ID NO:98 with human IgG4 constant domain, G4P:

(SEQ ID NO: 101)
QVQLVQSGAEVKKPGASVKVSCKASGYAFGSSWMNWVRQAPGQG
LEWMGWIYPGSGSANYSQKFQGRVTLTADKSTSTAYMELSSLRSE
DTATYYCARALQDYDGWFAYWGQGTLVTVSSASTKGPSVFPLAPC
SRSTSESTAALGCLVKDYFPEPVTVSWNSGALTSGVHTFPAVLQSSG
LYSLSSVVTVPSSSLGTKTYTCNVDHKPSNTKVDKRVESKYGPPCPP
CPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLG

One embodiment provides an anti-FLRT3 antibody of antigen-binding fragment having a light chain variable region having at least 50%, 60%, 70%, 80%, 85%, 90%, 95%, 99%, or more sequence identity to an amino acid sequence selected from the group consisting of SEQ ID NO: 17, 19, 21, 23, 25, 27, and 29, and a heavy chain variable region having at least 50%, 60%, 70%, 80%, 85%, 90%, 95%, 99%, or more sequence identity to an amino acid sequence selected from the group consisting of SEQ ID NO:38, 42, 46, 50, 54, 58, 62, 66, 70, 74, 78, 82, 86, 90, 94, and 98, In some embodiments, the antibody is humanized.

b. 18A7 i. Light Chain

One embodiment provides a humanized antibody or antigen binding fragment with a light chain variable region having at least 60, 65, 70, 75, 80, 85, 90, 95, 99, or 100% sequence identity with the following: DIVMTQSPSSLAMSVGQKVTMSCKSSQSLLNSSNQKNYLAWYQQKPGQSPKLLLYFASTRESGVPDRFIGSGSGTDFTLSISSVQAEDLADYF CQQHYSTPFTFGSGTKLEIK (SEQ ID NO:102)

The light chain CDRs of 18A7 are bolded and are as follows:

| | | |
|---|---|---|
| CDR1 | KSSQSLLNSSNQKNYLA | SEQ ID NO: 103 |
| CDR2 | FASTRES | SEQ ID NO: 104 |
| CDR3 | QQHYSTPFT | SEQ ID NO: 105 |

In another embodiment, SEQ ID NO:102 includes the sequence of human kappa constant domain:

(SEQ ID NO: 106)
DIVMTQSPSSLAMSVGQKVTMSCKSSQSLLNSSNQKNYLAWYQQK
PGQSPKLLLYFASTRESGVPDRFIGSGSGTDFTLSISSVQAEDLADYF
CQQHYSTPFTFGSGTKLEIKRTVAAPSVFIFPPSDEQLKSGTASVVCL
LNNFYPREAKVQWKVDNALQSGNSQESVTEQDSKDSTYSLSSTLTLS
KADYEKHKVYACEVTHQGLSSPVTKSFNRGEC ii. Heavy Chain One embodiment provides a humanized antibody or antigen binding fragment with a heavy chain variable region having at least 60, 65, 70, 75, 80, 85, 90, 95, 99, or 100% sequence identity with the following: EIQLQQSGAEL- VKPGASVKISCKASGHSFTGYNMNWVKQSHGKSLE WIGNINPYYGSTSYTQKFKGKATLTVDKSST-TAYMQLNSLTSEDSA VYYCARGGYDD-YFDYWGQGTTLTVSS (SEQ ID NO:107)

The heavy chain CDRs of 18A7 are bolded and are as follows:

| | | |
|---|---|---|
| CDR1 | GYNMN | SEQ ID NO: 108 |
| CDR2 | NINPYYGSTSYTQKFKG | SEQ ID NO: 109 |
| CDR3 | GGYDDYFDY | SEQ ID NO: 110 |

In another embodiment, SEQ ID NO:107 includes the sequence of human IgG1 constant domain:

(SEQ ID NO: 111)
EIQLQQSGAELVKPGASVKISCKASGHSFTGYNMNWVKQSHGKSLE
WIGNINPYYGSTSYTQKFKGKATLTVDKSSTTAYMQLNSLTSEDSA
VYYCARGGYDDYFDYWGQGTTLTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCKV
SNKALPAPIEKTISKAKGQPREPQVYTLPPSRDELTKNQVSLTCLVKG
FYPSDIAVEWESNGQPENNYKTTPPVLDSDGSFFLYSKLTVDKSRWQ
QGNVFSCSVMHEALHNHYTQKSLSLSPG

In one embodiment, SEQ ID NO:107 includes the sequence of human IgG1 constant domain, G1FES:

(SEQ ID NO: 112)
EIQLQQSGAELVKPGASVKISCKASGHSFTGYNMNWVKQSHGKSLE
WIGNINPYYGSTSYTQKFKGKATLTVDKSSTTAYMQLNSLTSEDSA
VYYCARGGYDDYFDYWGOGTTLTVSSASTKGPSVFPLAPSSKSTSG
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PEFEGGPSVFLFPPKPKDTLMISRTPEVTCVVVDVSHEDPEVKFNWY
VDGVEVHNAKTKPREEQYNSTYRVVSVLTVLHQDWLNGKEYKCKV
SNKALPASIEKTISKAKGQPREPQVYTLPPSRDELTKNQVSLTCLVKG
FYPSDIAVEWESNGQPENNYKTTPPVLDSDGSFFLYSKLTVDKSRWQ
QGNVFSCSVMHEALHNHYTQKSLSLSPG

In another embodiment, SEQ ID NO:107 includes human IgG4 constant domain, G4P:

(SEQ ID NO: 113)
EIQLQQSGAELVKPGASVKISCKASGHSFTGYNMNWVKQSHGKSLE
WIGNINPYYGSTSYTQKFKGKATLTVDKSSTTAYMQLNSLTSEDSA
VYYCARGGYDDYFDYWGQGTTLTVSSASTKGPSVFPLAPCSRSTSE
STAALGCLVKDYFPEPVTVSWNSGALTSGVHTFPAVLQSSGLYSLSS

-continued

VVTVPSSSLGTKTYTCNVDHKPSNTKVDKRVESKYGPPCPPCPAPEF
LGGPSVFLFPPKPKDTLMISRTPEVTCVVVDVSQEDPEVQFNWYVDG
VEVHNAKTKPREEQFNSTYRVVSVLTVLHQDWLNGKEYKCKVSNK
GLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGN
VFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:102, and a heavy chain variable region having at least 60, 65, 70, 75, 80, 85, 90, 95, 99, or 100% sequence identity to the amino acid according to SEQ ID NO:107.

In one embodiment, the antibody is humanized.

c. 1H5 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 114)
DIVMTQSHKFMSTSVGDRVTITCKASQDVGTAVAWYQQKPGQSPK
LLIYWASTRHTGVPDRFTGSGSGTDFTLTISNVQSEDLADYFCQQYS
SYPTFGGGTKLEIK

The light chain CDRs of 1H5 are bolded and are as follows:

| | | |
|---|---|---|
| CDR1 | KASQDVGTAVA | SEQ ID NO: 115 |
| CDR2 | WASTRHT | SEQ ID NO: 116 |
| CDR3 | QQYSSYPT | SEQ ID NO: 117 |

In another embodiment, SEQ ID NO:114 includes the sequence of human kappa constant domain:

(SEQ ID NO: 118)
DIVMTQSHKFMSTSVGDRVTITCKASQDVGTAVAWYQQKPGQSPK
LLIYWASTRHTGVPDRFTGSGSGTDFTLTISNVQSEDLADYFCQQYS
SYPTFGGGTKLEIKRTVAAPSVFIFPPSDEQLKSGTASVVCLLNNFYP
REAKVQWKVDNALQSGNSQESVTEQDSKDSTYSLSSTLTLSKADYE
KHKVYACEVTHQGLSSPVTKSFNRGEC ii. Heavy Chain One embodiment provides a humanized antibody or antigen binding fragment with a heavy chain variable region having at least 60, 65, 70, 75, 80, 85, 90, 95, 99, or 100% sequence identity with the following: EVQLQQSGPEL-VKPGASVKMSCKASGYTFTDYYMNWVKQSHGKSL EWIGRVNPSNGVTSYNQKFKGKAALTVDKSL STAYMQLNSLTSED SAVYYCARD-FLMDYWGQGTSVTVSS (SEQ ID NO:119)

The heavy chain CDRs of 1H5 are bolded and are as follows:

| | | |
|---|---|---|
| CDR1 | DYYMN | SEQ ID NO: 120 |
| CDR2 | RVNPSNGVTSYNQKFKG | SEQ ID NO: 121 |
| CDR3 | DFLMDY | SEQ ID NO: 122 |

In another embodiment, SEQ ID NO:119 includes the sequence of human IgG1 constant domain:

(SEQ ID NO: 123)
EVQLQQSGPELVKPGASVKMSCKASGYTFTDYYMNWVKQSHGKSL
EWIGRVNPSNGVTSYNQKFKGKAALTVDKSLSTAYMQLNSLTSED
SAVYYCARDFLMDYWGQGTSVTVSSASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPAPIEKTISKAKGQPREPQVYTLPPSRDELTKNQVSLTCLVKGF
YPSDIAVEWESNGQPENNYKTTPPVLDSDGSFFLYSKLTVDKSRWQQ
GNVFSCSVMHEALHNHYTQKSLSLSPG

In another embodiment, SEQ ID NO:119 includes the sequence of human IgG1 constant domain, G1FES:

(SEQ ID NO: 124)
EVQLQQSGPELVKPGASVKMSCKASGYTFTDYYMNWVKQSHGKSL
EWIGRVNPSNGVTSYNQKFKGKAALTVDKSLSTAYMQLNSLTSED
SAVYYCARDFLMDYWGQGTSVTVSSASTKGPSVFPLAPSSKSTSGG
TAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAP
EFEGGPSVFLFPPKPKDTLMISRTPEVTCVVVDVSHEDPEVKFNWYV
DGVEVHNAKTKPREEQYNSTYRVVSVLTVLHQDWLNGKEYKCKVS
NKALPASIEKTISKAKGQPREPQVYTLPPSRDELTKNQVSLTCLVKGF
YPSDIAVEWESNGQPENNYKTTPPVLDSDGSFFLYSKLTVDKSRWQQ
GNVFSCSVMHEALHNHYTQKSLSLSPG

In another embodiment, SEQ ID NO:119 includes the sequence of human IgG4 constant domain, G4P:

(SEQ ID NO: 125)
EVQLQQSGPELVKPGASVKMSCKASGYTFTDYYMNWVKQSHGKSL
EWIGRVNPSNGVTSYNQKFKGKAALTVDKSLSTAYMQLNSLTSED
SAVYYCARDFLMDYWGQGTSVTVSSASTKGPSVFPLAPCSRSTSEST
AALGCLVKDYFPEPVTVSWNSGALTSGVHTFPAVLQSSGLYSLSSVV
TVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVE
VHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVF
SCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:114, and a heavy chain variable region having at least 60, 65, 70, 75, 80, 85, 90, 95, 99, or 100% sequence identity to the amino acid according to SEQ ID NO:119.

In one embodiment, the antibody is humanized.

d. 2F7 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 126)
DIVMTQSHKFMSTSIGDRVNITCKASQDVGTAVAWFQQKPGQSPKL
LIYWASTRHTGVPDRFTGSGSGTDFTLTISNVQSEDLADYFCQQYSS
YPTFGAGTTLELK

The light chain CDRs of 2F7 are bolded and are as follows:

| | | |
|---|---|---|
| CDR1 | KASQDVGTAVA | SEQ ID NO: 115 |
| CDR2 | WASTRHT | SEQ ID NO: 116 |
| CDR3 | QQYSSYPT | SEQ ID NO: 117 |

In another embodiment, SEQ ID NO:126 includes the sequence of human kappa constant domain:

(SEQ ID NO: 127)
DIVMTQSHKFMSTSIGDRVNITCKASQDVGTAVAWFQQKPGQSPKL
LIYWASTRHTGVPDRFTGSGSGTDFTLTISNVQSEDLADYFCQQYSS
YPTFGAGTTLELKRTVAAPSVFIFPPSDEQLKSGTASVVCLLNNFYPR
EAKVQWKVDNALQSGNSQESVTEQDSKDSTYSLSSTLTLSKADYEK
HKVYACEVTHQGLSSPVTKSFNRGEC ii. Heavy Chain One embodiment provides a humanized antibody or antigen binding fragment with a heavy chain variable region having at least 60, 65, 70, 75, 80, 85, 90, 95, 99, or 100% sequence identity with the following:

(SEQ ID NO: 128)
EVQLQQSGPELVKPGASVKMSCKASGYTFTDYYMNWVKQSHGKSL
EWIGRVYPSNSGASYNQKFKGKATLTVDKSLSTAYMQLNSLTSEDS
AVYYCASSYYFDYWGQGTTLTVSS

The heavy chain CDRs of 2F7 are bolded and are as follows:

| | | |
|---|---|---|
| CDR1 | DYYMN | SEQ ID NO: 120 |
| CDR2 | RVYPSNSGASYNQKFKG | SEQ ID NO: 129 |
| CDR3 | YYFDY | SEQ ID NO: 130 |

In another embodiment, SEQ ID NO:128 includes the sequence of human IgG1 constant domain:

(SEQ ID NO: 131)
EVQLQQSGPELVKPGASVKMSCKASGYTFTDYYMNWVKQSHGKSL
EWIGRVYPSNSGASYNQKFKGKATLTVDKSLSTAYMQLNSLTSEDS
AVYYCASSYYFDYWGQGTTLTVSSASTKGPSVFPLAPSSKSTSGGTA
ALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDG
VEVHNAKTKPREEQYNSTYRVVSVLTVLHQDWLNGKEYKCKVSNK
ALPAPIEKTISKAKGQPREPQVYTLPPSRDELTKNQVSLTCLVKGFYP
SDIAVEWESNGQPENNYKTTPPVLDSDGSFFLYSKLTVDKSRWQQG
NVFSCSVMHEALHNHYTQKSLSLSPG

In another embodiment, SEQ ID NO:128 includes the sequence of human IgG1 constant domain, G1FES:

(SEQ ID NO: 132)
EVQLQQSGPELVKPGASVKMSCKASGYTFTDYYMNWVKQSHGKSL
EWIGRVYPSNSGASYNQKFKGKATLTVDKSLSTAYMQLNSLTSEDS
AVYYCASSYYFDYWGQGTTLTVSSASTKGPSVFPLAPSSKSTSGGTA
ALGCLVKDYFPEPVTVSWNSGALTSGVHTFPAVLQSSGLYSLSSVVT
VPSSSLGTQTYICNVNHKPSNTKVDKKVEPKSCDKTHTCPPCPAPEFE
GGPSVFLFPPKPKDTLMISRTPEVTCVVVDVSHEDPEVKFNWYVDGV
EVHNAKTKPREEQYNSTYRVVSVLTVLHQDWLNGKEYKCKVSNKA
LPASIEKTISKAKGQPREPQVYTLPPSRDELTKNQVSLTCLVKGFYPS
DIAVEWESNGQPENNYKTTPPVLDSDGSFFLYSKLTVDKSRWQQGN
VFSCSVMHEALHNHYTQKSLSLSPG

In another embodiment, SEQ ID NO:128 includes the sequence of human IgG4 constant domain, G4P:

(SEQ ID NO: 133)
EVQLQQSGPELVKPGASVKMSCKASGYTFTDYYMNWVKQSHGKSL
EWIGRVYPSNSGASYNQKFKGKATLTVDKSLSTAYMQLNSLTSEDS
AVYYCASSYYFDYWGQGTTLTVSSASTKGPSVFPLAPCSRSTSESTA
ALGCLVKDYFPEPVTVSWNSGALTSGVHTFPAVLQSSGLYSLSSVVT
VPSSSLGTKTYTCNVDHKPSNTKVDKRVESKYGPPCPPCPAPEFLGG
PSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIA
VEWESNGQPENNYKTTPPVLDSDGSFFLYSRLTVDKSRWQEGNVFS
CSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:126, and a heavy chain variable region having at least 60, 65, 70, 75, 80, 85, 90, 95, 99, or 100% sequence identity to the amino acid according to SEQ ID NO:128.

In one embodiment, the antibody is humanized.

e. 5C2 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 134)
DIVMTQSPSSLAMSVGQKVTMSCKSSQSLLNSSNQKNYLAWYQQK
PGQSPKLLVYFASTRESGVPDRFIGSGSGTDFTLTISSVQAEDLADYF
CQQHYSTPFTFGSGTKLEIK

The light chain CDRs of 5C2 are bolded and are as follows:

| | | |
|---|---|---|
| CDR1 | KSSQSLLNSSNQKNYLA | SEQ ID NO: 103 |
| CDR2 | FASTRES | SEQ ID NO: 104 |
| CDR3 | QQHYSTPFT | SEQ ID NO: 105 |

In another embodiment, SEQ ID NO:134 includes the sequence of human kappa constant domain:

(SEQ ID NO: 135)
DIVMTQSPSSLAMSVGQKVTMSCKSSQSLLNSSNQKNYLAWYQQK
PGQSPKLLVYFASTRESGVPDRFIGSGSGTDFTLTISSVQAEDLADYF
CQQHYSTPFTFGSGTKLEIKRTVAAPSVFIFPPSDEQLKSGTASVVCL
LNNFYPREAKVQWKVDNALQSGNSQESVTEQDSKDSTYSLSSTLTLS
KADYEKHKVYACEVTHQGLSSPVTKSFNRGEC ii. Heavy Chain One embodiment provides a humanized antibody or antigen binding fragment with a heavy chain variable region having at least 60, 65, 70, 75, 80, 85, 90, 95, 99, or 100% sequence identity with the following:

(SEQ ID NO: 136)
EIQLQQSGAELVKPGASVKISCKASGYSFTGYNMNWVKQSHGKSLE
WIGNINPYYGSTSYNQKFKGKATLTVNKSSSTAYMQLNSLTSEDSA
VYYCASGGYDDYFDYWGQGTTLTVSS

The heavy chain CDRs of 5C2 are bolded and are as follows:

| | | |
|---|---|---|
| CDR1 | GYNMN | SEQ ID NO: 108 |
| CDR2 | NINPYYGSTSYNQKFKG | SEQ ID NO: 137 |
| CDR3 | GGYDDYFDY | SEQ ID NO: 110 |

In another embodiment, SEQ ID NO:136 includes the sequence of human IgG1 constant domain:

(SEQ ID NO: 138)
EIQLQQSGAELVKPGASVKISCKASGYSFTGYNMNWVKQSHGKSLE
WIGNINPYYGSTSYNQKFKGKATLTVNKSSSTAYMQLNSLTSEDSA
VYYCASGGYDDYFDYWGQGTTLTVSSASTKGPSVFPLAPSSKSTSG

-continued

```
GTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWY
VDGVEVHNAKTKPREEQYNSTYRVVSVLTVLHQDWLNGKEYKCKV
SNKALPAPIEKTISKAKGQPREPQVYTLPPSRDELTKNQVSLTCLVKG
FYPSDIAVEWESNGQPENNYKTTPPVLDSDGSFFLYSKLTVDKSRWQ
QGNVFSCSVMHEALHNHYTQKSLSLSPG
```

In another embodiment, SEQ ID NO:136 includes the sequence of human IgG1 constant domain, G1FES:

(SEQ ID NO: 139)

EIQLQQSGAELVKPGASVKISCKASGYSFTGYNMNWVKQSHGKSLE

WIGNINPYYGGSTSYNQKFKGKATLTVNKSSSTAYMQLNSLTSEDSA

VYYCASGGYDDYFDYWGQGTTLTVSSASTKGPSVFPLAPSSKSTSG

GTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPA

PEFEGGPSVFLFPPKPKDTLMISRTPEVTCVVVDVSHEDPEVKFNWY

VDGVEVHNAKTKPREEQYNSTYRVVSVLTVLHQDWLNGKEYKCKV

SNKALPASIEKTISKAKGQPREPQVYTLPPSRDELTKNQVSLTCLVKG

FYPSDIAVEWESNGQPENNYKTTPPVLDSDGSFFLYSKLTVDKSRWQ

QGNVFSCSVMHEALHNHYTQKSLSLSPG

In another embodiment, SEQ ID NO:136 includes the sequence of human IgG4 constant domain, G4P:

(SEQ ID NO: 140)

EIQLQQSGAELVKPGASVKISCKASGYSFTGYNMNWVKQSHGKSLE

WIGNINPYYGGSTSYNQKFKGKATLTVNKSSSTAYMQLNSLTSEDSA

VYYCASGGYDDYFDYWGQGTTLTVSSASTKGPSVFPLAPCSRSTSES

TAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFL

GGPSVFLFPPKPKDTLMISRTPEVTCVVVDVSQEDPEVQFNWYVDGV

EVHNAKTKPREEQFNSTYRVVSVLTVLHQDWLNGKEYKCKVSNKG

LPSSIEKTISKAKGQPREPQVYTLPPSQEEMTKNQVSLTCLVKGFYPS

DIAVEWESNGQPENNYKTTPPVLDSDGSFFLYSRLTVDKSRWQEGN

VFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:134, and a heavy chain variable region having at least 60, 65, 70, 75, 80, 85, 90, 95, 99, or 100% sequence identity to the amino acid according to SEQ ID NO:136.

In one embodiment, the antibody is humanized.

f. 7H7 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 141)

DIVMTQSPSSLAMSVGQKVTMSCKSSQSLLNSSNQKNYLAWYQQK

PGQSPKLLVYFASTRESGVPDRFIGSGSGTDFTLTISSVQAEDLADYF

CQQHYSIPFTFGSGTKLEIK

The light chain CDRs of 7H7 are bolded and are as follows:

| | | |
|---|---|---|
| CDR1 | KSSQSLLNSSNQKNYLA | SEQ ID NO: 103 |
| CDR2 | FASTRES | SEQ ID NO: 104 |
| CDR3 | QQHYSIPFT | SEQ ID NO: 142 |

In another embodiment, SEQ ID NO:141 includes the sequence of human kappa constant domain:

ii. Heavy Chain (SEQ ID NO: 143)

DIVMTQSPSSLAMSVGQKVTMSCKSSQSLLNSSNQKNYLAWYQQK

PGQSPKLLVYFASTRESGVPDRFIGSGSGTDFTLTISSVQAEDLADYF

CQQHYSIPFTFGSGTKLEIKRTVAAPSVFIFPPSDEQLKSGTASVVCLL

NNFYPREAKVQWKVDNALQSGNSQESVTEQDSKDSTYSLSSTLTLS

KADYEKHKVYACEVTHQGLSSPVTKSFNRGEC

One embodiment provides a humanized antibody or antigen binding fragment with a heavy chain variable region having at least 60, 65, 70, 75, 80, 85, 90, 95, 99, or 100% sequence identity with the following:

(SEQ ID NO: 144)

EIQLQQSGAELVKPGASVKISCKASGYSFTGYNMNWVKQSHGKSLE

WIGNINPYYGGSTSYNQKFKGKATLTVDKSSNTAYMQLNSLTSEDSA

VYYCARWGYGYDDWYFDVWGAGTTVTVSS

The heavy chain CDRs of 7H7 are bolded and are as follows:

| | | |
|---|---|---|
| CDR1 | GYNMN | SEQ ID NO: 108 |
| CDR2 | NINPYYGGSTSYNQKFKG | SEQ ID NO: 137 |
| CDR3 | WGYGYDDWYFDV | SEQ ID NO: 145 |

In another embodiment, SEQ ID NO:144 includes the sequence of human IgG1 constant domain:

(SEQ ID NO: 146)

EIQLQQSGAELVKPGASVKISCKASGYSFTGYNMNWVKQSHGKSLE

WIGNINPYYGGSTSYNQKFKGKATLTVDKSSNTAYMQLNSLTSEDSA

VYYCARWGYGYDDWYFDVWGAGTTVTVSSASTKGPSVFPLAPSSK

STSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPP

-continued

CPAPELLGGPSVFLFPPKPKDTLMISRTPEVTCVVVDVSHEDPEVKFN

WYVDGVEVHNAKTKPREEQYNSTYRVVSVLTVLHQDWLNGKEYK

CKVSNKALPAPIEKTISKAKGQPREPQVYTLPPSRDELTKNQVSLTCL

VKGFYPSDIAVEWESNGQPENNYKTTPPVLDSDGSFFLYSKLTVDKS

RWQQGNVFSCSVMHEALHNHYTQKSLSLSPG

In another embodiment, SEQ ID NO:144 includes the sequence of human IgG1 constant domain, G1FES:

(SEQ ID NO: 147)

EIQLQQSGAELVKPGASVKISCKASGYSFTGYNMNWVKQSHGKSLE

WIGNINPYYGSTSYNQKFKGKATLTVDKSSNTAYMQLNSLTSEDSA

VYYCARWGYGYDDWYFDVWGAGTTVTVSSASTKGPSVFPLAPSSK

STSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPP

CPAPEFEGGPSVFLFPPKPKDTLMISRTPEVTCVVVDVSHEDPEVKFN

WYVDGVEVHNAKTKPREEQYNSTYRVVSVLTVLHQDWLNGKEYK

CKVSNKALPASIEKTISKAKGQPREPQVYTLPPSRDELTKNQVSLTCL

VKGFYPSDIAVEWESNGQPENNYKTTPPVLDSDGSFFLYSKLTVDKS

RWQQGNVFSCSVMHEALHNHYTQKSLSLSPG

In another embodiment, SEQ ID NO:144 includes the sequence of human IgG4 constant domain, G4P:

(SEQ ID NO: 148)

EIQLQQSGAELVKPGASVKISCKASGYSFTGYNMNWVKQSHGKSLE

WIGNINPYYGSTSYNQKFKGKATLTVDKSSNTAYMOLNSLTSEDSA

VYYCARWGYGYDDWYFDVWGAGTTVTVSSASTKGPSVFPLAPCSR

STSESTAALGCLVKDYFPEPVTVSWNSGALTSGVHTFPAVLQSSGLY

SLSSVVTVPSSSLGTKTYTCNVDHKPSNTKVDKRVESKYGPPCPPCP

APEFLGGPSVFLFPPKPKDTLMISRTPEVTCVVVDVSQEDPEVQFNW

YVDGVEVHNAKTKPREEQFNSTYRVVSVLTVLHQDWLNGKEYKCK

VSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRW

QEGNVFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:141, and a heavy chain variable region having at least 60, 65, 70, 75, 80, 85, 90, 95, 99, or 100% sequence identity to the amino acid according to SEQ ID NO:144.

In one embodiment, the antibody is humanized.

g. 10C6 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 134)

DIVMTQSPSSLAMSVGQKVTMSCKSSQSLLNSSNQKNYLAWYQQK

PGQSPKLLVYFASTRESGVPDRFIGSGSGTDFTLTISSVQAEDLADYF

CQQHYSTPFTFGSGTKLEIK

The light chain CDRs of 10C6 are bolded and are as follows:

| | | |
|---|---|---|
| CDR1 | KSSQSLLNSSNQKNYLA | SEQ ID NO: 103 |
| CDR2 | FASTRES | SEQ ID NO: 104 |
| CDR3 | QQHYSIPFT | SEQ ID NO: 142 |

In another embodiment, SEQ ID NO:134 includes the sequence of human kappa constant domain:

(SEQ ID NO: 135)

DIVMTQSPSSLAMSVGQKVTMSCKSSQSLLNSSNQKNYLAWYQQK

PGQSPKLLVYFASTRESGVPDRFIGSGSGTDFTLTISSVQAEDLADYF

CQQHYSTPFTFGSGTKLEIKRTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following:

(SEQ ID NO: 149)

EIQLQQSGAEMVKPGASVKISCKASGHSFTGYNMNWVKQSHEKSLE

WIGNINPYYGSTSYNQKFKGKATLTVDKSSSTAYMQLNSLTSEDSA

VYYCARGGYDDYFDYWGQGTTLTVSS

The heavy chain CDRs of 7H7 are bolded and are as follows:

| | | |
|---|---|---|
| CDR1 | GYNMN | SEQ ID NO: 108 |
| CDR2 | NINPYYGSTSYNQKFKG | SEQ ID NO: 137 |
| CDR3 | WGYGYDDWYFDV | SEQ ID NO: 110 |

In another embodiment, SEQ ID NO:149 includes the sequence of human IgG1 constant domain:

(SEQ ID NO: 150)

EIQLQQSGAEMVKPGASVKISCKASGHSFTGYNMNWVKQSHEKSLE

WIGNINPYYGSTSYNQKFKGKATLTVDKSSSTAYMQLNSLTSEDSA

VYYCARGGYDDYFDYWGQGTTLTVSSASTKGPSVFPLAPSSKSTSG

GTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWY

VDGVEVHNAKTKPREEQYNSTYRVVSVLTVLHQDWLNGKEYKCKV

-continued

SNKALPAPIEKTISKAKGQPREPQVYTLPPSRDELTKNQVSLTCLVKG

FYPSDIAVEWESNGQPENNYKTTPPVLDSDGSFFLYSKLTVDKSRWQ

QGNVFSCSVMHEALHNHYTQKSLSLSPG

In another embodiment, SEQ ID NO:149 includes the sequence of human IgG1 constant domain, G1FES:

(SEQ ID NO: 151)
EIQLQQSGAEMVKPGASVKISCKASGHSFTGYNMNWVKQSHEKSLE

WIGNINPYYGSTSYNQKFKGKATLTVDKSSSTAYMQLNSLTSEDSA

VYYCARGGYDDYFDYWGQGTTLTVSSASTKGPSVFPLAPSSKSTSG

GTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPA

PEFEGGPSVFLFPPKPKDTLMISRTPEVTCVVVDVSHEDPEVKFNWY

VDGVEVHNAKTKPREEQYNSTYRVVSVLTVLHQDWLNGKEYKCKV

SNKALPASIEKTISKAKGQPREPQVYTLPPSRDELTKNQVSLTCLVKG

FYPSDIAVEWESNGQPENNYKTTPPVLDSDGSFFLYSKLTVDKSRWQ

QGNVFSCSVMHEALHNHYTQKSLSLSPG

In another embodiment, SEQ ID NO:149 includes the sequence of human IgG4 constant domain, G4P:

(SEQ ID NO: 152)
EIQLQQSGAEMVKPGASVKISCKASGHSFTGYNMNWVKQSHEKSLE

WIGNINPYYGSTSYNQKFKGKATLTVDKSSSTAYMQLNSLTSEDSA

VYYCARGGYDDYFDYWGQGTTLTVSSASTKGPSVFPLAPCSRSTSE

STAALGCLVKDYFPEPVTVSWNSGALTSGVHTFPAVLQSSGLYSLSS

VVTVPSSSLGTKTYTCNVDHKPSNTKVDKRVESKYGPPCPPCPAPEF

LGGPSVFLFPPKPKDTLMISRTPEVTCVVVDVSQEDPEVQFNWYVDG

VEVHNAKTKPREEQFNSTYRVVSVLTVLHQDWLNGKEYKCKVSNK

GLPSSIEKTISKAKGQPREPQVYTLPPSQEEMTKNQVSLTCLVKGFYP

SDIAVEWESNGQPENNYKTTPPVLDSDGSFFLYSRLTVDKSRWQEGN

VFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:149, and a heavy chain variable region having at least 60, 65, 70, 75, 80, 85, 90, 95, 99, or 100% sequence identity to the amino acid according to SEQ ID NO:134.

In one embodiment, the antibody is humanized.

h. 12A4 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 153)
DIVMTQSHKFMSTSVGDRVSITCKASQDVGTAVTWYQQKPGLSPKL

LFYWASTRHTGVPDRFTGSGSGTDFTLTISNVQSEDLADYFCHQYS

NYPTFGGGTKLEIK

The light chain CDRs of 12A4 are bolded and are as follows:

| | | |
|---|---|---|
| CDR1 | KASQDVGTAVT | SEQ ID NO:154 |
| CDR2 | WASTRHT | SEQ ID NO:116 |
| CDR3 | HQYSNYPT | SEQ ID NO:155 |

In another embodiment, SEQ ID NO:134 includes the sequence of human kappa constant domain:

(SEQ ID NO: 156)
DIVMTQSHKFMSTSVGDRVSITCKASQDVGTAVTWYQQKPGLSPKL

LFYWASTRHTGVPDRFTGSGSGTDFTLTISNVQSEDLADYFCHQYS

NYPTFGGGTKLEIKRTVAAPSVFIFPPSDEQLKSGTASVVCLLNNFYP

REAKVQWKVDNALQSGNSQESVTEQDSKDSTYSLSSTLTLSKADYE

KHKVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following:

(SEQ ID NO: 157)
EVQLQQSGPELVKPGASVKMSCKASGYTFTDYYMNWVKQSHGKSL

EWIGRVNPSNGGTTYNQRFKGKATLTVDESLSTAYMQLNSLTSEDS

AVYYCARDFLMDYWGQGTSVTVSS

The heavy chain CDRs of 7H7 are bolded and are as follows:

| | | |
|---|---|---|
| CDR1 | DYYMN | SEQ ID NO: 120 |
| CDR2 | RVNPSNGGTTYNQRFKG | SEQ ID NO: 158 |
| CDR3 | DFLMDY | SEQ ID NO: 158 |

In another embodiment, SEQ ID NO:149 includes the sequence of human IgG1 constant domain:

(SEQ ID NO: 159)
EVQLQQSGPELVKPGASVKMSCKASGYTFTDYYMNWVKQSHGKSL

EWIGRVNPSNGGTTYNQRFKGKATLTVDESLSTAYMQLNSLTSEDS

AVYYCARDFLMDYWGQGTSVTVSSASTKGPSVFPLAPSSKSTSGGT

AALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDG

VEVHNAKTKPREEQYNSTYRVVSVLTVLHQDWLNGKEYKCKVSNK

-continued

ALPAPIEKTISKAKGQPREPQVYTLPPSRDELTKNQVSLTCLVKGFYP

SDIAVEWESNGQPENNYKTTPPVLDSDGSFFLYSKLTVDKSRWQQG

NVFSCSVMHEALHNHYTQKSLSLSPG

In another embodiment, SEQ ID NO:149 includes the sequence of human IgG1 constant domain, G1FES:

(SEQ ID NO: 160)
EVQLQQSGPELVKPGASVKMSCKASGYTFTDYYMNWVKQSHGKSL

EWIGRVNPSNGGTTYNQRFKGKATLTVDESLSTAYMQLNSLTSEDS

AVYYCARDFLMDYWGQGTSVTVSSASTKGPSVFPLAPSSKSTSGGT

AALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPEF

EGGPSVFLFPPKPKDTLMISRTPEVTCVVVDVSHEDPEVKFNWYVDG

VEVHNAKTKPREEQYNSTYRVVSVLTVLHQDWLNGKEYKCKVSNK

ALPASIEKTISKAKGQPREPQVYTLPPSRDELTKNQVSLTCLVKGFYP

SDIAVEWESNGQPENNYKTTPPVLDSDGSFFLYSKLTVDKSRWQQG

NVFSCSVMHEALHNHYTQKSLSLSPG

In another embodiment, SEQ ID NO:149 includes the sequence of human IgG4 constant domain, G4P:

(SEQ ID NO: 161)
EVQLQQSGPELVKPGASVKMSCKASGYTFTDYYMNWVKQSHGKSL

EWIGRVNPSNGGTTYNQRFKGKATLTVDESLSTAYMQLNSLTSEDS

AVYYCARDFLMDYWGQGTSVTVSSASTKGPSVFPLAPCSRSTSEST

AALGCLVKDYFPEPVTVSWNSGALTSGVHTFPAVLQSSGLYSLSSVV

TVPSSSLGTKTYTCNVDHKPSNTKVDKRVESKYGPPCPPCPAPEFLG

GPSVFLFPPKPKDTLMISRTPEVTCVVVDVSQEDPEVQFNWYVDGVE

VHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVF

SCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:153, and a heavy chain variable region having at least 60, 65, 70, 75, 80, 85, 90, 95, 99, or 100% sequence identity to the amino acid according to SEQ ID NO:157.

In one embodiment, the antibody is humanized.

i. 13B2 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 162)
ETTVTQSPASLSMAIGEKVTIRCITSTDIDDDMNWYQQKPGKPPKLLI

SEGNTLRPGVPSRFSSSGYGTDFVFTIENMLSEDVADYYCLQSDNLP

YTFGGGTKLEIK

The light chain CDRs of 13B2 are bolded and are as follows:

| | | |
|---|---|---|
| CDR1 | ITSTDIDDDMN | SEQ ID NO: 163 |
| CDR2 | EGNTLRP | SEQ ID NO: 164 |
| CDR3 | LQSDNLPYT | SEQ ID NO: 165 |

In another embodiment, SEQ ID NO:162 includes the sequence of human kappa constant domain:

(SEQ ID NO: 166)
ETTVTQSPASLSMAIGEKVTIRCITSTDIDDDMNWYQQKPGKPPKLLI

SEGNTLRPGVPSRFSSSGYGTDFVFTIENMLSEDVADYYCLQSDNLP

YTFGGGTKLEIKRTVAAPSVFIFPPSDEQLKSGTASVVCLLNNFYPRE

AKVQWKVDNALQSGNSQESVTEQDSKDSTYSLSSTLTLSKADYEKH

KVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following: EIQLQQSGTELVKPGASVKISCKASGYSFTGYNMNWMKQSHGMSLEWIGNINPYYGSTSYNQKFKGKATLTIDKSSSTAYMQLNSLTSEDSAVYYCARDRKNWEYFFDYWGQGTTLTVSS (SEQ ID NO:167)

The heavy chain CDRs of 13B2 are bolded and are as follows:

| | | |
|---|---|---|
| CDR1 | GYNMN | SEQ ID NO: 108 |
| CDR2 | NINPYYGSTSYNQKFKG | SEQ ID NO: 137 |
| CDR3 | DRKNWEYFFDY | SEQ ID NO: 168 |

In another embodiment, SEQ ID NO:167 includes the sequence of human IgG1 constant domain:

(SEQ ID NO: 169)
EIQLQQSGTELVKPGASVKISCKASGYSFTGYNMNWMKQSHGMSLE

WIGNINPYYGSTSYNQKFKGKATLTIDKSSSTAYMQLNSLTSEDSAV

YYCARDRKNWEYFFDYWGQGTTLTVSSASTKGPSVFPLAPSSKSTS

GGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCP

APELLGGPSVFLFPPKPKDTLMISRTPEVTCVVVDVSHEDPEVKFNW

YVDGVEVHNAKTKPREEQYNSTYRVVSVLTVLHQDWLNGKEYKCK

VSNKALPAPIEKTISKAKGQPREPQVYTLPPSRDELTKNQVSLTCLVK

-continued

GFYPSDIAVEWESNGQPENNYKTTPPVLDSDGSFFLYSKLTVDKSRW

QQGNVFSCSVMHEALHNHYTQKSLSLSPG

In another embodiment, SEQ ID NO:167 includes the sequence human IgG1 constant domain, G1FES:

(SEQ ID NO: 170)

EIQLQQSGTELVKPGASVKISCKASGYSFTGYNMNWMKQSHGMSLE

WIGNINPYYGGSTSYNQKFKGKATLTIDKSSSTAYMQLNSLTSEDSAV

YYCARDRKNWEYFFDYWGQGTTLTVSSASTKGPSVFPLAPSSKSTS

GGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCP

APEFEGGPSVFLFPPKPKDTLMISRTPEVTCVVVDVSHEDPEVKFNW

YVDGVEVHNAKTKPREEQYNSTYRVVSVLTVLHQDWLNGKEYKCK

VSNKALPASIEKTISKAKGQPREPQVYTLPPSRDELTKNQVSLTCLVK

GFYPSDIAVEWESNGQPENNYKTTPPVLDSDGSFFLYSKLTVDKSRW

QQGNVFSCSVMHEALHNHYTQKSLSLSPG

In another embodiment, SEQ ID NO:167 includes the sequence of human IgG4 constant domain, G4P:

(SEQ ID NO: 171)

EIQLQQSGTELVKPGASVKISCKASGYSFTGYNMNWMKQSHGMSLE

WIGNINPYYGGSTSYNQKFKGKATLTIDKSSSTAYMQLNSLTSEDSAV

YYCARDRKNWEYFFDYWGQGTTLTVSSASTKGPSVFPLAPCSRSTS

ESTAALGCLVKDYFPEPVTVSWNSGALTSGVHTFPAVLQSSGLYSLS

SVVTVPSSSLGTKTYTCNVDHKPSNTKVDKRVESKYGPPCPPCPAPE

FLGGPSVFLFPPKPKDTLMISRTPEVTCVVVDVSQEDPEVQFNWYVD

GVEVHNAKTKPREEQFNSTYRVVSVLTVLHQDWLNGKEYKCKVSN

KGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEG

NVFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:162, and a heavy chain variable region having at least 60, 65, 70, 75, 80, 85, 90, 95, 99, or 100% sequence identity to the amino acid according to SEQ ID NO:167.

In one embodiment, the antibody is humanized.

j. 14D3 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 172)

DIVMTQSHKFMSTSVGDRVSITCKASQDLSTAVAWYQQKPGQSPKL

LIYSASYRYTGVPDRFTGSGSGTDFTFTISSVQAEDLAVYYCQQHYS

TPLTFGAGTKLELK

The light chain CDRs of 14D3 are bolded and are as follows:

| | | |
|---|---|---|
| CDR1 | KASQDLSTAVA | SEQ ID NO: 173 |
| CDR2 | SASYRYT | SEQ ID NO: 174 |
| CDR3 | QQHYSTPLT | SEQ ID NO: 175 |

In another embodiment, SEQ ID NO:172 includes the sequence of human kappa constant domain:

(SEQ ID NO: 176)

DIVMTQSHKFMSTSVGDRVSITCKASQDLSTAVAWYQQKPGQSPKL

LIYSASYRYTGVPDRFTGSGSGTDFTFTISSVQAEDLAVYYCQQHYS

TPLTFGAGTKLELKRTVAAPSVFIFPPSDEQLKSGTASVVCLLNNFYP

REAKVQWKVDNALQSGNSQESVTEQDSKDSTYSLSSTLTLSKADYE

KHKVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following: EIQLQQSGAELVKPGASVKISCKASGYSFTGYNMNWVKQSHGKSLE WIGNITPYYGSASYNQKFKGKATLTVDKSSSTAYMQLNSLTSEDSA VYYCARRSYDYDENAMDYWGQGTSVTVSS (SEQ ID NO:177)

The heavy chain CDRs of 13B2 are bolded and are as follows:

| | | |
|---|---|---|
| CDR1 | GYNMN | SEQ ID NO: 108 |
| CDR2 | NITPYYGSASYNQKFKG | SEQ ID NO: 178 |
| CDR3 | RSYDYDENAMDY | SEQ ID NO: 179 |

In another embodiment, SEQ ID NO:177 includes the sequence human IgG1 constant domain:

(SEQ ID NO: 180)

EIQLQQSGAELVKPGASVKISCKASGYSFTGYNMNWVKQSHGKSLE

WIGNITPYYGSASYNQKFKGKATLTVDKSSSTAYMQLNSLTSEDSA

VYYCARRSYDYDENAMDYWGQGTSVTVSSASTKGPSVFPLAPSSKS

TSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFN

WYVDGVEVHNAKTKPREEQYNSTYRVVSVLTVLHQDWLNGKEYK

CKVSNKALPAPIEKTISKAKGQPREPQVYTLPPSRDELTKNQVSLTCL

VKGFYPSDIAVEWESNGQPENNYKTTPPVLDSDGSFFLYSKLTVDKS

RWQQGNVFSCSVMHEALHNHYTQKSLSLSPG

In another embodiment, SEQ ID NO:177 includes the sequence of human IgG1 constant domain, G1FES:

(SEQ ID NO: 181)

EIQLQQSGAELVKPGASVKISCKASGYSFTGYNMNWVKQSHGKSLE

WIGNITPYYGSASYNQKFKGKATLTVDKSSSTAYMOLNSLTSEDSA

-continued

VYYCARRSYDYDENAMDYWGQGTSVTVSSASTKGPSVFPLAPSSKS

TSGGTAALGCLVKDYFPEPVTVSWNSGALTSGVHTFPAVLQSSGLYS

LSSVVTVPSSSLGTQTYICNVNHKPSNTKVDKKVEPKSCDKTHTCPP

CPAPEFEGGPSVFLFPPKPKDTLMISRTPEVTCVVVDVSHEDPEVKFN

WYVDGVEVHNAKTKPREEQYNSTYRVVSVLTVLHQDWLNGKEYK

CKVSNKALPASIEKTISKAKGQPREPQVYTLPPSRDELTKNQVSLTCL

VKGFYPSDIAVEWESNGQPENNYKTTPPVLDSDGSFFLYSKLTVDKS

RWQQGNVFSCSVMHEALHNHYTQKSLSLSPG

In another embodiment, SEQ ID NO:177 includes the sequence of human IgG4 constant domain, G4P:

(SEQ ID NO: 182)
EIQLQQSGAELVKPGASVKISCKASGYSFTGYNMNWVKQSHGKSLEWIG

NITPYYGSASYNQKFKGKATLTVDKSSSTAYMQLNSLTSEDSAVYYCAR

RSYDYDENAMDYWGQGTSVTVSSASTKGPSVFPLAPCSRSTSESTAALG

CLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:172, and a heavy chain variable region having at least 60, 65, 70, 75, 80, 85, 90, 95, 99, or 100% sequence identity to the amino acid according to SEQ ID NO:177.

In one embodiment, the antibody is humanized.

k. 20C3 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 183)
QIVLTQSPAIMSASPGEKVTMTCSASSSVSYMHWYQQKSGTSPKRWI

YDTSKLASGVPARFSGSGSGTSYSLTISSMEAEDAATYYCQQWSGN

PYTFGGGTKLEIK

The light chain CDRs of 20C3 are bolded and are as follows:

| | | |
|---|---|---|
| CDR1 | SASSSVSYMH | SEQ ID NO: 184 |
| CDR2 | DTSKLAS | SEQ ID NO: 185 |
| CDR3 | QQWSGNPYT | SEQ ID NO: 186 |

In another embodiment, SEQ ID NO:183 includes the sequence of human kappa constant domain:

(SEQ ID NO: 187)
QIVLTQSPAIMSASPGEKVTMTCSASSSVSYMHWYQQKSGTSPKRWI

YDTSKLASGVPARFSGSGSGTSYSLTISSMEAEDAATYYCQQWSGN

PYTFGGGTKLEIKRTVAAPSVFIFPPSDEQLKSGTASVVCLLNNFYPR

EAKVQWKVDNALQSGNSQESVTEQDSKDSTYSLSSTLTLSKADYEK

HKVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following:

(SEQ ID NO: 188)
EVKLEESGGGLVQPGGSMKLSCVVSGFTFSNYWMNWVRQSPEKGL

EWVAQIRLKSDNYATHYAESVKGRFTISRDDSKSSVYLQMNNLRA

EDTGIYYCTGESNIYYGYFDYWGQGTTLTVSS

The heavy chain CDRs of 20C3 are bolded and are as follows:

| | | |
|---|---|---|
| CDR1 | NYWMN | SEQ ID NO: 189 |
| CDR2 | QIRLKSDNYATHYAESVKG | SEQ ID NO: 190 |
| CDR3 | ESNIYYGYFDY | SEQ ID NO: 191 |

In another embodiment, SEQ ID NO:188 includes the sequence of human IgG1 constant domain:

(SEQ ID NO: 192)
EVKLEESGGGLVQPGGSMKLSCVVSGFTFSNYWMNWVRQSPEKGL

EWVAQIRLKSDNYATHYAESVKGRFTISRDDSKSSVYLQMNNLRA

EDTGIYYCTGESNIYYGYFDYWGQGTTLTVSSASTKGPSVFPLAPSS

KSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVK

FNWYVDGVEVHNAKTKPREEQYNSTYRVVSVLTVLHQDWLNGKE

YKCKVSNKALPAPIEKTISKAKGQPREPQVYTLPPSRDELTKNQVSLT

CLVKGFYPSDIAVEWESNGQPENNYKTTPPVLDSDGSFFLYSKLTVD

KSRWQQGNVFSCSVMHEALHNHYTQKSLSLSPG

In another embodiment, SEQ ID NO:188 includes the sequence of human IgG1 constant domain, G1FES:

(SEQ ID NO: 193)
EVKLEESGGGLVQPGGSMKLSCVVSGFTFSNYWMNWVRQSPEKGL

EWVAQIRLKSDNYATHYAESVKGRFTISRDDSKSSVYLQMNNLRA

EDTGIYYCTGESNIYYGYFDYWGQGTTLTVSSASTKGPSVFPLAPSS

KSTSGGTAALGCLVKDYFPEPVTVSWNSGALTSGVHTFPAVLQSSGL

-continued

YSLSSVVTVPSSSLGTQTYICNVNHKPSNTKVDKKVEPKSCDKTHTC

PPCPAPEFEGGPSVFLFPPKPKDTLMISRTPEVTCVVVDVSHEDPEVK

FNWYVDGVEVHNAKTKPREEQYNSTYRVVSVLTVLHQDWLNGKE

YKCKVSNKALPASIEKTISKAKGQPREPQVYTLPPSRDELTKNQVSLT

CLVKGFYPSDIAVEWESNGQPENNYKTTPPVLDSDGSFFLYSKLTVD

KSRWQQGNVFSCSVMHEALHNHYTQKSLSLSPG

In another embodiment, SEQ ID NO:188 includes the sequence of human IgG4 constant domain, G4P:

(SEQ ID NO: 194)
EVKLEESGGGLVQPGGSMKLSCVVSGFTFSNYWMNWVRQSPEKGL

EWVAQIRLKSDNYATHYAESVKGRFTISRDDSKSSVYLQMNNLRA

EDTGIYYCTGESNIYYGYFDYWGQGTTLTVSSASTKGPSVFPLAPCS

RSTSESTAALGCLVKDYFPEPVTVSWNSGALTSGVHTFPAVLOSSGL

YSLSSVVTVPSSSLGTKTYTCNVDHKPSNTKVDKRVESKYGPPCPPC

PAPEFLGGPSVFLFPPKPKDTLMISRTPEVTCVVVDVSQEDPEVQFNW

YVDGVEVHNAKTKPREEQFNSTYRVVSVLTVLHQDWLNGKEYKCK

VSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRW

QEGNVFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:183, and a heavy chain variable region having at least 60, 65, 70, 75, 80, 85, 90, 95, 99, or 100% sequence identity to the amino acid according to SEQ ID NO:188.

In one embodiment, the antibody is humanized.

l. 15G11 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 195)
DIQMTQSPASQSASLGESVTITCLASQTIGTWLAWYQQKPGKSPQLL

IYAATSLADGVPSRFSGSGSGTKFSFKISSLQAEDFVSYYCQQLYSNP

YTFGGGTKLEIK

The light chain CDRs of 15G11 are bolded and are as follows:

| | | |
|---|---|---|
| CDR1 | LASQTIGTWLA | SEQ ID NO: 196 |
| CDR2 | AATSLAD | SEQ ID NO: 197 |
| CDR3 | QQLYSNPYT | SEQ ID NO: 198 |

In another embodiment, SEQ ID NO:195 includes the sequence of human kappa constant domain:

(SEQ ID NO: 199)
DIQMTQSPASQSASLGESVTITCLASQTIGTWLAWYQQKPGKSPQLL

IYAATSLADGVPSRFSGSGSGTKFSFKISSLQAEDFVSYYCQQLYSNP

YTFGGGTKLEIKRTVAAPSVFIFPPSDEQLKSGTASVVCLLNNFYPRE

AKVQWKVDNALQSGNSQESVTEQDSKDSTYSLSSTLTLSKADYEKH

KVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following:

(SEQ ID NO: 200)
EIQLQQSGAELVKPGASVKISCKASGYSFTGYNMNWVKQSHGKSLE

WIGNITPYYGSTFYNQKFKGKATLTVDKSSSTAYMQLNSLTSEDSA

VYYCARRDYYGSSYGSSYFDYWGQGTTLTVSS

The heavy chain CDRs of 15G11 are bolded and are as follows:

| | | |
|---|---|---|
| CDR1 | GYNMN | SEQ ID NO: 108 |
| CDR2 | NITPYYGSTFYNQKFKG | SEQ ID NO: 201 |
| CDR3 | RDYYGSSYGSSYFDY | SEQ ID NO: 202 |

In another embodiment, SEQ ID NO:200 includes the sequence of human IgG1 constant domain:

(SEQ ID NO: 203)
EIQLQQSGAELVKPGASVKISCKASGYSFTGYNMNWVKQSHGKSLE

WIGNITPYYGSTFYNQKFKGKATLTVDKSSSTAYMQLNSLTSEDSA

VYYCARRDYYGSSYGSSYFDYWGQGTTLTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPELLGGPSVFLFPPKPKDTLMISRTPEVTCVVVDVSHEDPEV

KFNWYVDGVEVHNAKTKPREEQYNSTYRVVSVLTVLHQDWLNGK

EYKCKVSNKALPAPIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

In another embodiment, SEQ ID NO:200 includes the sequence of human IgG1 constant domain, G1FES:

(SEQ ID NO: 204)
EIQLQQSGAELVKPGASVKISCKASGYSFTGYNMNWVKQSHGKSLE

WIGNITPYYGSTFYNQKFKGKATLTVDKSSSTAYMQLNSLTSEDSA

VYYCARRDYYGSSYGSSYFDYWGQGTTLTVSSASTKGPSVFPLAPS

SKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHT

CPPCPAPEFEGGPSVFLFPPKPKDTLMISRTPEVTCVVVDVSHEDPEV

-continued

KFNWYVDGVEVHNAKTKPREEQYNSTYRVVSVLTVLHQDWLNGK

EYKCKVSNKALPASIEKTISKAKGQPREPQVYTLPPSRDELTKNQVSL

TCLVKGFYPSDIAVEWESNGQPENNYKTTPPVLDSDGSFFLYSKLTV

DKSRWQQGNVFSCSVMHEALHNHYTQKSLSLSPG

In another embodiment, SEQ ID NO:200 includes the sequence of human IgG4 constant domain, G4P:

(SEQ ID NO: 205)
EIQLQQSGAELVKPGASVKISCKASGYSFTGYNMNWVKQSHGKSLE

WIGNITPYYGSTFYNQKFKGKATLTVDKSSSTAYMQLNSLTSEDSA

VYYCARRDYYGSSYGSSYFDYWGOGTTLTVSSASTKGPSVFPLAPC

SRSTSESTAALGCLVKDYFPEPVTVSWNSGALTSGVHTFPAVLQSSG

LYSLSSVVTVPSSSLGTKTYTCNVDHKPSNTKVDKRVESKYGPPCPP

CPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKC

KVSNKGLPSSIEKTISKAKGQPREPQVYTLPPSQEEMTKNQVSLTCLV

KGFYPSDIAVEWESNGQPENNYKTTPPVLDSDGSFFLYSRLTVDKSR

WQEGNVFSCSVMHEALHNHYTQKSLSLSLG

One embodiment provides an anti-FLRT3 antibody with a light chain variable region having at least 60, 65, 70, 75, 80, 85, 90, 95, 99, or 100% sequence identity to the amino acid according to SEQ ID NO:195, and a heavy chain variable region having at least 60, 65, 70, 75, 80, 85, 90, 95, 99, or 100% sequence identity to the amino acid according to SEQ ID NO:200.

In one embodiment, the antibody is humanized.

m. 17A1 i. Light Chain

One embodiment provides a humanized antibody or antigen binding fragment with a light chain variable region having at least 60, 65, 70, 75, 80, 85, 90, 95, 99, or 100% sequence identity with the following:

(SEQ ID NO: 206)
DIVMTQSHKFMSTSVGDRVSITCKASQDVGTAVAWYQQKPGQSPK

LLIYWASTRHTGVPDRFTGSGSGTDFALTISNVQSADLAYYFCQQYS

NYPTFGGGTKLEIK

The light chain CDRs of 17A7 are bolded and are as follows:

| | | |
|---|---|---|
| CDR1 | KASQDVGTAVA | SEQ ID NO: 115 |
| CDR2 | WASTRHT | SEQ ID NO: 116 |
| CDR3 | QQYSNYPT | SEQ ID NO: 207 |

In another embodiment, SEQ ID NO:206 includes the sequence of human kappa constant domain:

(SEQ ID NO: 208)
DIVMTQSHKFMSTSVGDRVSITCKASQDVGTAVAWYQQKPGQSPK

LLIYWASTRHTGVPDRFTGSGSGTDFALTISNVQSADLAYYFCQQYS

-continued

NYPTFGGGTKLEIKRTVAAPSVFIFPPSDEQLKSGTASVVCLLNNFYP

REAKVQWKVDNALQSGNSQESVTEQDSKDSTYSLSSTLTLSKADYE

KHKVYACEVTHQGLSSPVTKSFNRGEC ii. Heavy Chain

One embodiment provides a humanized antibody or antigen binding fragment with a heavy chain variable region having at least 60, 65, 70, 75, 80, 85, 90, 95, 99, or 100% sequence identity with the following:

(SEQ ID NO: 209)
EVQLQQSGPELVKPGASVKMSCKASGYTFTDYYMNWVKQSHGKSL

EWIGRVNPSNGGTTYNQKFKGKATLTVDKSLSTAYMQLNSLTSED

SAVYYCARNFLMDYWGQGTSVTVSS

The heavy chain CDRs of 17A1 are bolded and are as follows:

| | | |
|---|---|---|
| CDR1 | DYYMN | SEQ ID NO: 120 |
| CDR2 | RVNPSNGGTTYNQKFKG | SEQ ID NO: 210 |
| CDR3 | NFLMDY | SEQ ID NO: 211 |

In another embodiment, SEQ ID NO:209 includes the sequence of human IgG1 constant domain:

(SEQ ID NO: 212)
EVQLQQSGPELVKPGASVKMSCKASGYTFTDYYMNWVKQSHGKSL

EWIGRVNPSNGGTTYNQKFKGKATLTVDKSLSTAYMQLNSLTSED

SAVYYCARNFLMDYWGQGTSVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYV

DGVEVHNAKTKPREEQYNSTYRVVSVLTVLHQDWLNGKEYKCKVS

NKALPAPIEKTISKAKGQPREPQVYTLPPSRDELTKNQVSLTCLVKGF

YPSDIAVEWESNGQPENNYKTTPPVLDSDGSFFLYSKLTVDKSRWQQ

GNVFSCSVMHEALHNHYTQKSLSLSPG

In another embodiment, SEQ ID NO:209 includes the sequence human IgG1 constant domain, G1FES:

(SEQ ID NO: 213)
EVQLQQSGPELVKPGASVKMSCKASGYTFTDYYMNWVKQSHGKSL

EWIGRVNPSNGGTTYNQKFKGKATLTVDKSLSTAYMQLNSLTSED

SAVYYCARNFLMDYWGQGTSVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAP

EFEGGPSVFLFPPKPKDTLMISRTPEVTCVVVDVSHEDPEVKFNWYV

DGVEVHNAKTKPREEQYNSTYRVVSVLTVLHQDWLNGKEYKCKVS

NKALPASIEKTISKAKGQPREPQVYTLPPSRDELTKNQVSLTCLVKGF

-continued

```
YPSDIAVEWESNGQPENNYKTTPPVLDSDGSFFLYSKLTVDKSRWQQ

GNVFSCSVMHEALHNHYTQKSLSLSPG
```

In another embodiment, SEQ ID NO:209 includes the sequence of human IgG4 constant domain, G4P:

```
                                        (SEQ ID NO: 214)
EVQLQQSGPELVKPGASVKMSCKASGYTFTDYYMNWVKQSHGKSL

EWIGRVNPSNGGTTYNQKFKGKATLTVDKSLSTAYMQLNSLTSED

SAVYYCARNFLMDYWGQGTSVTVSSASTKGPSVFPLAPCSRSTSEST

AALGCLVKDYFPEPVTVSWNSGALTSGVHTFPAVLQSSGLYSLSSVV

TVPSSSLGTKTYTCNVDHKPSNTKVDKRVESKYGPPCPPCPAPEFLG

GPSVFLFPPKPKDTLMISRTPEVTCVVVDVSQEDPEVQFNWYVDGVE

VHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVF

SCSVMHEALHNHYTQKSLSLSLG
```

One embodiment provides an anti-FLRT3 antibody with a light chain variable region having at least 60, 65, 70, 75, 80, 85, 90, 95, 99, or 100% sequence identity to the amino acid according to SEQ ID NO:206, and a heavy chain variable region having at least 60, 65, 70, 75, 80, 85, 90, 95, 99, or 100% sequence identity to the amino acid according to SEQ ID NO:209.

In one embodiment, the antibody is humanized.

The activity of an antibody or antigen binding fragment thereof that is specific for FLRT3 can be determined using functional assays that are known in the art, and include the assays discussed below. Typically, the assays include determining if the antibody or antigen binding fragment thereof increases (i.e., agonist) or decreases (i.e., antagonist) signaling through FLRT3.

In some embodiments, the disclosed antibodies and antigen binding fragments thereof immunospecifically bind to human or mouse FLRT3. In some embodiments, the antibody binds to an extracellular domain of human or mouse FLRT3.

For example, molecules are provided that can immunospecifically bind to FLRT3:

(I) arrayed on the surface of a cell (especially a live cell);
(II) arrayed on the surface of a cell (especially a live cell) at an endogenous concentration;
(III) arrayed on the surface of a live cell, and modulates binding between FLRT3 and a ligand thereof,
(IV) arrayed on the surface of a live cell, and reduces or inhibits immune response by FLRT3;
(V) arrayed on the surface of a live cell, wherein the cell is a tumor cell;
(VI) combinations of I-IV and V;
(VII) combinations of I-III and V; and
(VIII) arrayed on the surface of a live myeloid or lymphoid derived cancer cells (AML or ALL), and enhances apoptosis and differentiation resulting in reduced self-renewal of cancer stem cells.

To prepare an antibody or antigen binding fragment thereof that specifically binds to FLRT3 purified proteins, polypeptides, fragments, fusions, or epitopes to FLRT3 or polypeptides expressed from nucleic acid sequences thereof, can be used. The antibodies or antigen binding fragments thereof can be prepared using any suitable methods known in the art such as those discussed in more detail below.

a. Human and Humanized Antibodies

In some embodiments, the antibodies are humanized antibodies. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', $F(ab')_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

b. Single-Chain Antibodies

In some embodiments, the antibodies are single-chain antibodies. Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

c. Monovalent Antibodies

In some embodiments, the antibodies are monovalent antibodies. In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the $F(ab')_2$ fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The $F(ab')_2$ fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

d. Hybrid Antibodies

In some embodiments, the antibodies are hybrid antibodies. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

e. Conjugates or Fusions of Antibody Fragments

In some embodiments, the antibodies are conjugates or fusions of antibody fragments. The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor®, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

2. Proteins and Polypeptides a. Protein and Polypeptide Compositions

The immunomodulatory or binding agent can be a FLRT3 protein, polypeptide, or fusion protein. For example, the immunomodulatory agent or binding moiety can be an isolated or recombinant protein or polypeptide, or functional fragment, variant, or fusion protein thereof of FLRT3.

The FLRT3 protein or polypeptide, or functional fragment, variant, or fusion protein thereof can be an agonist or an antagonist. For example, in some embodiments an antagonist of FLRT3 is a FLRT3 polypeptide or a fragment or fusion protein thereof that binds to a ligand of FLRT3. The polypeptide can be a soluble fragment, for example the extracellular domain of FLRT3, or a functional fragment thereof, or a fusion protein thereof. In some embodiments, a soluble ligand of FLRT3 may serve as an antagonist, decreasing FLRT3 mediated signal transduction.

The activity of a protein or polypeptide of FLRT3, or any fragment, variant or fusion protein thereof can be determined using functional assays that are known in the art, and include the assays discussed below. Typically, the assays include determining if the protein, polypeptide or fragment, variant or fusion protein thereof increases (i.e., agonist) or decreases (i.e., antagonist) signaling through the FLRT3 receptor. In some embodiments, the assay includes determining if the protein, polypeptide or fragment, variant, or fusion protein thereof increases (i.e., agonist) or decreases (i.e., antagonist) the immune response associated with FLRT3. Typically, the assays include determining if the protein, polypeptide or fragment, variant, or fusion protein thereof increases (i.e., agonist) or decreases (i.e., antagonist) signaling through FLRT3. In some embodiments, the assay includes determining if the protein, polypeptide or fragment, variant, or fusion protein thereof decreases (i.e., agonist) or increases (i.e., antagonist) an immune response regulated by FLRT3. In some embodiments, the assay includes determining if the protein, polypeptide or fragment, variant, or fusion protein thereof increases (i.e., antagonist) the apoptosis and differentiation of acute myeloid leukemia cells and acute lymphoblastic leukemia cells resulting in reduced self-renewal capacity of AML and ALL stem cells.

Nucleic acid and polypeptide sequences for FLRT3 are known in the art and exemplary protein and peptide sequences are provided above. The sequences can be used, as discussed in more detail below, by one of skill in the art to prepare any protein or polypeptide of FLRT3, or any fragment, variant, or fusion protein thereof. Generally, the proteins, polypeptides, fragments, variants, and fusions thereof of FLRT3 are expressed from nucleic acids that include sequences that encode a signal sequence. The signal sequence is generally cleaved from the immature polypeptide to produce the mature polypeptide lacking the signal sequence. The signal sequence can be replaced by the signal sequence of another polypeptide using standard molecule biology techniques to affect the expression levels, secretion, solubility, or other property of the polypeptide FLRT3 proteins with and without a signal sequence are disclosed. It is understood that in some cases, the mature protein as it is known or described in the art, i.e., the protein sequence without the signal sequence, is a putative mature protein.

During normal cell expression, a signal sequence can be removed by a cellular peptidase to yield a mature protein. The sequence of the mature protein can be determined or confirmed using methods that are known in the art.

i. Fragments

As used herein, a fragment of FLRT3 refers to any subset of the polypeptide that is at least one amino acid shorter than full length protein. Useful fragments include those that retain the ability to bind to their natural ligand or ligands. A polypeptide that is a fragment of any full-length FLRT3 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural ligand respectively as compared to the full-length protein.

Fragments of FLRT3 include cell free fragments. Cell free polypeptides can be fragments of full-length, transmembrane, polypeptides that may be shed, secreted or otherwise extracted from the producing cells. Cell free fragments of polypeptides can include some or all of the extracellular domain of the polypeptide, and lack some or all of the intracellular and/or transmembrane domains of the full-length protein. In one embodiment, polypeptide fragments include the entire extracellular domain of the full-length protein. In other embodiments, the cell free fragments of the polypeptides include fragments of the extracellular domain that retain biological activity of full-length protein. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is the only functional domain of the fragment (e.g., the ligand binding domain).

ii. Variants

Variants of FLRT3, and fragments thereof are also provided. In some embodiments, the variant is at least 50, 60, 70, 80, 85, 90, 95, 96, 97, 98, or 99 percent identical to any one of SEQ ID NO:2-5. Useful variants include those that increase biological activity, as indicated by any of the assays described herein, or that increase half-life or stability of the protein. The protein and polypeptides of FLRT3, and fragments, variants, and fusion proteins thereof can be engineered to increase biological activity. For example, in some embodiments, a FLRT3 polypeptide, protein, or fragment, variant or fusion thereof has been modified with at least one amino acid substitution, deletion, or insertion that increases a function thereof.

Finally, variant polypeptides can be engineered to have an increased half-life relative to wild type. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of affinity for the receptor on the half-life of proteins, polypeptides, fragments, or fusions thereof at serum and endosomal pH.

iii. Fusion Proteins

Fusion polypeptides have a first fusion partner including all or a part of a human or mouse FLRT3 polypeptide fused to a second polypeptide directly or via a linker peptide sequence that is fused to the second polypeptide. In one embodiment, the ECD of human or mouse FLRT3 or a fragment thereof is fused to a second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

$$N—R_1—R_2—R_3—C$$

wherein "N" represents the N-terminus of the fusion protein, "C" represents the C-terminus of the fusion protein. In some embodiments, "$R_1$" is a polypeptide or protein of FLRT3 or fragment or variant thereof, "$R_2$" is an optional peptide/polypeptide linker domain, and "$R_3$" is a second polypeptide. Alternatively, $R_3$ may be a polypeptide or protein of FLRT3, or fragment or variant thereof and $R_1$ may be a second polypeptide. In some embodiments, the FLRT3 polypeptide is the extracellular domain.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

In some embodiments, the fusion protein includes the extracellular domain of FLRT3, or a fragment or variant thereof, fused to an Ig Fc region. Recombinant Ig fusion proteins can be prepared by fusing the coding region of the extracellular domain or a fragment or variant thereof to the Fc region of human IgG1, IgG2, IgG3 or IgG4 or mouse IgG2a, or other suitable Ig domain, as described previously (Chapoval, et al., *Methods Mol. Med.,* 45:247-255 (2000)).

One embodiment provides a fusion protein having 80%, 85%, 90%, 95%, 99%, or 100% sequence identity to FLRT3 Fc (IgG1 Fc; wild type) (SEQ ID NO:215):

(SEQ ID NO: 215)
MISAAWSIFLIGTKIGLFLQVAPLSVMAKSCPSVCRCDAGFIYCND
RFLTSIPTGIPEDATTLYLONNQINNAGIPSDLKNLLKVERIYLYH
NSLDEFPTNLPKYVKELHLQENNIRTITYDSLSKIPYLEELHLDDN
SVSAVSIEEGAFRDSNYLRLLFLSRNHLSTIPWGLPRTIEELRLDD
NRISTISSPSLOGLTSLKRLVLDGNLLNNHGLGDKVFENLVNLTEL
SLVRNSLTAAPVNLPGTNLRKLYLQDNHINRVPPNAFSYLROLYRL
DMSNNNLSNLPQGIFDDLDNITQLILRNNPWYCGCKMKWVRDWLOS
LPVKVNVRGLMCQAPEKVRGMAIKDLNAELFDCKDSGIVSTIQITT
AIPNTVYPAQGQWPAPVTKOPDIKNPKLTKDHQTTGSPSRKTITIT
VKSVTSDTIHISWKLALPMTALRLSWLKLGHSPAFGSITETIVTGE
RSEYLVTALEPDSPYKVCMVPMETSNLYLFDETPVCIETETAPLRM
YNPTTTLNREQEKEPYKNPNLPLVPRGSDKTHTCPPCPAPELLGGP
SVFLFPPKPKDTLMISRTPEVTCVVVDVSHEDPEVKENWYVDGVEV
HNAKTKPREEQYNSTYRVVSVLTVLHODWLNGKEYKCKVSNKALPA
PIEKTISKAKGQPREPQVYTLPPSRDELTKNQVSLTCLVKGFYPSD
IAVEWESNGOPENNYKTTPPVLDSDGSFFLYSKLTVDKSRWOOGNV
FSCSVMHEALHNHYTOKSLSLSPG.

The underlined sequence is the signal sequence. The bolded sequence is a linker, and the double underlined sequence is the Fc domain of wild type IgG1. In one embodiment, the fusion protein does not have a signal sequence.

One embodiment provides a fusion protein having 80%, 85%, 90%, 95%, 99%, or 100% sequence identity to FLRT3 Fe (IgG1 Fc; FES)

(SEQ ID NO: 216)
MISAAWSIFLIGTKIGLFLQVAPLSVMAKSCPSVCRCDAGFIYCND
RFLTSIPTGIPEDATTLYLQNNQINNAGIPSDLKNLLKVERIYLYH
NSLDEFPTNLPKYVKELHLQENNIRTITYDSLSKIPYLEELHLDDN
SVSAVSIEEGAFRDSNYLRLLFLSRNHLSTIPWGLPRTIEELRLDD
NRISTISSPSLQGLTSLKRLVLDGNLLNNHGLGDKVFENLVNLTEL
SLVRNSLTAAPVNLPGTNLRKLYLQDNHINRVPPNAFSYLRQLYRL
DMSNNNLSNLPQGIFDDLDNITQLILRNNPWYCGCKMKWVRDWLQS
LPVKVNVRGLMCQAPEKVRGMAIKDLNAELFDCKDSGIVSTIQITT
AIPNTVYPAQGQWPAPVTKQPDIKNPKLTKDHQTTGSPSRKTITIT
VKSVTSDTIHISWKLALPMTALRLSWLKLGHSPAFGSITETIVTGE
RSEYLVTALEPDSPYKVCMVPMETSNLYLFDETPVCIETETAPLRM
YNPTTTLNREQEKEPYKNPNLPLVPRGSDKTHTCPPCPAPEFEGGP
SVFLFPPKPKDTLMISRTPEVTCVVVDVSHEDPEVKENWYVDGVEV
HNAKTKPREEQYNSTYRVVSVLTVLHQDWLNGKEYKCKVSNKALPA
SIEKTISKAKGQPREPQVYTLPPSRDELTKNQVSLTCLVKGFYPSD
IAVEWESNGQPENNYKTTPPVLDSDGSFFLYSKLTVDKSRWQQGNV
FSCSVMHEALHNHYTQKSLSLSPG.

The underlined sequence is the signal sequence. The bolded sequence is a linker, and the double underlined sequence is the Fc domain of mutated IgG1 (IgG1-FES). In one embodiment, the fusion protein does not have a signal sequence.

One embodiment provides a fusion protein having 80%, 85%, 90%, 95%, 99%, or 100% sequence identity to FLRT3 Fe (IgG4 Fc; G4P) (SEQ ID NO:217):

(SEQ ID NO: 217)
MISAAWSIFLIGTKIGLFLQVAPLSVMAKSCPSVCRCDAGFIYCND
RFLTSIPTGIPEDATTLYLQNNQINNAGIPSDLKNLLKVERIYLYH
NSLDEFPTNLPKYVKELHLQENNIRTITYDSLSKIPYLEELHLDDN
SVSAVSIEEGAFRDSNYLRLLFLSRNHLSTIPWGLPRTIEELRLDD
NRISTISSPSLQGLTSLKRLVLDGNLLNNHGLGDKVFFNLVNLTEL
SLVRNSLTAAPVNLPGTNLRKLYLQDNHINRVPPNAFSYLRQLYRL
DMSNNNLSNLPQGIFDDLDNITQLILRNNPWYCGCKMKWVRDWLQS
LPVKVNVRGLMCQAPEKVRGMAIKDLNAELFDCKDSGIVSTIQITT
AIPNTVYPAQGQWPAPVTKQPDIKNPKLTKDHQTTGSPSRKTITIT
VKSVTSDTIHISWKLALPMTALRLSWLKLGHSPAFGSITETIVTGE
RSEYLVTALEPDSPYKVCMVPMETSNLYLFDETPVCIETETAPLRM
YNPTTTLNREQEKEPYKNPNLPESKYGPPCPPCPAPEFLGGPSVEL

-continued

FPPKPKDTLMISRTPEVTCVVVDVSQEDPEVQENWYVDGVEVHNAK

TKPREEQFNSTYRVVSVLTVLHQDWLNGKEYKCKVSNKGLPSSIEK

TISKAKGQPREPQVYTLPPSQEEMTKNQVSLTCLVKGFYPSDIAVE

WESNGQPENNYKTTPPVLDSDGSFFLYSRLTVDKSRWQEGNVESCS

VMHEALHNHYTQKSLSLSLG*.

The underlined sequence is the signal sequence. The double underlined sequence is hG4P Fe (G4P).

iv. Polypeptide Modifications

The polypeptides and fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The polypeptides and fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e., pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N═C═N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

v. Modified Binding Properties

Binding properties of the proteins, polypeptides, fragments, variants and fusions thereof are relevant to the dose and dose regimen to be administered. In one embodiment the disclosed proteins, polypeptides, fragments, variants and fusions thereof have binding properties to FLRT3 or an FLRT3 ligand that demonstrate a higher term, or higher percentage, of occupancy of a binding site (e.g., on the ligand) relative to other receptor molecules that bind thereto. In other embodiments, the disclosed proteins, polypeptides, fragments, variants and fusions thereof have reduced binding affinity to FLRT3 relative to wild type protein.

In some embodiments the proteins, polypeptides, fragments, variants and fusions thereof have a relatively high affinity for FLRT3 and may therefore have a relatively slow off rate. In other embodiments, the proteins polypeptides, fragments, variants and fusions thereof are administered intermittently over a period of days, weeks or months to dampen immune responses which are allowed to recover prior to the next administration, which may serve to alter the immune response without completely turning the immune response on or off and may avoid long term side effects.

3. Isolated Nucleic Acid Molecules

Isolated nucleic acid sequences encoding the FLRT3 proteins, polypeptides, fragments, variants and fusions thereof are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the proteins, polypeptides, fragments, variants and fusions thereof may be optimized for expression in the expression host of choice. Codons may be substituted with alternative codons encoding the same amino acid to account for differences in codon usage between the mammal from which the nucleic acid sequence is derived and the expression host. In this manner, the nucleic acids may be synthesized using expression host-preferred codons.

Nucleic acids can be in sense or antisense orientation, or can be complementary to a reference sequence encoding a polypeptide or protein of FLRT3. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

4. Vectors and Host Cells

Vectors encoding the proteins, polypeptides, fragments, variants and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen® (Madison, WI), Clontech® (Palo Alto, CA), Stratagene® (La Jolla, CA), and Invitrogen Life Technologies® (Carlsbad, CA).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak®, New Haven, CT), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, $C_H2$ and $C_H3$ regions of a human immunoglobulin $C\gamma1$ chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

5. Small Molecules

The immunomodulatory agent can be a small molecule. Small molecules agonists and antagonists FLRT3 are known in the art or can be identified using routine screening methods.

In some embodiments, screening assays can include random screening of large libraries of test compounds. Alternatively, the assays may be used to focus on particular classes of compounds suspected of modulating the level of FLRT3. Assays can include determinations of FLRT3 mediated signaling activity. Other assays can include determinations of nucleic acid transcription or translation, mRNA levels, mRNA stability, mRNA degradation, transcription rates, and translation rates.

D. Pharmaceutical Compositions

Pharmaceutical compositions including the disclosed immunomodulatory agents are provided. Pharmaceutical compositions containing the immunomodulatory agent can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being affected.

For the disclosed immunomodulatory agents, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the immunomodulatory agent is administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In some embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712, which are incorporated herein by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), methacrylic acid copolymer (Eudragit L30D™), cellulose acetate phthalate coating (Aquateric™), cellulose acetate phthalate (CAP), methacrylic acid-co-methyl methacrylate (Eudragit L™), methacrylic acid—methyl methacrylate copolymer (1:2) (Eudragit S™), and pharmaceutical glaze (Shellac™). These coatings may be used as mixed films.

3. Formulations for Topical Administration

The disclosed immunomodulatory agents can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent™ nebulizer (Mallinckrodt® Inc, St. Louis, Mo.); the Acorn II® nebulizer (Marquest® Medical Products, Englewood, Colo.); the Ventolin® metered dose inhaler (GSK®, Research Triangle Park, N.C.); and the Spinhaler® powder inhaler (Fisons® Corp., Bedford, Mass.). Nektar®, Alkermes® and Mannkind® all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The immunomodulatory agents disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release,* 5:13-22 (1987); Mathiowitz, et al., *Reactive Polymers,* 6:275-283 (1987); and Mathiowitz, et al., *J. Appl. Polymer Sci.,* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

A. Methods of Making Antibodies

The disclosed antibodies can be generated in cell culture, in phage, or in various animals, including but not limited to cows, rabbits, goats, mice, rats, hamsters, guinea pigs, sheep, dogs, cats, monkeys, chimpanzees, and apes. Therefore, in one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles And Practice* (Academic Press, 1993); *Current Protocols In Immunology* (John Wiley & Sons, most recent edition).

FLRT3 deficient ("knockout) mice or wild type mice can be utilized for the generation of high affinity mAbs against FLRT3 using proprietary immunization techniques.

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., *Mol. Immunol.* 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides, or fusion proteins of FLRT3. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic peptide. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems®, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method consists of a two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

B. Methods for Producing Proteins

The disclosed proteins, polypeptides, fragments, variants and fusions thereof can be manufactured using conventional techniques that are known in the art. Isolated fusion proteins can be obtained by, for example, chemical synthesis or by recombinant production in a host cell. To recombinantly produce a protein, polypeptide, fragment, variant or fusion thereof, a nucleic acid containing a nucleotide sequence encoding the protein, polypeptide, fragment, variant or fusion thereof can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the protein, polypeptide, fragment, variant or fusion thereof. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express fusion proteins. Viral based expression systems are well known in the art and include, but are not limited to, baculoviral, SV40, retroviral, or vaccinia based viral vectors.

Mammalian cell lines that stably express proteins, polypeptides, fragments, variants or fusions thereof, can be produced using expression vectors with appropriate control elements and a selectable marker. For example, the eukaryotic expression vectors pCR3.1 (Invitrogen Life Technologies) and p91023(B) (see Wong et al. (1985) Science 228: 810-815) are suitable for expression of proteins, polypeptides, fragments, variants or fusions thereof, in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza® Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a protein, polypeptide, fragment, variant or fusion thereof, can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Proteins, polypeptides, fragments, variants or fusions thereof, can be isolated using, for example, chromatographic methods such as affinity chromatography, ion exchange chromatography, hydrophobic interaction chromatography, DEAE ion exchange, gel filtration, and hydroxylapatite chromatography. In some embodiments, proteins, polypeptides, fragments, variants or fusions thereof can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak®) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Fusion proteins can additionally be engineered to contain a secretory signal (if there is not a secretory signal already present) that causes the Proteins, polypeptides, fragments, variants or fusions thereof to be secreted by the cells in which it is produced. The secreted Proteins, polypeptides, fragments, variants or fusions thereof can then conveniently be isolated from the cell media.

C. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) Science 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992.

IV. Assays and Antibody Screening

One embodiment provides assays for antibody screening. Assays for antibody screening include:

1. Analysis of binding affinity of FLRT3-Fc to ligands in comparison to FLRT3.
2. Functional assays to confirm FLRT3-Fc prevents signaling by FLRT3 expressing cells. Reporter cells may be utilized for these assays, or primary FLRT3+ cells are another option.

A. Phase Screening

1. Phase I screening: screen for mAb binding to cell lines transfected to express cell surface FLRT3. Additionally, mAbs should have the capacity to bind endogenously expressed FLRT3 on the surface of primary human cell subsets, or endogenously expressed. These mAbs should be highly specific for FLRT3.
2. Phase II screening: FLRT3 specific mAbs should block the binding of FLRT3 to its ligands.
3. Phase III screening: Functional assays to confirm that FLRT3 mAbs or combination of mAbs modulate FLRT3 mediated signaling. These assays will utilize cell lines that express endogenous FLRT3, or primary cells such as human monocytes, macrophages and dendritic cell subsets or any other leukocyte populations that express FLRT3 to assess function in the presence of FLRT3 mAbs. Additionally, reporter cells lines may be used to determine if signaling pathways such as NF-kB (NF-kB reporter) or NFAT (NFAT reporter) are altered following culture with FLRT3 mAbs.
4. Phase IV screening: Functional assays to determine if FLRT3 mAbs are capable of inducing antibody dependent cell cytotoxicity (ADCC), complement dependent cytotoxicity (CDC) or cellular apoptosis through other mechanisms, of FLRT3 expressing cell lines. In particular, FLRT3 mAbs will be tested for the ability to deplete through one of these methods leukemia cell lines, known to express FLRT3 on the cell surface. FLRT3 mAbs may also be engineered to deplete FLRT3 expressing cells and tested as described later in this document through known methods.
5. Phase V screening: Functional assays to determine if FLRT3 mAbs are capable of delivering or inducing a positive or negative signal (agonist) via FLRT3 into FLRT3 expressing cells to stimulate or inhibit cellular function, respectively. Cell lines that endogenously express FLRT3, or transfectants of cell lines will be assessed for activation or inhibition following culture with FLRT3. In other assays, reporter cell lines will be used to determine whether FLRT3 mAbs enhance or dampen positive signaling pathways such as NF-kB (NF-kB reporter) or other known cell signaling reporters. Induction of apoptosis in cell lines will also be evaluated Phase II and III assays can be used to predict the concentrations of FLRT3 mAb(s) required to block physiological levels of ligands in vivo.

V. Method of Use

The disclosed antagonists or agonists of FLRT3 mediated signaling can be used to modulate immune responses in subjects in need of such treatment.

In one embodiment, the FLRT3 binding moieties induce, promote, or enhance ligand binding to FLRT3 and induce, promote, or enhance proliferation or activation of FLRT3+ immunosuppressive cells or cause depletion of these cells.

In one embodiment, the FLRT3 binding moieties inhibit, reduce or block ligand binding to FLRT3 and inhibit, reduce, or block FLRT3+ immunosuppressive cells or cause depletion of these cells.

Exemplary methods are discussed in more detail below.

A. Immune Response Stimulation

1. Therapeutic Strategies

Methods of inducing or enhancing an immune response in a subject are provided. Typically, the methods include administering a subject an effective amount of a FLRT3 immunomodulatory agent or binding moiety, or cells primed ex vivo with the FLRT3 immunomodulatory agent or binding moiety. The immune response can be, for example, inhibition of suppressive immune signals from for example, Treg and MDSC at a tumor site.

Alternatively, the immunomodulatory agent can stimulate signal transduction through FLRT3 and promote or enhance an immune response.

In some embodiments, the FLRT3 immunomodulatory agents or binding moieties can be used to block suppressive immune cells to tumor microenvironments. In another embodiment, the FLRT3 immunomodulatory agent or binding moieties can be used to inhibit, reduce, or block tumor metastasis. In some embodiments, the agent can reduce or inhibit the activity of Tregs, reduce the production of cytokines such as IL-10 from Tregs, reduce the differentiation of Tregs, reduce the number of Tregs, reduce the ratio of Tregs within an immune cell population, or reduce the survival of Tregs. The immunomodulatory agent or binding moiety can be administered to a subject in need thereof in an effective amount to overcome T cell exhaustion and/or T cell anergy. Overcoming T cell exhaustion or T cell anergy can be determined by measuring T cell function using known techniques.

The methods can be used in vivo or ex vivo to inhibit, reduce, or block suppressive immune responses and thereby have a stimulating therapeutic effect.

In some embodiments, the agent, or nucleic acid encoding the agent, is administered directly to the subject. In some embodiments, the agent or nucleic acid encoding the agent, is contacted with cells (e.g., immune cells) ex vivo, and the treated cells are administered to the subject (e.g., adoptive transfer). The agents can enable a more robust immune response to be possible. The disclosed compositions are useful to stimulate or enhance immune responses involving T cells by inhibiting, reducing or blocking suppressive immune signal transduction through FLRT3.

The immunomodulatory agents utilized for increasing an immune response are typically those that reduce FLRT3 expression, ligand binding, crosslinking, suppressive signaling, or a combination thereof. For example, the agent can be an antagonist of FLRT3, such as an antagonist (blocking) anti-FLRT3 antibody or antigen binding fragment thereof. The agent can also be a FLRT3 polypeptide, for example, a soluble polypeptide, or fusion protein thereof that can serve as a decoy receptor for one or more FLRT3 ligands or receptors.

FLRT3 blockade, for example using function blocking anti-FLRT3 antibodies, can be an alternative agent or complementary agent to soluble FLRT3 polypeptides and fusion proteins. For example, in some embodiments, FLRT3 blockade is combined with a decoy receptor such as soluble FLRT3 or fusion protein thereof. The combined treatment (e.g., FLRT3-Fc and FLRT3 blockade) may be complementary.

In some embodiments, immune response stimulating therapy (e.g., in the treatment of cancer or infections) includes depletion of FLRT3+ cells.

Development and identification of FLRT3 depleting mAbs can be carried out according to known construction and screening methods including those discussed herein. See, for example, Reff, et al, Blood. Vol 83, No 2, 1994: pp 435-445, which describes preparation of an anti-CD20 chimeric antibody that binds to human C1q, and mediates complement-dependent cell lysis (CDCC) in the presence of human complement, and anti-body-dependent cellular cytotoxicity (ADCC) with human effector cells. Rituximab destroys B cells and is therefore used to treat diseases which are characterized by overactive, dysfunctional, or excessive numbers of B cells. Other B cell-depleting antibodies include ocrelizumab and ofatumumab. In another example, CD3 Abs can preferentially target and deplete activated effector T cells while preserving CD4+Foxp3+ Tregs. The antibodies transiently deplete T cells although they display no or little complement-dependent and antibody-dependent cellular cytotoxicity. Redirected cell lysis due to the ability to crosslink CD3 molecules expressed by two different cells (cytotoxic CD8+ T cells on one side and other target T cells on the other side) has been shown, however, T cell depletion mostly results from AICD (reviewed in You, Front Immunol. 2015; 6: 242).

2. Subjects to be Treated a. Treatment of Cancer

The disclosed compositions and methods can be used to treat cancer. Generally, the agents are used to stimulate or enhance an immune response to cancer in the subject by administering to the subject an amount of an immunomodulatory agent, for example any one of the disclosed antibodies or antigen-binding fragments or fusion proteins that inhibits, reduces, or blocks FLRT3 expression, ligand binding, crosslinking, suppressive signaling, or a combination thereof. The immunomodulatory agent can bind FLRT3 and promote or enhance an immune response by stimulating signal transduction through FLRT3. The method can reduce or more symptoms of the cancer.

In one embodiment the FLRT3 immunomodulatory agents or binding moieties inhibit, reduce, or block FLRT3 and ligand binding and thereby inhibit, reduce, or block Treg and MDSC suppressive functions at a tumor site.

In another embodiment, the FLRT3 immunomodulatory agents or binding moieties inhibit, reduce, or block FLRT3 and deplete the suppressive immune cells, for example in a tumor microenvironment.

In another embodiment, the FLRT3 immunomodulatory agents or binding moieties inhibit, reduce, or block FLRT3 and ligand binding and thereby inhibit, reduce, or block trafficking of suppressive immune cells to a tumor microenvironment and thereby inhibit, reduce, or block tumor metastasis.

Cancer cells acquire a characteristic set of functional capabilities during their development through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

The disclosed compositions and methods are particularly useful for the treatment of cancers that are associated with cells that express abnormally high levels of FLRT3 or FLRT3 specific binding partner, including a ligand or counter-receptor.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Treatment of Infections

The disclosed compositions and methods can be used to treat infections and infectious diseases. Generally, the agents are used to stimulate or enhance an immune response to infection in the subject by administering to the subject an amount of an immunomodulatory agent that modulates FLRT3 expression, ligand binding, crosslinking, suppressive signaling, or a combination thereof including but not limited to any one of the disclosed antibodies or antigen-binding fragments or fusion proteins. In one embodiment, the immunomodulatory agent inhibits, reduces, or blocks a suppressive immune signal transduction through FLRT3. In another embodiment, the immunomodulatory agent induces, promotes, or enhances an immune response by inducing, promoting, or enhancing signal transduction through FLRT3. The method can reduce one or more symptoms of the infection.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa*, or *Mycobacterium.*

In some embodiments, the disclosed compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HV), a human T-lymphotrophic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective viral agent would be beneficial to an animal or human subject. Thus, the disclosed compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) and other viral infections, caused by, for example, HTLV, hepatitis virus, respiratory syncytial virus, vaccinia virus, and rabies virus. The molecules can be administered topically to treat viral skin diseases such as herpes lesions or shingles, or genital warts. The molecules can also be administered systemically to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.*

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia*, rhizophus), *Sporothrix* (*schenkii*), *Blastomyces* (*dermatitidis*), *Paracoccidioides* (*brasiliensis*), *Coccidioides* (*immitis*) and *Histoplasma* (*capsulatuma*), *Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia*, or *Trypanosoma*, etc.

B. Immune Response Inhibiting

1. Therapeutic Strategies

Methods of reducing or inhibiting an immune response in a subject are provided. Typically, the methods include administering a subject an effective amount of any one of the disclosed antibodies or antigen-binding fragments or fusion proteins, or cells primed ex vivo with these immunomodulatory agents. The immune response can be, for example, promoting or enhancing a suppressive immune response. In one embodiment, the disclosed compositions promote, enhance, or activate Tregs, increase the production of cytokines such as IL-10 from Tregs, increase the differentiation of Tregs, increase the number of Tregs, increase the ratio of Tregs within an immune cell population, or increase the survival of Tregs. to provide an immune suppressive response.

In another embodiment, the immunomodulatory agent promotes a suppressive immune response by inducing, promoting, or enhancing signal transduction through FLRT3.

The methods can be used in vivo or ex vivo as immune response-inhibiting therapeutic applications. Thus, in some embodiments, the agent, or nucleic acid encoding the agent, is administered directly to the subject. In some embodiments, the agent or nucleic acid encoding the agent, is contacted with cells (e.g., immune cells) ex vivo, and the treat cells are administered to the subject (e.g. adoptive transfer). In general, the disclosed immunomodulatory agents can be used for treating a subject having or being predisposed to any disease or disorder to which the subject's immune system mounts an overactive or inappropriate immune response. The agents can enable a less robust immune response to be possible. The disclosed compositions are useful to reduce or inhibit immune responses involving T cells.

The immunomodulatory agents utilized for reducing an immune response are typically those that increase FLRT3 expression, ligand binding, crosslinking, FLRT3 mediated signaling, or a combination thereof. For example, the agent can be an agonist of FLRT3, such as an agonist (stimulating) anti-FLRT3 antibody or antigen binding fragment thereof.

a. Inflammatory Responses

The disclosed compositions and methods can be used to treat inflammation. Generally, the agents are used to reduce or inhibit an immune response in the subject by administering to the subject an amount of an immunomodulatory agent that modulates FLRT3 expression, ligand binding, crosslinking, suppressive signaling, or a combination thereof. The method can reduce or more symptoms of the inflammation. In inflammation can be acute, chronic, or persistent inflammation.

In some embodiments, the immunomodulatory agents slow down the immune system. For example, agent can be used to control hyper-inflammatory response causing damage healthy tissues. Accordingly, in some embodiments, the agents are administered to a subject undergoing a hyper-inflammatory response. In such cases, controlling excessive immune responses can be beneficial to the subject.

A method for treating an inflammatory response in a subject in need thereof comprising administering an effective amount of any one of the antibodies or antigen-binding fragments or fusion proteins to treat the inflammatory response.

b. Inflammatory and Autoimmune Diseases/Disorders

Agents that modulate FLRT3 expression, ligand binding, crosslinking, suppressive signaling, or a combination thereof can also be used to treat inflammatory or autoimmune diseases and disorders. Representative inflammatory or autoimmune diseases/disorders include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, Graft versus host disease, grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments the inflammation or autoimmune disease is caused by a pathogen or is the result of an infection.

One embodiment provides a method of treating inflammation in a subject in need thereof comprising administering an effective amount of any one of the disclosed antibodies or antigen-binding fragments or fusion proteins to treat the inflammation.

A method for treating an autoimmune disease in a subject in need thereof comprising administering an effective amount of any one of the disclosed antibodies or antigen-binding fragments or fusion proteins to treat the autoimmune disease.

VI. Combination Therapies

The disclosed immunomodulatory agents can be administered to a subject in need thereof alone or in combination with one or more additional therapeutic agents. In some embodiments, the immunomodulatory agent and the additional therapeutic agent are administered separately, but simultaneously. The immunomodulatory agent and the additional therapeutic agent can also be administered as part of the same composition. In other embodiments, the immunomodulatory agent and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6, 7, 14, 21, 28, 35, or 48 days prior to a first administration of second agent. The immunomodulatory agent can be the first or the second therapeutic agent.

The immunomodulatory agent and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutic, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Increasing Immune Responses

1. Antimicrobials

For example, FLRT3 immunomodulatory agents can be used in a preventive or prophylactic role in the treatment and prevention of disease as discussed above, and also in the context of severe trauma injuries like major burn, open bone fracture, accidental amputation or other wounds. Therefore, the FLRT3 immunomodulatory agents can be administered to the subject in combination with an antimicrobial such as an antibiotic, an antifungal, an antiviral, an antiparasitic, or essential oil.

In some embodiments, the subject is administered the FLRT3 immunomodulatory agent and/or the antimicrobial at time of admission to the hospital to prevent further bacterial, fungal or viral complications. The antibiotic can target pathogens and the FLRT3 immunomodulatory agent can stimulate the immune system to provide an enhanced response to treat or prevent further infection or disease.

2. Chemotherapeutic Agents

The FLRT3 immunomodulatory agents can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ (2) and combinations thereof.

3. Other Immunomodulators a. PD-1 Antagonists

In some embodiments, FLRT3 immunomodulatory agents are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A,* 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., *Clin. Cancer Res.,* 14:3044-3051 (2008).

Exemplary anti-B7-H1 (also referred to as anti-PD-L1) antibodies include, but are not limited to, those described in the following U.S. Pat. Nos. 8,383,796, 9,102,725, 9,273,135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147 all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity, Vol.* 27, pp. 111-122, (2007)). Such fragments also include the soluble ECD portion of the PD-1 protein that includes mutations, such as the A99L mutation, that increases binding to the natural ligands (Molnar et al., *PNAS,* 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal,* 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.,* 277:7363-7368 (2002). Such small organics could be administered alone or together with an anti-CTLA4 antibody to reduce inhibitory signal transduction of T cells.

4. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide, and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu XQ, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S—(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled “Cyclophosphamide analogs useful as anti-tumor agents” which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev. Immunol. 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. bevacizumab (Avastin®), VEGF-Trap) (see, for example, Li et al., Vascular endothelial growth factor blockade reduces intratumoral regulatory T cells and enhances the efficacy of a GM-CSF-secreting cancer immunotherapy. Clin *Cancer Res.* 2006 Nov. 15; 12(22):6808-16), anthracyclines, oxaliplatin, doxorubicin, TLR4 antagonists, and IL-18 antagonists.

B. Reducing Immune Responses

1. Immunosuppressive Agents

In some embodiments, the immune response, or inflammatory/autoimmune disease/disorder is treated by administering to the subject a FLRT3 immunomodulatory agent and a second agent that is an immune suppressant. Immunosuppressive agents include, but are not limited to antibodies against other lymphocyte surface markers (e.g., CD40, alpha-4 integrin) or against cytokines, fusion proteins (e.g., CTLA-4-Ig (Orencia®), TNFR-Ig (Enbrel®)), TNF-α blockers such as etanercept (Enbrel®), infliximab (Remicade®), certolizumab (Cimzia®), and adalimumab (Humira®), cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

The therapeutic agent can be a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the therapeutic agent is a CTLA-4-Ig fusion protein known as belatacept. Belatacept contains two amino acid substitutions (L104E and A29Y) that markedly increase its avidity to CD86 in vivo. In another embodiment, the therapeutic agent is Maxy-4.

In another embodiment, the therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. Cyclophosphamide (CTX) is the primary drug used for diffuse proliferative glomerulonephritis in patients with renal lupus.

The therapeutic agent can be administered in an effective amount to reduce the blood or serum levels of anti-double stranded DNA (anti-ds DNA) auto antibodies and/or to reduce proteinuria in a patient in need thereof.

In another embodiment, the therapeutic agent increases the amount of adenosine in the serum, see for example, WO 08/147482. For example, the second therapeutic agent can be CD73-Ig, recombinant CD73, or another agent (e.g., a cytokine or monoclonal antibody or small molecule) that increases the expression of CD73, see for example WO 04/084933. In another embodiment the therapeutic agent is Interferon-beta.

The therapeutic agent can be a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-1β, TNF-α, TGF-beta, IFN-γ, IL-18 IL-17, IL-6, IL-23, IL-22, IL-21, and MMPs. In another embodiment, the therapeutic agent is a small molecule that interacts with Tregs, enhances Treg activity, promotes or enhances IL-10 secretion by Tregs, increases the number of Tregs, increases the suppressive capacity of Tregs, or combinations thereof.

In some embodiments, the composition increases Treg activity or production. Exemplary Treg enhancing agents include but are not limited to glucocorticoid fluticasone, salmeteroal, antibodies to IL-12, IFN-γ, and IL-4; vitamin D3, and dexamethasone, and combinations thereof.

In some embodiments, the therapeutic agent is an antibody, for example, a functions blocking antibody against a proinflammatory molecule such as IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. In some embodiments, the language "rapamycin compound" as used herein does not include FK506-like compounds.

2. Anti-inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

VII. Kits

The disclosed FLRT3 immunomodulatory agents can be packaged in a hermetically sealed container, such as an ampoule or sachet, indicating the quantity. The agent can be supplied as a dry sterilized lyophilized powder or water free concentrate in a hermetically sealed container and can be reconstituted, e.g., with water or saline to the appropriate concentration for administration to a subject. For example, the agent can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized agent can be stored at between 2 and 8° C. in their original container and are typically administered within 12 hours, or within 6 hours, or within 5 hours, or within 3 hours, or within 1 hour after being reconstituted.

In an alternative embodiment, agent can be supplied in liquid form in a hermetically sealed container indicating the quantity and concentration. In some embodiments, the liquid form of the agent supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the agent.

Pharmaceutical packs and kits including one or more containers filled with agent are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more FLRT3 immunomodulatory agents. In particular embodiments, a kit also includes one or more other prophylactic or therapeutic agents useful for the treatment of cancer, in one or more containers. In other embodiments, a kit also includes one or more anti-inflammatory agents useful for the treatment inflammatory and autoimmune diseases, in one or more containers.

EXAMPLES

Example 1: FLRT3's Immunosuppression In Vitro is Comparable to PD-L1

Figure 1B:
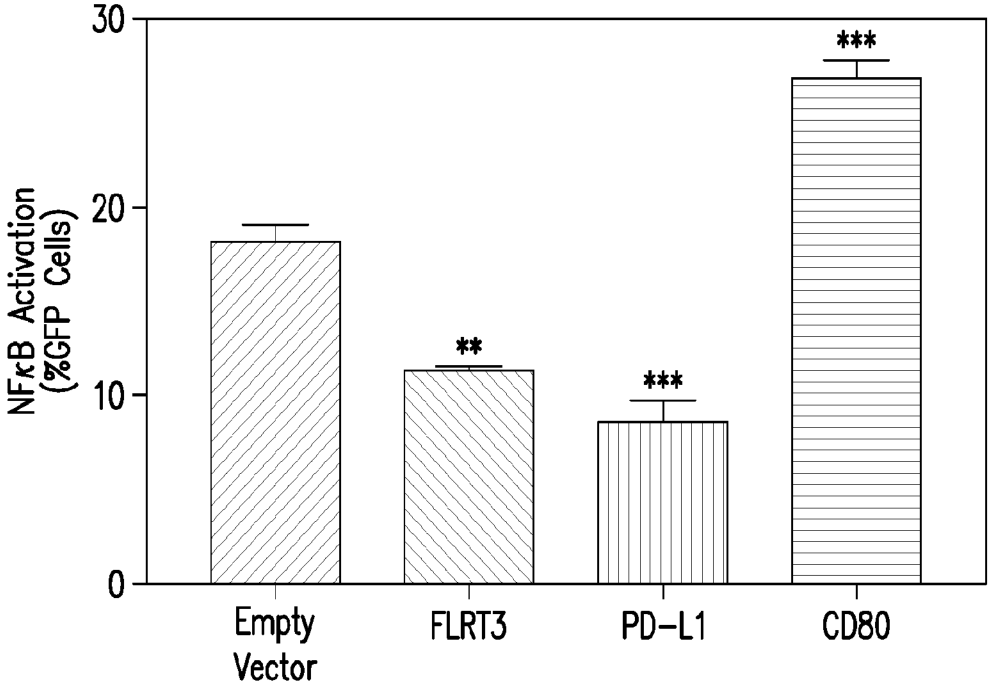
Figure 1C:
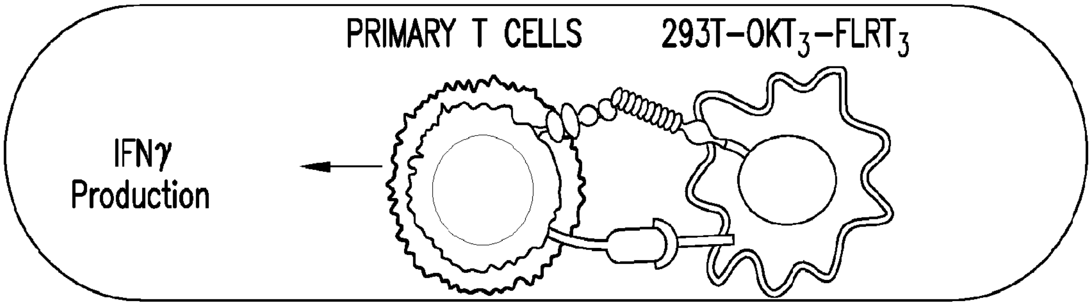
Figure 1D:
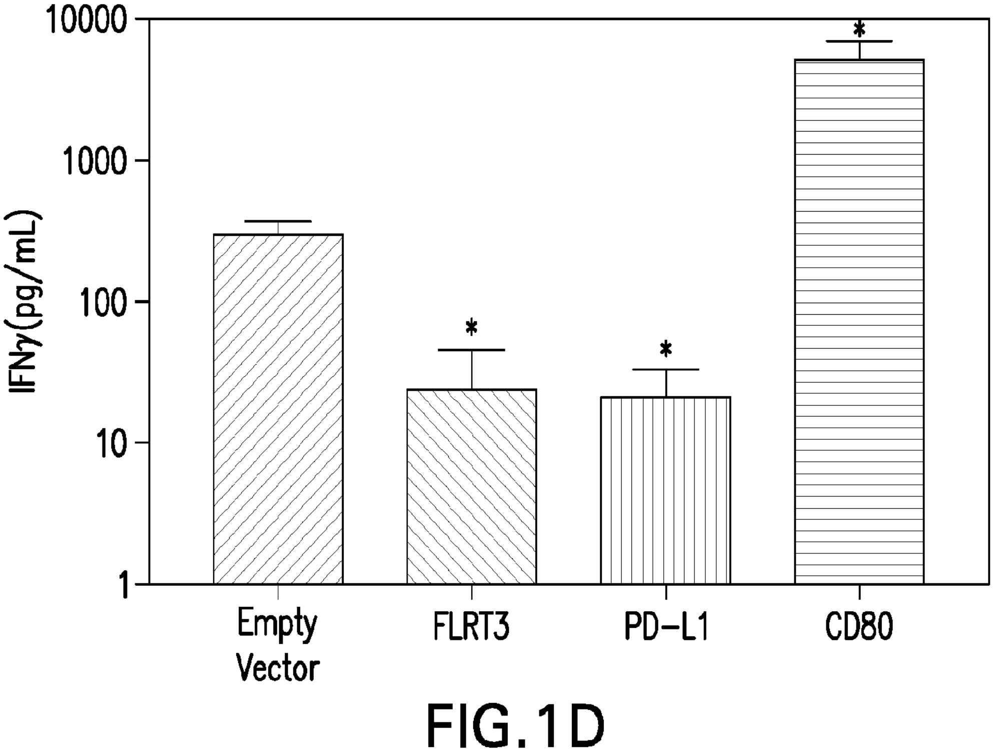

To determine if FLRT3 is as immunosuppressive as PD-L1, cell-based assays were performed to determine NF-κB activation or IFN-g secretion in the presence of cells expressing human CD3 antibody single chain variable fragment (OKT3) and FLRT3, PD-L1, empty vector negative control or CD80 positive control (FIGS. 1A and C). FLRT3 expression results in a comparable decrease in NF-κB-GFP-reporter fluorescence compared to PD-L1 in Jurkat T cells expressing the FLRT3 binding partner UNC5B (FIG. 1B). FLRT3 expression also results in a comparable decrease in IFNγ production compared to PD-L1 when using purified primary healthy donor T cells (FIG. 1D).

Example 2: FLRT3 is Expressed in Mouse and Human Cancers

Figure 2A:
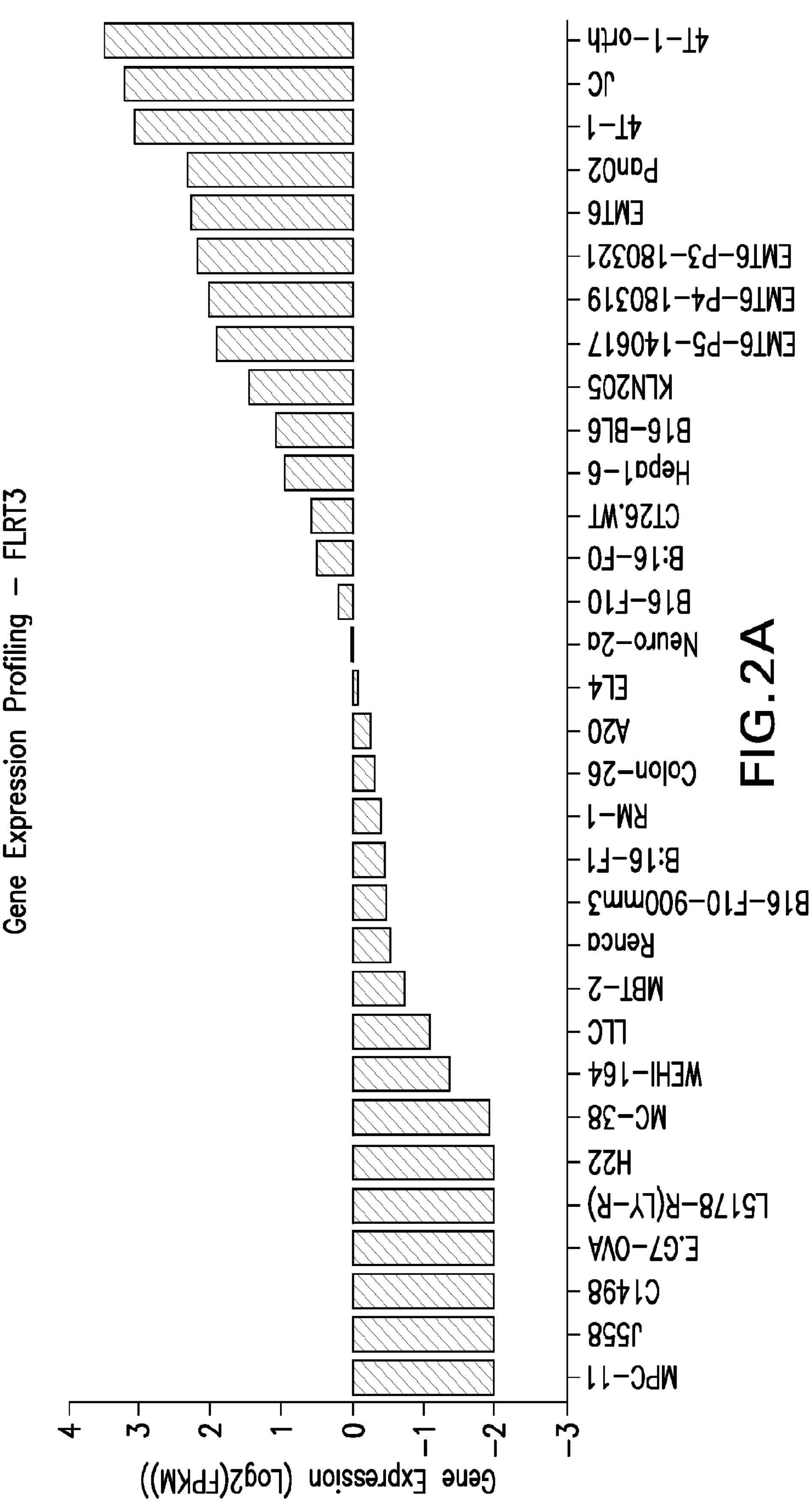
FIGS. 2A-2B shows FLRT3 is expressed in mouse and human cancers.
Figure 2B:
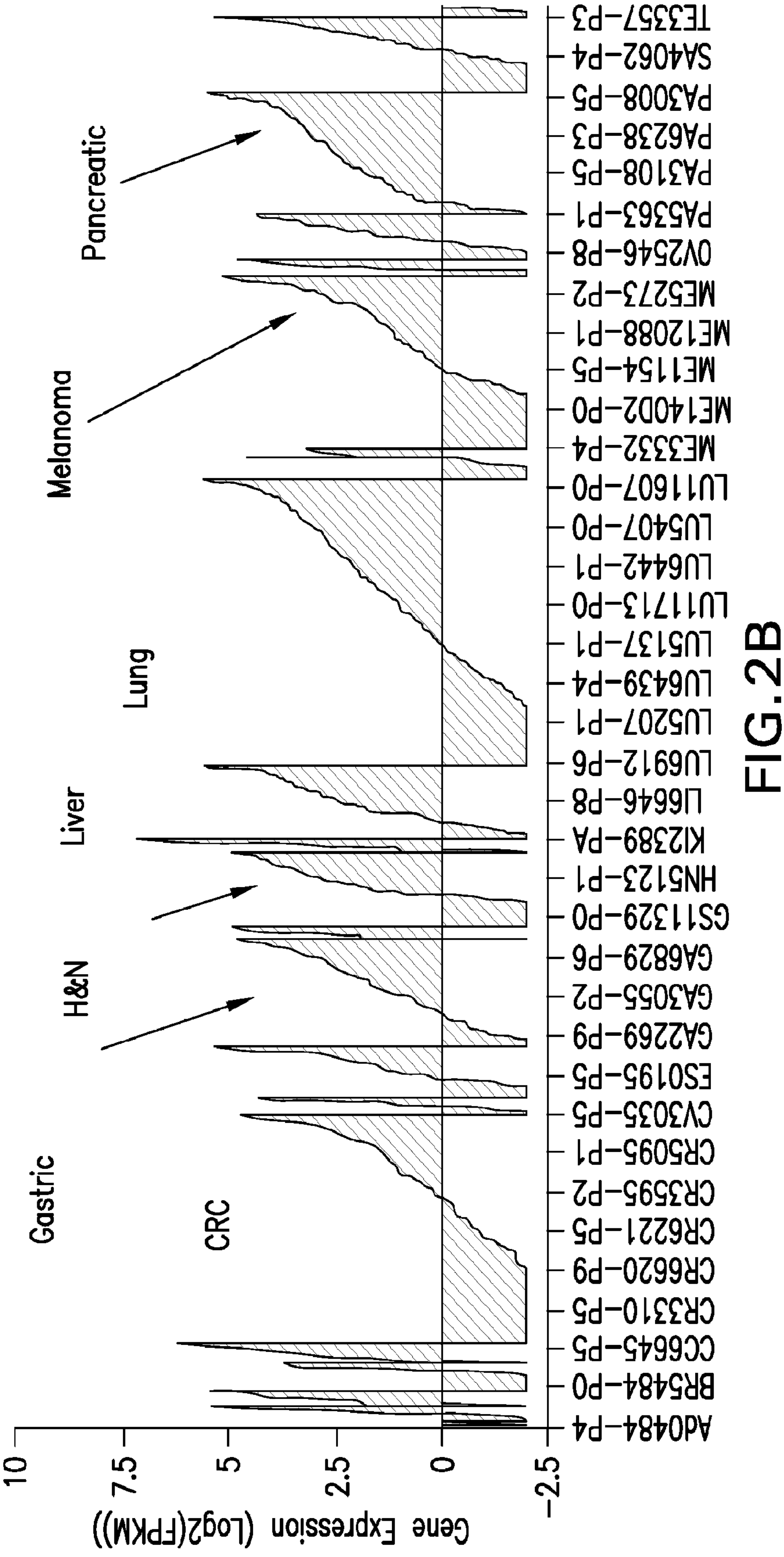
Figure 3:
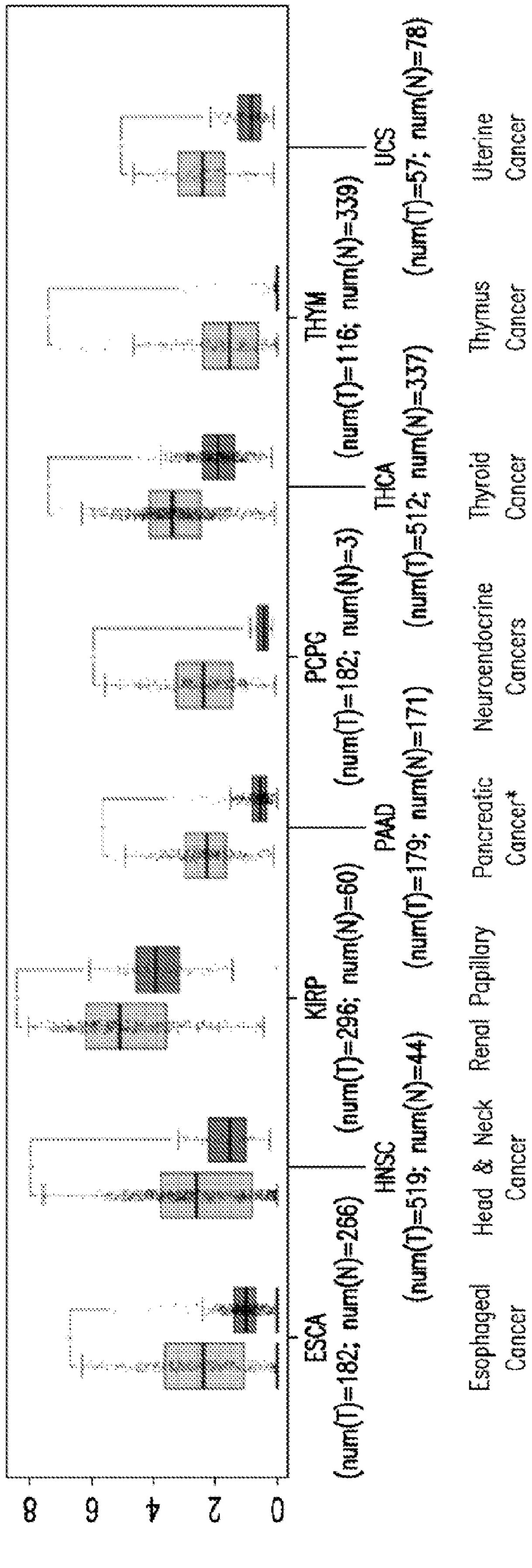
FIG. 3 shows FLRT3 expression is significantly increased in several human cancer types.
Figure 4A:
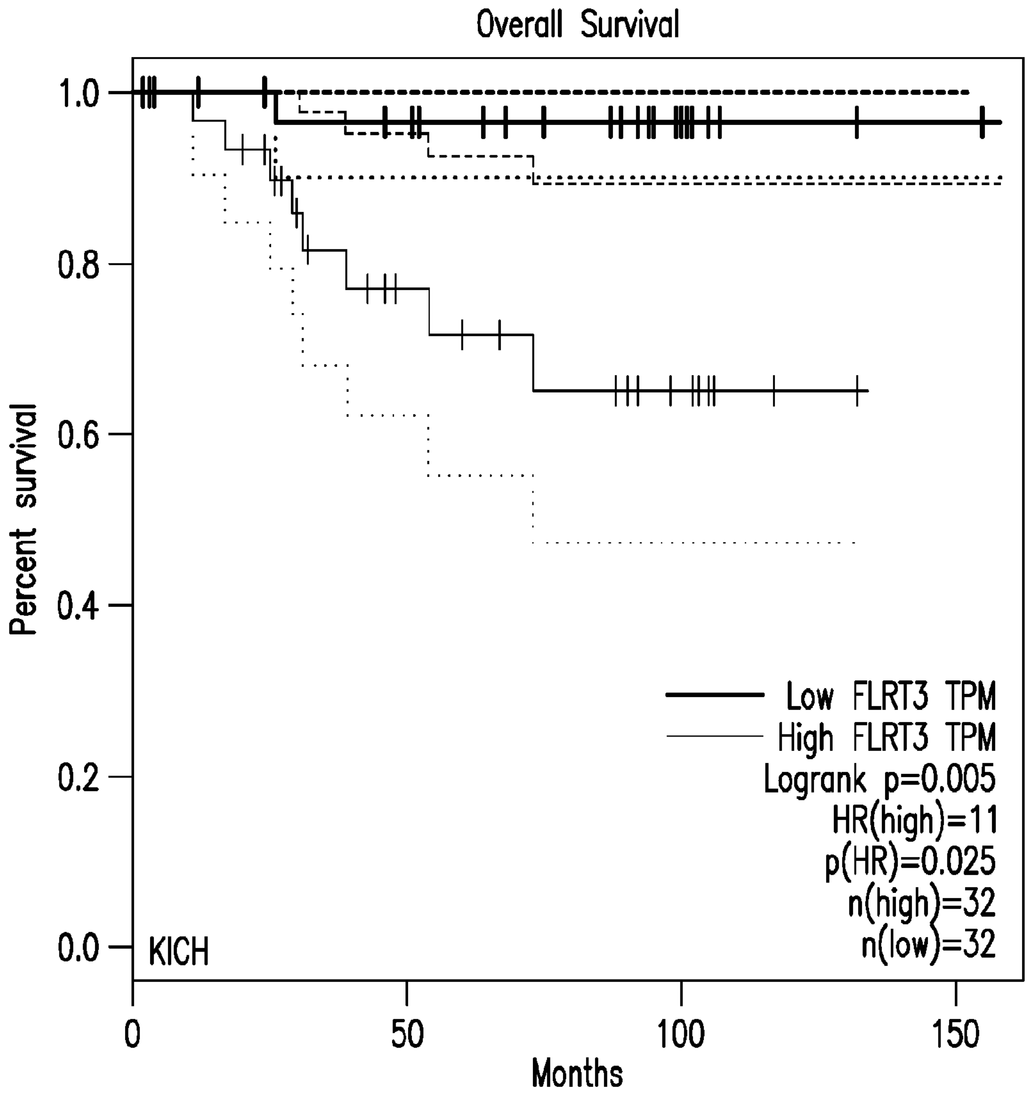
FIGS. 4A-4C show FLRT3 high expression correlates with reduced overall survival in kidney (A4), pancreatic (4B) and lung (4C) cancers.
Figure 4B:
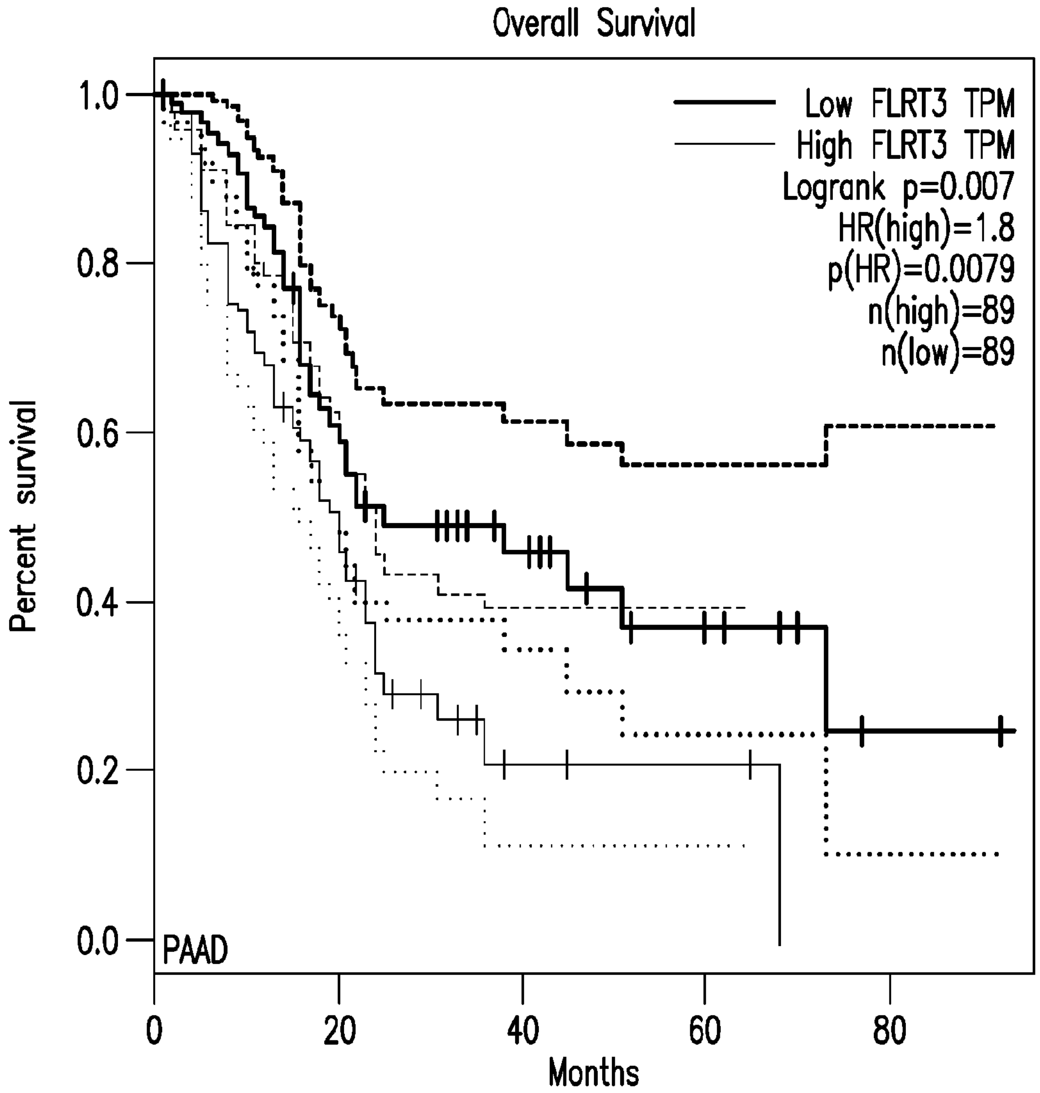
Figure 4C:
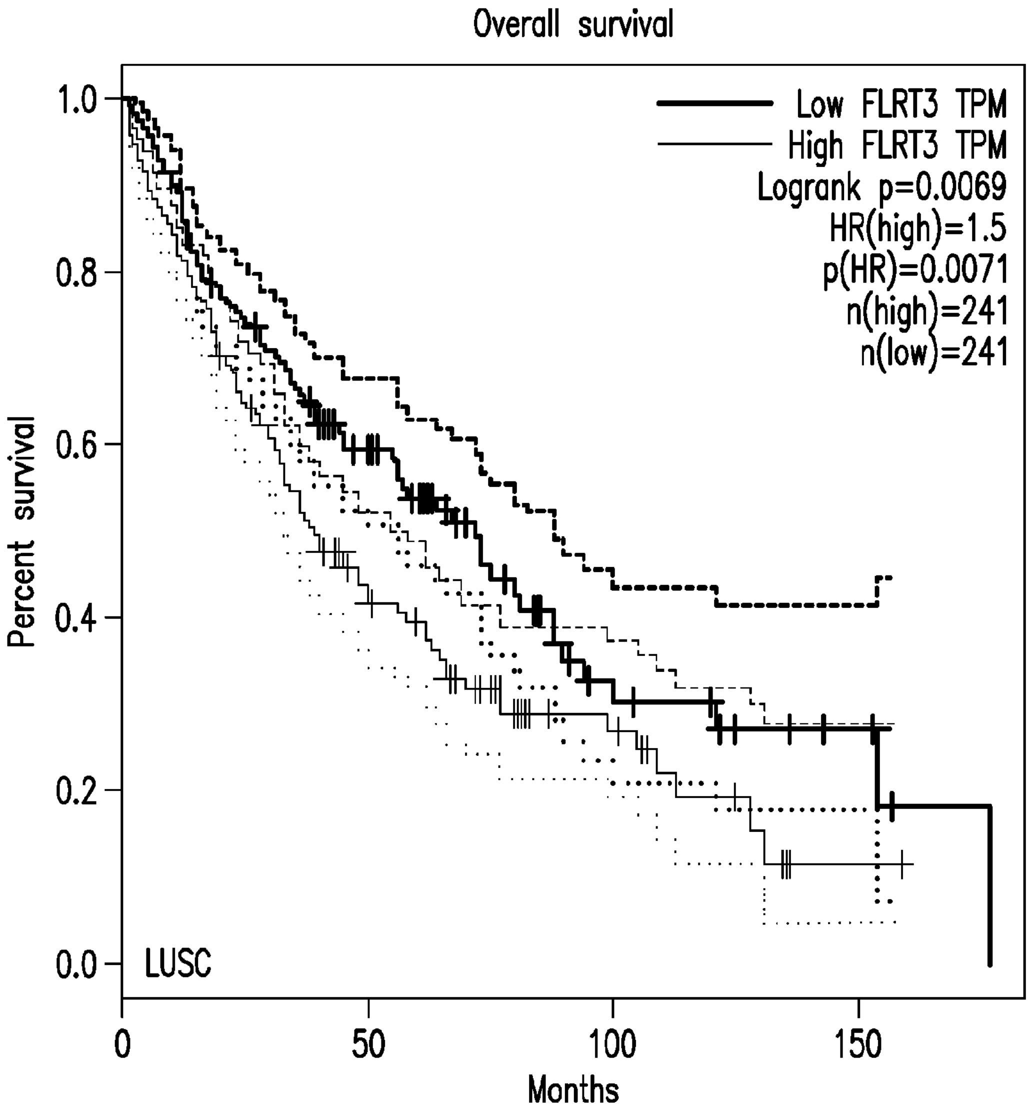
Figure 5A:
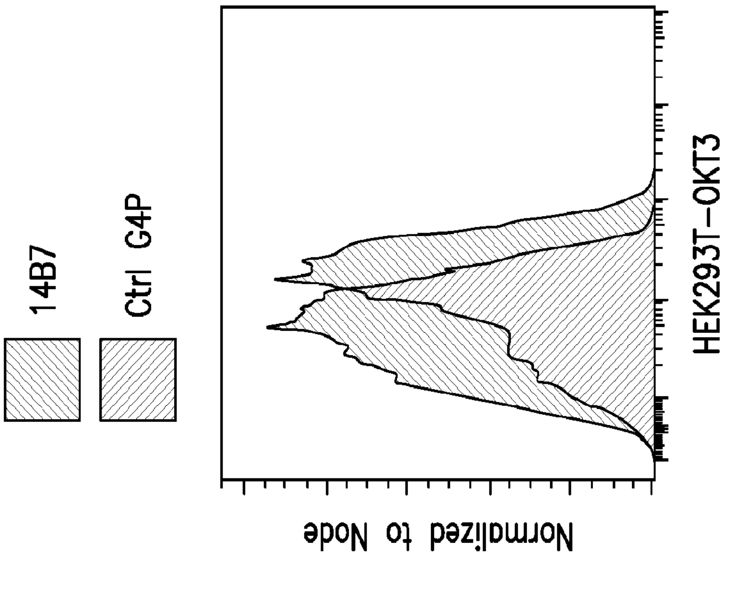
FIGS. 5A-5I plots showing FLRT3 expression analyses on cell lines using FLRT3 (monoclonal antibody) mAb 14B7.
Figure 5B:
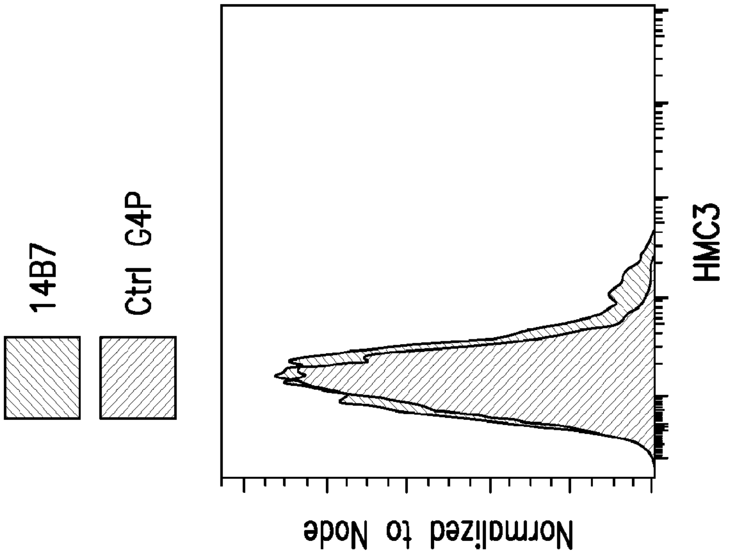
Figure 5C:
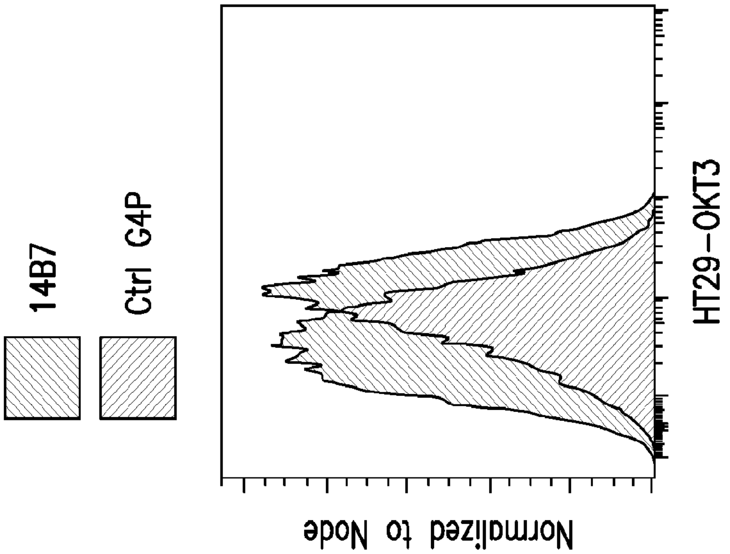
Figure 5F:
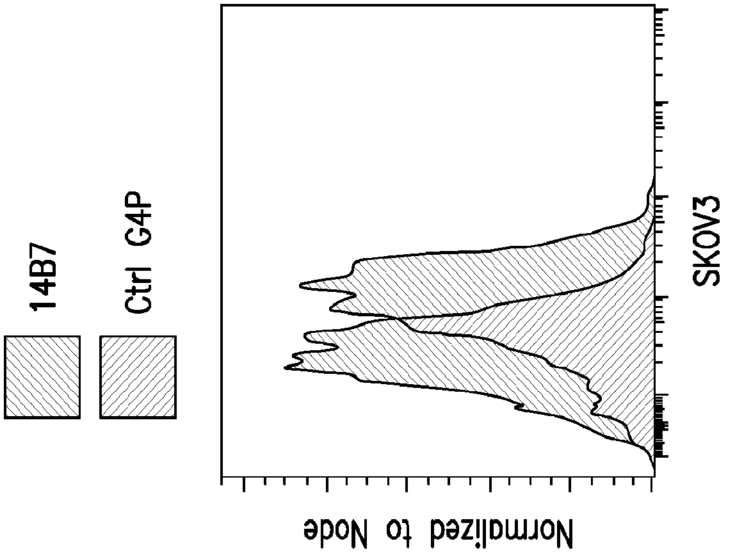
Figure 5E:
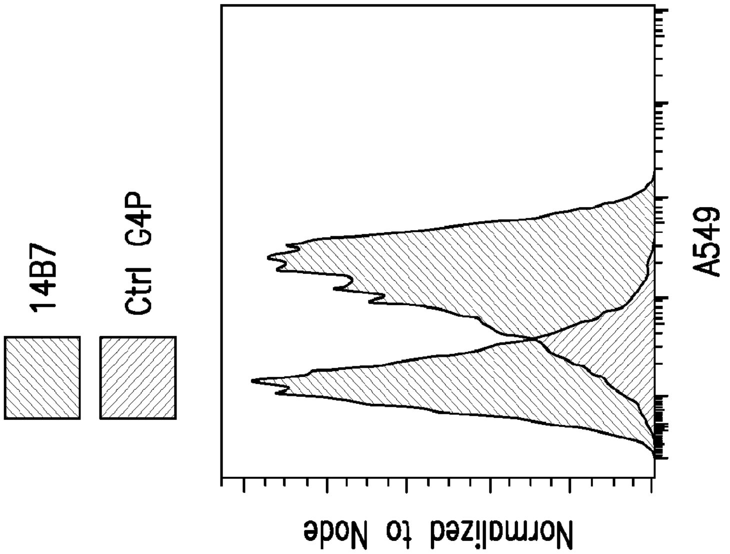
Figure 5D:
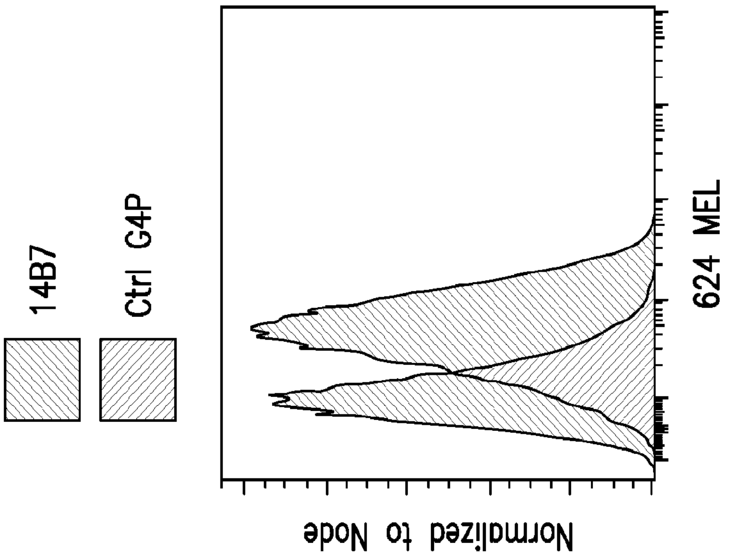
Figure 5G:
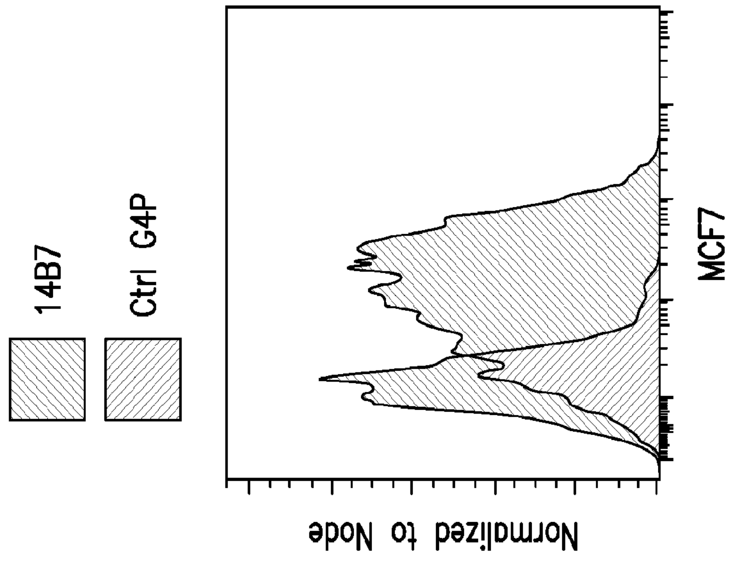
Figure 5H:
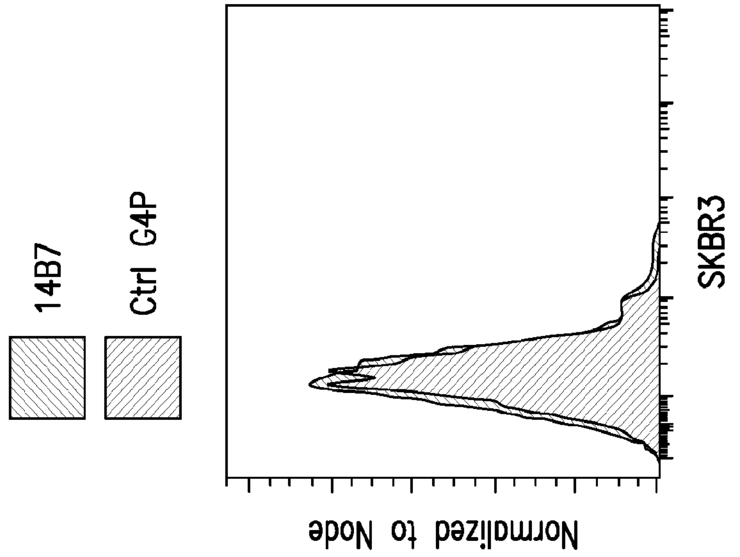
Figure 5I:
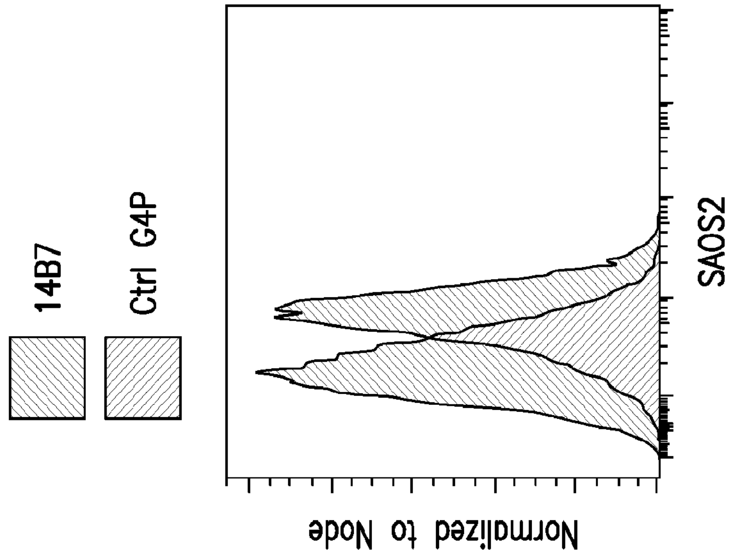

FLRT3 was shown to be expressed in mouse and human cancers. FIG. 2 shows FLRT3 RNA sequence data from mouse cancer passages in immunodeficient mice. The top mouse tumors expressing FLRT3 were breast (4T1, TC, EMT6) and pancreatic (Pan02) tumors (FIG. 2A), while the top human tumors expressing FLRT3 were pancreatic, gastric, H&N, liver, lung, and several others tumors (FIG. 2B). FIGS. 3 and 4 show FLRT3 RNA expression data from the human cancer patients. Significantly ($p<0.01$) increased expression of FLRT3 was also shown in esophageal carcinoma, head and neck squamous, kidney renal papillary carcinoma, pancreatic adenocarcinoma, pheochromocytoma, thyroid carcinoma, thymoma, and others FIG. 3). Overall survival studies showed that high expression of FLRT3 Correlates with reduced overall survival in kidney chromophobe, pancreatic adedocarcinoma and lung squamous cell carcinoma (FIG. 4A-4C). Furthermore, cancer cell lines stained with the 14B7 antibody were assessed for expression of FLRT3. A human kidney and colon cell lines engineered to stably overexpress membrane OKT3 (anti-CD3 monoclonal antibody) scFV sequence, HEK293T-OKT3 (FIG. 5A) and HT29-OKT3 (FIG. 5C) respectively, were shown to express low levels of FLRT3, whereas there was no expression in microglial HMC3 cells (FIG. 5B). A549 (lung, FIG. 5E), MCF7 (breast, FIG. 5G), SKOV3 (ovarian, FIG. 5F) were shown to have relatively higher expression of FLRT3. This data is in line with the RNA database.

Example 3: FLRT3 Overexpression Increases Tumor Growth in NSG Mouse Model

Tumor volumes were measured every two to three days post inoculation with empty vector (EV) or FLRT3-HT29-

Figure 6A:
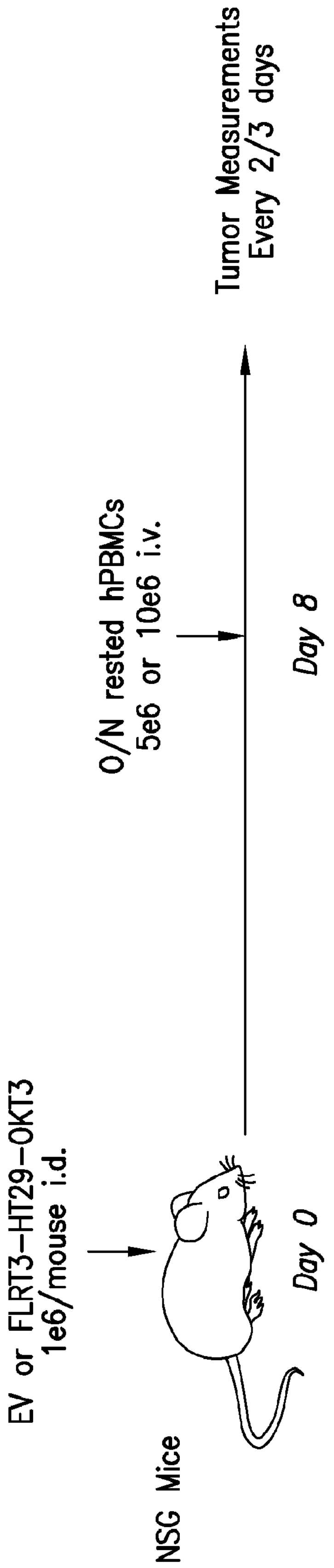
FIGS. 6A-6C show FLRT3 overexpression increased tumor growth in the NSG mouse model.
Figure 6B:
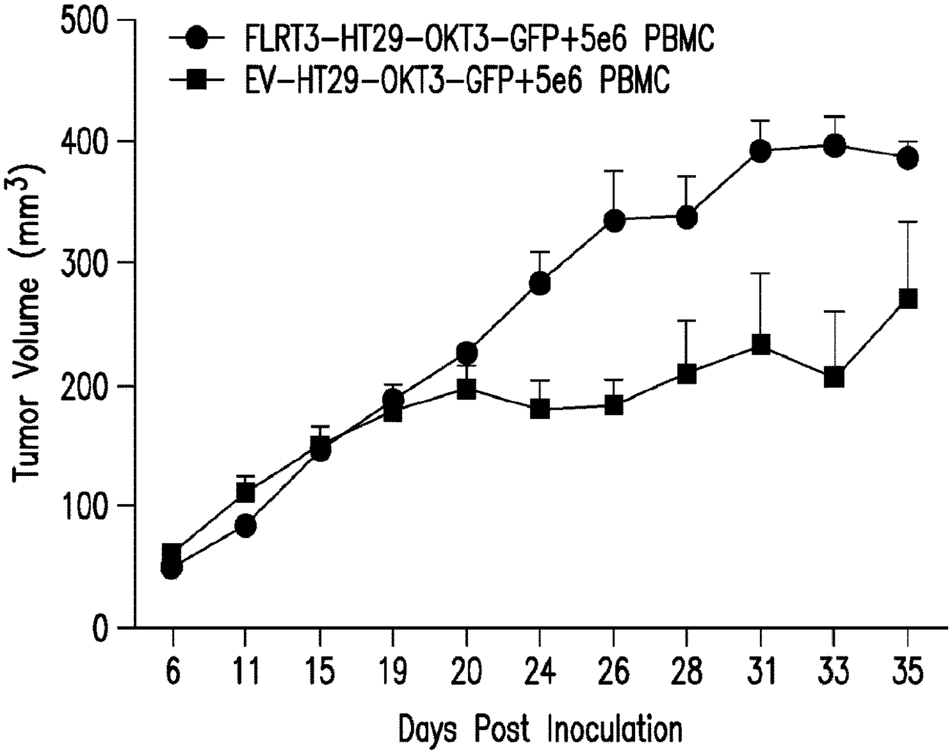
Figure 6C:
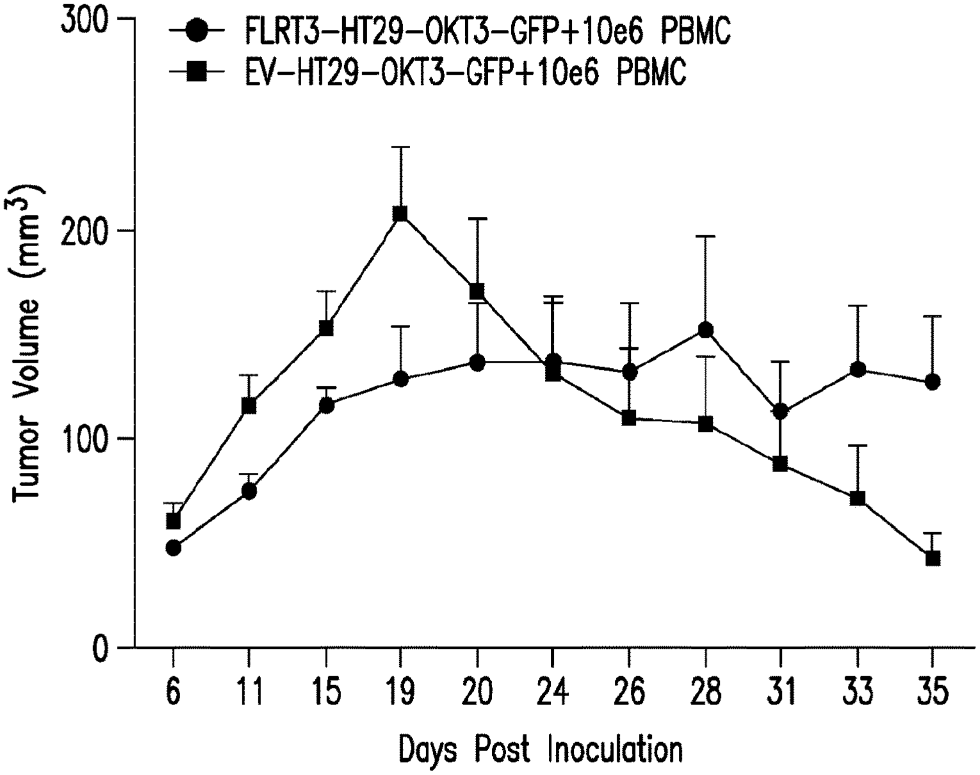

OKT3 in immunodeficient NSG (NOD scid gamma) mice to determine the effect of FLRT3 overexpression on human PBMCs (FIG. 6A). In the HT29-OKT3+ NSG model, FLRT3 augments in vivo tumor growth in the presence of 5e6 (FIG. 6B) and 10e6 (FIG. 6C) human peripheral blood mononuclear cells (PBMC). The strong immune response seen in the 10e6 PBMCs group partially masked the inhibitory effects of FLRT3.

Figure 7A:
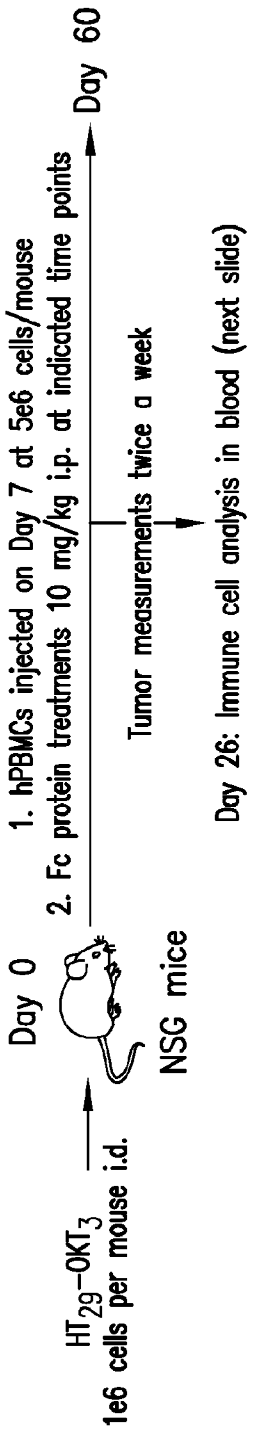
FIGS. 7A-7B show soluble FLRT3 protects against GvHD.
Figure 7B:
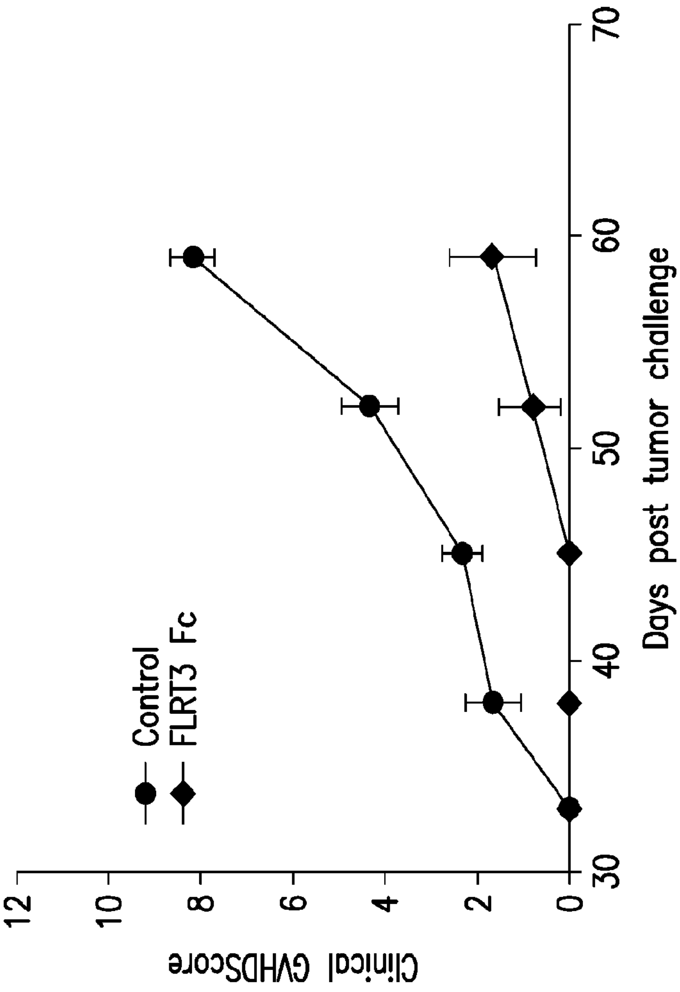
Figure 8A:
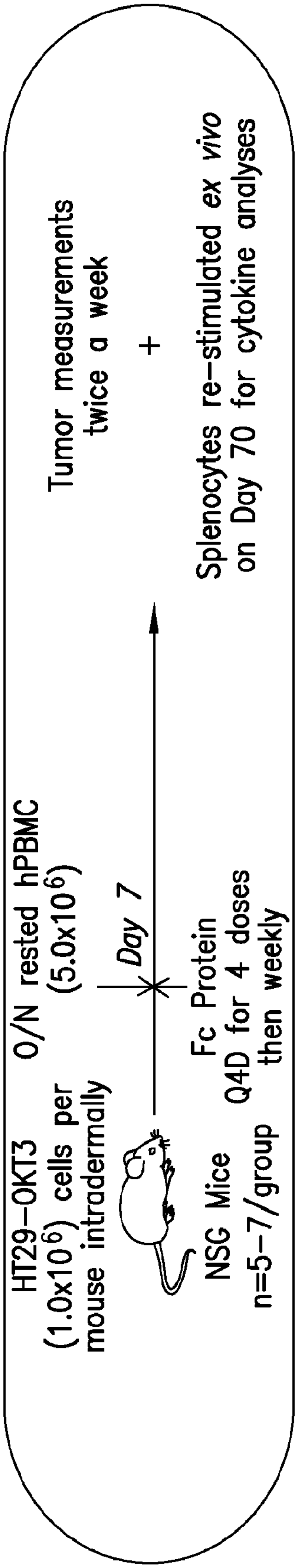
FIGS. 8A-8F show soluble FLRT3 increased tumor growth in humanized models and inhibits immune function.
Figure 8B:
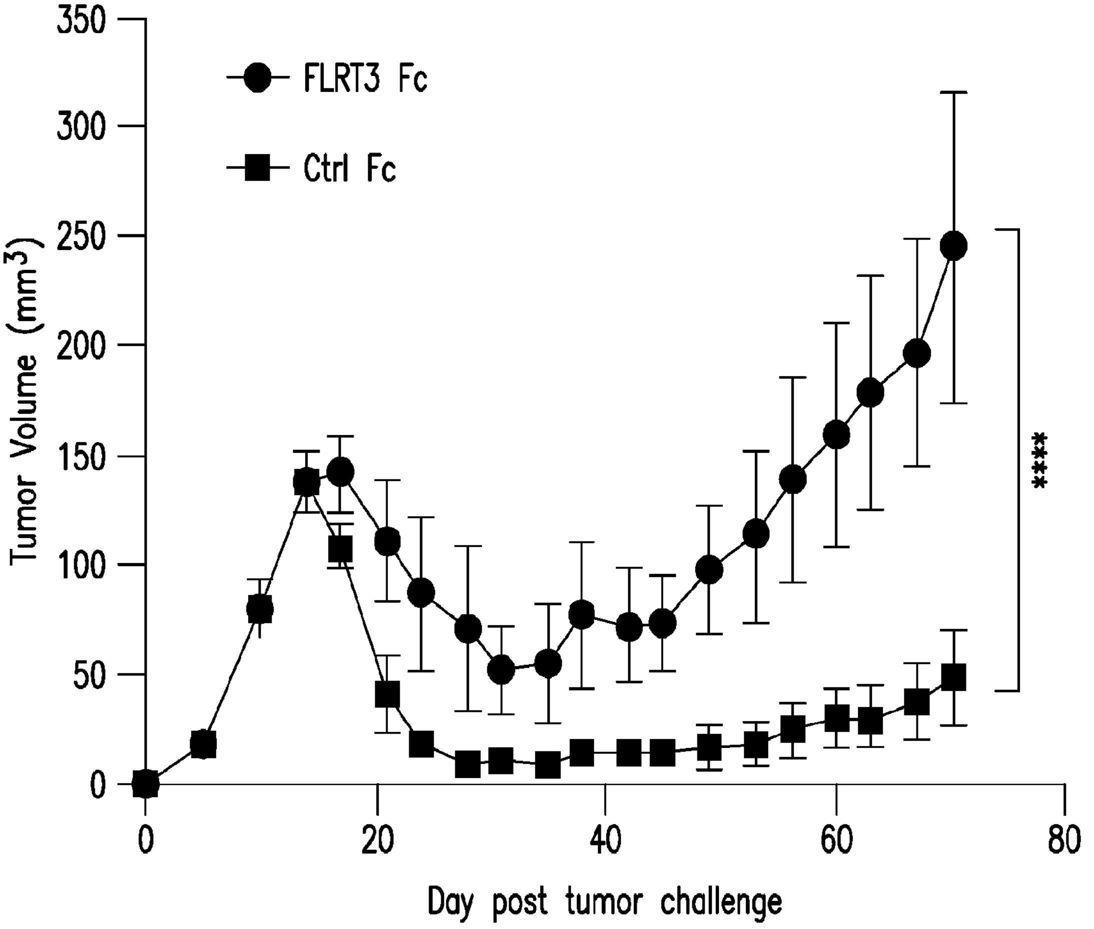
Figure 8E:
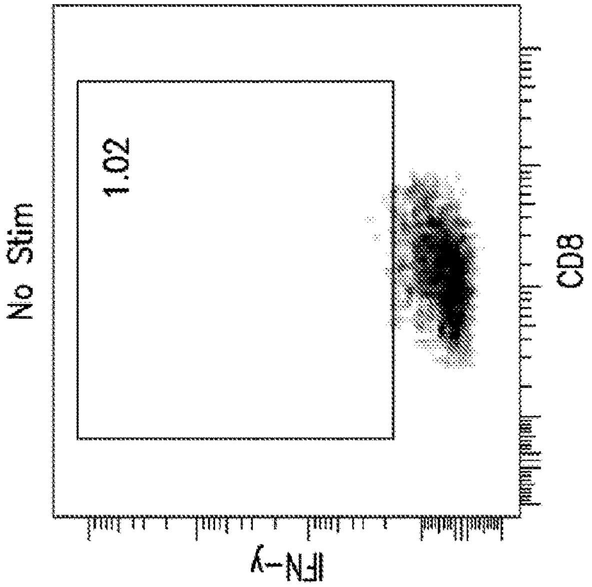
Figure 8D:
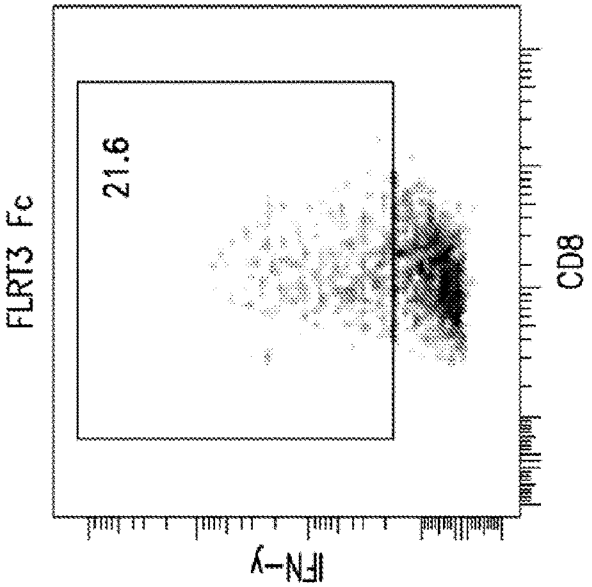
Figure 8C:
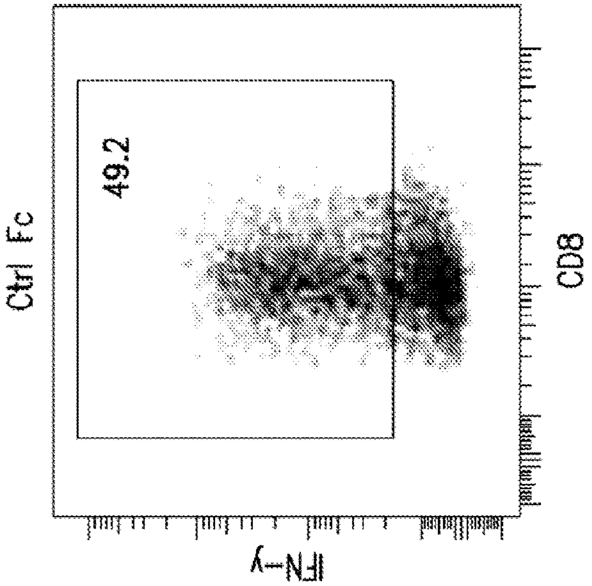
Figure 8F:
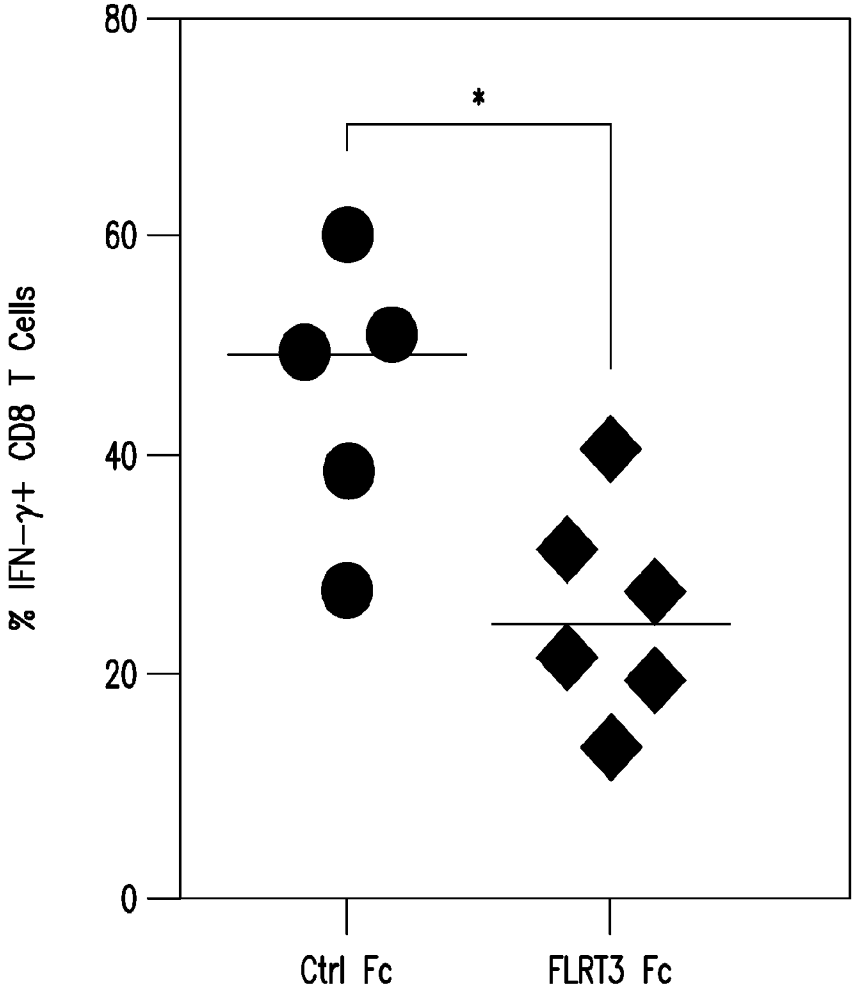
Figure 8I:
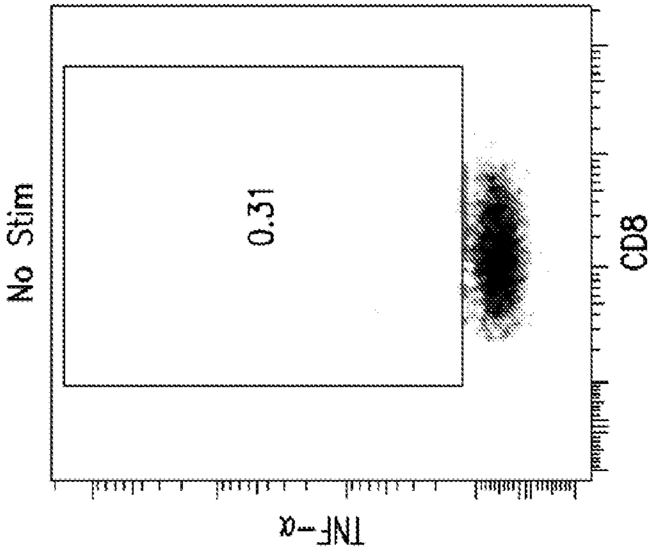
Figure 8H:
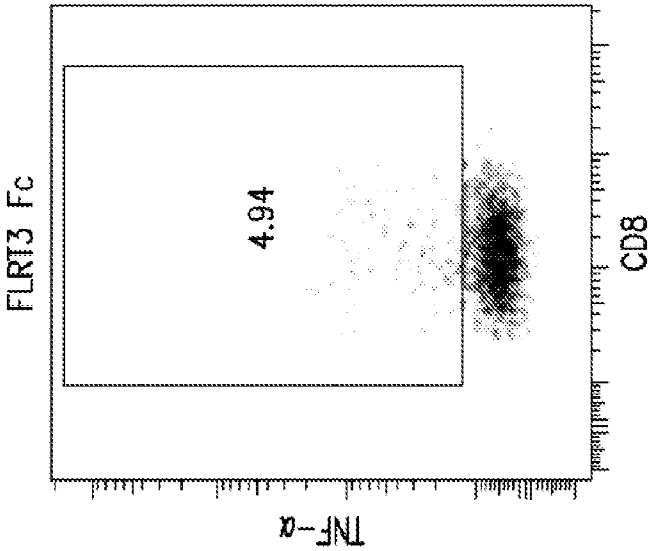
Figure 8G:
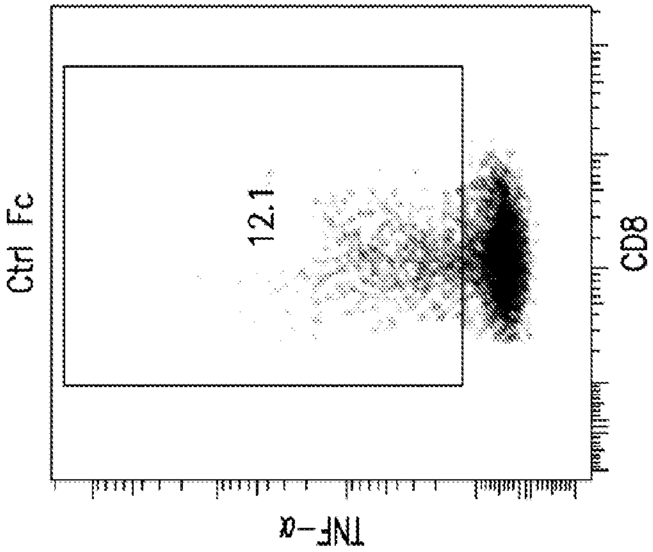
Figure 8J:
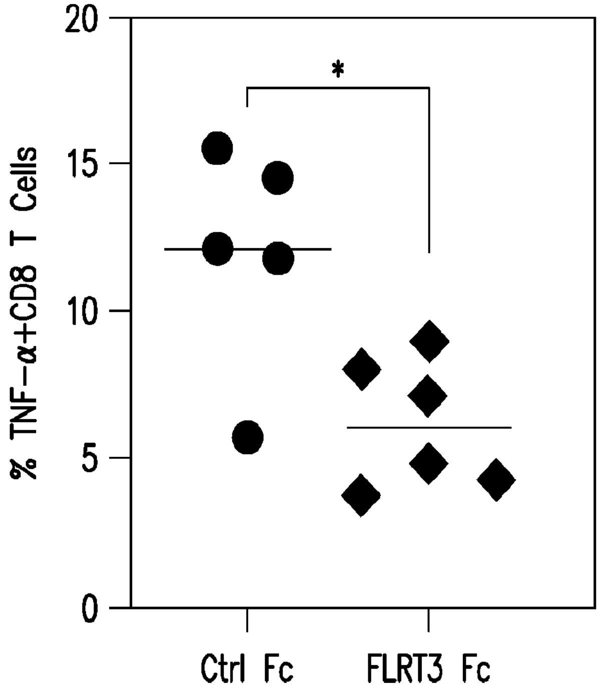
Figure 8K:
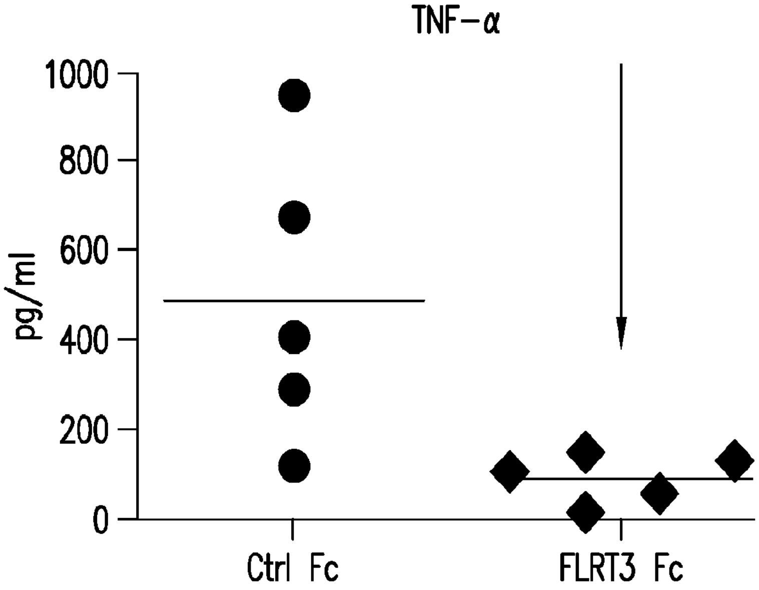
FIG. 8K-8P are bar graphs showing the effects of FLRT3 Fc on cytokine production.
Figures 8L, 8M, 8N:
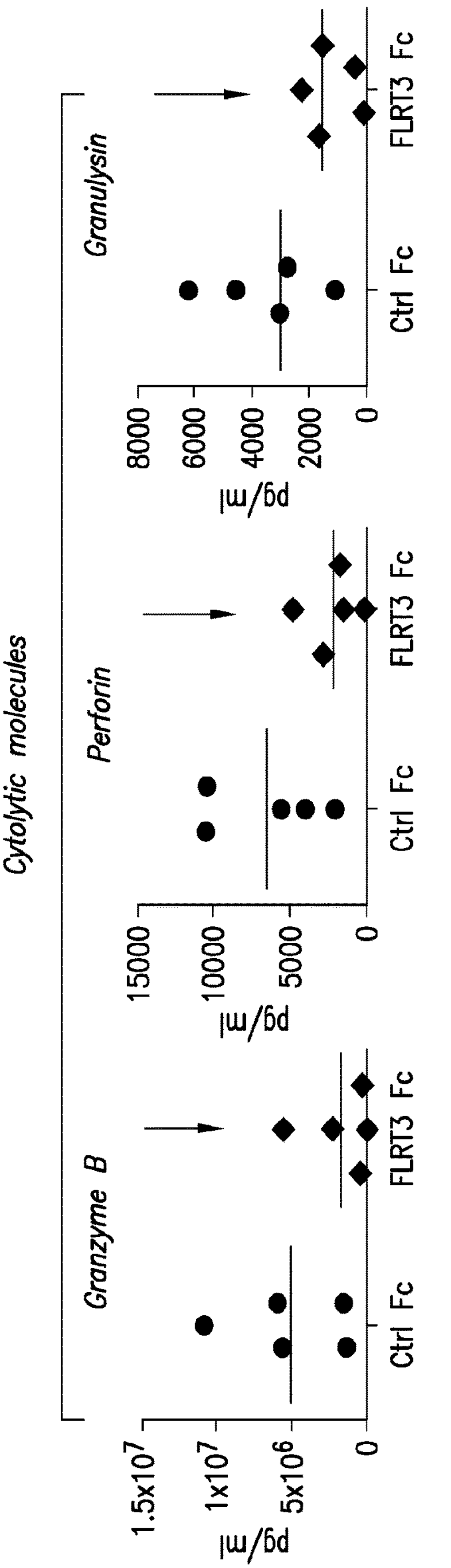
Figure 8O:
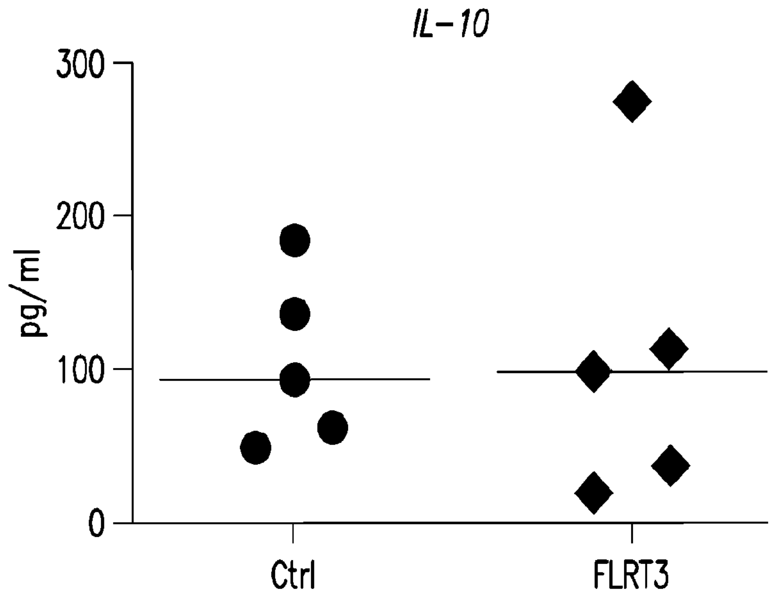
Figure 8P:
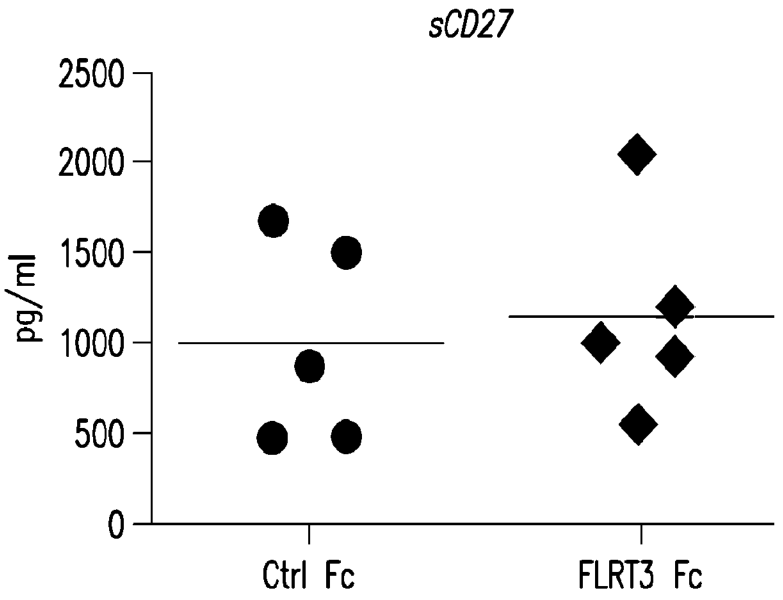
Figure 8Q:
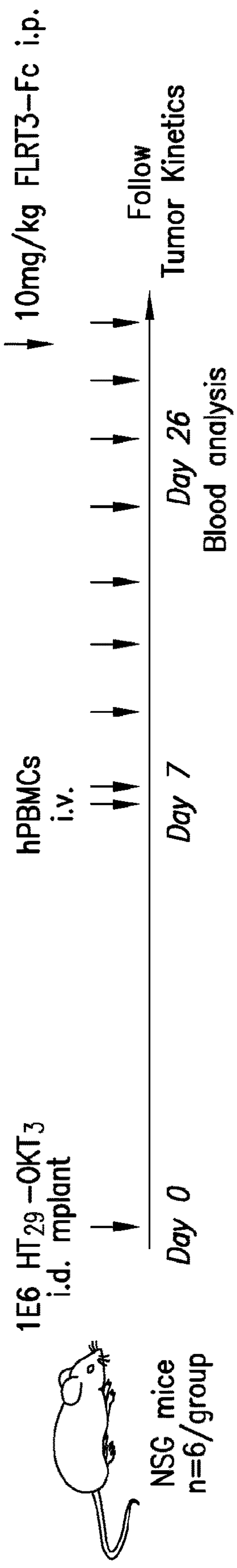
FIG. 8Q is an illustration of the protocol used to treat mice to determine tumor measurements.
Figure 8R:
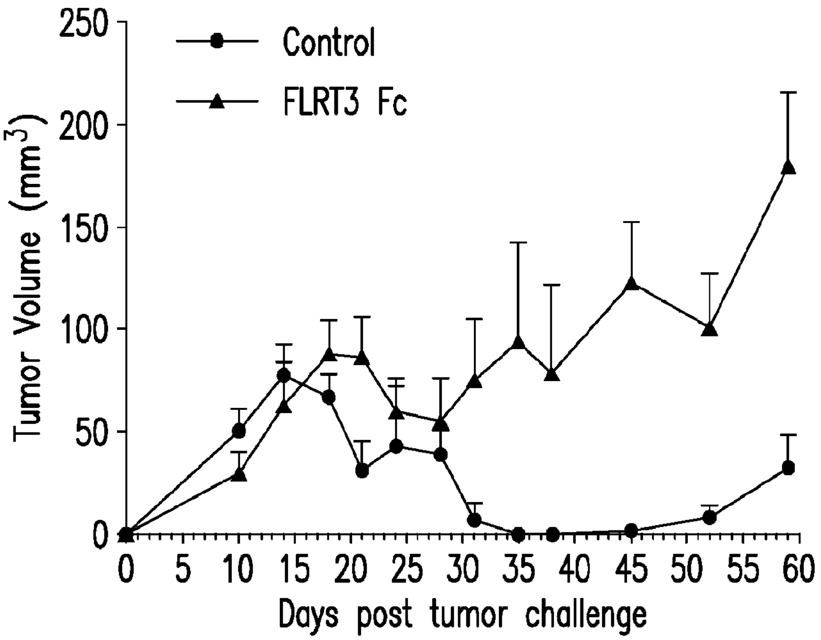
FIG. 8R is a line graph showing the effect of soluble FLRT3 on HT29-OKT3 tumor growth.
Figure 8S:
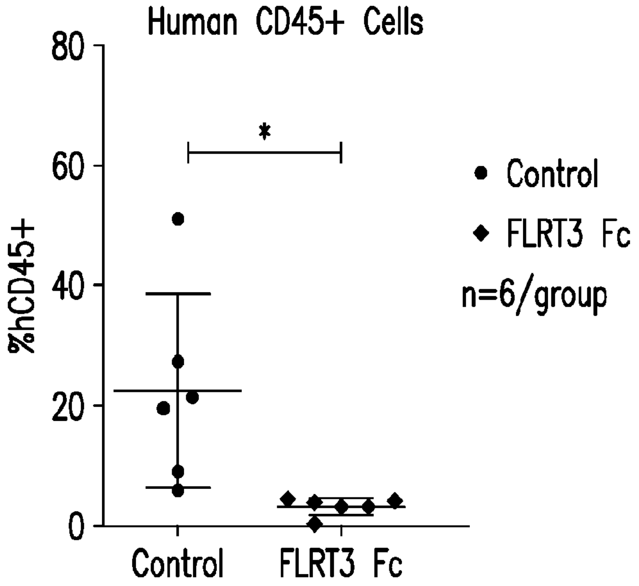
FIGS. 8S-8T are dot plots showing the effect of FLRT3 Fc on human CD45+ cells (8S) and T cell subsets (8T).
Figure 8T:
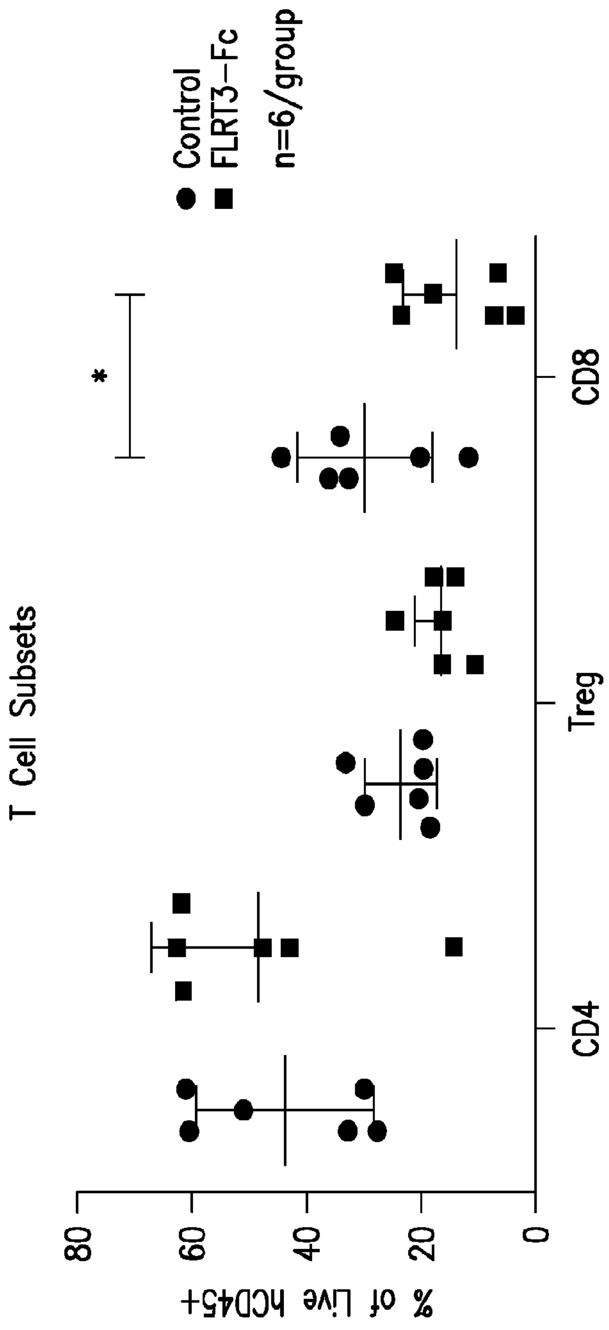

Example 4: Soluble FLRT3 Increased Tumor Growth in Humanized Models and Inhibits Immune Function Mice inoculated with HT29-OKT3 were treated with hPBMCs and soluble FLRT3 (FLRT3-Fc) and tumor volume was measured twice a week for up to 60 days (FIG. 7A). Clinical graft versus host disease (GvHD) scores showed that soluble FLRT3 protects the NSG mice against GvHD (FIG. 7B). Treatment of HT-29 colorectal cancer tumor bearing mice with soluble FLRT3 Fc fusion protein (FIG. 8A) resulted in increased tumor growth (FIG. 8B). Immune cell analysis showed that soluble FLRT3 Fc fusion protein caused immune suppression of IFN-g and TNF production in CD8 T cells by intracellular cytokine staining analysis (FIG. 8C-8J). Analysis of serum from mice also demonstrated inhibition of cytolytic cytokines including TNF, Granzyme B, Perforin and Granulysin (FIG. 8K-8P). In a similar repeat study of the HT-29 colorectal tumor model (FIG. 8Q), FLRT3 overexpression also increased tumor growth (FIG. 8R) that correlated with decreased human CD45+ cells (FIG. 8S) and decreased CD8 T cells (FIG. 8T) in the blood.

Example 5: FLRT3 Promotes Tumor Growth in Humanized In Vivo Models

Figure 9A:
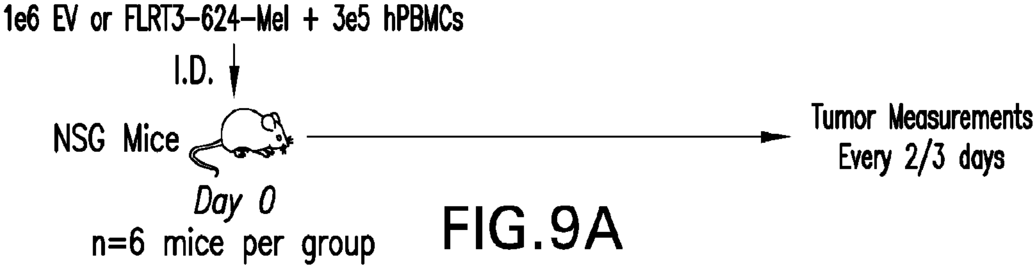
FIGS. 9A-9B show FLRT3 promotes growth of 624Mel in a humanized mouse model.
Figure 9B:
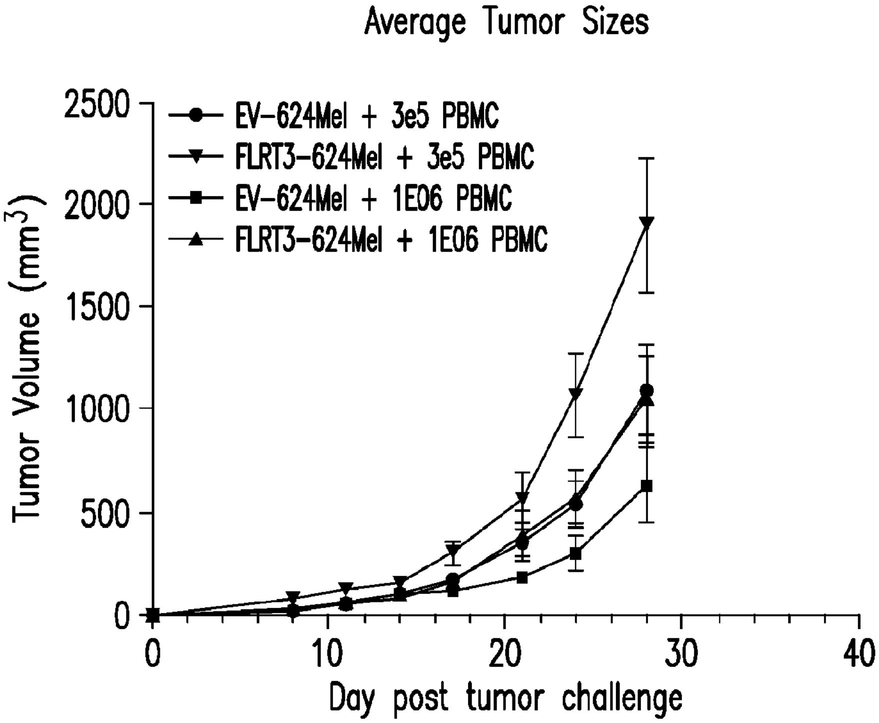
Figure 9C:
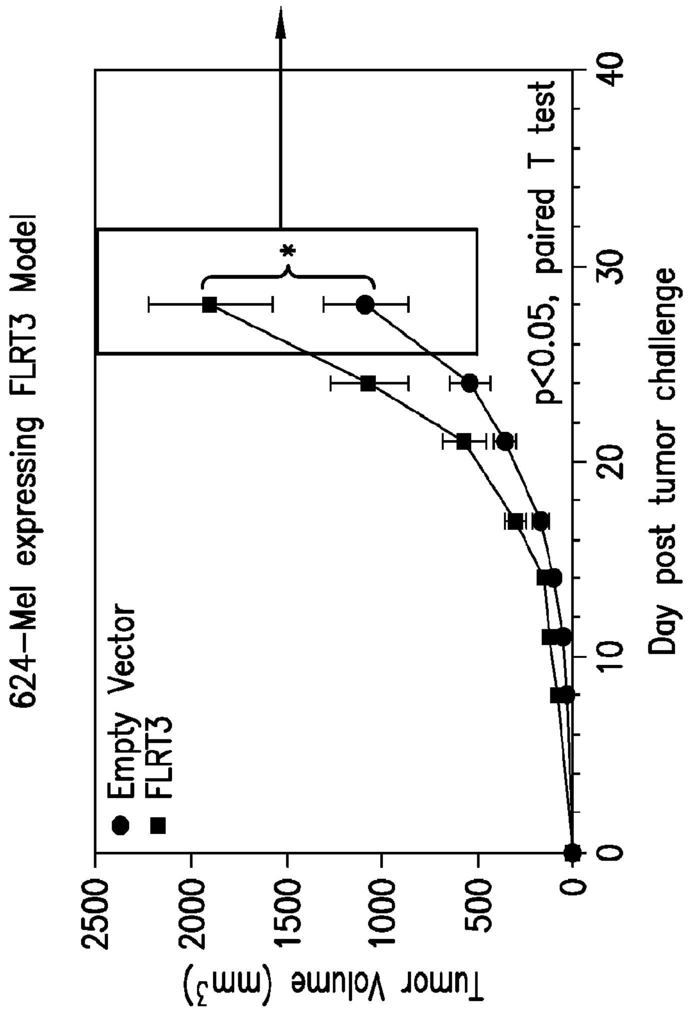
FIG. 9C is a line graph showing the effect of FLRT3 on tumor size.
Figure 9D:
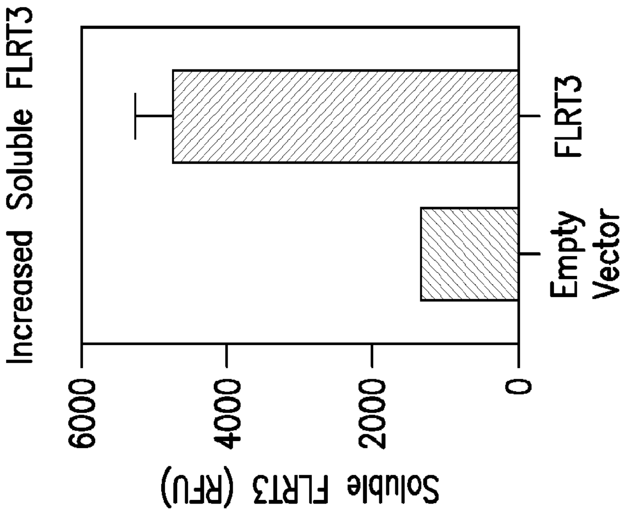
FIG. 9D is a bar graph showing levels of soluble FLRT3 in the 624Mel tumor model.

Tumor measurements of mice inoculated with empty vector control or FLRT3 overexpressing 624Mel tumor cells and hPBMCs (FIG. 9A) showed that FLRT3 promotes growth of 624Mel in a humanized model (FIG. 9B). In another model with 624Mel overexpressing FLRT3 or empty vector control, soluble FLRT3 was detected in mice 624Mel-FLRT3 implanted mice (FIGS. 9C and 9D). This data suggests that soluble FLRT3 may promote tumor growth and restrict immune activity locally and systemically.

Example 6: FLRT3 Antibodies Identified by Binding to hFLRT3 on Cells

Figure 10:
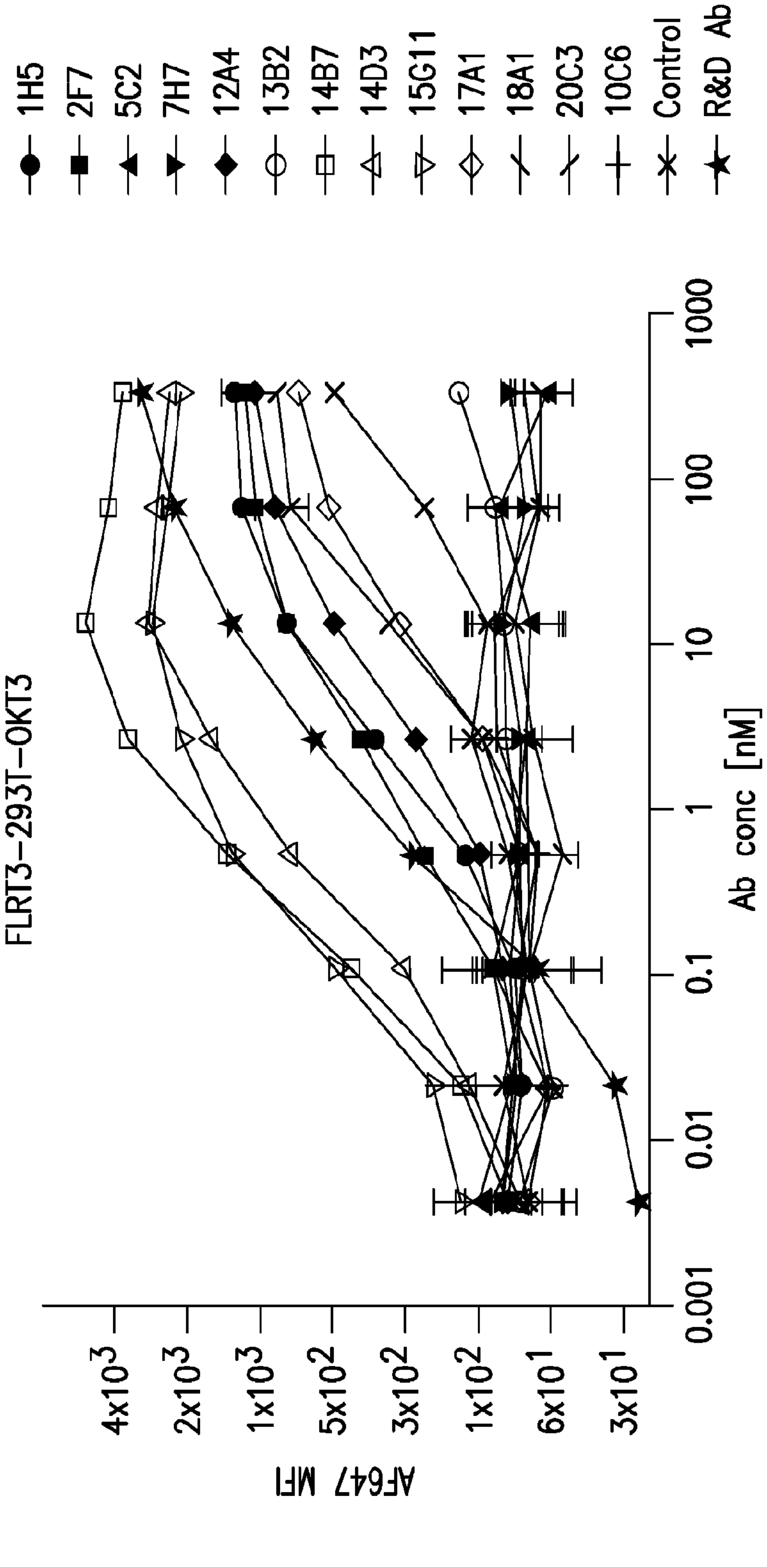
FIG. 10 are line graphs showing monoclonal antibodies identified by binding to hFLRT3 on 293T-OKT3 cells (13A) as compared to EV-293T-OKT3 (13B).

Thirteen FLRT3 antibodies were isolated and binding was assessed in a FACS assay. Eight out of 13 antibodies bound specifically to FLRT3 in a dose-dependent manner (FIG. 10). Out of the eight antibodies, three bound more strongly than the other five. Binding activity was comparable or better than the commercial FLRT3 antibody. Table 1 shows the $K_D$ values for the isolated FLRT3 recombinant monoclonal antibodies. The 14B7 antibody shows the highest affinity of all the antibodies shown.

TABLE 1

Affinity measurements with FLRT3-His monomeric fusion protein.

| Variant # | $K_D$ (M) | $K_D$ (nM) | kon (1/Ms) | kdis (1/s) | Full R^2 |
|---|---|---|---|---|---|
| 13B2 | 2.91E+23 | N/A | 8.20E+04 | 4.89E+27 | 0.000 |
| 14B7 | 3.49E−1B | 0.349 | 4.36E+05 | 1.38E−04 | 0.997 |
| 7H7 | 1.00E−12 | 0.001 | 6.05E+04 | 1.00E−07 | 0.898 |
| 15G11 | 7.91E−11 | 0.079 | 6.46E+05 | 3.66E−05 | 0.919 |
| 17A1 | 1.82E−08 | 18.200 | 1.21E+05 | 1.54E−04 | 0.969 |
| 20C3 | 2.21E−09 | 2.210 | 8.62E+04 | 2.07E−04 | 0.954 |
| 12A4 | 2.18E−10 | 0.218 | 1.33E+05 | 3.24E−05 | 0.981 |
| 14D3 | 3.79E−07 | 379.000 | 3.72E+05 | 1.59E−02 | 0.703 |
| 10C6 | 0.00E+00 | N/A | 0.00E+00 | 0.00E+00 | 0.000 |
| 18A7 | 0.00E+00 | N/A | 0.00E+00 | 0.00E+00 | 0.000 |
| 1H5 | 1.90E−10 | 0.190 | 1.40E+05 | 1.60E−05 | 0.974 |
| 2F7 | 2.43E−09 | 7.700 | 1.77E+05 | 1.35E−04 | 0.960 |
| 5C2 | 1.66E−06 | 1660.000 | 2.49E+03 | 4.12E−03 | 0.327 |

Figure 11:
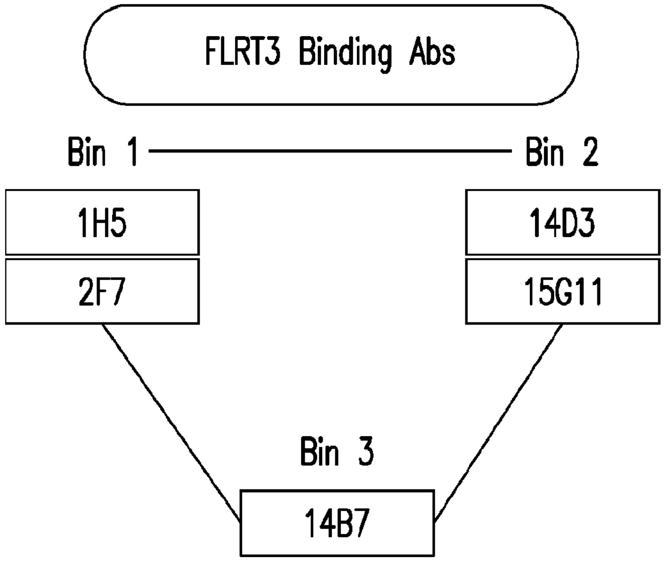
FIG. 11 is an illustration showing that FLRT3 antibodies fall into three bins.

Further analysis of the binding studies indicated that FLRT3 antibodies fall into 3 bins. As indicated in Table 2, 1H5 and 21F7 share a bin, 141D3 and 15G11 share a bin and 141B7 is in its own bin (FIG. 11).

TABLE 2

FLRT3 monoclonal antibodies fall into three bins.

| Ab# | | 1H5 | 2F7 | 5C2 | 14B7 | 14D3 | 15G11 |
|---|---|---|---|---|---|---|---|
| 1X Kinetic | 0.0322 | 0.947 | 0.9903 | 0.0741 | 1.7334 | 0.9472 | 1.2773 |
| 1H5 | −0.259 | −0.0568 | −0.0098 | −0.2598 | 1.2013 | 0.549 | 0.9702 |
| 2F7 | −0.4517 | −0.1158 | −0.0655 | −0.3981 | 1.0567 | 0.3798 | 0.7982 |
| 5C2 | −0.0822 | 0.7828 | 0.8388 | −0.0066 | 1.5617 | 0.8325 | 1.1788 |
| 14B7 | −0.0044 | 0.6708 | 0.7714 | 0.0014 | 0.0294 | 0.6214 | 1.073 |
| 14D3 | −0.1754 | 0.6438 | 0.7501 | −0.1005 | 1.3635 | −0.0406 | 0.1963 |
| 15G11 | −0.3792 | 0.4671 | 0.5733 | −0.2545 | 1.1351 | −0.2608 | −0.0482 |

Figure 12A:
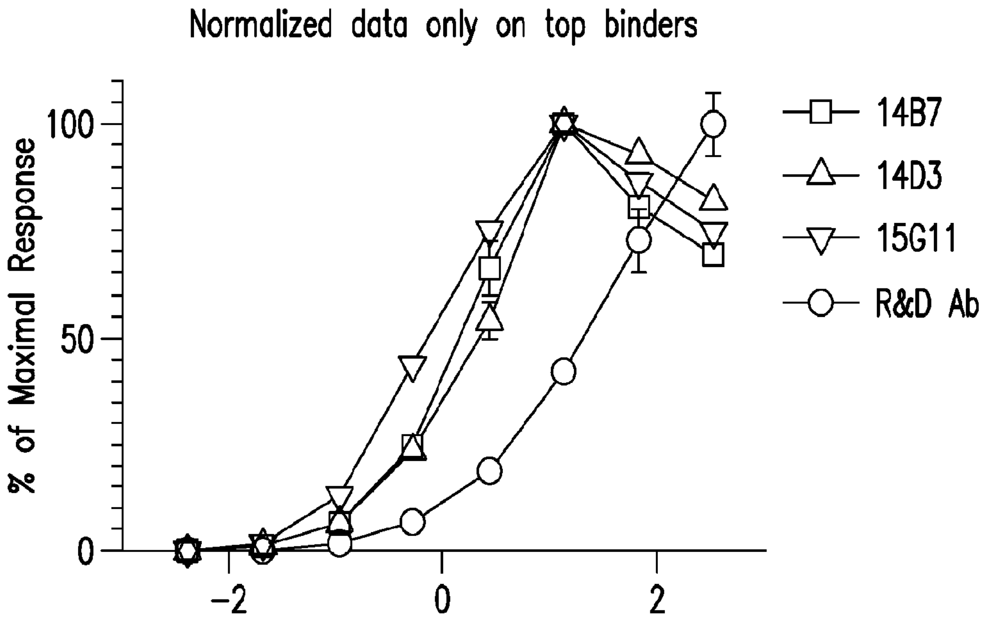
FIGS. 12A-12B show binding EC50 values of top binders to 293T-hFLRT3 cells.
Figure 12B:
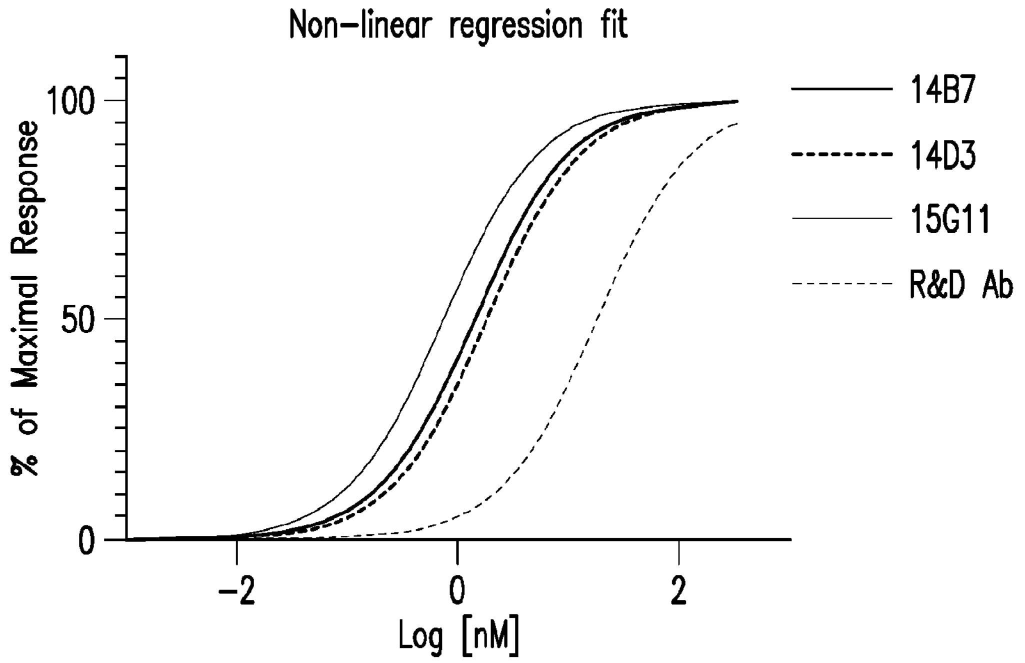

A binding curve for the top 3 mAb was performed for binding to human FLRT3 transfected cells 293T cells (FIG. 12A), and EC50 values for top 3 binders were calculated based on non-linear regression fit (FIG. 12B). MFI values of each group were normalized within that group—i.e. largest value 100% and smallest value 0%. EC50 values for 141B7<1.5 nM, for 141D3, 15G11<5 nM in two separate experiments (Table 3).

TABLE 3

| EC$_{50}$ values of top binders. | | |
|---|---|---|
| | EC50 Values (nM) | |
| Clone/Ab | Exp 1 | Exp 2 |
| 14B7 | 1.41 | 1.35 |
| 14D3 | 1.82 | 3.24 |
| 15G11 | 0.74 | 2.27 |
| R&D Ab | 18.17 | 6.40 |
| 12A4 (weak binder for comparison) | 15.69 | 17.71 |

Figure 13:
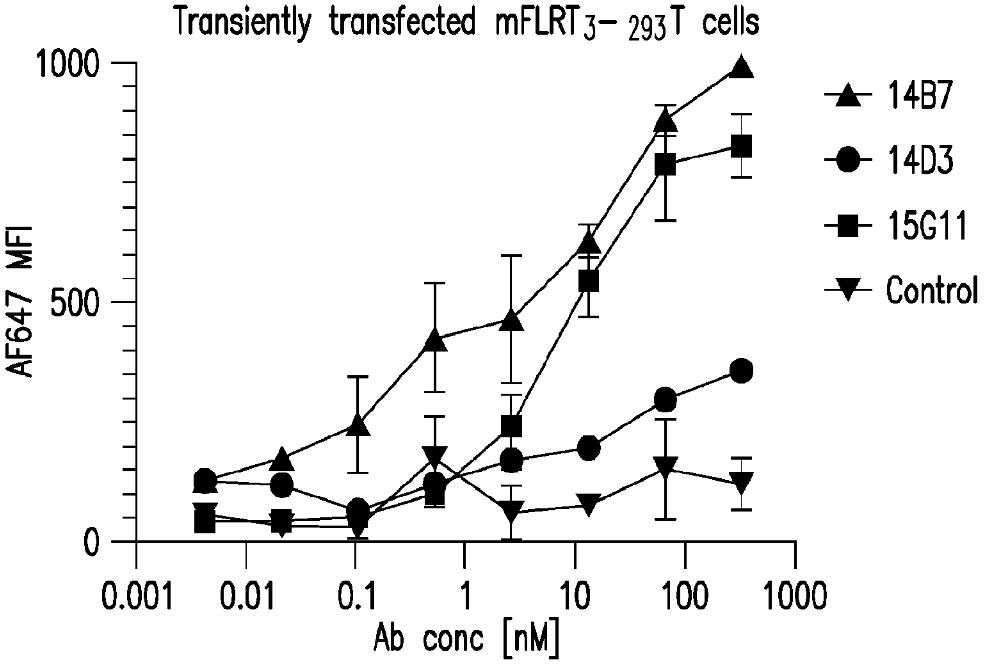
FIG. 13 is a line graph showing 14B3 binds to mouse FLRT3 on 239T-OKT3-mFLRT3 cells.

Binding of antibodies to mFLRT3 was tested on transiently transfected 293T cells. The antibody 14B7 showed strong binding to mouse FLRT3 (FIG. 13). Antibodies 14D3 and 15G11 showed weak binding at higher antibody concentrations.

Example 8: 14B7 Disrupts Unc5B-FLRT3 Interaction

Figure 14A:
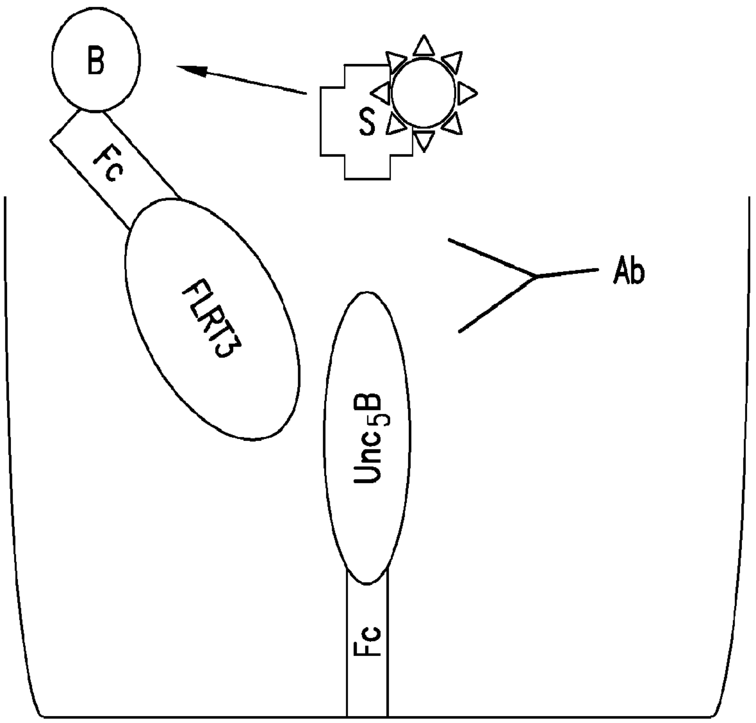
FIGS. 14A-14C show 14B7 disrupts Unc5B-FLRT3 interaction in ELISA assays.
Figure 14B:
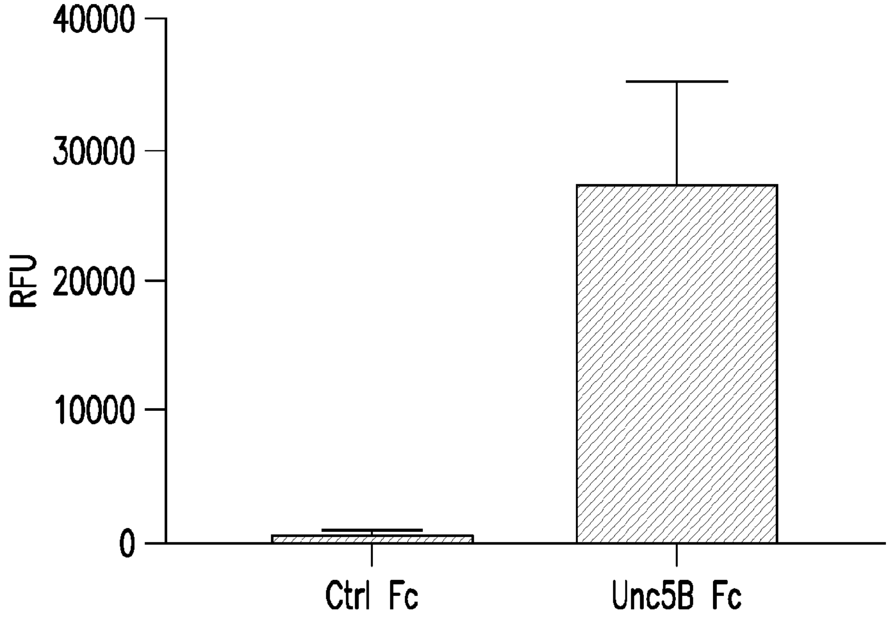
Figure 14C:
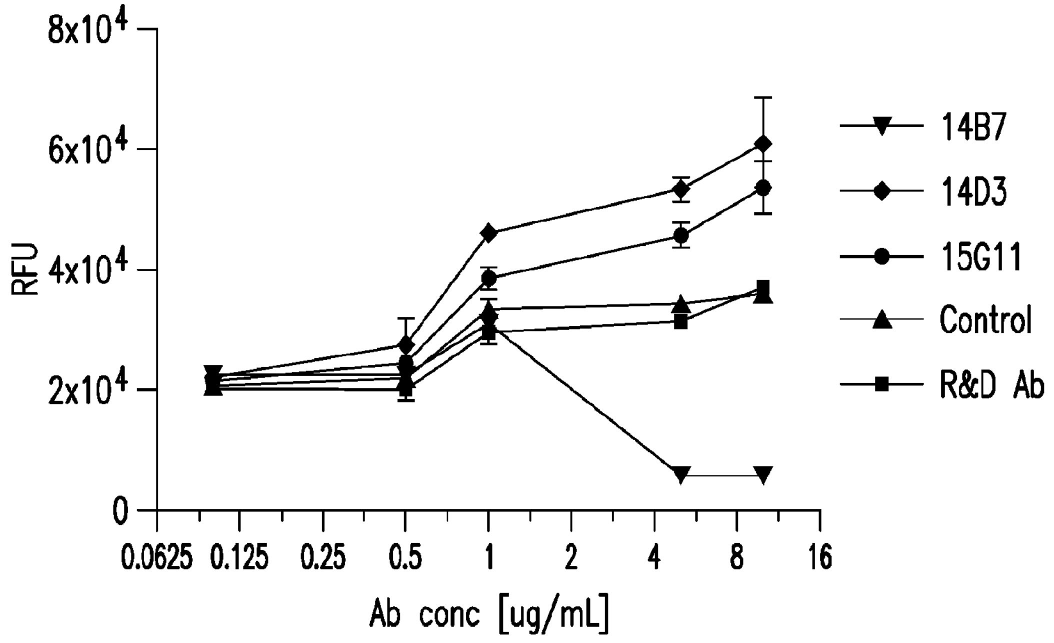

The FLRT3 antibodies were tested for their ability to block FLRT3-Unc5B interaction in ELISA assays (FIG. 14A). The binding of FLRT3-Fc biotin to Unc5B-Fc was confirmed in the absence of blocking mAbs (FIG. 14B). Testing FLRT3 Fc binding to UNC5B Fc was performed in presence of increasing concentrations of antibodies and 14B7 was shown to block the interaction of Unc5B-FLRT3 at 5 and 10 μg/mL (FIG. 14C).

Figure 15A:
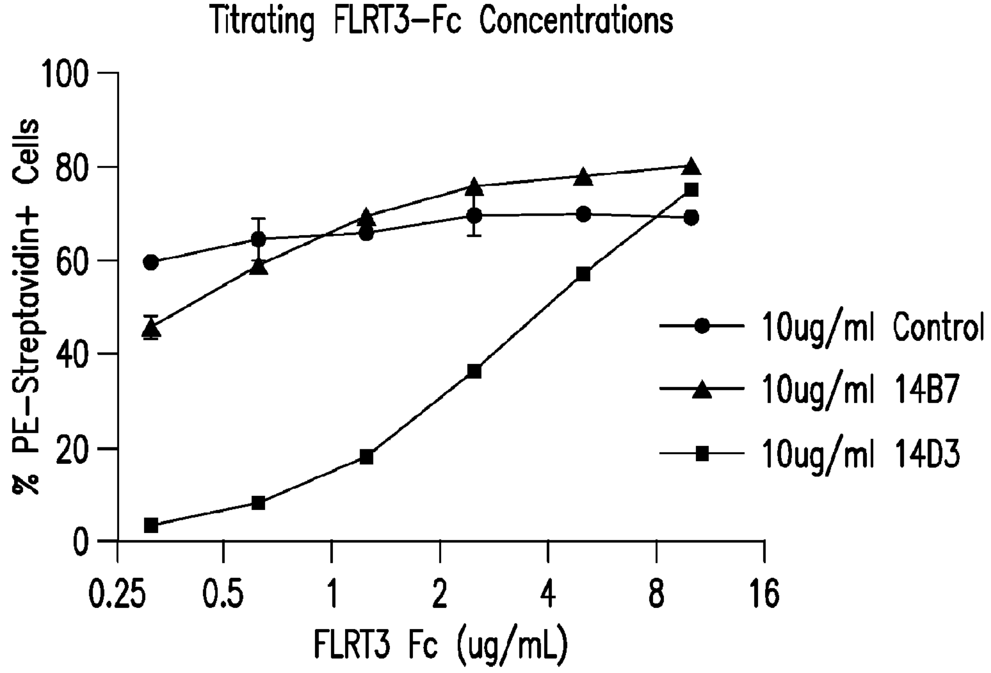
FIGS. 15A-15B show 14B7 disrupts FLRT3-Unc5B interaction in cell-based assays.
Figure 15B:
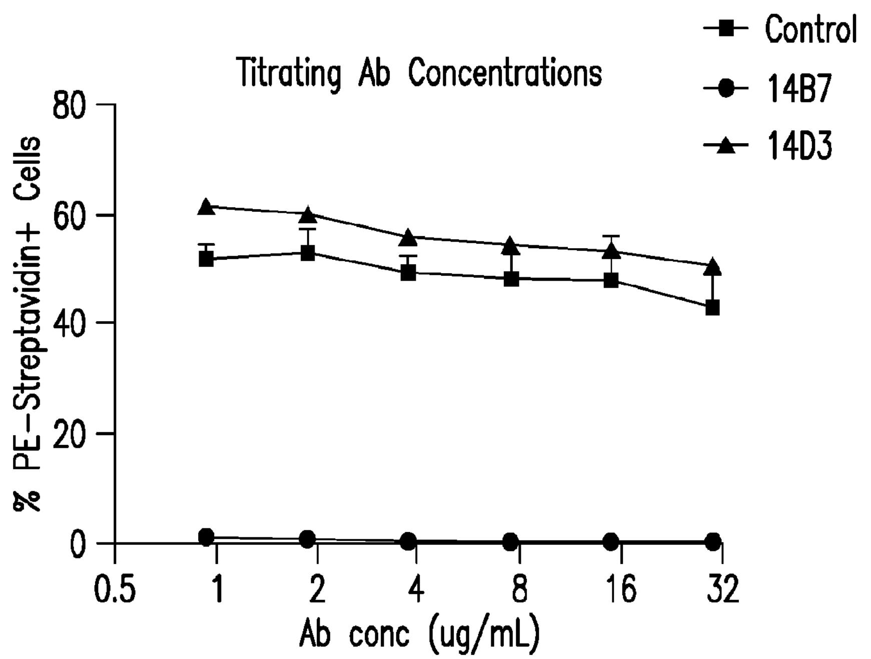
Figure 16A:
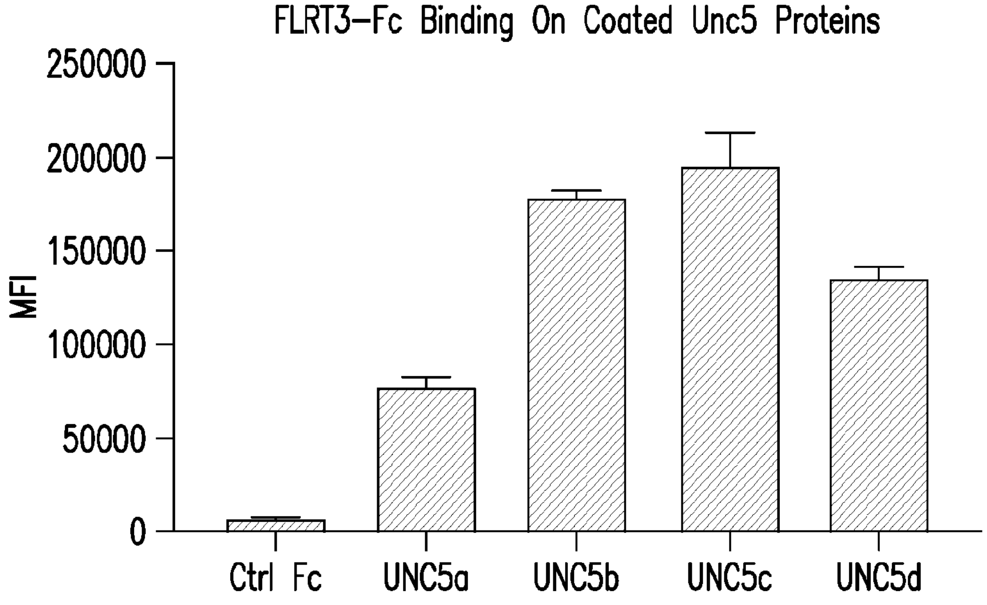
FIGS. 16A-16E show 14B7 blocks other FLRT3-Unc5 interactions.
Figure 16B:
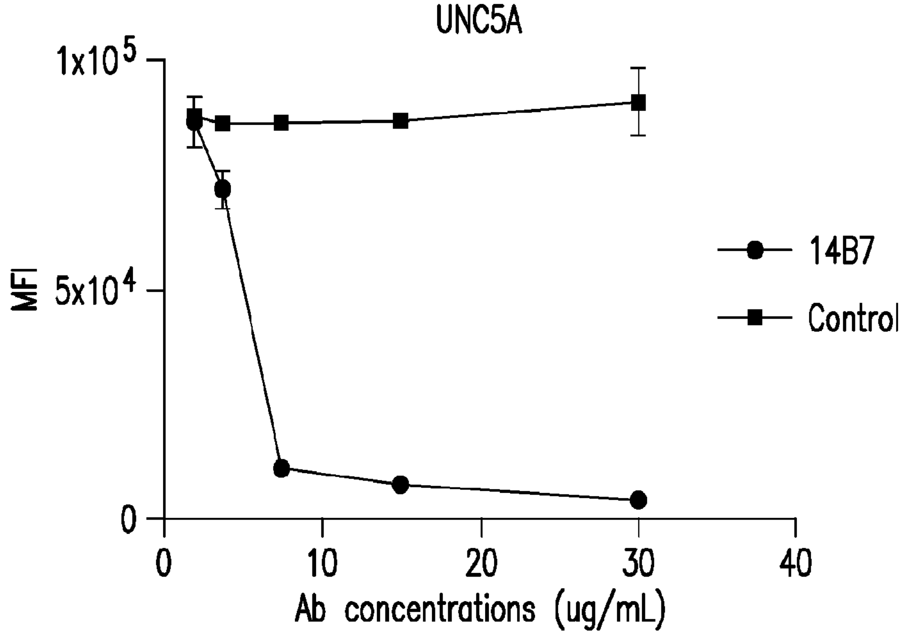
Figure 16C:
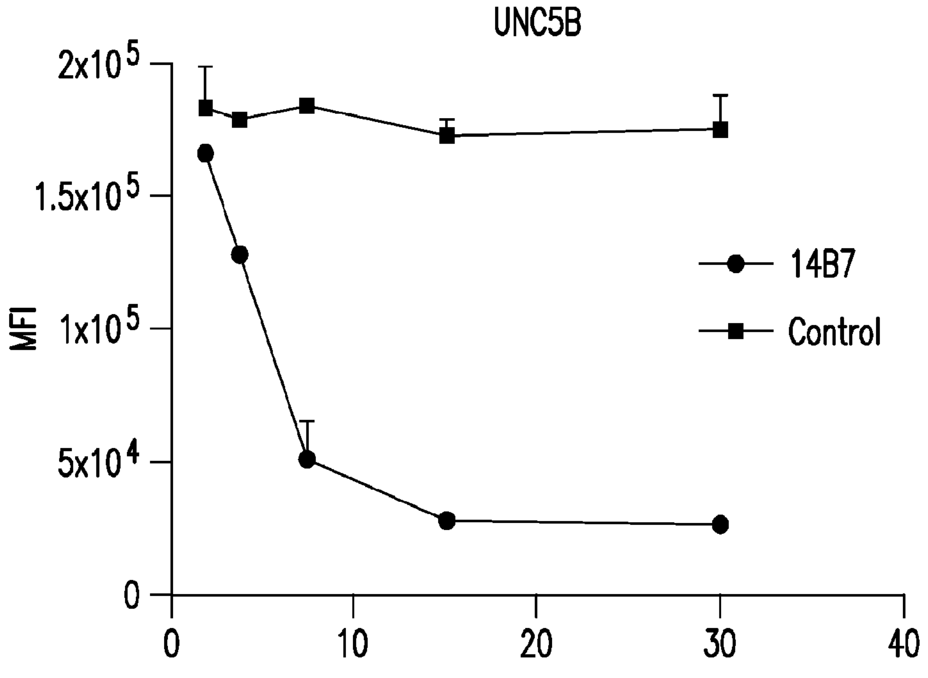
Figure 16D:
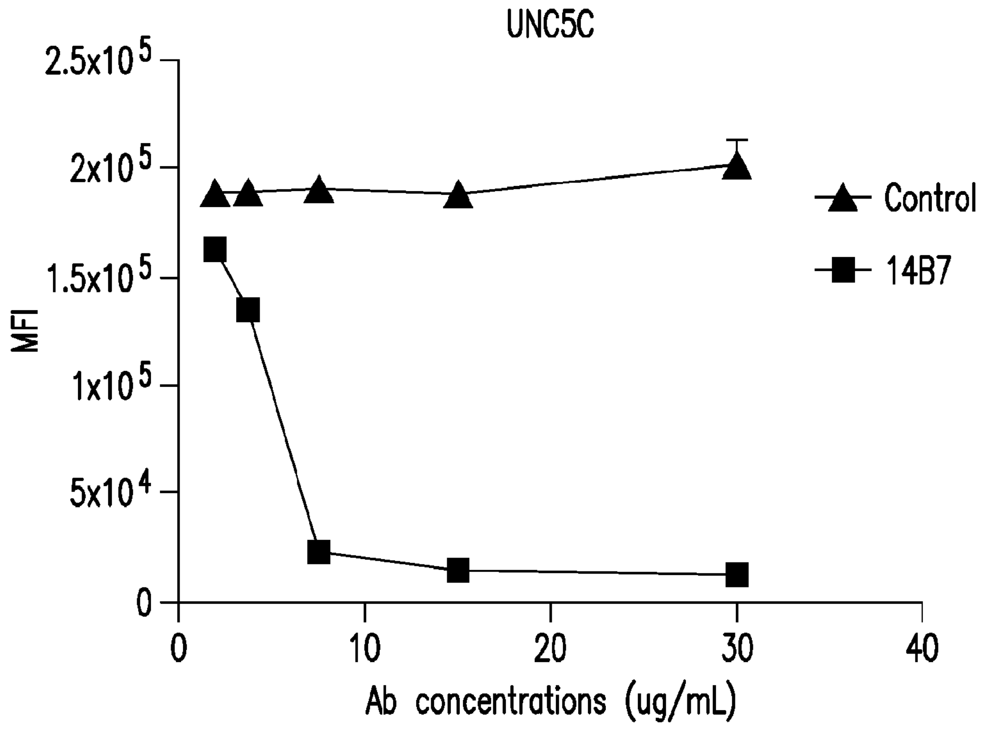
Figure 16E:
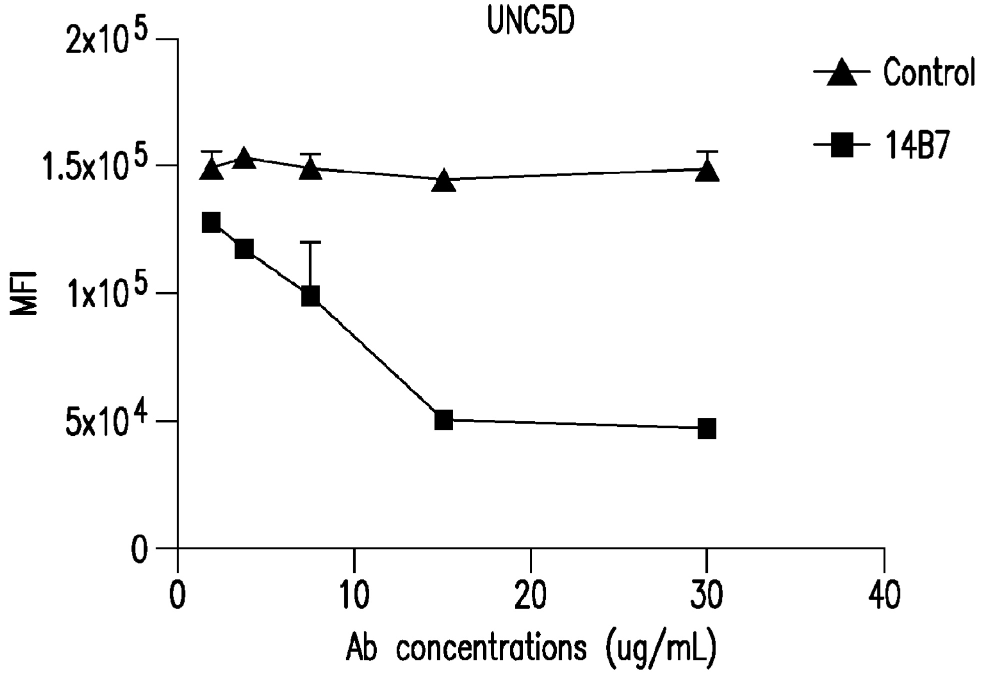

The titration of increasing concentrations of soluble FLRT3 showed that 14B7 blocked FLRT3-Unc5B binding in ELISA assays. The data was confirmed by flow cytometry at titrating concentrations of incubated FLRT3-Fc (FIG. 15A). The 14B7 antibody blocked Unc5B-FLRT3 binding in this assay at as low as 0.9 μg/mL concentration (FIG. 15B). FLRT3 was shown to also bind to Unc5A, Unc5C, and Unc5D in ELISA assay (FIG. 16A). Antibody 14B7 blocked FLRT3 binding to all Unc5 proteins (FIG. 16B-16E).

Example 9: 14B7 Disrupts Binding of Unc5B-Fc Biotin to FLRT3-Fc

Figure 17A:
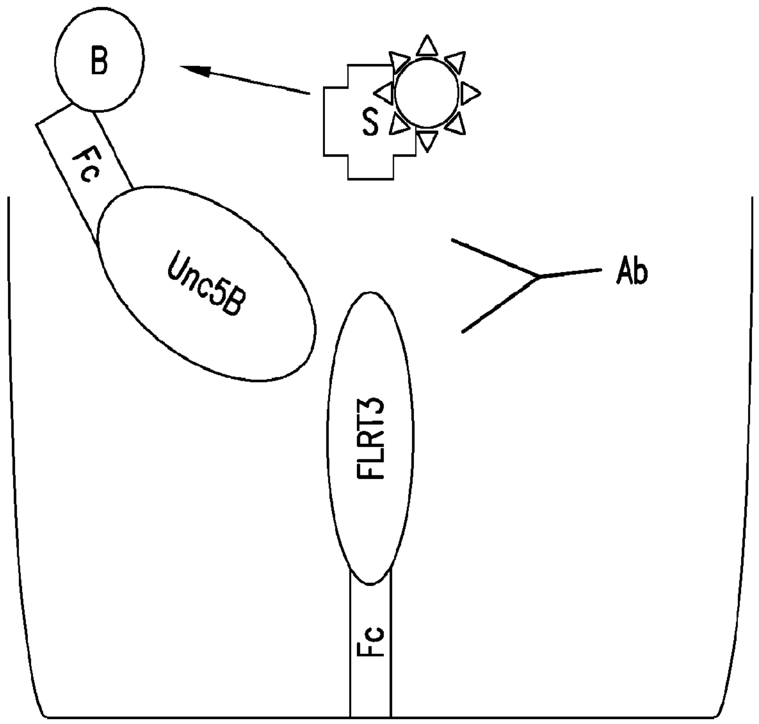
FIGS. 17A-17C show 14B7 disrupts Unc5B-FLRT3 interaction in ELISA assays.
Figure 17B:
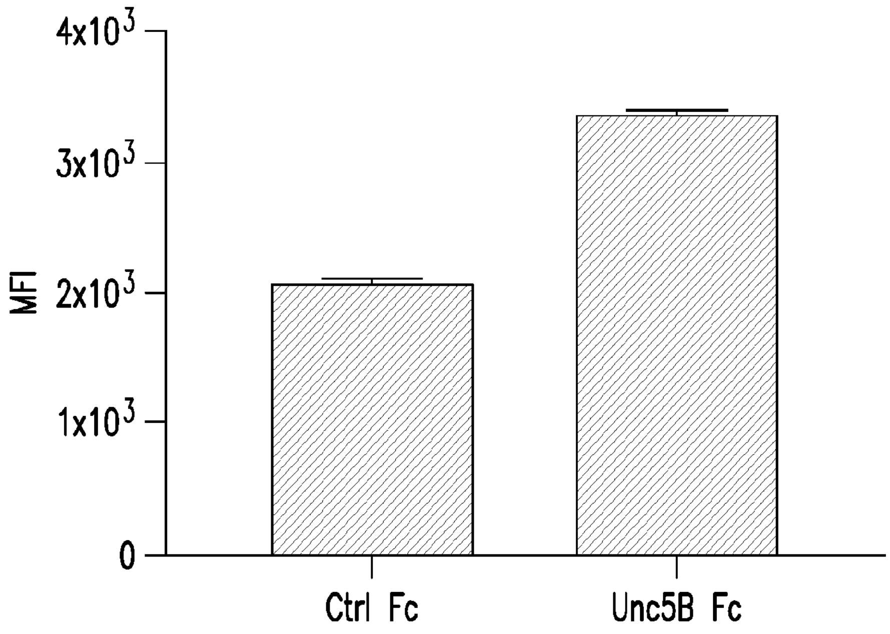
Figure 17C:
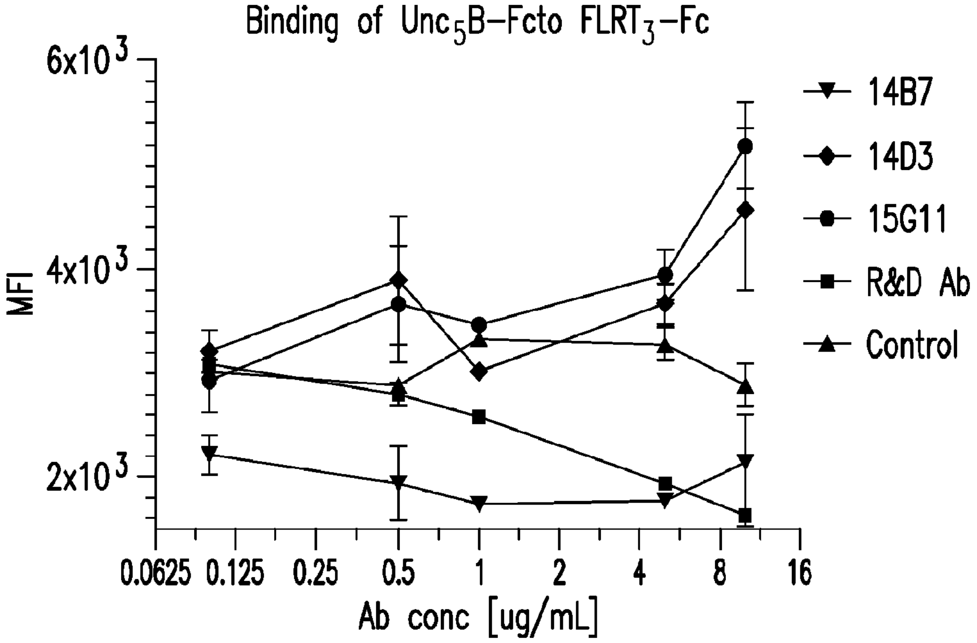
Figure 18:
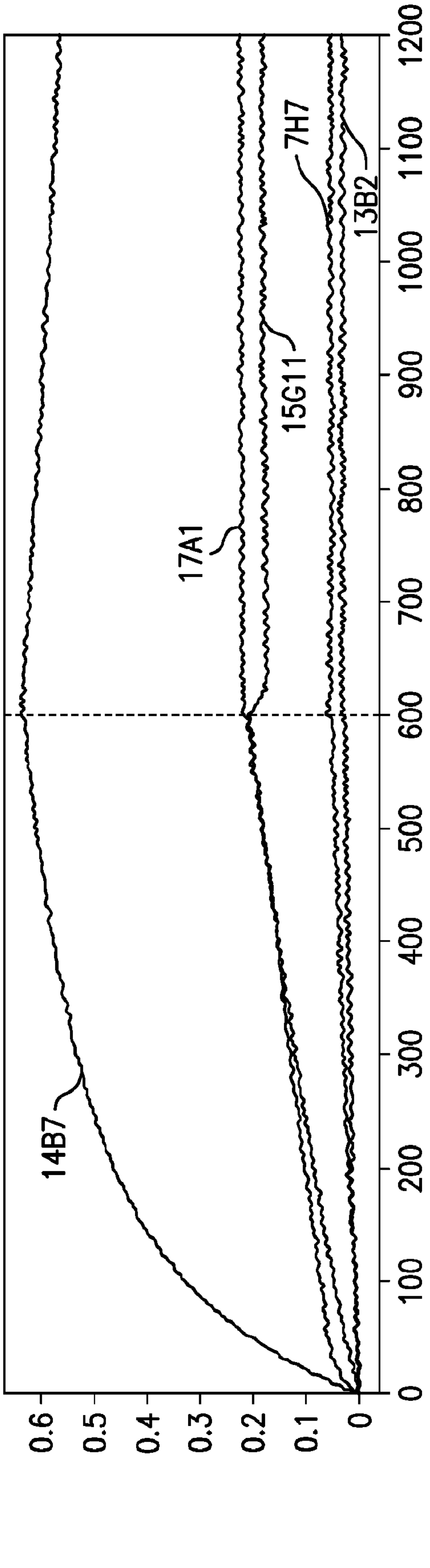
FIG. 18 shows binding curves of FLRT3 antibodies to FLRT3 monomer by octet.

Similar to example 8, but in reverse orientation (FIG. 17A), binding of Unc5B-Fc biotin to FLRT3-Fc was confirmed (FIG. 17B), and tested in presence of increasing concentrations of antibodies (FIG. 17C). ELISA assays showed that 14B7 disrupted Unc5B-FLRT3 interaction in at all concentrations tested (FIG. 17C). In an Octet analysis, the binding curves of FLRT3 antibodies to FLRT3 monomer showed that 14B7 was consistently a top binder (FIG. 18).

Example 10: FLRT3 Antibodies Bind to A549 Cells that Express Endogenous hFLRT3

Figure 19:
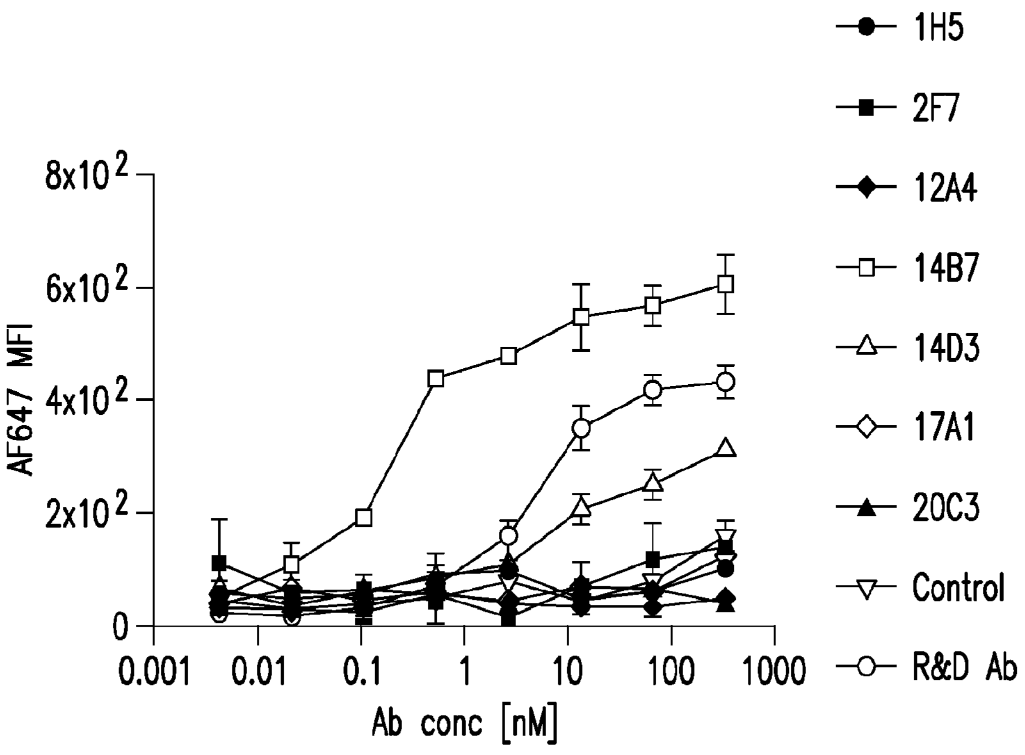
FIG. 19 is a line graph showing FLRT3 antibodies bind to A549 cells that express endogenous hFLRT3.
Figure 20A:
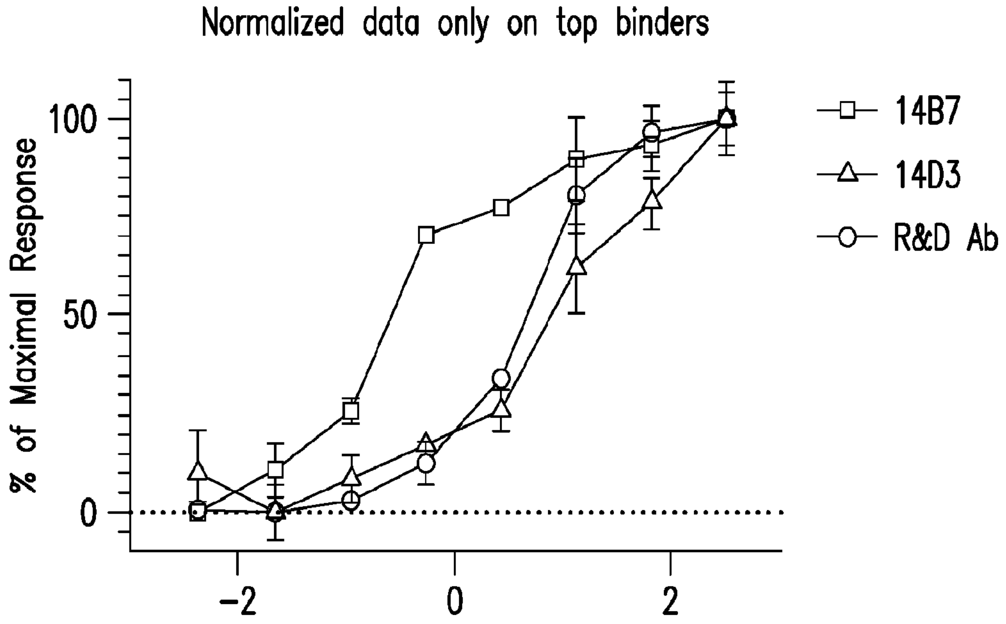
FIGS. 20A-20B show binding EC50 values for A549 cells.
Figure 20B:
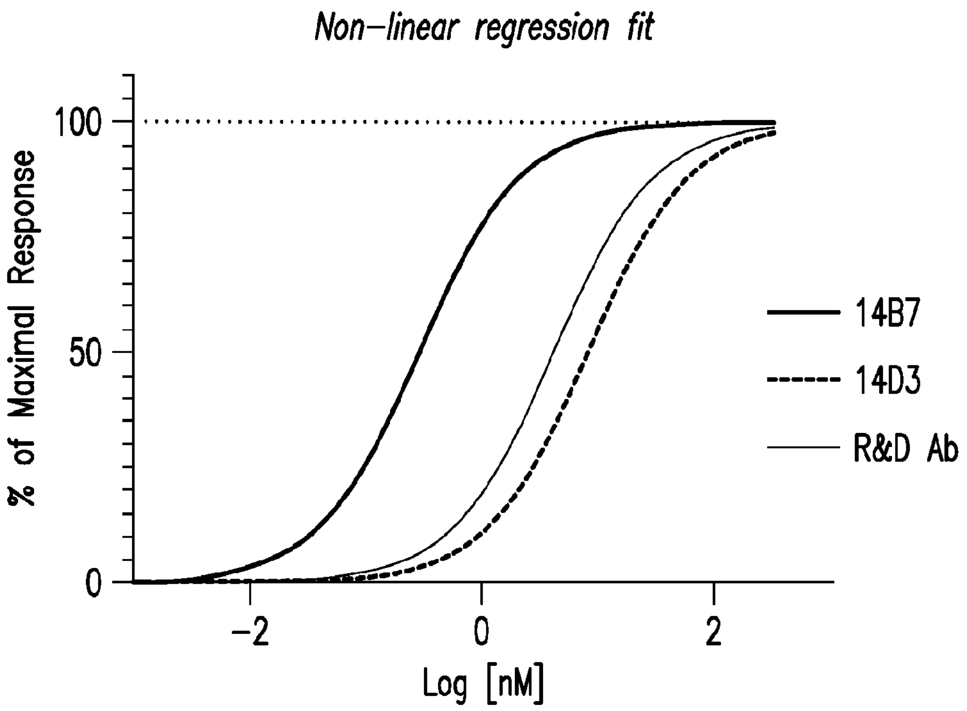

Increasing concentrations of FLRT3 antibodies bound to A549 cells that express endogenous hFLRT3 (FIG. 19). Binding curves for the top three antibodies were performed (FIG. 20A). MFI values of each group were normalized within that group—i.e. largest value 100% and smallest value 0% (FIG. 20A). EC50 values were calculated based on non-linear regression fit (FIG. 20B). EC50 value of 14B7 was less than 1 nM demonstrating stronger binding than the other antibodies (Table 4).

TABLE 4

| EC50 values of top binders in A549 cells. | |
|---|---|
| Clone/Ab | EC50 Values (nM) |
| 14B7 | 0.29 |
| 14D3 | 8.21 |
| R&D Ab | 4.29 |
| 12A4 (weak binder for comparison) | 251 |

Example 11: FLRT3 Suppresses IFN-γ Production in 293T-OKT3-FLRT3 Assay

Figure 21A:
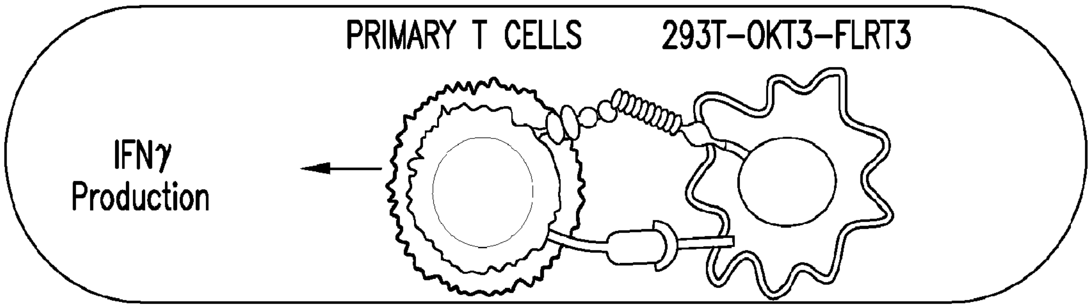
FIGS. 21A-21I show FLRT3 inhibition of T cells.
Figure 21B:
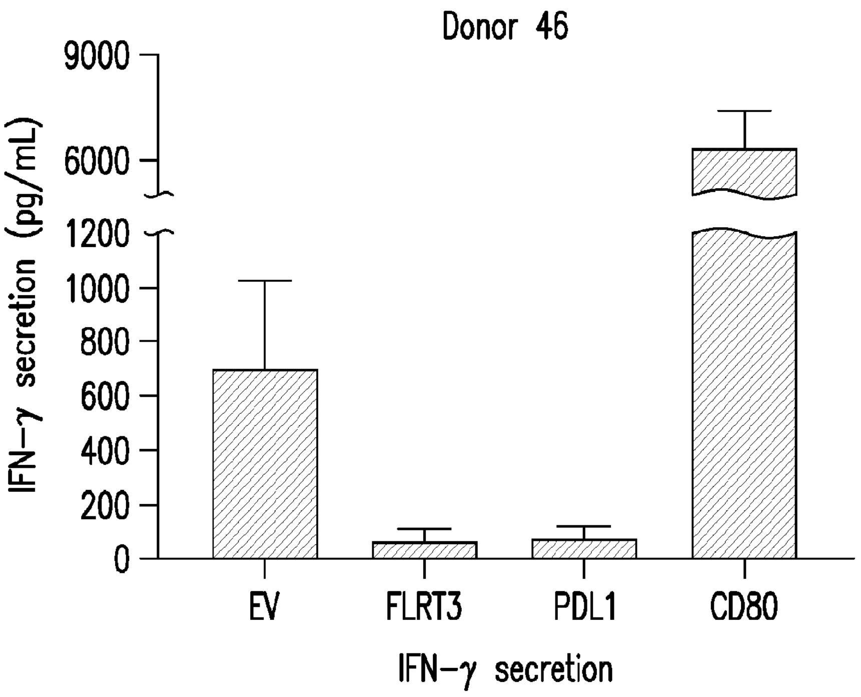
Figure 21C:
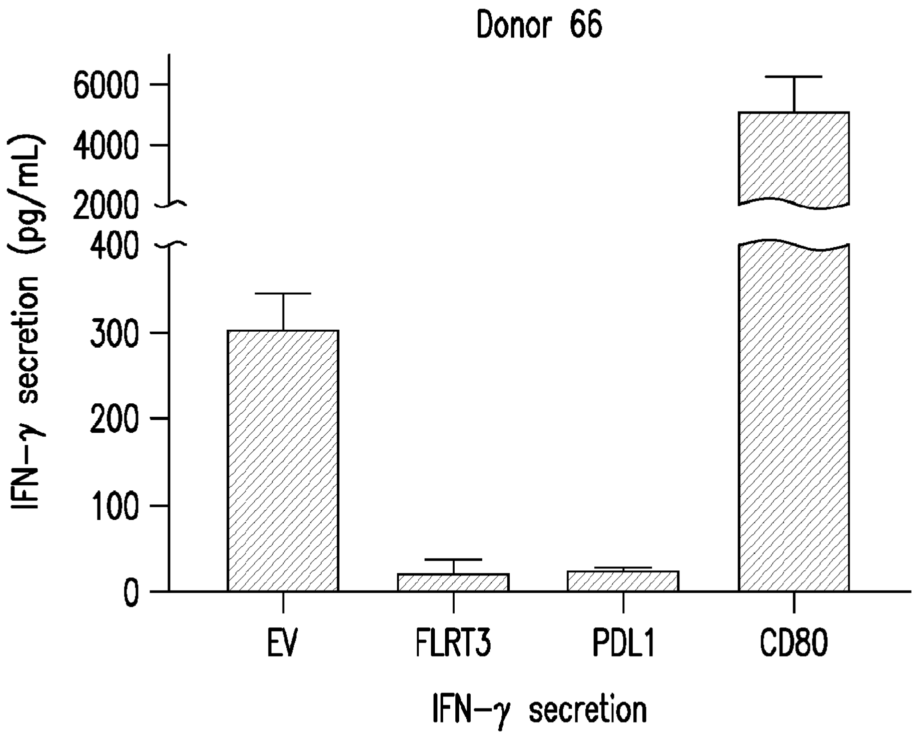
Figure 21D:
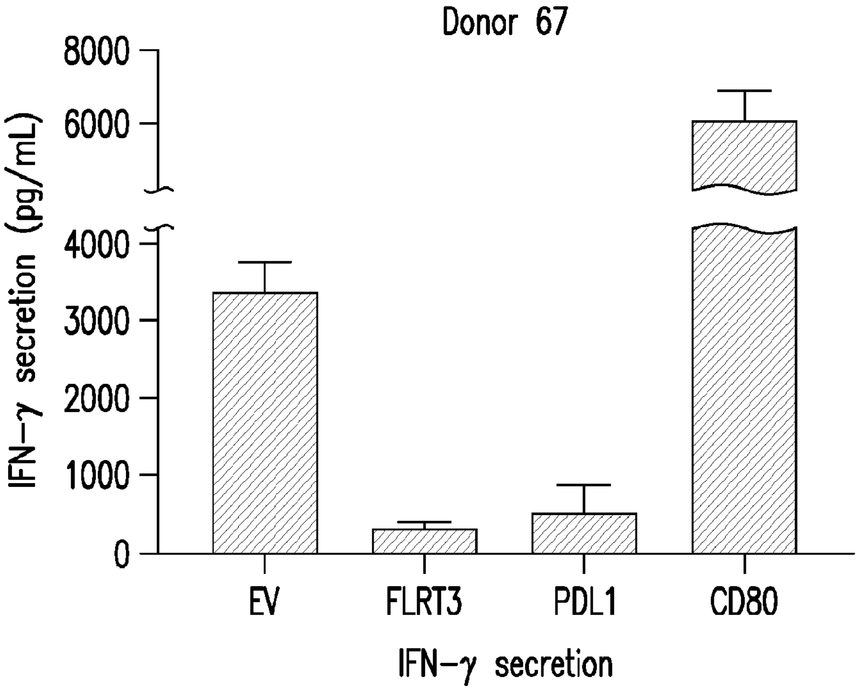
Figure 21E:
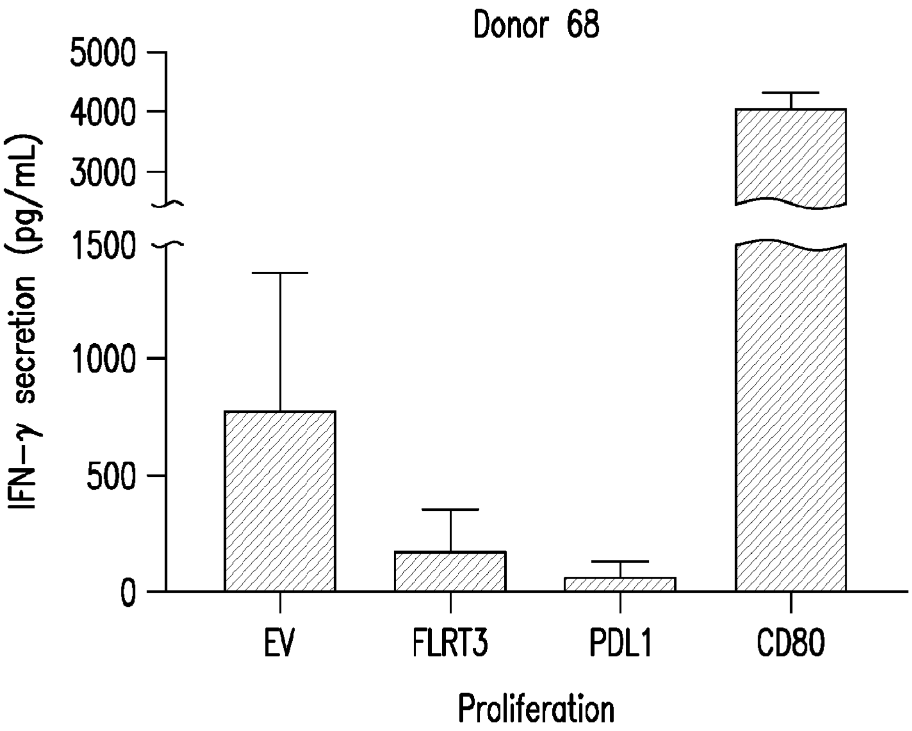
Figure 21F:
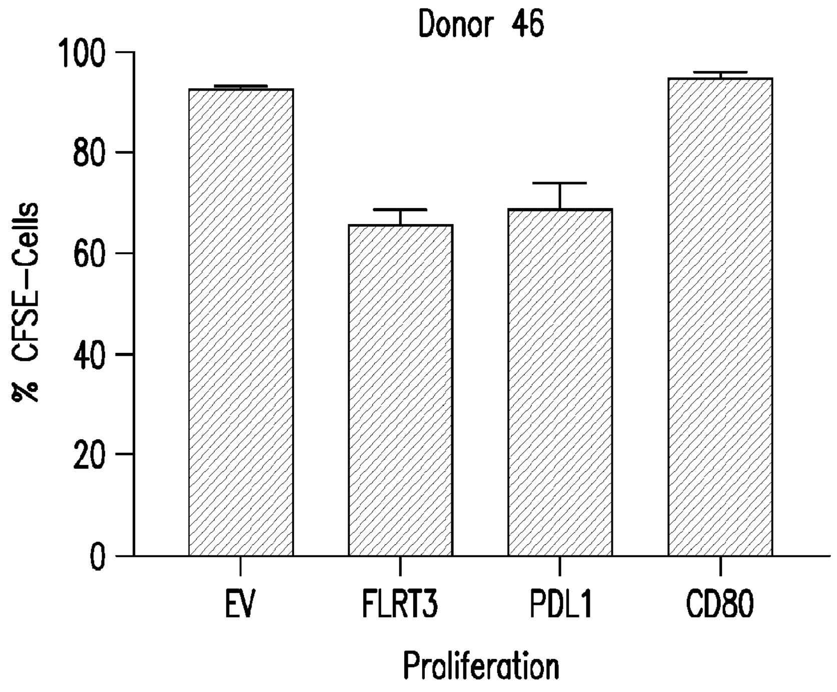
Figure 21G:
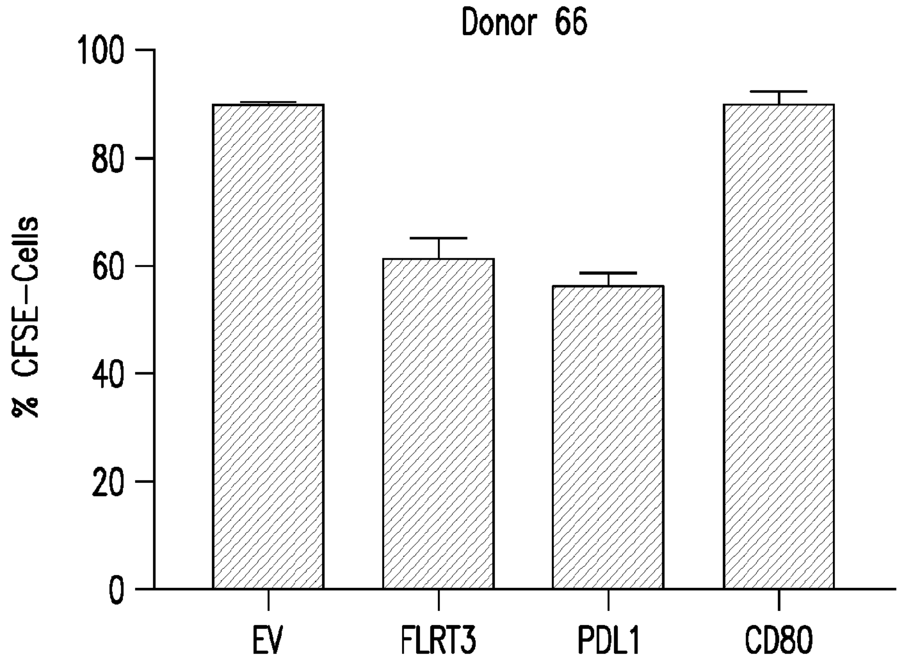
Figure 21H:
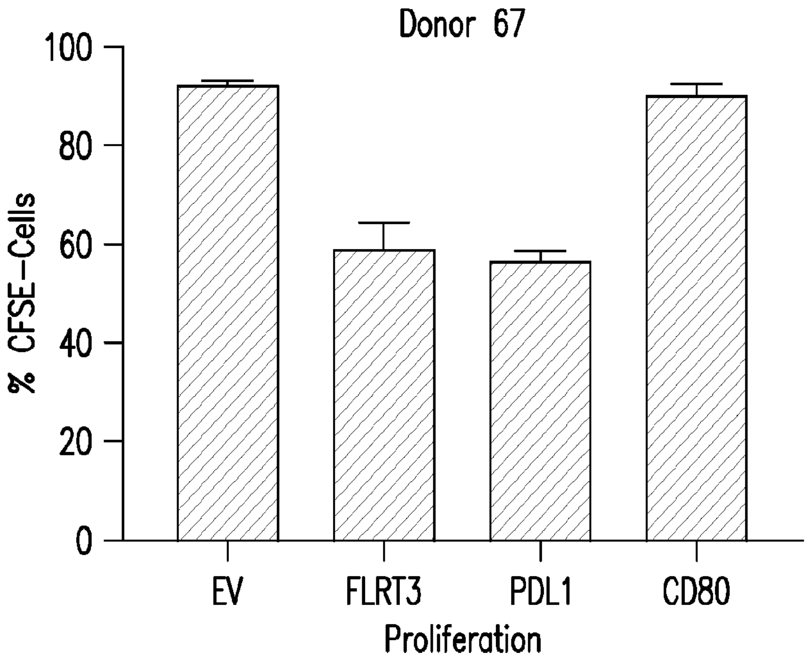
Figure 21I:
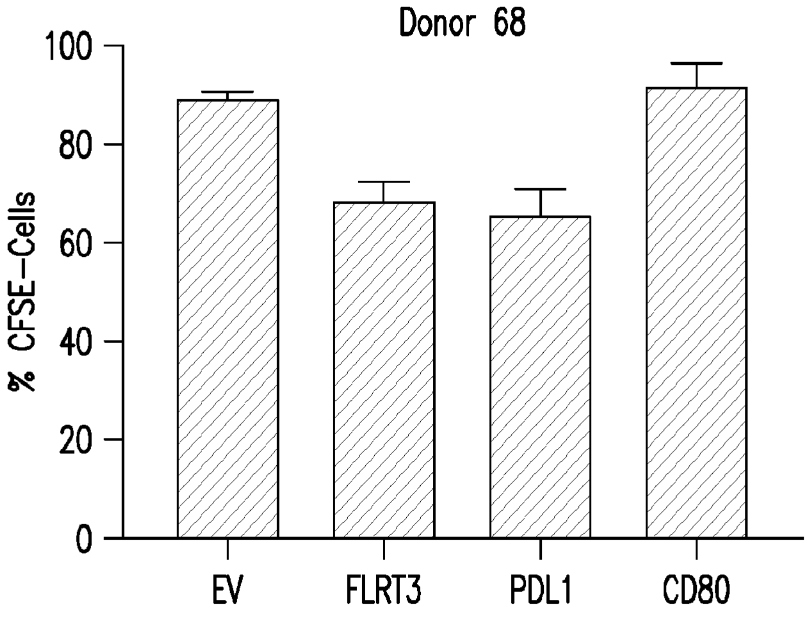
Figure 22A:
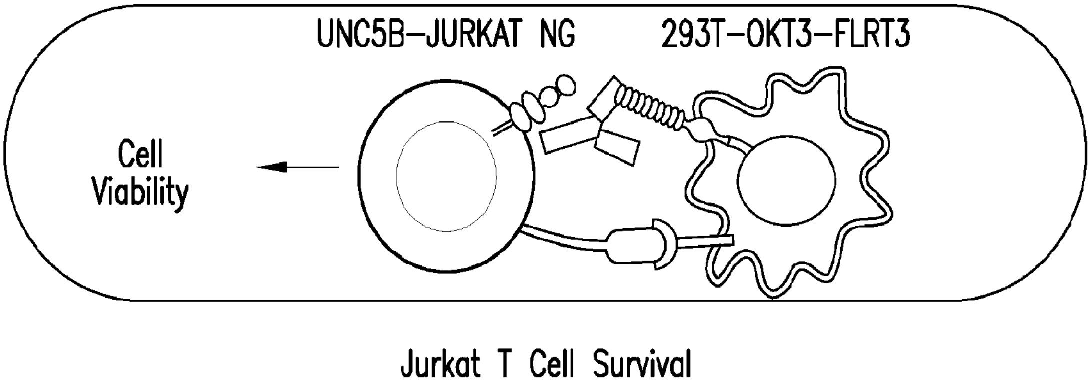
FIGS. 22A-22D show FLRT3 antibodies reverse cell death and NF-kB-GFP reporter signaling in Jurkat T cells.
Figure 22B:
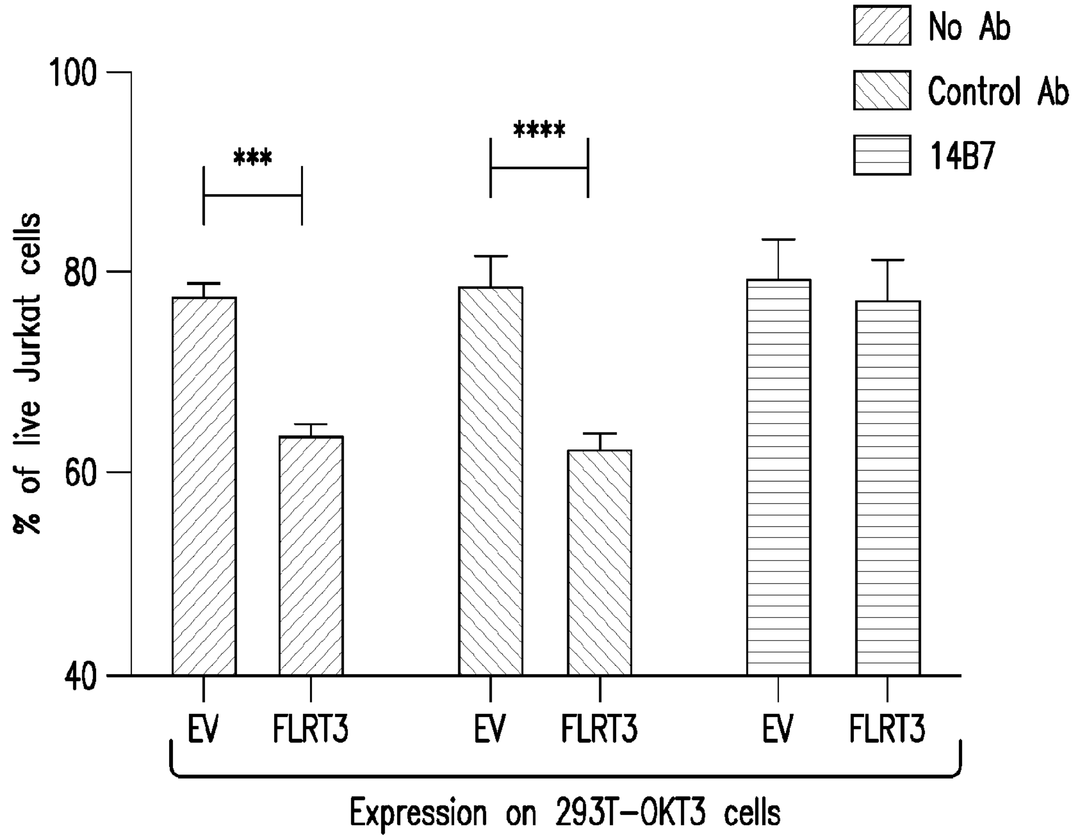
Figure 22C:
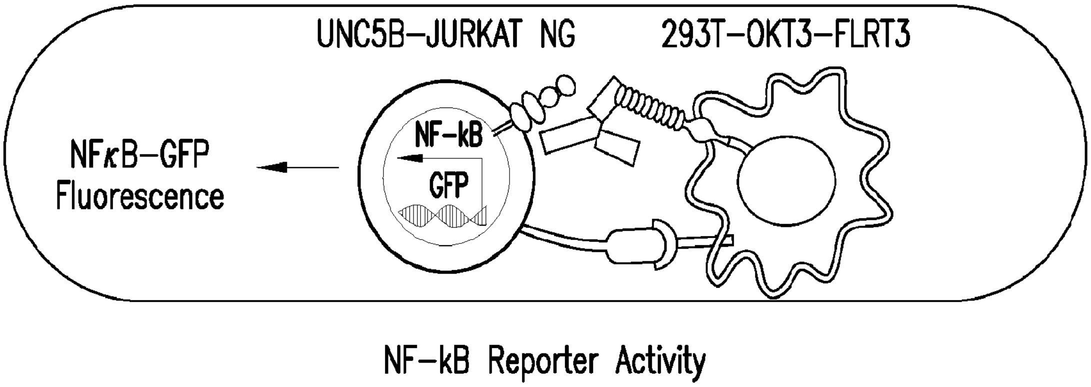
Figure 22D:
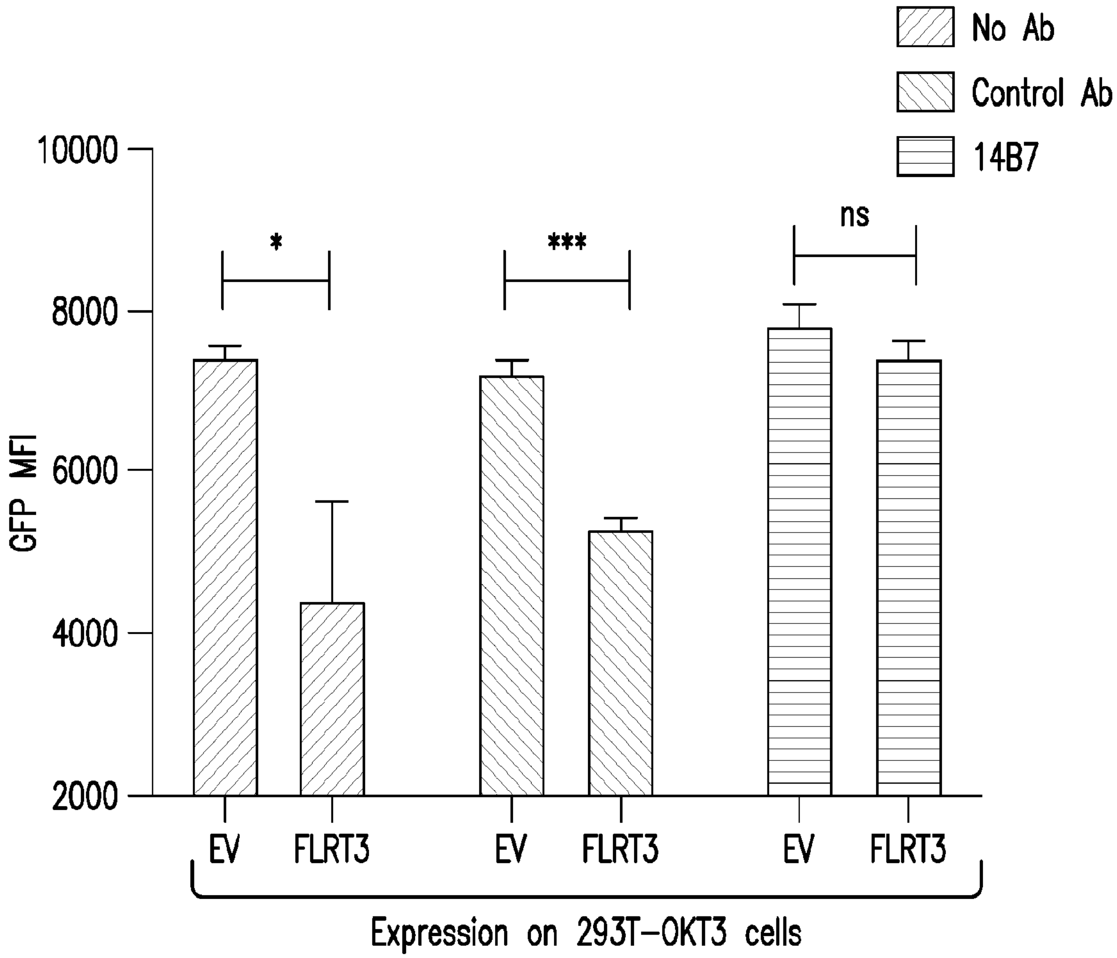

Similar to the assays described in Example 1, FLRT3, PDL1 inhibitory control, empty vector negative control and CD80 stimulatory control was expressed on 293T-OKT3 cells and co-cultured with total PBMCs (FIG. 21A) from multiple donors for evaluation of T cell IFN-g secretion (FIGS. 21B-E) and T cell proliferation based on CFSE dilution (FIG. 21F-I). These data demonstrated that FLRT3 suppressed T cell effector function based on inhibition of IFN-g secretion similarly to PD-L1. Whereas, T cell proliferation was less inhibited, once again similar to PD-L1 effects.

Example 12: FLRT3 Antibodies Reverse Inhibition of T Cells

To determine if FLRT3 antibodies could reverse T cell mediated suppression, assays were performed similar to Example 1. Jurkat T cells that were transduced to express Unc5B and contained an NF-kB-GFP reporter were co-cultured with 293T-OKT3 cells overexpressing either FLRT3 or empty vector control (EV), and with FLRT3 antibody 14B7 or control antibody (FIG. 22A-22D). These assays demonstrated the FLRT3 expression reduced Jurkat T cell viability and NF-kB-GFP reporter activity (FIG. 22A-22D). When 14B7 antibody was added to the culture, Jurkat T cell viability and NF-kB-GFP reporter activity were restored (FIG. 22A-22D).

Figure 23A:
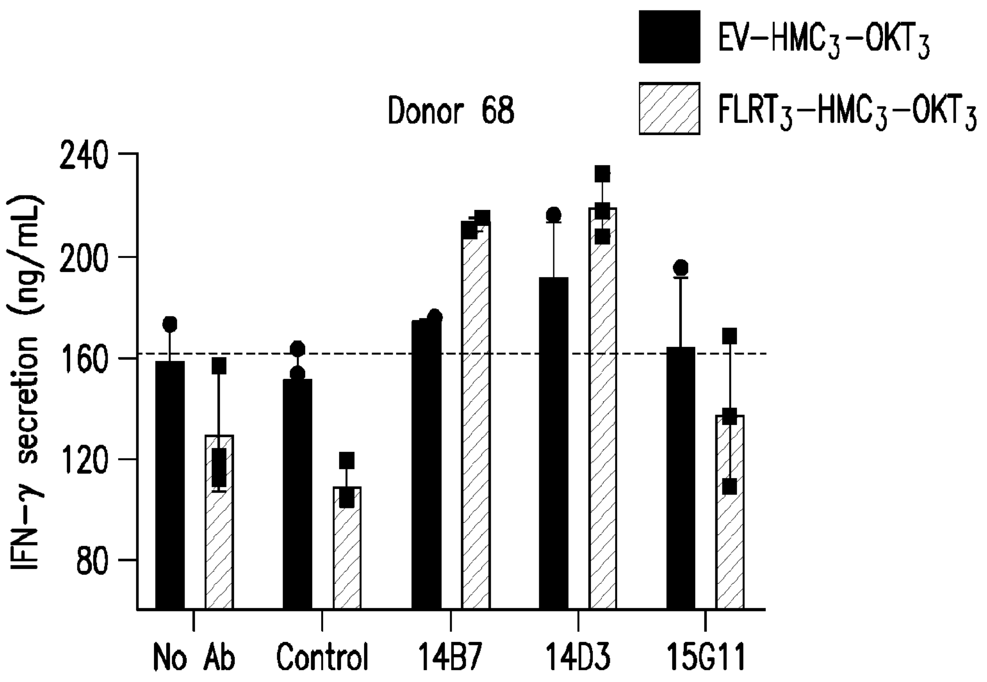
FIGS. 23A-23B show FLRT3 antibodies reverse inhibition of T cells.
Figure 23B:
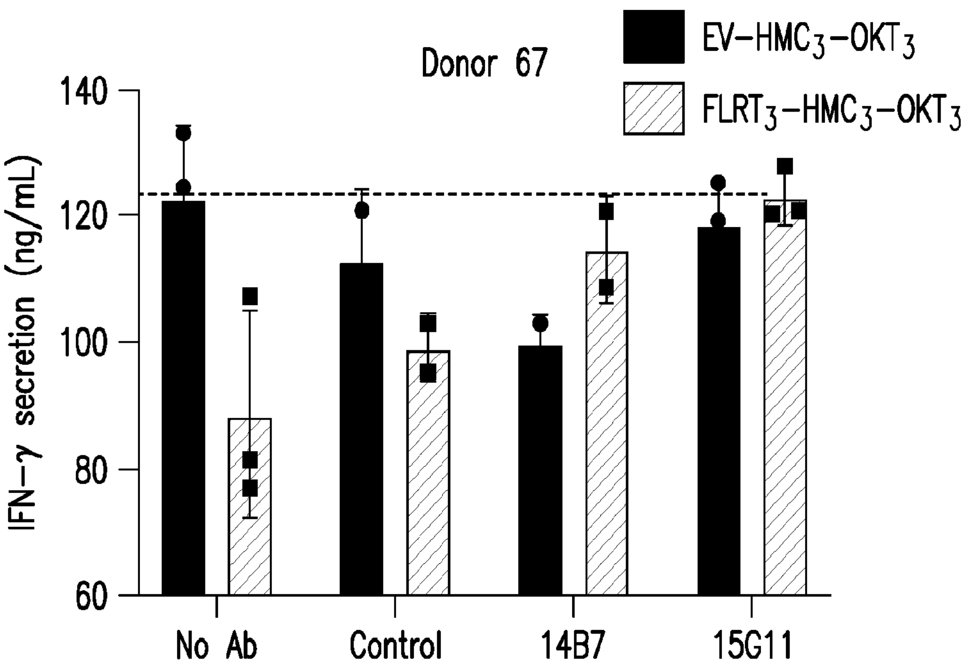

Total PBMCs from two different donors, Donor 68 (FIG. 23A) and Donor 67 (FIG. 23B) were activated in the presence of HMC3-OKT3 cells overexpressing FLRT3 or empty vector control, and with FLRT3 antibodies or control antibodies. Four days later, supernatants were collected and IFN-γ production was analyzed by ELISA. Antibody 14B7 reversed the FLRT3 mediated inhibitory effects on IFN-γ in both donors in comparison to the control antibody.

Figure 24A:
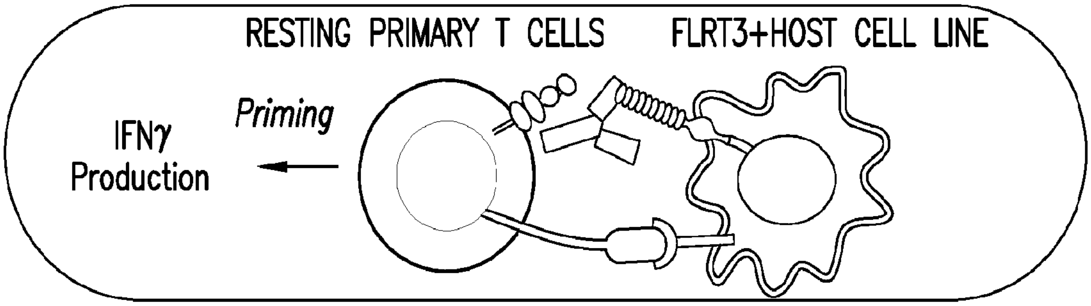
FIGS. 24A-24J show 14B7 promotes T cell priming and activation.
Figure 24B:
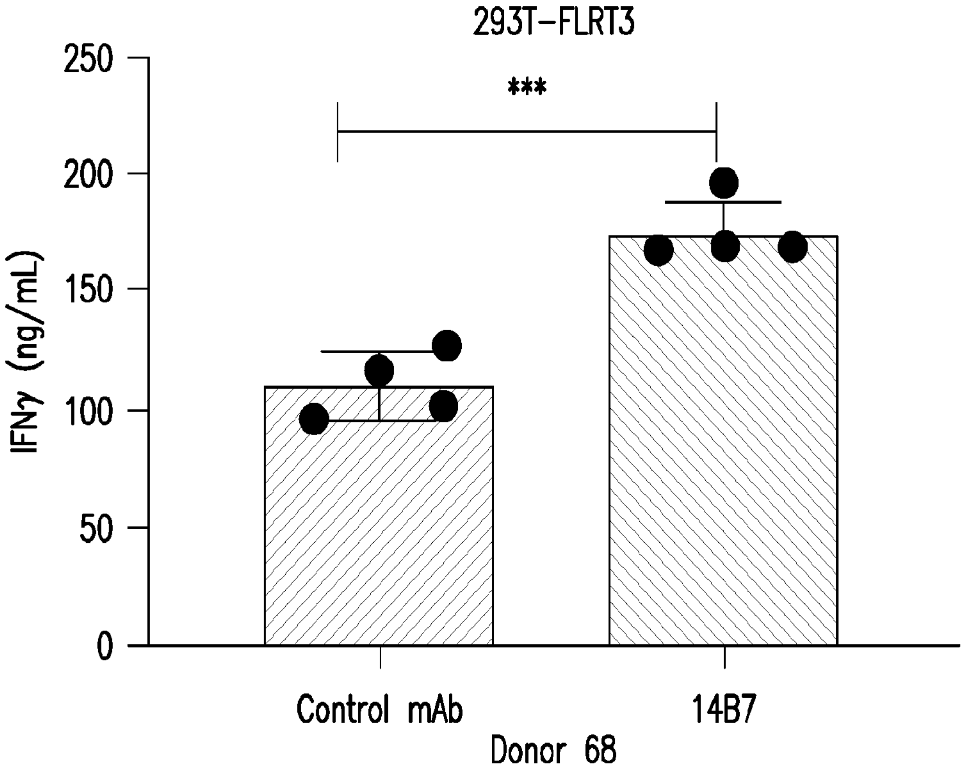
Figure 24C:
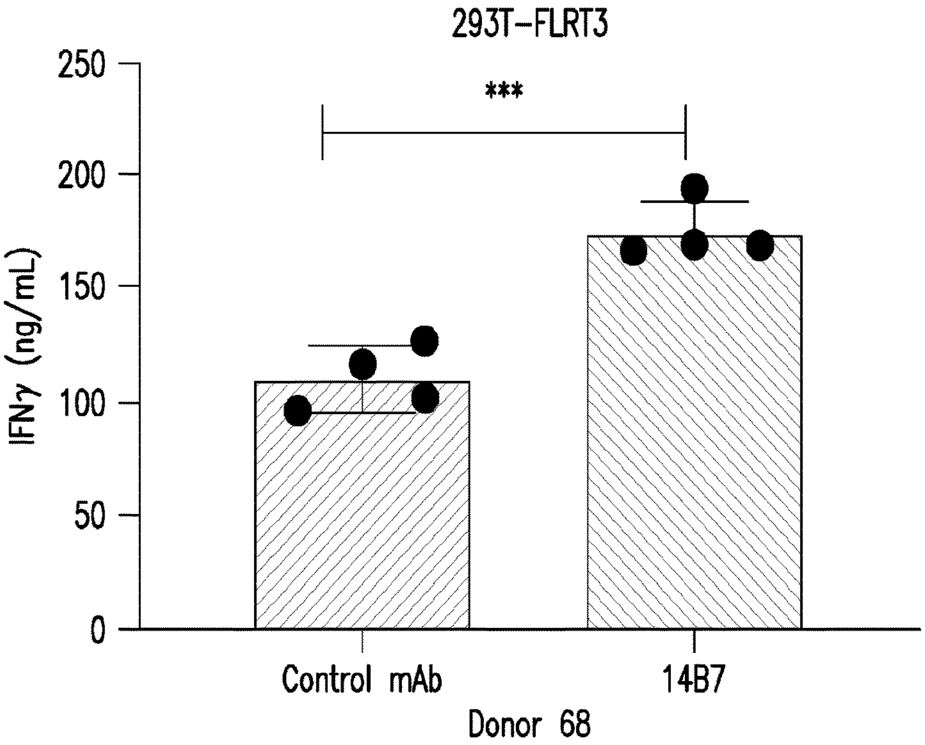
Figure 24D:
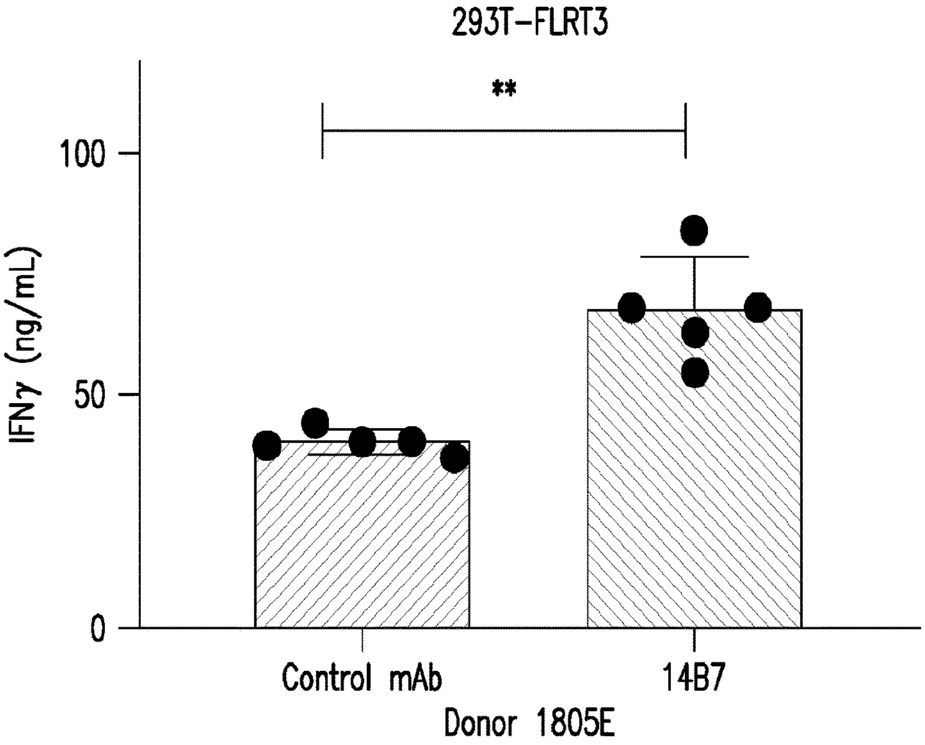
Figure 24E:
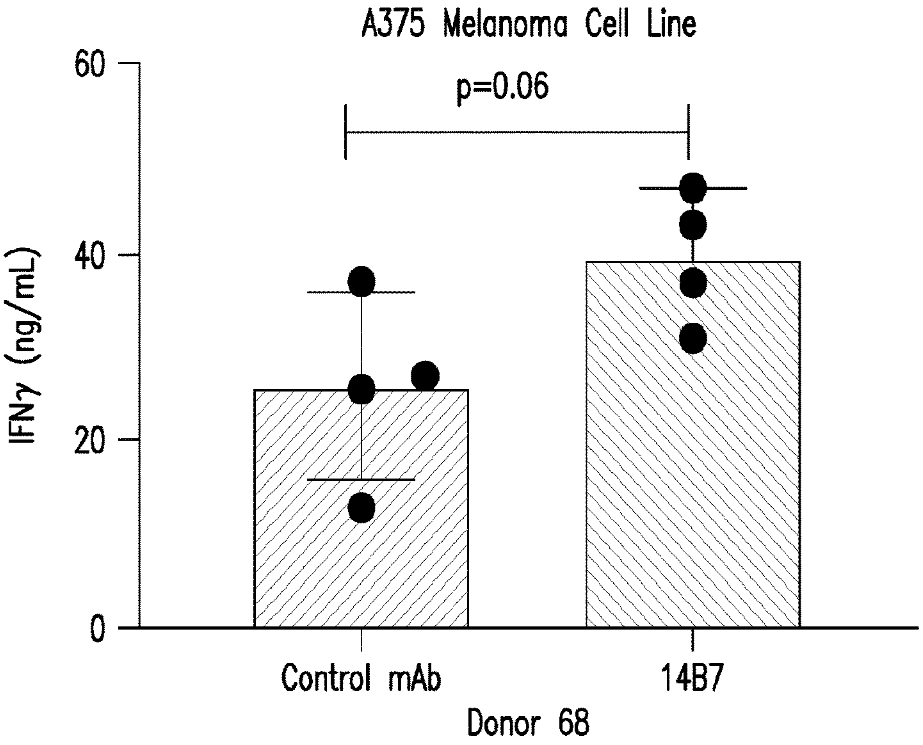
Figure 24F:
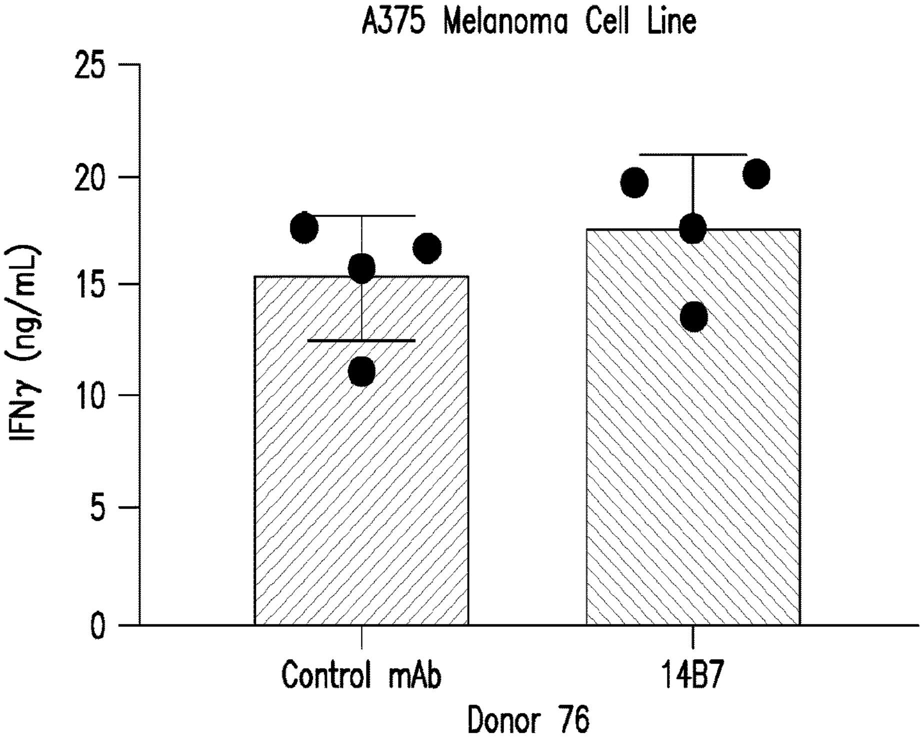
Figure 24G:
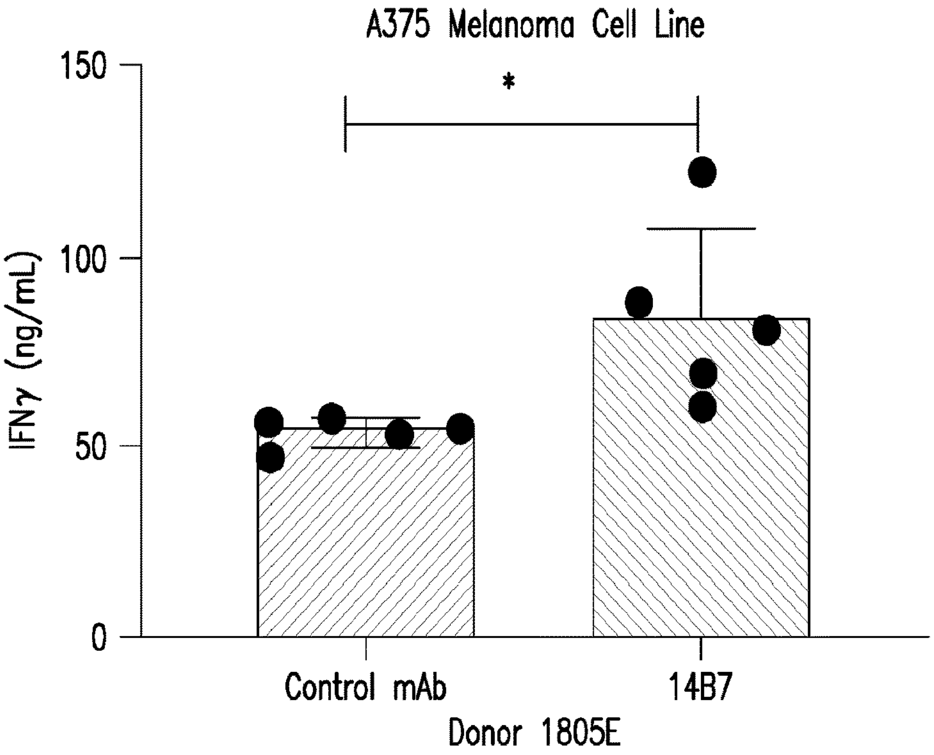
Figure 24H:
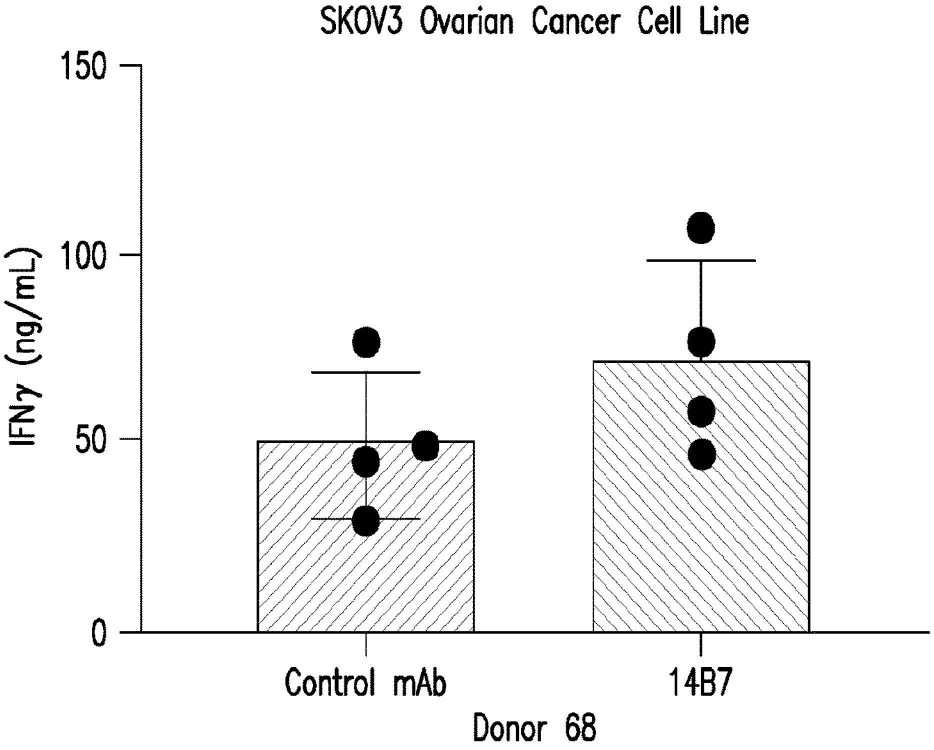
Figure 24I:
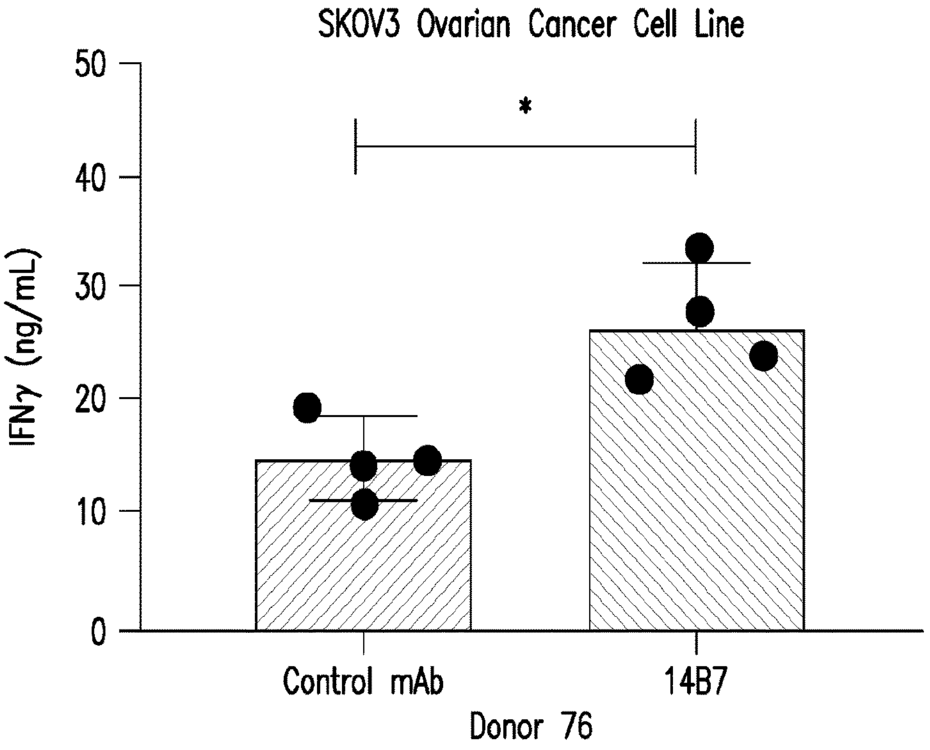
Figure 24J:
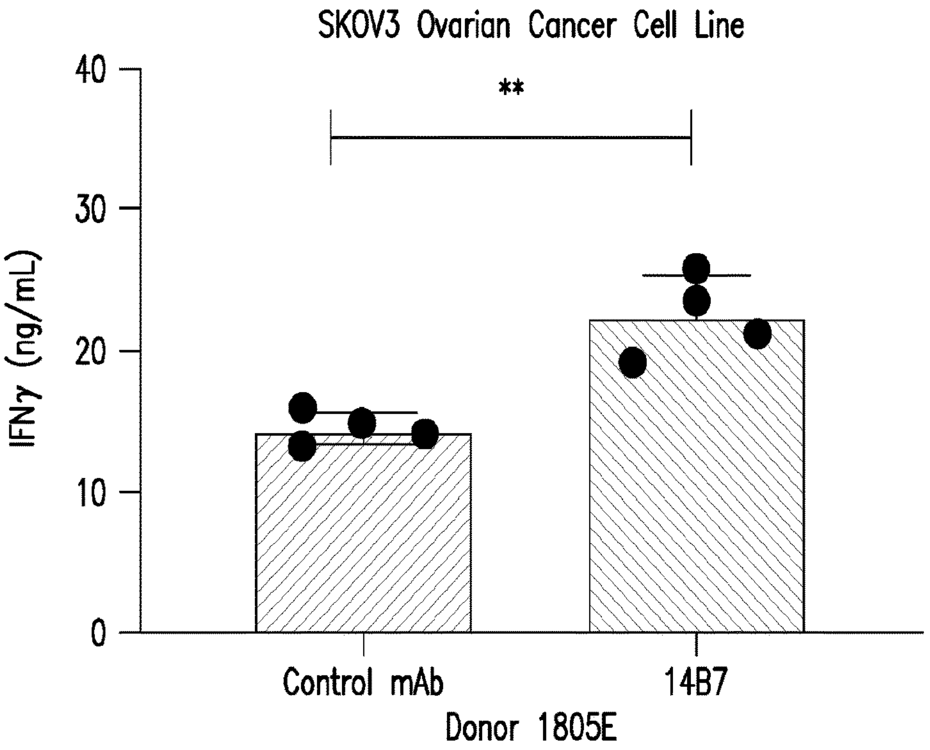

Additional donors PBMCs were co-cultured with FLRT3 overexpressing or endogenously expressing cell lines with FLRT3 antibody 14B7 or control to determine if blockade of FLRT3 robustly promoted T cell activity during T cell priming and activation (FIG. 24A). Donors 68, 76 and 1805E were culture with 293T-FLRT overexpressing cells (without OKT3) (FIG. 24B-24D), A549 lung cancer cells that endogenously express FLRT3 (FIG. 24E-24G), and SKOV3 ovarian cancer cells that endogenously express FLRT3 (FIG. 24H-24J). Following co-culture, supernatant levels of IFN-g were determined by ELISA. These results indicate that 14B7 blockade of FLRT3 enhanced T cell priming, activation, and IFN-g secretion.

Figure 25A:
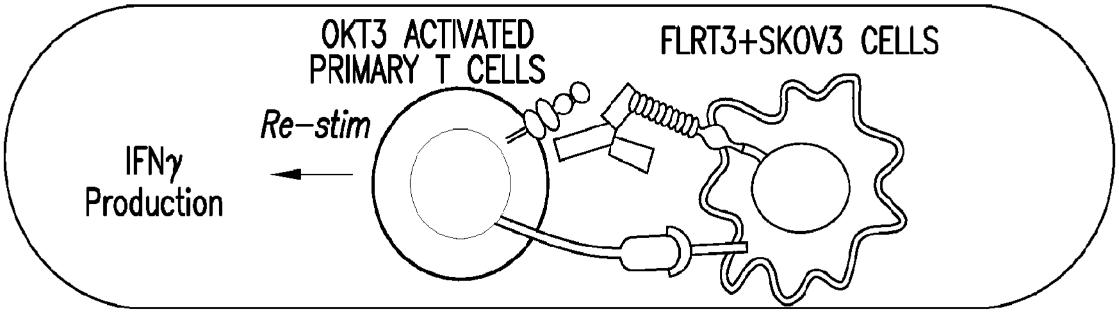
FIGS. 25A-25D show 14B7 promotes T cell effector function.
Figure 25B:
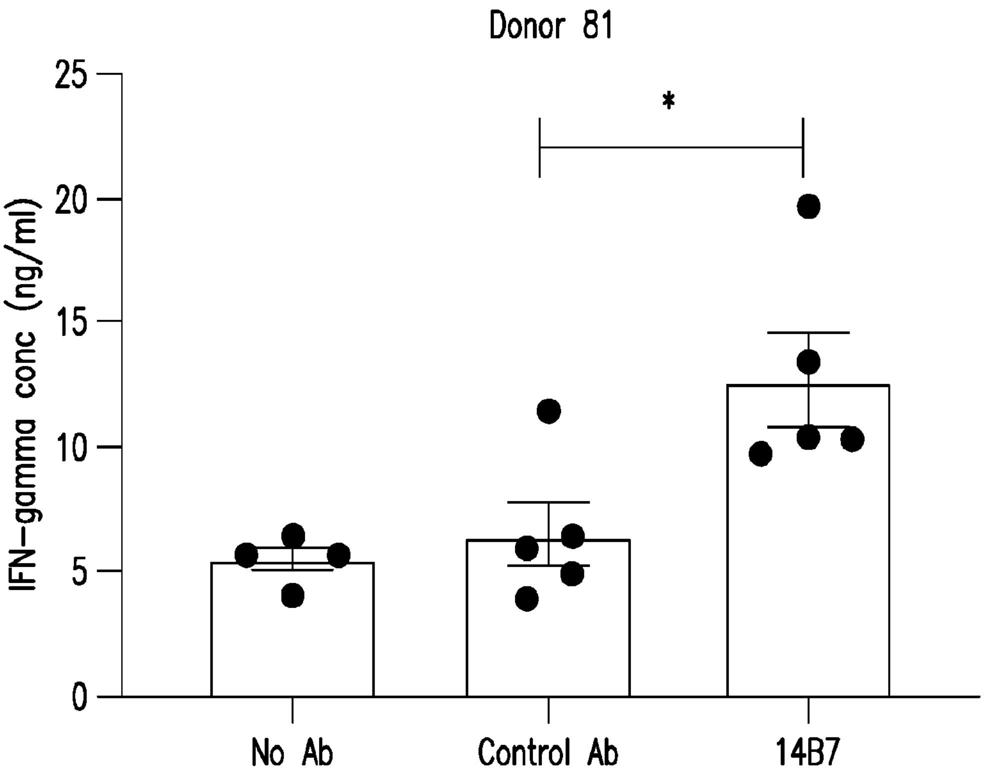
Figure 25C:
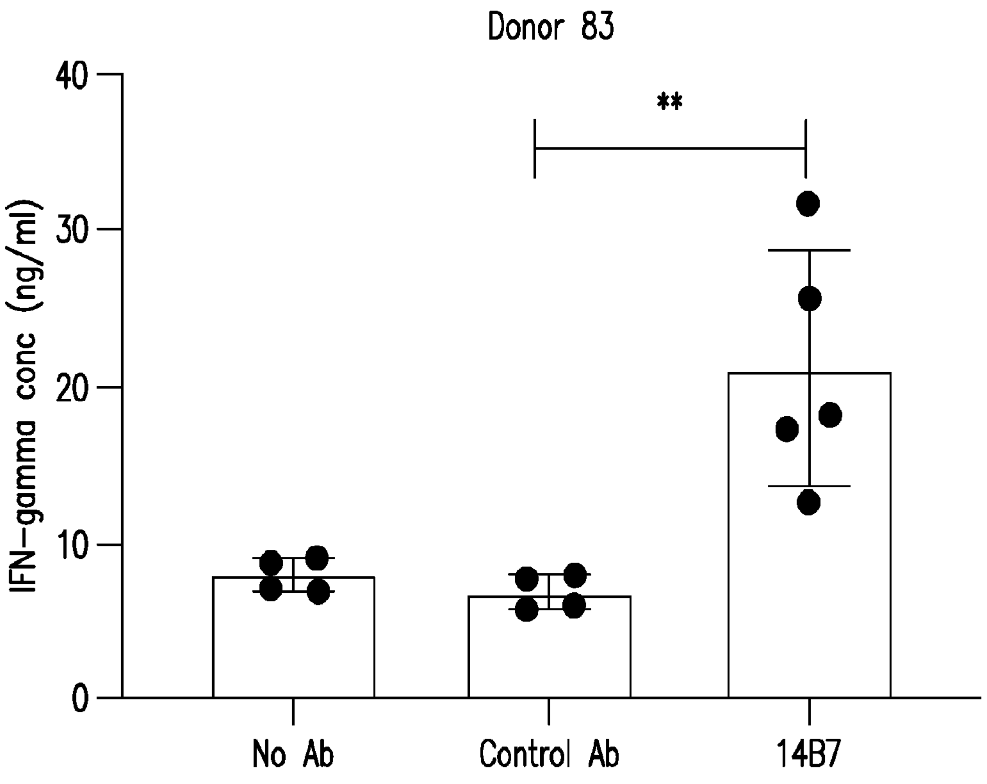
Figure 25D:
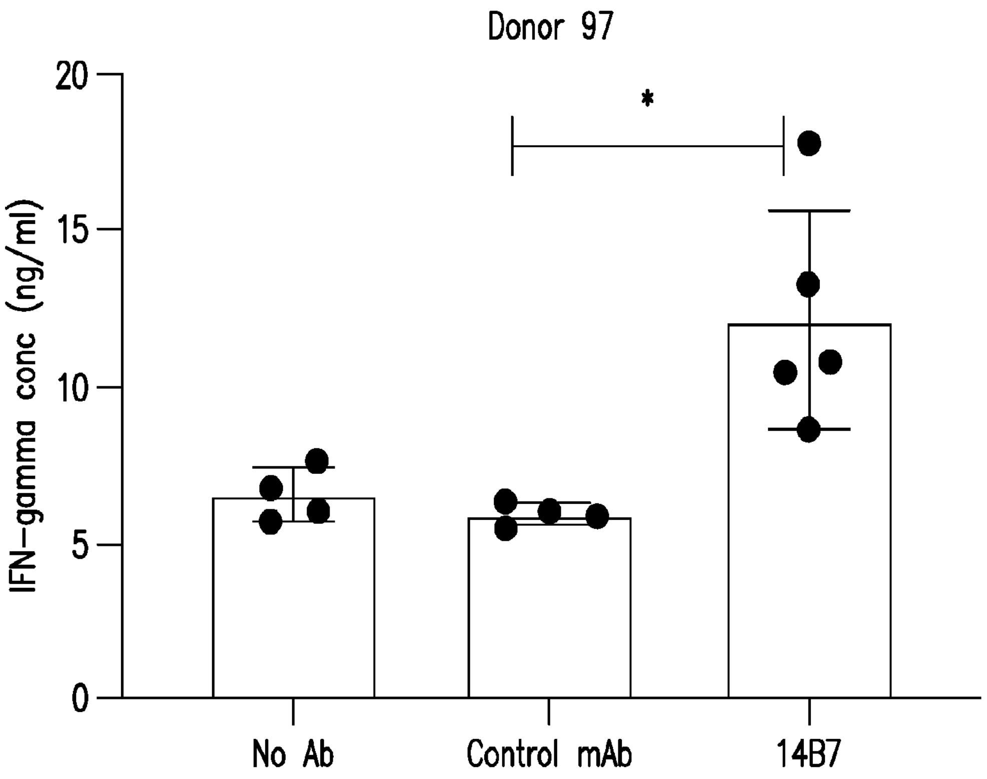

In a similar assay as above but modified to test whether FLRT3 blockade by 14B7 augments T cell activity during the effector phase, T cells were pre-activated, then re-stimulated with SKOV3 ovarian cancer cells that endogenously express FLRT3 in the presence of anti-CD3+anti-CD28 immunocult beads in the presence of 14B7 or control antibodies (FIG. 25A). Three different donors were evaluated and all three demonstrated an increased in IFN-g secretion in the presence of 14B7 in comparison to control antibody (FIG. 25B-25D).

Example 13: 14B7 Inhibits Growth of FLRT3+ Tumors and Cancer Cells Naturally Expressing FLRT3

Figure 26A:
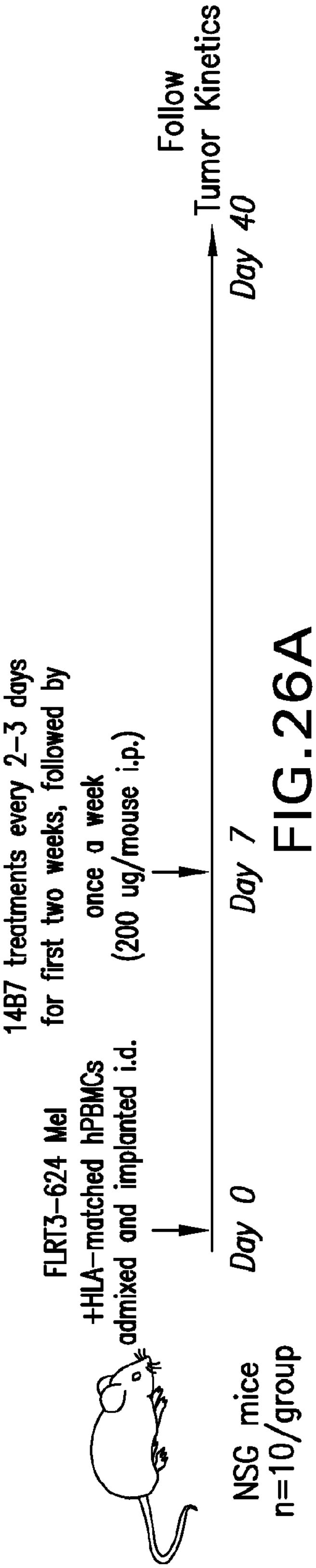
FIGS. 26A-26C show 14B7 inhibits growth of FLRT3+ 624-Mel tumors.
Figure 26B:
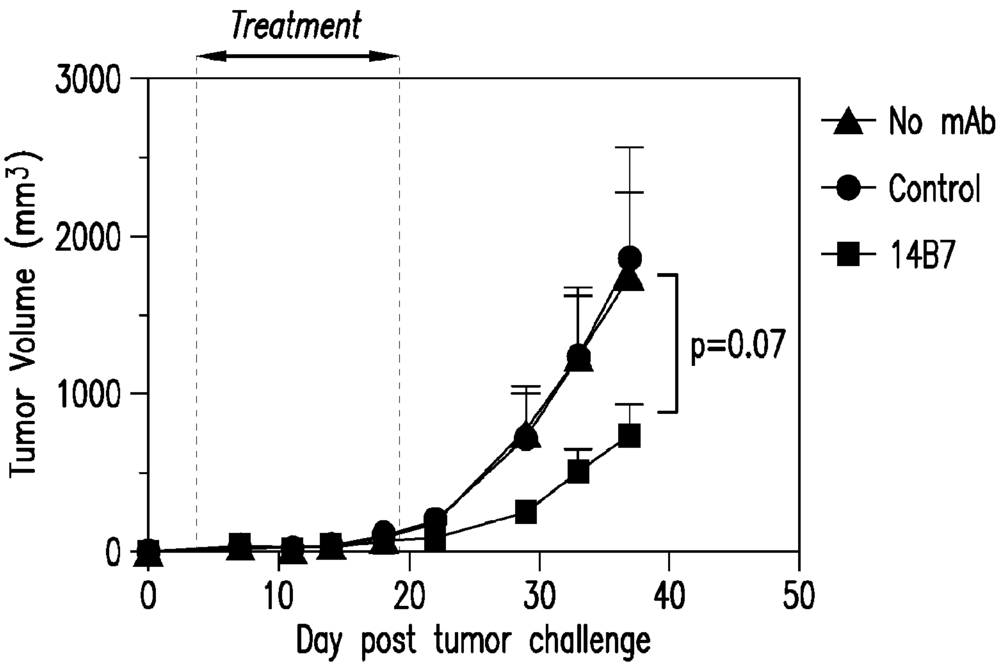
Figure 26C:
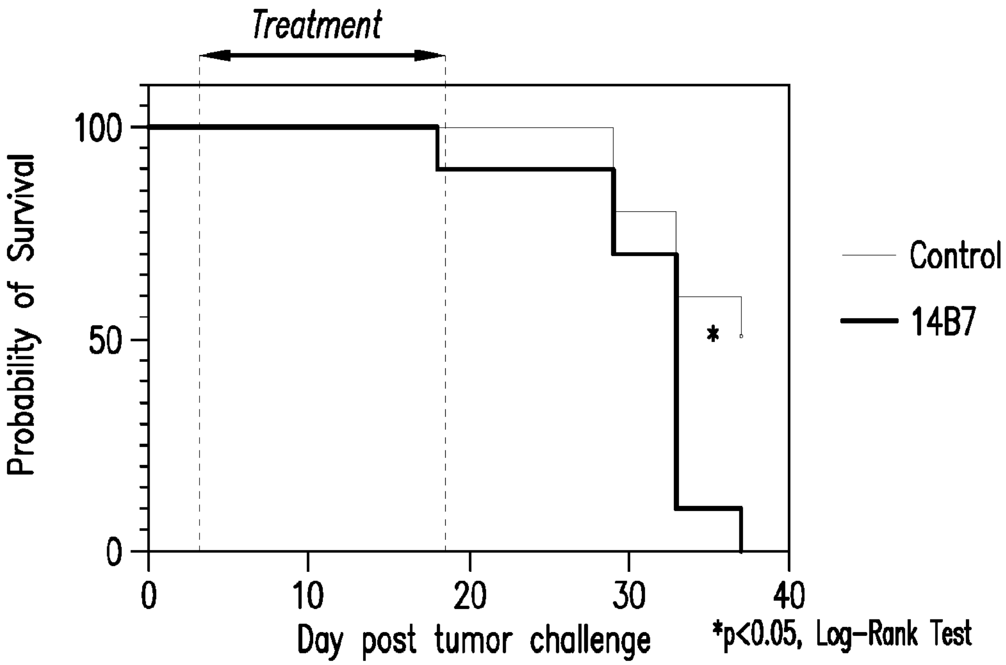
Figure 27A:
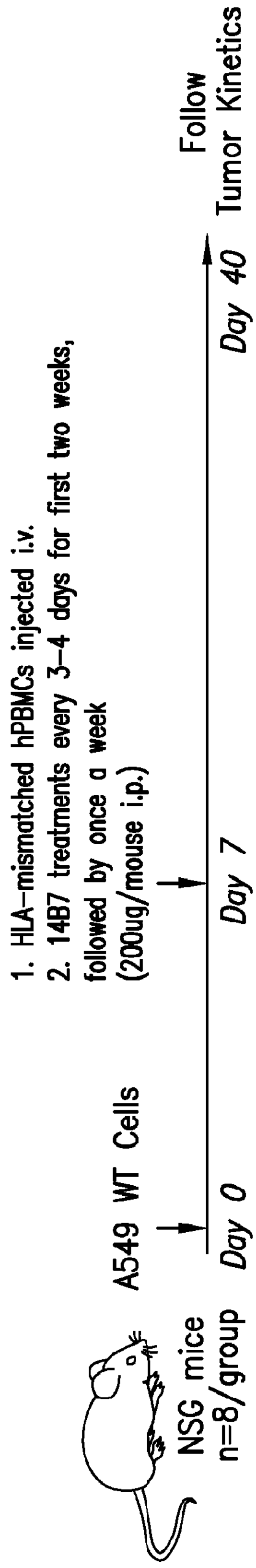
FIGS. 27A-27C shows 14B7 inhibits growth of A549 tumors that naturally express FLRT3.
Figure 27B:
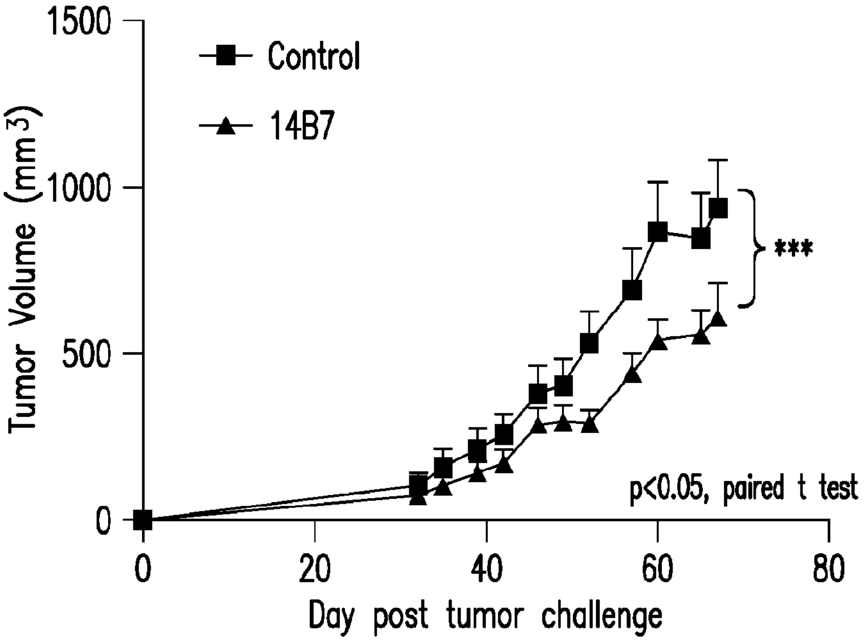
Figure 27C:
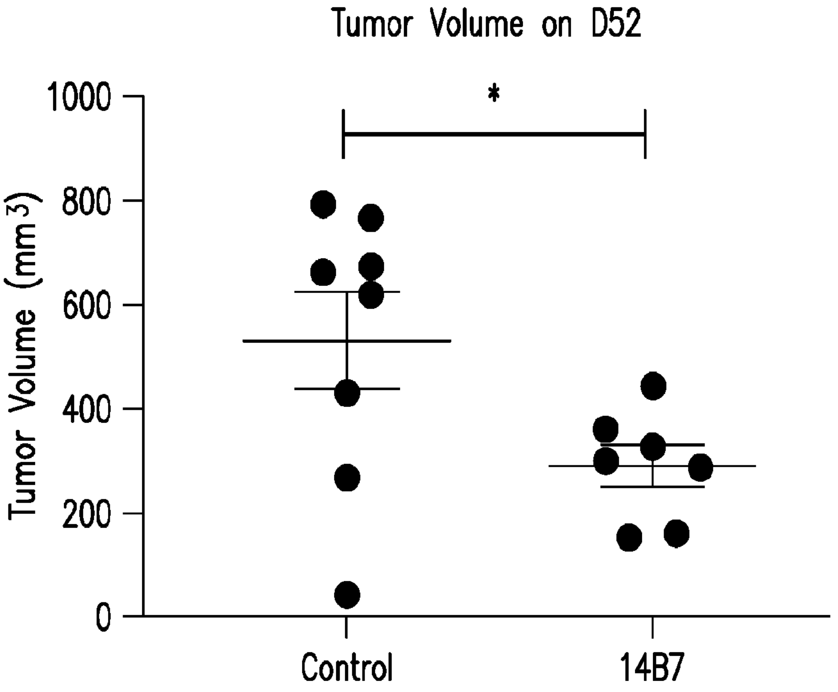
Figure 28A:
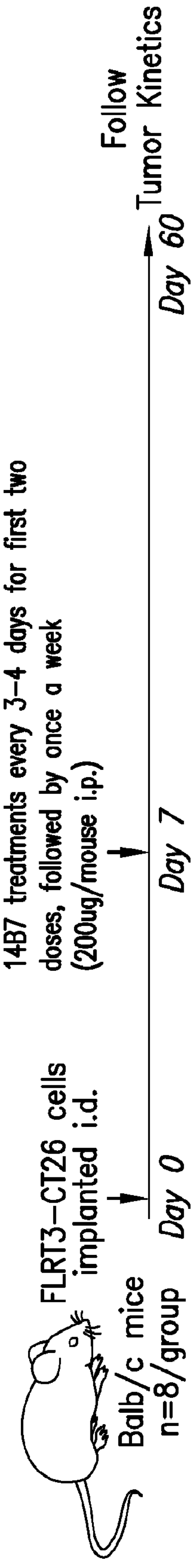
FIGS. 28A-28B shows 14B7 inhibits growth of CT26 tumors that are transduced to overexpress FLRT3.
Figure 28B:
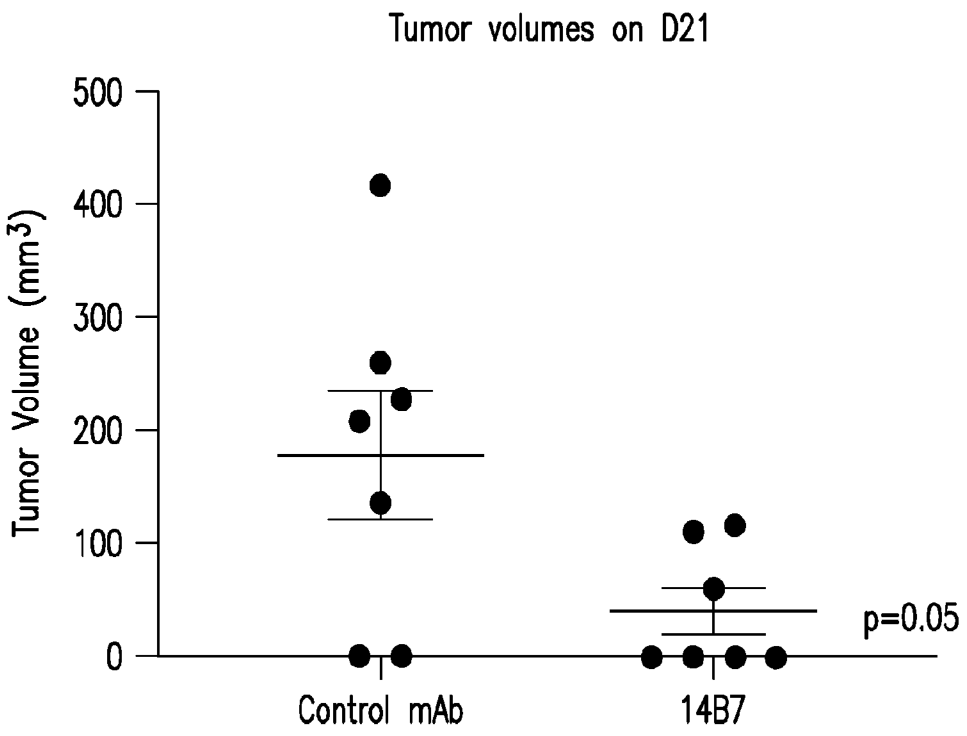

Tumor kinetics studies of NSG mice with FLRT3 over-expressing-624Mel-tumors and HLA-matched hPBMCs admixed and implanted were analyzed up to 40 days post treatment (FIG. 26A). Antibody 14B7 decreased tumor growth of FLRT3+ 624Mel tumors (FIG. 26B) and increased the probability of survival for the mice (FIG. 26C). Tumor kinetics studies of NSG mice with A549 WT cells that endogenously express FLRT3, plus HLA-mismatched human PBMCs administered 7 days later, showed that 14B7 decreased tumor growth in A549 tumors naturally expressing FLRT3 (FIGS. 27A-27C). A tumor growth study in syngeneic Balb/c mice that are fully immune competent were implanted with CT26 tumor cells that were transduced to overexpress FLRT3, and treated with 14B7 or control antibody (FIG. 28A). Tumor growth assessed on day 21 showed a significant reduction in CT26 tumor growth in the presence of 14B7 FLRT3 blockade (FIG. 28B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize or be able to ascertain using no more than routine experimentation, many equivalents to the specific embodiments of the invention described herein. Such equivalents are intended to be encompassed by the following claims.

We claim:

1. An anti-FLRT3 antibody or antigen-binding fragment thereof comprising:

a) a light chain variable region comprising SEQ ID NO: 17, and b) a heavy chain variable region comprising SEQ ID NO: 50 wherein the antibody of antigen-binding fragment thereof binds to FLRT3.

2. The antibody or antigen-binding fragment of claim 1, further comprising one or more constant domains from an immunoglobulin constant region.

3. The antibody or antigen-binding fragment of claim 1, wherein the antibody is humanized.

4. A method for treating a tumor in a subject in need thereof, comprising administering a therapeutically effective amount of the antibody or antigen-binding fragment thereof of claim 1 to the subject to reduce tumor burden in the subject.

5. The method of claim 4, wherein the tumor is a colorectal tumor, a lymphoma tumor, or an ovarian tumor.

6. A method for promoting an immune response in a subject in need thereof, comprising administering an effective amount of the antibody of claim 1 in an amount effective to promote an immune response in the subject.

7. The method of claim 6, wherein the promoted immune response retards tumor growth, inhibits tumor-mediated immune suppression, eliminates tumors, depletes or blocks the activity of tumor-associated macrophages (TAMs), decreases TAM-mediated immune suppression, reduces or reverses T cell suppression, increases T cell proliferation, or a combination thereof.

8. A method of treating an autoimmune disease in subject in need thereof, comprising administering an effective amount of the antibody or antigen-binding fragment of claim 1.

9. A pharmaceutical composition comprising the antibody or antigen-binding fragment thereof according to claim 1, and a pharmaceutically acceptable excipient.

* * * * *

```
                          SEQUENCE LISTING


<160> NUMBER OF SEQ ID NOS: 217

<210> SEQ ID NO 1
<211> LENGTH: 3830
<212> TYPE: DNA
<213> ORGANISM: Homo sapiens

<400> SEQUENCE: 1

cttcttcagc cactgcgagg tgaagcttta aacttcagac ttggaggtgg gctgtgtgca     60

gtaaactgga atgctctccc tcgctcactc ctcagtgtag gagtgatctg aagcaggaca    120

agctcagcct gcagctgccg tgggctttgt gtggactgga cgcagagctt gggagacggg    180

ggagggctat tactccaatt cactgtcaat ggaattacag ctatagcggc agtgtatata    240

ggattgcttt ttctcgtctt cctgggttct gaagtaacgg aagctacctt gtataaagac    300

ctcaacactg ctgaccatga tcagcgcagc ctggagcatc ttcctcatcg ggactaaaat    360

tgggctgttc cttcaagtag cacctctatc agttatggct aaatcctgtc catctgtgtg    420

tcgctgcgat gcgggtttca tttactgtaa tgatcgcttt ctgacatcca ttccaacagg    480

aataccagag gatgctacaa ctctctacct tcagaacaac caaataaata atgctgggat    540

tccttcagat ttgaaaaact tgctgaaagt agaaagaata tacctatacc acaacagttt    600

agatgaattt cctaccaacc tcccaaagta tgtaaaagag ttacatttgc aagaaaataa    660

cataaggact atcacttatg attcactttc aaaaattccc tatctggaag aattacattt    720

agatgacaac tctgtctctg cagttagcat agaagaggga gcattccgag acagcaacta    780

tctccgactg cttttcctgt cccgtaatca ccttagcaca attccctggg gtttgcccag    840

gactatagaa gaactacgct tggatgataa tcgcatatcc actatttcat caccatctct    900

tcaaggtctc actagtctaa aacgcctggt tctagatgga aacctgttga acaatcatgg    960

tttaggtgac aaagttttct tcaacctagt taatttgaca gagctgtccc tggtgcggaa   1020

ttccctgact gctgcaccag taaaccttcc aggcacaaac ctgaggaagc tttatcttca   1080

agataaccac atcaatcggg tgcccccaaa tgctttttct tatctaaggc agctctatcg   1140

actggatatg tccaataata acctaagtaa tttacctcag ggtatctttg atgatttgga   1200

caatataaca caactgattc ttcgcaacaa tccctggtat tgcgggtgca agatgaaatg   1260

ggtacgtgac tggttacaat cactacctgt gaaggtcaac gtgcgtgggc tcatgtgcca   1320
```

```
agccccagaa aaggttcgtg ggatggctat taaggatctc aatgcagaac tgtttgattg   1380
taaggacagt gggattgtaa gcaccattca gataaccact gcaataccca acacagtgta   1440
tcctgcccaa ggacagtggc cagctccagt gaccaaacag ccagatatta agaaccccaa   1500
gctcactaag gatcaccaaa ccacagggag tccctcaaga aaaacaatta caattactgt   1560
gaagtctgtc acctctgata ccattcatat ctcttggaaa cttgctctac ctatgactgc   1620
tttgagactc agctggctta aactgggcca tagcccggca tttggatcta taacagaaac   1680
aattgtaaca ggggaacgca gtgagtactt ggtcacagcc ctggagcctg attcacccta   1740
taaagtatgc atggttccca tggaaaccag caacctctac ctatttgatg aaactcctgt   1800
ttgtattgag actgaaactg cacccttcg aatgtacaac cctacaacca ccctcaatcg    1860
agagcaagag aaagaacctt acaaaaaccc caatttacct ttggctgcca tcattggtgg   1920
ggctgtggcc ctggttacca ttgcccttct tgctttagtg tgttggtatg ttcataggaa   1980
tggatcgctc ttctcaagga actgtgcata tagcaaaggg aggagaagaa aggatgacta   2040
tgcagaagct ggcactaaga aggacaactc tatcctggaa atcagggaaa cttcttttca   2100
gatgttacca ataagcaatg aacccatctc gaaggaggag tttgtaatac acaccatatt   2160
tcctcctaat ggaatgaatc tgtacaaaaa caatcacagt gaaagcagta gtaaccgaag   2220
ctacagagac agtggtattc cagactcaga tcactcacac tcatgatgct gaaggactca   2280
cagcagactt gtgttttggg ttttttaaac ctaagggagg tgatggtagg aaccctgttc   2340
tactgcaaaa cactggaaaa agagactgaa aaaaagcaat gtactgtaca tttgccatat   2400
aatttatatt taagaacttt ttattaaaag tttcaaattt caggttactg ctgcgattga   2460
tgtagtggag atgcctgaac acaattctat attttagtat tttttagtaa tttgtactgt   2520
attttccttg caaatattgg agttataaac catttacttt gtgttctact gagtaagatg   2580
acttgttgac tgtgaaagtg aattttcttg ctgtgtcgaa caatcaggac tgcattcata   2640
tgagatcctt gtagtataag cacaggccat tttcacttt ggtattaata aaatgtaaaa    2700
aaaaaaaact ggctgaatgg ctgaatgaga taaaatttaa ttttaaaaaa tggttatgaa   2760
ataatgttcc aattattaaa tttgtattat cccagtggta ttcaataaat caaaatgtgt   2820
gaagtaatgg gcaatatcaa acttcctgca tatctccatt tttgctctag gcaaattaat   2880
tatccttaaa aaagttaagc atatcttctg aactgaatac atcagctggc ataaaaggag   2940
catgaagtct gttaaagcca ttgtcagcaa agctttgaaa ataaaggact tcacaaaaac   3000
ggtaatgtaa atgtgcttcc aagttggggg gaaaatgtgt acttaggaaa acatggaaac   3060
ttagacttgt atagtgtaat gaacacaaat accaaaactg cattttggtt ttgcctatac   3120
catcctgatt tttgaaaagt gaattataaa cacaaaattg ttagtgttta tgatgttttt   3180
atcataaagg atgtcagaga aactttatgc atattaaaaa tgtaatgtaa ttataagcga   3240
ttcccctcaa caatccagag aaagtagttc tttaaataag agataattta aagaaaaata   3300
aatactagac atcaaattta gatctggttt atgtcaaagg ttttaacact gtacataaat   3360
gttcaattta cttttacaaa gatcaagaat actgcccatt actgtcacaa ttttccagat   3420
attatataat gaactcgtaa tgtaacattt ccttctagct tcctactgaa ttgtgagctg   3480
ttacttgttg aaaaaccata tcacttttct gttgccatga ttttttttt ttcaacaaaa    3540
aaccaaagtg cattgtacgc cctttggcca gtcttgtatg tgccttgatc caacgctaca   3600
tgtattcagc ttttaaaact ccacaaattt ttcatactcc ttaaatatga aaaattatgg   3660
```

```
tcttattgct gaataaaact tttaaaaagt acagaataat tgtgcttgct ttttcaggat   3720

tgtgttacta tcactaagta gcaaattgcc cagcacatta gtcctaaacg tcccatgtat   3780

ttttctaggc ataaaaataa aagttggcta aaaattttaa aaaatcaaca              3830


<210> SEQ ID NO 2
<211> LENGTH: 649
<212> TYPE: PRT
<213> ORGANISM: Homo sapiens

<400> SEQUENCE: 2

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350
```

```
Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Leu Ala Ala Ile Ile Gly Gly Ala Val Ala Leu Val Thr Ile Ala Leu
    530                 535                 540

Leu Ala Leu Val Cys Trp Tyr Val His Arg Asn Gly Ser Leu Phe Ser
545                 550                 555                 560

Arg Asn Cys Ala Tyr Ser Lys Gly Arg Arg Arg Lys Asp Asp Tyr Ala
                565                 570                 575

Glu Ala Gly Thr Lys Lys Asp Asn Ser Ile Leu Glu Ile Arg Glu Thr
            580                 585                 590

Ser Phe Gln Met Leu Pro Ile Ser Asn Glu Pro Ile Ser Lys Glu Glu
        595                 600                 605

Phe Val Ile His Thr Ile Phe Pro Pro Asn Gly Met Asn Leu Tyr Lys
    610                 615                 620

Asn Asn His Ser Glu Ser Ser Ser Asn Arg Ser Tyr Arg Asp Ser Gly
625                 630                 635                 640

Ile Pro Asp Ser Asp His Ser His Ser
                645


<210> SEQ ID NO 3
<211> LENGTH: 500
<212> TYPE: PRT
<213> ORGANISM: Homo sapiens

<400> SEQUENCE: 3

Lys Ser Cys Pro Ser Val Cys Arg Cys Asp Ala Gly Phe Ile Tyr Cys
1               5                   10                  15

Asn Asp Arg Phe Leu Thr Ser Ile Pro Thr Gly Ile Pro Glu Asp Ala
            20                  25                  30

Thr Thr Leu Tyr Leu Gln Asn Asn Gln Ile Asn Asn Ala Gly Ile Pro
        35                  40                  45

Ser Asp Leu Lys Asn Leu Leu Lys Val Glu Arg Ile Tyr Leu Tyr His
    50                  55                  60

Asn Ser Leu Asp Glu Phe Pro Thr Asn Leu Pro Lys Tyr Val Lys Glu
```

-continued

```
65                  70                  75                  80

Leu His Leu Gln Glu Asn Asn Ile Arg Thr Ile Thr Tyr Asp Ser Leu
                85                  90                  95

Ser Lys Ile Pro Tyr Leu Glu Glu Leu His Leu Asp Asp Asn Ser Val
            100                 105                 110

Ser Ala Val Ser Ile Glu Glu Gly Ala Phe Arg Asp Ser Asn Tyr Leu
        115                 120                 125

Arg Leu Leu Phe Leu Ser Arg Asn His Leu Ser Thr Ile Pro Trp Gly
    130                 135                 140

Leu Pro Arg Thr Ile Glu Glu Leu Arg Leu Asp Asp Asn Arg Ile Ser
145                 150                 155                 160

Thr Ile Ser Ser Pro Ser Leu Gln Gly Leu Thr Ser Leu Lys Arg Leu
                165                 170                 175

Val Leu Asp Gly Asn Leu Leu Asn Asn His Gly Leu Gly Asp Lys Val
            180                 185                 190

Phe Phe Asn Leu Val Asn Leu Thr Glu Leu Ser Leu Val Arg Asn Ser
        195                 200                 205

Leu Thr Ala Ala Pro Val Asn Leu Pro Gly Thr Asn Leu Arg Lys Leu
    210                 215                 220

Tyr Leu Gln Asp Asn His Ile Asn Arg Val Pro Pro Asn Ala Phe Ser
225                 230                 235                 240

Tyr Leu Arg Gln Leu Tyr Arg Leu Asp Met Ser Asn Asn Asn Leu Ser
                245                 250                 255

Asn Leu Pro Gln Gly Ile Phe Asp Asp Leu Asp Asn Ile Thr Gln Leu
            260                 265                 270

Ile Leu Arg Asn Asn Pro Trp Tyr Cys Gly Cys Lys Met Lys Trp Val
        275                 280                 285

Arg Asp Trp Leu Gln Ser Leu Pro Val Lys Val Asn Val Arg Gly Leu
    290                 295                 300

Met Cys Gln Ala Pro Glu Lys Val Arg Gly Met Ala Ile Lys Asp Leu
305                 310                 315                 320

Asn Ala Glu Leu Phe Asp Cys Lys Asp Ser Gly Ile Val Ser Thr Ile
                325                 330                 335

Gln Ile Thr Thr Ala Ile Pro Asn Thr Val Tyr Pro Ala Gln Gly Gln
            340                 345                 350

Trp Pro Ala Pro Val Thr Lys Gln Pro Asp Ile Lys Asn Pro Lys Leu
        355                 360                 365

Thr Lys Asp His Gln Thr Thr Gly Ser Pro Ser Arg Lys Thr Ile Thr
    370                 375                 380

Ile Thr Val Lys Ser Val Thr Ser Asp Thr Ile His Ile Ser Trp Lys
385                 390                 395                 400

Leu Ala Leu Pro Met Thr Ala Leu Arg Leu Ser Trp Leu Lys Leu Gly
                405                 410                 415

His Ser Pro Ala Phe Gly Ser Ile Thr Glu Thr Ile Val Thr Gly Glu
            420                 425                 430

Arg Ser Glu Tyr Leu Val Thr Ala Leu Glu Pro Asp Ser Pro Tyr Lys
        435                 440                 445

Val Cys Met Val Pro Met Glu Thr Ser Asn Leu Tyr Leu Phe Asp Glu
    450                 455                 460

Thr Pro Val Cys Ile Glu Thr Glu Thr Ala Pro Leu Arg Met Tyr Asn
465                 470                 475                 480

Pro Thr Thr Thr Leu Asn Arg Glu Gln Glu Lys Glu Pro Tyr Lys Asn
                485                 490                 495
```

```
Pro Asn Leu Pro
            500


<210> SEQ ID NO 4
<211> LENGTH: 649
<212> TYPE: PRT
<213> ORGANISM: Mus musculus

<400> SEQUENCE: 4

Met Ile Ser Pro Ala Trp Ser Leu Phe Leu Ile Gly Thr Lys Ile Gly
1               5                   10                  15

Leu Phe Phe Gln Val Ala Pro Leu Ser Val Val Ala Lys Ser Cys Pro
            20                  25                  30

Ser Val Cys Arg Cys Asp Ala Gly Phe Ile Tyr Cys Asn Asp Arg Ser
        35                  40                  45

Leu Thr Ser Ile Pro Val Gly Ile Pro Glu Asp Ala Thr Thr Leu Tyr
    50                  55                  60

Leu Gln Asn Asn Gln Ile Asn Asn Val Gly Ile Pro Ser Asp Leu Lys
65                  70                  75                  80

Asn Leu Leu Lys Val Gln Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Gly Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu His Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Ser Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Ser Ala Glu Leu
            340                 345                 350

Phe Asp Cys Lys Asp Ser Gly Ile Val Ser Thr Ile Gln Ile Thr Thr
```

```
        355                 360                 365

Ala Ile Pro Asn Thr Ala Tyr Pro Ala Gln Gly Gln Trp Pro Ala Pro
    370                 375                 380

Val Thr Lys Gln Pro Asp Ile Lys Asn Pro Lys Leu Ile Lys Asp Gln
385                 390                 395                 400

Arg Thr Thr Gly Ser Pro Ser Arg Lys Thr Ile Leu Ile Thr Val Lys
                405                 410                 415

Ser Val Thr Pro Asp Thr Ile His Ile Ser Trp Arg Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Glu Ser Pro Tyr Arg Val Cys Met Val
465                 470                 475                 480

Pro Met Glu Thr Ser Asn Leu Tyr Leu Phe Asp Glu Thr Pro Val Cys
                485                 490                 495

Ile Glu Thr Gln Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Leu Ala Ala Ile Ile Gly Gly Ala Val Ala Leu Val Ser Ile Ala Leu
    530                 535                 540

Leu Ala Leu Val Cys Trp Tyr Val His Arg Asn Gly Ser Leu Phe Ser
545                 550                 555                 560

Arg Asn Cys Ala Tyr Ser Lys Gly Arg Arg Arg Lys Asp Asp Tyr Ala
                565                 570                 575

Glu Ala Gly Thr Lys Lys Asp Asn Ser Ile Leu Glu Ile Arg Glu Thr
            580                 585                 590

Ser Phe Gln Met Leu Pro Ile Ser Asn Glu Pro Ile Ser Lys Glu Glu
        595                 600                 605

Phe Val Ile His Thr Ile Phe Pro Pro Asn Gly Met Asn Leu Tyr Lys
    610                 615                 620

Asn Asn Leu Ser Glu Ser Ser Ser Asn Arg Ser Tyr Arg Asp Ser Gly
625                 630                 635                 640

Ile Pro Asp Ser Asp His Ser His Ser
                645


<210> SEQ ID NO 5
<211> LENGTH: 500
<212> TYPE: PRT
<213> ORGANISM: Mus musculus

<400> SEQUENCE: 5

Lys Ser Cys Pro Ser Val Cys Arg Cys Asp Ala Gly Phe Ile Tyr Cys
1               5                   10                  15

Asn Asp Arg Ser Leu Thr Ser Ile Pro Val Gly Ile Pro Glu Asp Ala
            20                  25                  30

Thr Thr Leu Tyr Leu Gln Asn Asn Gln Ile Asn Asn Val Gly Ile Pro
        35                  40                  45

Ser Asp Leu Lys Asn Leu Leu Lys Val Gln Arg Ile Tyr Leu Tyr His
    50                  55                  60

Asn Ser Leu Asp Glu Phe Pro Thr Asn Leu Pro Lys Tyr Val Lys Glu
65                  70                  75                  80
```

```
Leu His Leu Gln Glu Asn Asn Ile Arg Thr Ile Thr Tyr Asp Ser Leu
                85                  90                  95

Ser Lys Ile Pro Tyr Leu Glu Glu Leu His Leu Asp Asp Asn Ser Val
            100                 105                 110

Ser Ala Val Ser Ile Glu Glu Gly Ala Phe Arg Asp Ser Asn Tyr Leu
        115                 120                 125

Arg Leu Leu Phe Leu Ser Arg Asn His Leu Ser Thr Ile Pro Gly Gly
    130                 135                 140

Leu Pro Arg Thr Ile Glu Glu Leu Arg Leu Asp Asp Asn Arg Ile Ser
145                 150                 155                 160

Thr Ile Ser Ser Pro Ser Leu His Gly Leu Thr Ser Leu Lys Arg Leu
                165                 170                 175

Val Leu Asp Gly Asn Leu Leu Asn Asn His Gly Leu Gly Asp Lys Val
            180                 185                 190

Phe Phe Asn Leu Val Asn Leu Thr Glu Leu Ser Leu Val Arg Asn Ser
        195                 200                 205

Leu Thr Ala Ala Pro Val Asn Leu Pro Gly Thr Ser Leu Arg Lys Leu
    210                 215                 220

Tyr Leu Gln Asp Asn His Ile Asn Arg Val Pro Pro Asn Ala Phe Ser
225                 230                 235                 240

Tyr Leu Arg Gln Leu Tyr Arg Leu Asp Met Ser Asn Asn Asn Leu Ser
                245                 250                 255

Asn Leu Pro Gln Gly Ile Phe Asp Asp Leu Asp Asn Ile Thr Gln Leu
            260                 265                 270

Ile Leu Arg Asn Asn Pro Trp Tyr Cys Gly Cys Lys Met Lys Trp Val
        275                 280                 285

Arg Asp Trp Leu Gln Ser Leu Pro Val Lys Val Asn Val Arg Gly Leu
    290                 295                 300

Met Cys Gln Ala Pro Glu Lys Val Arg Gly Met Ala Ile Lys Asp Leu
305                 310                 315                 320

Ser Ala Glu Leu Phe Asp Cys Lys Asp Ser Gly Ile Val Ser Thr Ile
                325                 330                 335

Gln Ile Thr Thr Ala Ile Pro Asn Thr Ala Tyr Pro Ala Gln Gly Gln
            340                 345                 350

Trp Pro Ala Pro Val Thr Lys Gln Pro Asp Ile Lys Asn Pro Lys Leu
        355                 360                 365

Ile Lys Asp Gln Arg Thr Thr Gly Ser Pro Ser Arg Lys Thr Ile Leu
    370                 375                 380

Ile Thr Val Lys Ser Val Thr Pro Asp Thr Ile His Ile Ser Trp Arg
385                 390                 395                 400

Leu Ala Leu Pro Met Thr Ala Leu Arg Leu Ser Trp Leu Lys Leu Gly
                405                 410                 415

His Ser Pro Ala Phe Gly Ser Ile Thr Glu Thr Ile Val Thr Gly Glu
            420                 425                 430

Arg Ser Glu Tyr Leu Val Thr Ala Leu Glu Pro Glu Ser Pro Tyr Arg
        435                 440                 445

Val Cys Met Val Pro Met Glu Thr Ser Asn Leu Tyr Leu Phe Asp Glu
    450                 455                 460

Thr Pro Val Cys Ile Glu Thr Gln Thr Ala Pro Leu Arg Met Tyr Asn
465                 470                 475                 480

Pro Thr Thr Thr Leu Asn Arg Glu Gln Glu Lys Glu Pro Tyr Lys Asn
                485                 490                 495

Pro Asn Leu Pro
```

500

<210> SEQ ID NO 6
<211> LENGTH: 1651
<212> TYPE: PRT
<213> ORGANISM: Homo sapiens

<400> SEQUENCE: 6

Met Lys Trp Lys His Val Pro Phe Leu Val Met Ile Ser Leu Leu Ser
1 5 10 15

Leu Ser Pro Asn His Leu Phe Leu Ala Gln Leu Ile Pro Asp Pro Glu
20 25 30

Asp Val Glu Arg Gly Asn Asp His Gly Thr Pro Ile Pro Thr Ser Asp
35 40 45

Asn Asp Asp Asn Ser Leu Gly Tyr Thr Gly Ser Arg Leu Arg Gln Glu
50 55 60

Asp Phe Pro Pro Arg Ile Val Glu His Pro Ser Asp Leu Ile Val Ser
65 70 75 80

Lys Gly Glu Pro Ala Thr Leu Asn Cys Lys Ala Glu Gly Arg Pro Thr
85 90 95

Pro Thr Ile Glu Trp Tyr Lys Gly Gly Glu Arg Val Glu Thr Asp Lys
100 105 110

Asp Asp Pro Arg Ser His Arg Met Leu Leu Pro Ser Gly Ser Leu Phe
115 120 125

Phe Leu Arg Ile Val His Gly Arg Lys Ser Arg Pro Asp Glu Gly Val
130 135 140

Tyr Val Cys Val Ala Arg Asn Tyr Leu Gly Glu Ala Val Ser His Asn
145 150 155 160

Ala Ser Leu Glu Val Ala Ile Leu Arg Asp Asp Phe Arg Gln Asn Pro
165 170 175

Ser Asp Val Met Val Ala Val Gly Glu Pro Ala Val Met Glu Cys Gln
180 185 190

Pro Pro Arg Gly His Pro Glu Pro Thr Ile Ser Trp Lys Lys Asp Gly
195 200 205

Ser Pro Leu Asp Asp Lys Asp Glu Arg Ile Thr Ile Arg Gly Gly Lys
210 215 220

Leu Met Ile Thr Tyr Thr Arg Lys Ser Asp Ala Gly Lys Tyr Val Cys
225 230 235 240

Val Gly Thr Asn Met Val Gly Glu Arg Glu Ser Glu Val Ala Glu Leu
245 250 255

Thr Val Leu Glu Arg Pro Ser Phe Val Lys Arg Pro Ser Asn Leu Ala
260 265 270

Val Thr Val Asp Asp Ser Ala Glu Phe Lys Cys Glu Ala Arg Gly Asp
275 280 285

Pro Val Pro Thr Val Arg Trp Arg Lys Asp Asp Gly Glu Leu Pro Lys
290 295 300

Ser Arg Tyr Glu Ile Arg Asp Asp His Thr Leu Lys Ile Arg Lys Val
305 310 315 320

Thr Ala Gly Asp Met Gly Ser Tyr Thr Cys Val Ala Glu Asn Met Val
325 330 335

Gly Lys Ala Glu Ala Ser Ala Thr Leu Thr Val Gln Glu Pro Pro His
340 345 350

Phe Val Val Lys Pro Arg Asp Gln Val Val Ala Leu Gly Arg Thr Val
355 360 365

```
Thr Phe Gln Cys Glu Ala Thr Gly Asn Pro Gln Pro Ala Ile Phe Trp
    370                 375                 380

Arg Arg Glu Gly Ser Gln Asn Leu Leu Phe Ser Tyr Gln Pro Pro Gln
385                 390                 395                 400

Ser Ser Ser Arg Phe Ser Val Ser Gln Thr Gly Asp Leu Thr Ile Thr
                405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
        435                 440                 445

Ile Ala Asp Arg Pro Pro Pro Val Ile Arg Gln Gly Pro Val Asn Gln
    450                 455                 460

Thr Val Ala Val Asp Gly Thr Phe Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
            500                 505                 510

Arg Tyr Ala Lys Leu Gly Asp Thr Gly Arg Tyr Thr Cys Ile Ala Ser
        515                 520                 525

Thr Pro Ser Gly Glu Ala Thr Trp Ser Ala Tyr Ile Glu Val Gln Glu
    530                 535                 540

Phe Gly Val Pro Val Gln Pro Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
            580                 585                 590

Ser Tyr Ile Ile Glu Ala Phe Ser His Ala Ser Gly Ser Ser Trp Gln
        595                 600                 605

Thr Val Ala Glu Asn Val Lys Thr Glu Thr Ser Ala Ile Lys Gly Leu
    610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
        675                 680                 685

Ser Ser Ile Glu Val His Trp Thr Val Asp Gln Gln Ser Gln Tyr Ile
    690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                725                 730                 735

Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
        755                 760                 765

Lys Thr Leu Glu Glu Ala Pro Ser Ala Pro Pro Gln Gly Val Thr Val
    770                 775                 780

Ser Lys Asn Asp Gly Asn Gly Thr Ala Ile Leu Val Ser Trp Gln Pro
```

-continued 785 790 795 800

Pro Pro Glu Asp Thr Gln Asn Gly Met Val Gln Glu Tyr Lys Val Trp
805 810 815

Cys Leu Gly Asn Glu Thr Arg Tyr His Ile Asn Lys Thr Val Asp Gly
820 825 830

Ser Thr Phe Ser Val Val Ile Pro Phe Leu Val Pro Gly Ile Arg Tyr
835 840 845

Ser Val Glu Val Ala Ala Ser Thr Gly Ala Gly Ser Gly Val Lys Ser
850 855 860

Glu Pro Gln Phe Ile Gln Leu Asp Ala His Gly Asn Pro Val Ser Pro
865 870 875 880

Glu Asp Gln Val Ser Leu Ala Gln Gln Ile Ser Asp Val Val Lys Gln
885 890 895

Pro Ala Phe Ile Ala Gly Ile Gly Ala Ala Cys Trp Ile Ile Leu Met
900 905 910

Val Phe Ser Ile Trp Leu Tyr Arg His Arg Lys Lys Arg Asn Gly Leu
915 920 925

Thr Ser Thr Tyr Ala Gly Ile Arg Lys Val Pro Ser Phe Thr Phe Thr
930 935 940

Pro Thr Val Thr Tyr Gln Arg Gly Gly Glu Ala Val Ser Ser Gly Gly
945 950 955 960

Arg Pro Gly Leu Leu Asn Ile Ser Glu Pro Ala Ala Gln Pro Trp Leu
965 970 975

Ala Asp Thr Trp Pro Asn Thr Gly Asn Asn His Asn Asp Cys Ser Ile
980 985 990

Ser Cys Cys Thr Ala Gly Asn Gly Asn Ser Asp Ser Asn Leu Thr Thr
995 1000 1005

Tyr Ser Arg Pro Ala Asp Cys Ile Ala Asn Tyr Asn Asn Gln Leu
1010 1015 1020

Asp Asn Lys Gln Thr Asn Leu Met Leu Pro Glu Ser Thr Val Tyr
1025 1030 1035

Gly Asp Val Asp Leu Ser Asn Lys Ile Asn Glu Met Lys Thr Phe
1040 1045 1050

Asn Ser Pro Asn Leu Lys Asp Gly Arg Phe Val Asn Pro Ser Gly
1055 1060 1065

Gln Pro Thr Pro Tyr Ala Thr Thr Gln Leu Ile Gln Ser Asn Leu
1070 1075 1080

Ser Asn Asn Met Asn Asn Gly Ser Gly Asp Ser Gly Glu Lys His
1085 1090 1095

Trp Lys Pro Leu Gly Gln Gln Lys Gln Glu Val Ala Pro Val Gln
1100 1105 1110

Tyr Asn Ile Val Glu Gln Asn Lys Leu Asn Lys Asp Tyr Arg Ala
1115 1120 1125

Asn Asp Thr Val Pro Pro Thr Ile Pro Tyr Asn Gln Ser Tyr Asp
1130 1135 1140

Gln Asn Thr Gly Gly Ser Tyr Asn Ser Ser Asp Arg Gly Ser Ser
1145 1150 1155

Thr Ser Gly Ser Gln Gly His Lys Lys Gly Ala Arg Thr Pro Lys
1160 1165 1170

Val Pro Lys Gln Gly Gly Met Asn Trp Ala Asp Leu Leu Pro Pro
1175 1180 1185

Pro Pro Ala His Pro Pro Pro His Ser Asn Ser Glu Glu Tyr Asn
1190 1195 1200

Ile Ser Val Asp Glu Ser Tyr Asp Gln Glu Met Pro Cys Pro Val
1205 1210 1215

Pro Pro Ala Arg Met Tyr Leu Gln Gln Asp Glu Leu Glu Glu Glu
1220 1225 1230

Glu Asp Glu Arg Gly Pro Thr Pro Pro Val Arg Gly Ala Ala Ser
1235 1240 1245

Ser Pro Ala Ala Val Ser Tyr Ser His Gln Ser Thr Ala Thr Leu
1250 1255 1260

Thr Pro Ser Pro Gln Glu Glu Leu Gln Pro Met Leu Gln Asp Cys
1265 1270 1275

Pro Glu Glu Thr Gly His Met Gln His Gln Pro Asp Arg Arg Arg
1280 1285 1290

Gln Pro Val Ser Pro Pro Pro Pro Pro Arg Pro Ile Ser Pro Pro
1295 1300 1305

His Thr Tyr Gly Tyr Ile Ser Gly Pro Leu Val Ser Asp Met Asp
1310 1315 1320

Thr Asp Ala Pro Glu Glu Glu Glu Asp Glu Ala Asp Met Glu Val
1325 1330 1335

Ala Lys Met Gln Thr Arg Arg Leu Leu Leu Arg Gly Leu Glu Gln
1340 1345 1350

Thr Pro Ala Ser Ser Val Gly Asp Leu Glu Ser Ser Val Thr Gly
1355 1360 1365

Ser Met Ile Asn Gly Trp Gly Ser Ala Ser Glu Glu Asp Asn Ile
1370 1375 1380

Ser Ser Gly Arg Ser Ser Val Ser Ser Ser Asp Gly Ser Phe Phe
1385 1390 1395

Thr Asp Ala Asp Phe Ala Gln Ala Val Ala Ala Ala Ala Glu Tyr
1400 1405 1410

Ala Gly Leu Lys Val Ala Arg Arg Gln Met Gln Asp Ala Ala Gly
1415 1420 1425

Arg Arg His Phe His Ala Ser Gln Cys Pro Arg Pro Thr Ser Pro
1430 1435 1440

Val Ser Thr Asp Ser Asn Met Ser Ala Ala Val Met Gln Lys Thr
1445 1450 1455

Arg Pro Ala Lys Lys Leu Lys His Gln Pro Gly His Leu Arg Arg
1460 1465 1470

Glu Thr Tyr Thr Asp Asp Leu Pro Pro Pro Pro Val Pro Pro Pro
1475 1480 1485

Ala Ile Lys Ser Pro Thr Ala Gln Ser Lys Thr Gln Leu Glu Val
1490 1495 1500

Arg Pro Val Val Val Pro Lys Leu Pro Ser Met Asp Ala Arg Thr
1505 1510 1515

Asp Arg Ser Ser Asp Arg Lys Gly Ser Ser Tyr Lys Gly Arg Glu
1520 1525 1530

Val Leu Asp Gly Arg Gln Val Val Asp Met Arg Thr Asn Pro Gly
1535 1540 1545

Asp Pro Arg Glu Ala Gln Glu Gln Gln Asn Asp Gly Lys Gly Arg
1550 1555 1560

Gly Asn Lys Ala Ala Lys Arg Asp Leu Pro Pro Ala Lys Thr His
1565 1570 1575

Leu Ile Gln Glu Asp Ile Leu Pro Tyr Cys Arg Pro Thr Phe Pro
1580 1585 1590

Thr Ser Asn Asn Pro Arg Asp Pro Ser Ser Ser Ser Ser Met Ser
1595 1600 1605

Ser Arg Gly Ser Gly Ser Arg Gln Arg Glu Gln Ala Asn Val Gly
1610 1615 1620

Arg Arg Asn Ile Ala Glu Met Gln Val Leu Gly Gly Tyr Glu Arg
1625 1630 1635

Gly Glu Asp Asn Asn Glu Glu Leu Glu Glu Thr Glu Ser
1640 1645 1650

<210> SEQ ID NO 7
<211> LENGTH: 1474
<212> TYPE: PRT
<213> ORGANISM: Homo sapiens

<400> SEQUENCE: 7

Met Ala Arg Leu Ala Ala Val Leu Trp Asn Leu Cys Val Thr Ala Val
1 5 10 15

Leu Val Thr Ser Ala Thr Gln Gly Leu Ser Arg Ala Gly Leu Pro Phe
20 25 30

Gly Leu Met Arg Arg Glu Leu Ala Cys Glu Gly Tyr Pro Ile Glu Leu
35 40 45

Arg Cys Pro Gly Ser Asp Val Ile Met Val Glu Asn Ala Asn Tyr Gly
50 55 60

Arg Thr Asp Asp Lys Ile Cys Asp Ala Asp Pro Phe Gln Met Glu Asn
65 70 75 80

Val Gln Cys Tyr Leu Pro Asp Ala Phe Lys Ile Met Ser Gln Arg Cys
85 90 95

Asn Asn Arg Thr Gln Cys Val Val Val Ala Gly Ser Asp Ala Phe Pro
100 105 110

Asp Pro Cys Pro Gly Thr Tyr Lys Tyr Leu Glu Val Gln Tyr Asp Cys
115 120 125

Val Pro Tyr Lys Val Glu Gln Lys Val Phe Val Cys Pro Gly Thr Leu
130 135 140

Gln Lys Val Leu Glu Pro Thr Ser Thr His Glu Ser Glu His Gln Ser
145 150 155 160

Gly Ala Trp Cys Lys Asp Pro Leu Gln Ala Gly Asp Arg Ile Tyr Val
165 170 175

Met Pro Trp Ile Pro Tyr Arg Thr Asp Thr Leu Thr Glu Tyr Ala Ser
180 185 190

Trp Glu Asp Tyr Val Ala Ala Arg His Thr Thr Thr Tyr Arg Leu Pro
195 200 205

Asn Arg Val Asp Gly Thr Gly Phe Val Val Tyr Asp Gly Ala Val Phe
210 215 220

Tyr Asn Lys Glu Arg Thr Arg Asn Ile Val Lys Tyr Asp Leu Arg Thr
225 230 235 240

Arg Ile Lys Ser Gly Glu Thr Val Ile Asn Thr Ala Asn Tyr His Asp
245 250 255

Thr Ser Pro Tyr Arg Trp Gly Gly Lys Thr Asp Ile Asp Leu Ala Val
260 265 270

Asp Glu Asn Gly Leu Trp Val Ile Tyr Ala Thr Glu Gly Asn Asn Gly
275 280 285

Arg Leu Val Val Ser Gln Leu Asn Pro Tyr Thr Leu Arg Phe Glu Gly
290 295 300

Thr Trp Glu Thr Gly Tyr Asp Lys Arg Ser Ala Ser Asn Ala Phe Met
305 310 315 320

```
Val Cys Gly Val Leu Tyr Val Leu Arg Ser Val Tyr Val Asp Asp Asp
                325                 330                 335

Ser Glu Ala Ala Gly Asn Arg Val Asp Tyr Ala Phe Asn Thr Asn Ala
            340                 345                 350

Asn Arg Glu Glu Pro Val Ser Leu Thr Phe Pro Asn Pro Tyr Gln Phe
        355                 360                 365

Ile Ser Ser Val Asp Tyr Asn Pro Arg Asp Asn Gln Leu Tyr Val Trp
    370                 375                 380

Asn Asn Tyr Phe Val Val Arg Tyr Ser Leu Glu Phe Gly Pro Pro Asp
385                 390                 395                 400

Pro Ser Ala Gly Pro Ala Thr Ser Pro Pro Leu Ser Thr Thr Thr Thr
                405                 410                 415

Ala Arg Pro Thr Pro Leu Thr Ser Thr Ala Ser Pro Ala Ala Thr Thr
            420                 425                 430

Pro Leu Arg Arg Ala Pro Leu Thr Thr His Pro Val Gly Ala Ile Asn
        435                 440                 445

Gln Leu Gly Pro Asp Leu Pro Pro Ala Thr Ala Pro Val Pro Ser Thr
    450                 455                 460

Arg Arg Pro Pro Ala Pro Asn Leu His Val Ser Pro Glu Leu Phe Cys
465                 470                 475                 480

Glu Pro Arg Glu Val Arg Arg Val Gln Trp Pro Ala Thr Gln Gln Gly
                485                 490                 495

Met Leu Val Glu Arg Pro Cys Pro Lys Gly Thr Arg Gly Ile Ala Ser
            500                 505                 510

Phe Gln Cys Leu Pro Ala Leu Gly Leu Trp Asn Pro Arg Gly Pro Asp
        515                 520                 525

Leu Ser Asn Cys Thr Ser Pro Trp Val Asn Gln Val Ala Gln Lys Ile
    530                 535                 540

Lys Ser Gly Glu Asn Ala Ala Asn Ile Ala Ser Glu Leu Ala Arg His
545                 550                 555                 560

Thr Arg Gly Ser Ile Tyr Ala Gly Asp Val Ser Ser Ser Val Lys Leu
                565                 570                 575

Met Glu Gln Leu Leu Asp Ile Leu Asp Ala Gln Leu Gln Ala Leu Arg
            580                 585                 590

Pro Ile Glu Arg Glu Ser Ala Gly Lys Asn Tyr Asn Lys Met His Lys
        595                 600                 605

Arg Glu Arg Thr Cys Lys Asp Tyr Ile Lys Ala Val Val Glu Thr Val
    610                 615                 620

Asp Asn Leu Leu Arg Pro Glu Ala Leu Glu Ser Trp Lys Asp Met Asn
625                 630                 635                 640

Ala Thr Glu Gln Val His Thr Ala Thr Met Leu Leu Asp Val Leu Glu
                645                 650                 655

Glu Gly Ala Phe Leu Leu Ala Asp Asn Val Arg Glu Pro Ala Arg Phe
            660                 665                 670

Leu Ala Ala Lys Glu Asn Val Val Leu Glu Val Thr Val Leu Asn Thr
        675                 680                 685

Glu Gly Gln Val Gln Glu Leu Val Phe Pro Gln Glu Glu Tyr Pro Arg
    690                 695                 700

Lys Asn Ser Ile Gln Leu Ser Ala Lys Thr Ile Lys Gln Asn Ser Arg
705                 710                 715                 720

Asn Gly Val Val Lys Val Val Phe Ile Leu Tyr Asn Asn Leu Gly Leu
                725                 730                 735
```

```
Phe Leu Ser Thr Glu Asn Ala Thr Val Lys Leu Ala Gly Glu Ala Gly
            740                 745                 750

Pro Gly Gly Pro Gly Gly Ala Ser Leu Val Val Asn Ser Gln Val Ile
        755                 760                 765

Ala Ala Ser Ile Asn Lys Glu Ser Ser Arg Val Phe Leu Met Asp Pro
    770                 775                 780

Val Ile Phe Thr Val Ala His Leu Glu Asp Lys Asn His Phe Asn Ala
785                 790                 795                 800

Asn Cys Ser Phe Trp Asn Tyr Ser Glu Arg Ser Met Leu Gly Tyr Trp
                805                 810                 815

Ser Thr Gln Gly Cys Arg Leu Val Glu Ser Asn Lys Thr His Thr Thr
            820                 825                 830

Cys Ala Cys Ser His Leu Thr Asn Phe Ala Val Leu Met Ala His Arg
        835                 840                 845

Glu Ile Tyr Gln Gly Arg Ile Asn Glu Leu Leu Leu Ser Val Ile Thr
    850                 855                 860

Trp Val Gly Ile Val Ile Ser Leu Val Cys Leu Ala Ile Cys Ile Ser
865                 870                 875                 880

Thr Phe Cys Phe Leu Arg Gly Leu Gln Thr Asp Arg Asn Thr Ile His
                885                 890                 895

Lys Asn Leu Cys Ile Asn Leu Phe Leu Ala Glu Leu Leu Phe Leu Val
            900                 905                 910

Gly Ile Asp Lys Thr Gln Tyr Glu Ile Ala Cys Pro Ile Phe Ala Gly
        915                 920                 925

Leu Leu His Tyr Phe Phe Leu Ala Ala Phe Ser Trp Leu Cys Leu Glu
    930                 935                 940

Gly Val His Leu Tyr Leu Leu Leu Val Glu Val Phe Glu Ser Glu Tyr
945                 950                 955                 960

Ser Arg Thr Lys Tyr Tyr Tyr Leu Gly Gly Tyr Cys Phe Pro Ala Leu
                965                 970                 975

Val Val Gly Ile Ala Ala Ala Ile Asp Tyr Arg Ser Tyr Gly Thr Glu
            980                 985                 990

Lys Ala Cys Trp Leu Arg Val Asp  Asn Tyr Phe Ile Trp  Ser Phe Ile
        995                 1000                1005

Gly Pro  Val Ser Phe Val Ile  Val Val Asn Leu Val  Phe Leu Met
    1010                1015                1020

Val Thr  Leu His Lys Met Ile  Arg Ser Ser Ser Val  Leu Lys Pro
    1025                1030                1035

Asp Ser  Ser Arg Leu Asp Asn  Ile Lys Ser Trp Ala  Leu Gly Ala
    1040                1045                1050

Ile Ala  Leu Leu Phe Leu Leu  Gly Leu Thr Trp Ala  Phe Gly Leu
    1055                1060                1065

Leu Phe  Ile Asn Lys Glu Ser  Val Val Met Ala Tyr  Leu Phe Thr
    1070                1075                1080

Thr Phe  Asn Ala Phe Gln Gly  Val Phe Ile Phe Val  Phe His Cys
    1085                1090                1095

Ala Leu  Gln Lys Lys Val His  Lys Glu Tyr Ser Lys  Cys Leu Arg
    1100                1105                1110

His Ser  Tyr Cys Cys Ile Arg  Ser Pro Pro Gly Gly  Thr His Gly
    1115                1120                1125

Ser Leu  Lys Thr Ser Ala Met  Arg Ser Asn Thr Arg  Tyr Tyr Thr
    1130                1135                1140

Gly Thr  Gln Ser Arg Ile Arg  Arg Met Trp Asn Asp  Thr Val Arg
```

1145 1150 1155

Lys Gln Thr Glu Ser Ser Phe Met Ala Gly Asp Ile Asn Ser Thr
1160 1165 1170

Pro Thr Leu Asn Arg Gly Thr Met Gly Asn His Leu Leu Thr Asn
1175 1180 1185

Pro Val Leu Gln Pro Arg Gly Gly Thr Ser Pro Tyr Asn Thr Leu
1190 1195 1200

Ile Ala Glu Ser Val Gly Phe Asn Pro Ser Ser Pro Pro Val Phe
1205 1210 1215

Asn Ser Pro Gly Ser Tyr Arg Glu Pro Lys His Pro Leu Gly Gly
1220 1225 1230

Arg Glu Ala Cys Gly Met Asp Thr Leu Pro Leu Asn Gly Asn Phe
1235 1240 1245

Asn Asn Ser Tyr Ser Leu Arg Ser Gly Asp Phe Pro Pro Gly Asp
1250 1255 1260

Gly Gly Pro Glu Pro Pro Arg Gly Arg Asn Leu Ala Asp Ala Ala
1265 1270 1275

Ala Phe Glu Lys Met Ile Ile Ser Glu Leu Val His Asn Asn Leu
1280 1285 1290

Arg Gly Ser Ser Ser Ala Ala Lys Gly Pro Pro Pro Pro Glu Pro
1295 1300 1305

Pro Val Pro Pro Val Pro Gly Gly Gly Gly Glu Glu Glu Ala Gly
1310 1315 1320

Gly Pro Gly Gly Ala Asp Arg Ala Glu Ile Glu Leu Leu Tyr Lys
1325 1330 1335

Ala Leu Glu Glu Pro Leu Leu Leu Pro Arg Ala Gln Ser Val Leu
1340 1345 1350

Tyr Gln Ser Asp Leu Asp Glu Ser Glu Ser Cys Thr Ala Glu Asp
1355 1360 1365

Gly Ala Thr Ser Arg Pro Leu Ser Ser Pro Pro Gly Arg Asp Ser
1370 1375 1380

Leu Tyr Ala Ser Gly Ala Asn Leu Arg Asp Ser Pro Ser Tyr Pro
1385 1390 1395

Asp Ser Ser Pro Glu Gly Pro Ser Glu Ala Leu Pro Pro Pro Pro
1400 1405 1410

Pro Ala Pro Pro Gly Pro Pro Glu Ile Tyr Tyr Thr Ser Arg Pro
1415 1420 1425

Pro Ala Leu Val Ala Arg Asn Pro Leu Gln Gly Tyr Tyr Gln Val
1430 1435 1440

Arg Arg Pro Ser His Glu Gly Tyr Leu Ala Ala Pro Gly Leu Glu
1445 1450 1455

Gly Pro Gly Pro Asp Gly Asp Gly Gln Met Gln Leu Val Thr Ser
1460 1465 1470

Leu

<210> SEQ ID NO 8
<211> LENGTH: 945
<212> TYPE: PRT
<213> ORGANISM: Homo sapiens

<400> SEQUENCE: 8

Met Gly Ala Arg Ser Gly Ala Arg Gly Ala Leu Leu Leu Ala Leu Leu
1 5 10 15

Leu Cys Trp Asp Pro Arg Leu Ser Gln Ala Gly Thr Asp Ser Gly Ser

```
            20                  25                  30

Glu Val Leu Pro Asp Ser Phe Pro Ser Ala Pro Ala Glu Pro Leu Pro
        35                  40                  45

Tyr Phe Leu Gln Glu Pro Gln Asp Ala Tyr Ile Val Lys Asn Lys Pro
    50                  55                  60

Val Glu Leu Arg Cys Arg Ala Phe Pro Ala Thr Gln Ile Tyr Phe Lys
65                  70                  75                  80

Cys Asn Gly Glu Trp Val Ser Gln Asn Asp His Val Thr Gln Glu Gly
                85                  90                  95

Leu Asp Glu Ala Thr Gly Leu Arg Val Arg Glu Val Gln Ile Glu Val
            100                 105                 110

Ser Arg Gln Gln Val Glu Glu Leu Phe Gly Leu Glu Asp Tyr Trp Cys
        115                 120                 125

Gln Cys Val Ala Trp Ser Ser Ala Gly Thr Thr Lys Ser Arg Arg Ala
    130                 135                 140

Tyr Val Arg Ile Ala Tyr Leu Arg Lys Asn Phe Asp Gln Glu Pro Leu
145                 150                 155                 160

Gly Lys Glu Val Pro Leu Asp His Glu Val Leu Leu Gln Cys Arg Pro
                165                 170                 175

Pro Glu Gly Val Pro Val Ala Glu Val Glu Trp Leu Lys Asn Glu Asp
            180                 185                 190

Val Ile Asp Pro Thr Gln Asp Thr Asn Phe Leu Leu Thr Ile Asp His
        195                 200                 205

Asn Leu Ile Ile Arg Gln Ala Arg Leu Ser Asp Thr Ala Asn Tyr Thr
    210                 215                 220

Cys Val Ala Lys Asn Ile Val Ala Lys Arg Arg Ser Thr Thr Ala Thr
225                 230                 235                 240

Val Ile Val Tyr Val Asn Gly Gly Trp Ser Ser Trp Ala Glu Trp Ser
                245                 250                 255

Pro Cys Ser Asn Arg Cys Gly Arg Gly Trp Gln Lys Arg Thr Arg Thr
            260                 265                 270

Cys Thr Asn Pro Ala Pro Leu Asn Gly Gly Ala Phe Cys Glu Gly Gln
        275                 280                 285

Ala Phe Gln Lys Thr Ala Cys Thr Thr Ile Cys Pro Val Asp Gly Ala
    290                 295                 300

Trp Thr Glu Trp Ser Lys Trp Ser Ala Cys Ser Thr Glu Cys Ala His
305                 310                 315                 320

Trp Arg Ser Arg Glu Cys Met Ala Pro Pro Pro Gln Asn Gly Gly Arg
                325                 330                 335

Asp Cys Ser Gly Thr Leu Leu Asp Ser Lys Asn Cys Thr Asp Gly Leu
            340                 345                 350

Cys Met Gln Asn Lys Lys Thr Leu Ser Asp Pro Asn Ser His Leu Leu
        355                 360                 365

Glu Ala Ser Gly Asp Ala Ala Leu Tyr Ala Gly Leu Val Val Ala Ile
    370                 375                 380

Phe Val Val Val Ala Ile Leu Met Ala Val Gly Val Val Val Tyr Arg
385                 390                 395                 400

Arg Asn Cys Arg Asp Phe Asp Thr Asp Ile Thr Asp Ser Ser Ala Ala
                405                 410                 415

Leu Thr Gly Gly Phe His Pro Val Asn Phe Lys Thr Ala Arg Pro Ser
            420                 425                 430

Asn Pro Gln Leu Leu His Pro Ser Val Pro Pro Asp Leu Thr Ala Ser
        435                 440                 445
```

```
Ala Gly Ile Tyr Arg Gly Pro Val Tyr Ala Leu Gln Asp Ser Thr Asp
    450                 455                 460

Lys Ile Pro Met Thr Asn Ser Pro Leu Leu Asp Pro Leu Pro Ser Leu
465                 470                 475                 480

Lys Val Lys Val Tyr Ser Ser Ser Thr Thr Gly Ser Gly Pro Gly Leu
                485                 490                 495

Ala Asp Gly Ala Asp Leu Leu Gly Val Leu Pro Pro Gly Thr Tyr Pro
            500                 505                 510

Ser Asp Phe Ala Arg Asp Thr His Phe Leu His Leu Arg Ser Ala Ser
        515                 520                 525

Leu Gly Ser Gln Gln Leu Leu Gly Leu Pro Arg Asp Pro Gly Ser Ser
    530                 535                 540

Val Ser Gly Thr Phe Gly Cys Leu Gly Gly Arg Leu Ser Ile Pro Gly
545                 550                 555                 560

Thr Gly Val Ser Leu Leu Val Pro Asn Gly Ala Ile Pro Gln Gly Lys
                565                 570                 575

Phe Tyr Glu Met Tyr Leu Leu Ile Asn Lys Ala Glu Ser Thr Leu Pro
            580                 585                 590

Leu Ser Glu Gly Thr Gln Thr Val Leu Ser Pro Ser Val Thr Cys Gly
        595                 600                 605

Pro Thr Gly Leu Leu Leu Cys Arg Pro Val Ile Leu Thr Met Pro His
    610                 615                 620

Cys Ala Glu Val Ser Ala Arg Asp Trp Ile Phe Gln Leu Lys Thr Gln
625                 630                 635                 640

Ala His Gln Gly His Trp Glu Glu Val Val Thr Leu Asp Glu Glu Thr
                645                 650                 655

Leu Asn Thr Pro Cys Tyr Cys Gln Leu Glu Pro Arg Ala Cys His Ile
            660                 665                 670

Leu Leu Asp Gln Leu Gly Thr Tyr Val Phe Thr Gly Glu Ser Tyr Ser
        675                 680                 685

Arg Ser Ala Val Lys Arg Leu Gln Leu Ala Val Phe Ala Pro Ala Leu
    690                 695                 700

Cys Thr Ser Leu Glu Tyr Ser Leu Arg Val Tyr Cys Leu Glu Asp Thr
705                 710                 715                 720

Pro Val Ala Leu Lys Glu Val Leu Glu Leu Glu Arg Thr Leu Gly Gly
                725                 730                 735

Tyr Leu Val Glu Glu Pro Lys Pro Leu Met Phe Lys Asp Ser Tyr His
            740                 745                 750

Asn Leu Arg Leu Ser Leu His Asp Leu Pro His Ala His Trp Arg Ser
        755                 760                 765

Lys Leu Leu Ala Lys Tyr Gln Glu Ile Pro Phe Tyr His Ile Trp Ser
    770                 775                 780

Gly Ser Gln Lys Ala Leu His Cys Thr Phe Thr Leu Glu Arg His Ser
785                 790                 795                 800

Leu Ala Ser Thr Glu Leu Thr Cys Lys Ile Cys Val Arg Gln Val Glu
                805                 810                 815

Gly Glu Gly Gln Ile Phe Gln Leu His Thr Thr Leu Ala Glu Thr Pro
            820                 825                 830

Ala Gly Ser Leu Asp Thr Leu Cys Ser Ala Pro Gly Ser Thr Val Thr
        835                 840                 845

Thr Gln Leu Gly Pro Tyr Ala Phe Lys Ile Pro Leu Ser Ile Arg Gln
    850                 855                 860
```

Lys Ile Cys Asn Ser Leu Asp Ala Pro Asn Ser Arg Gly Asn Asp Trp
865 870 875 880

Arg Met Leu Ala Gln Lys Leu Ser Met Asp Arg Tyr Leu Asn Tyr Phe
885 890 895

Ala Thr Lys Ala Ser Pro Thr Gly Val Ile Leu Asp Leu Trp Glu Ala
900 905 910

Leu Gln Gln Asp Asp Gly Asp Leu Asn Ser Leu Ala Ser Ala Leu Glu
915 920 925

Glu Met Gly Lys Ser Glu Met Leu Val Ala Val Ala Thr Asp Gly Asp
930 935 940

Cys
945

<210> SEQ ID NO 9
<211> LENGTH: 760
<212> TYPE: PRT
<213> ORGANISM: Artificial Sequence
<220> FEATURE:
<223> OTHER INFORMATION: Engineered antibody from hybridoma

<400> SEQUENCE: 9

Met Ile Ser Ala Ala Trp Ser Ile Phe Leu Ile Gly Thr Lys Ile Gly
1 5 10 15

Leu Phe Leu Gln Val Ala Pro Leu Ser Val Met Ala Lys Ser Cys Pro
20 25 30

Ser Val Cys Arg Cys Asp Ala Gly Phe Ile Tyr Cys Asn Asp Arg Phe
35 40 45

Leu Thr Ser Ile Pro Thr Gly Ile Pro Glu Asp Ala Thr Thr Leu Tyr
50 55 60

Leu Gln Asn Asn Gln Ile Asn Asn Ala Gly Ile Pro Ser Asp Leu Lys
65 70 75 80

Asn Leu Leu Lys Val Glu Arg Ile Tyr Leu Tyr His Asn Ser Leu Asp
85 90 95

Glu Phe Pro Thr Asn Leu Pro Lys Tyr Val Lys Glu Leu His Leu Gln
100 105 110

Glu Asn Asn Ile Arg Thr Ile Thr Tyr Asp Ser Leu Ser Lys Ile Pro
115 120 125

Tyr Leu Glu Glu Leu His Leu Asp Asp Asn Ser Val Ser Ala Val Ser
130 135 140

Ile Glu Glu Gly Ala Phe Arg Asp Ser Asn Tyr Leu Arg Leu Leu Phe
145 150 155 160

Leu Ser Arg Asn His Leu Ser Thr Ile Pro Trp Gly Leu Pro Arg Thr
165 170 175

Ile Glu Glu Leu Arg Leu Asp Asp Asn Arg Ile Ser Thr Ile Ser Ser
180 185 190

Pro Ser Leu Gln Gly Leu Thr Ser Leu Lys Arg Leu Val Leu Asp Gly
195 200 205

Asn Leu Leu Asn Asn His Gly Leu Gly Asp Lys Val Phe Phe Asn Leu
210 215 220

Val Asn Leu Thr Glu Leu Ser Leu Val Arg Asn Ser Leu Thr Ala Ala
225 230 235 240

Pro Val Asn Leu Pro Gly Thr Asn Leu Arg Lys Leu Tyr Leu Gln Asp
245 250 255

Asn His Ile Asn Arg Val Pro Pro Asn Ala Phe Ser Tyr Leu Arg Gln
260 265 270

```
Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Leu Val Pro Arg Gly Ser Asp Lys Thr His Thr Cys Pro Pro Cys Pro
    530                 535                 540

Ala Pro Glu Leu Leu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
        595                 600                 605

Gln Tyr Asn Ser Thr Tyr Arg Val Val Ser Val Leu Thr Val Leu His
    610                 615                 620

Gln Asp Trp Leu Asn Gly Lys Glu Tyr Lys Cys Lys Val Ser Asn Lys
625                 630                 635                 640

Ala Leu Pro Ala Pro Ile Glu Lys Thr Ile Ser Lys Ala Lys Gly Gln
                645                 650                 655

Pro Arg Glu Pro Gln Val Tyr Thr Leu Pro Pro Ser Arg Asp Glu Leu
            660                 665                 670

Thr Lys Asn Gln Val Ser Leu Thr Cys Leu Val Lys Gly Phe Tyr Pro
        675                 680                 685

Ser Asp Ile Ala Val Glu Trp Glu Ser Asn Gly Gln Pro Glu Asn Asn
```

```
    690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly
        755                 760


<210> SEQ ID NO 10
<211> LENGTH: 760
<212> TYPE: PRT
<213> ORGANISM: Artificial Sequence
<220> FEATURE:
<223> OTHER INFORMATION: Engineered antibody from hybridoma

<400> SEQUENCE: 10

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
```

```
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Leu Val Pro Arg Gly Ser Asp Lys Thr His Thr Cys Pro Pro Cys Pro
    530                 535                 540

Ala Pro Glu Phe Glu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
        595                 600                 605

Gln Tyr Asn Ser Thr Tyr Arg Val Val Ser Val Leu Thr Val Leu His
    610                 615                 620

Gln Asp Trp Leu Asn Gly Lys Glu Tyr Lys Cys Lys Val Ser Asn Lys
625                 630                 635                 640

Ala Leu Pro Ala Ser Ile Glu Lys Thr Ile Ser Lys Ala Lys Gly Gln
                645                 650                 655

Pro Arg Glu Pro Gln Val Tyr Thr Leu Pro Pro Ser Arg Asp Glu Leu
            660                 665                 670

Thr Lys Asn Gln Val Ser Leu Thr Cys Leu Val Lys Gly Phe Tyr Pro
        675                 680                 685

Ser Asp Ile Ala Val Glu Trp Glu Ser Asn Gly Gln Pro Glu Asn Asn
    690                 695                 700

Tyr Lys Thr Thr Pro Pro Val Leu Asp Ser Asp Gly Ser Phe Phe Leu
705                 710                 715                 720
```

```
Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly
        755                 760


<210> SEQ ID NO 11
<211> LENGTH: 756
<212> TYPE: PRT
<213> ORGANISM: Artificial Sequence
<220> FEATURE:
<223> OTHER INFORMATION: Engineered antibody from hybridoma

<400> SEQUENCE: 11

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320
```

```
Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Glu Ser Lys Tyr Gly Pro Pro Cys Pro Pro Cys Pro Ala Pro Glu Phe
    530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser Gln Glu Asp Pro Glu Val Gln Phe Asn Trp Tyr Val Asp Gly Val
            580                 585                 590

Glu Val His Asn Ala Lys Thr Lys Pro Arg Glu Glu Gln Phe Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Gly Leu Pro Ser
625                 630                 635                 640

Ser Ile Glu Lys Thr Ile Ser Lys Ala Lys Gly Gln Pro Arg Glu Pro
                645                 650                 655

Gln Val Tyr Thr Leu Pro Pro Ser Gln Glu Glu Met Thr Lys Asn Gln
            660                 665                 670

Val Ser Leu Thr Cys Leu Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Tyr Ser Arg Leu
705                 710                 715                 720

Thr Val Asp Lys Ser Arg Trp Gln Glu Gly Asn Val Phe Ser Cys Ser
                725                 730                 735
```

Val Met His Glu Ala Leu His Asn His Tyr Thr Gln Lys Ser Leu Ser
740 745 750

Leu Ser Leu Gly
755

<210> SEQ ID NO 12
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 12

Asp Ile Gln Met Asn Gln Ser Pro Ser Ser Leu Ser Ala Ser Leu Gly
1 5 10 15

Asp Thr Ile Thr Ile Ala Cys Arg Ala Ser Gln Asn Ile Asp Ile Trp
20 25 30

Leu Ser Trp Tyr Gln Gln Lys Pro Gly Ser Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Leu Gln Gly Gln Ser Phe Pro Phe
85 90 95

Thr Phe Gly Ser Gly Thr Lys Leu Glu Ile Lys
100 105

<210> SEQ ID NO 13
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 13

Arg Ala Ser Gln Asn Ile Asp Ile Trp Leu Ser
1 5 10

<210> SEQ ID NO 14
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 14

Lys Ala Ser Asn Leu His Thr
1 5

<210> SEQ ID NO 15
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 15

Leu Gln Gly Gln Ser Phe Pro Phe Thr
1 5

<210> SEQ ID NO 16
<211> LENGTH: 214

<212> TYPE: PRT
<213> ORGANISM: Artificial Sequence
<220> FEATURE:
<223> OTHER INFORMATION: Engineered antibody from hybridoma

<400> SEQUENCE: 16

```
Asp Ile Gln Met Thr Gln Ser Pro Ser Ser Val Ser Ala Ser Leu Gly
1               5                   10                  15

Asp Arg Val Thr Ile Thr Cys Arg Ala Ser Gln Asn Ile Asp Ile Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 17

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ile Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
                85                  90                  95

Thr Phe Gly Ser Gly Thr Lys Leu Glu Ile Lys
            100                 105
```

<210> SEQ ID NO 18
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 18

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ile Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 19
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 19

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Thr Asn
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
```

```
                85                  90                  95

Thr Phe Gly Ser Gly Thr Lys Leu Glu Ile Lys
            100                 105


<210> SEQ ID NO 20
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Thr Asn
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 21
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ile Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Thr Pro Phe
                85                  90                  95

Thr Phe Gly Ser Gly Thr Lys Leu Glu Ile Lys
            100                 105


<210> SEQ ID NO 22
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 22

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Thr Asn
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Phe Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 23
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 23

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ile Trp
            20                  25                  30

Leu Ser Trp Tyr Gln Gln Lys Pro Gly Lys Ala Pro Lys Leu Leu Ile
        35                  40                  45
```

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Gly Gln Ser Thr Pro Phe
85 90 95

Thr Phe Gly Ser Gly Thr Lys Leu Glu Ile Lys
100 105

<210> SEQ ID NO 24
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 24

Asp Ile Gln Met Thr Gln Ser Pro Ser Ser Val Ser Ala Ser Val Gly
1 5 10 15

Asp Arg Val Thr Ile Thr Cys Arg Ala Ser Gln Asn Ile Asp Ile Trp
20 25 30

Leu Ser Trp Tyr Gln Gln Lys Pro Gly Lys Ala Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Gly Gln Ser Thr Pro Phe
85 90 95

Thr Phe Gly Ser Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 25
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 25

Asp Ile Gln Met Thr Gln Ser Pro Ser Ser Val Ser Ala Ser Val Gly
1 5 10 15

Asp Arg Val Thr Ile Thr Cys Arg Ala Ser Gln Asn Ile Asp Thr Asn

```
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Thr Pro Phe
                85                  90                  95

Thr Phe Gly Ser Gly Thr Lys Leu Glu Ile Lys
            100                 105


<210> SEQ ID NO 26
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Thr Asn
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 27
```

Asp Ile Gln Met Thr Gln Ser Pro Ser Ser Val Ser Ala Ser Val Gly
1 5 10 15

Asp Arg Val Thr Ile Thr Cys Arg Ala Ser Gln Asn Ile Asp Ser Trp
20 25 30

Leu Ser Trp Tyr Gln Gln Lys Pro Gly Lys Ala Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Gly Gln Ser Phe Pro Phe
85 90 95

Thr Phe Gly Ser Gly Thr Lys Leu Glu Ile Lys
100 105

<210> SEQ ID NO 28
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 28

Asp Ile Gln Met Thr Gln Ser Pro Ser Ser Val Ser Ala Ser Val Gly
1 5 10 15

Asp Arg Val Thr Ile Thr Cys Arg Ala Ser Gln Asn Ile Asp Ser Trp
20 25 30

Leu Ser Trp Tyr Gln Gln Lys Pro Gly Lys Ala Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Gly Gln Ser Phe Pro Phe
85 90 95

Thr Phe Gly Ser Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 29
<211> LENGTH: 107
<212> TYPE: PRT
<213> ORGANISM: Artificial Sequence
<220> FEATURE:

<223> OTHER INFORMATION: Engineered antibody from hybridoma

<400> SEQUENCE: 29

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ser Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Thr Pro Phe
                85                  90                  95

Thr Phe Gly Ser Gly Thr Lys Leu Glu Ile Lys
            100                 105
```

<210> SEQ ID NO 30
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 30

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asn Ile Asp Ser Trp
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Gln Ser Thr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 31

<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 31

Gln Val Gln Leu Gln Gln Ser Gly Pro Glu Leu Val Lys Pro Gly Ala
1 5 10 15

Ser Val Asn Ile Ser Cys Lys Ala Ser Gly Tyr Ala Phe Gly Asn Ser
20 25 30

Trp Met Asn Trp Val Lys Gln Arg Pro Gly Lys Gly Leu Glu Trp Ile
35 40 45

Gly Trp Ile Tyr Pro Gly Asp Gly Asn Ala Asn Tyr Asn Gly Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Ala Leu Tyr Asp Tyr Asp Gly Trp Phe Ala Tyr Trp Gly Gln
100 105 110

Gly Thr Leu Val Thr Val Ser Ala
115 120

<210> SEQ ID NO 32
<211> LENGTH: 5
<212> TYPE: PRT
<213> ORGANISM: Artificial Sequence
<220> FEATURE:
<223> OTHER INFORMATION: Engineered antibody from hybridoma

<400> SEQUENCE: 32

Asn Ser Trp Met Asn
1 5

<210> SEQ ID NO 33
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 33

Trp Ile Tyr Pro Gly Asp Gly Asn Ala Asn Tyr Asn Gly Lys Phe Lys
1 5 10 15

Gly

<210> SEQ ID NO 34
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 34

Ala Leu Tyr Asp Tyr Asp Gly Trp Phe Ala Tyr
1 5 10

<210> SEQ ID NO 35
<211> LENGTH: 449
<212> TYPE: PRT
<213> ORGANISM: Artificial Sequence
<220> FEATURE:

<223> OTHER INFORMATION: Engineered antibody from hybridoma

<400> SEQUENCE: 35

Gln Val Gln Leu Gln Gln Ser Gly Pro Glu Leu Val Lys Pro Gly Ala
1               5                   10                  15

Ser Val Asn Ile Ser Cys Lys Ala Ser Gly Tyr Ala Phe Gly Asn Ser
            20                  25                  30

Trp Met Asn Trp Val Lys Gln Arg Pro Gly Lys Gly Leu Glu Trp Ile
        35                  40                  45

Gly Trp Ile Tyr Pro Gly Asp Gly Asn Ala Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 36
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 36

Gln Val Gln Leu Gln Gln Ser Gly Pro Glu Leu Val Lys Pro Gly Ala
1 5 10 15

Ser Val Asn Ile Ser Cys Lys Ala Ser Gly Tyr Ala Phe Gly Asn Ser
20 25 30

Trp Met Asn Trp Val Lys Gln Arg Pro Gly Lys Gly Leu Glu Trp Ile
35 40 45

Gly Trp Ile Tyr Pro Gly Asp Gly Asn Ala Asn Tyr Asn Gly Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Phe Cys
85 90 95

Ala Arg Ala Leu Tyr Asp Tyr Asp Gly Trp Phe Ala Tyr Trp Gly Gln
100 105 110

Gly Thr Leu Val Thr Val Ser Ala Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Phe Glu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys

```
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 37
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 37

Gln Val Gln Leu Gln Gln Ser Gly Pro Glu Leu Val Lys Pro Gly Ala
1               5                   10                  15

Ser Val Asn Ile Ser Cys Lys Ala Ser Gly Tyr Ala Phe Gly Asn Ser
            20                  25                  30

Trp Met Asn Trp Val Lys Gln Arg Pro Gly Lys Gly Leu Glu Trp Ile
        35                  40                  45

Gly Trp Ile Tyr Pro Gly Asp Gly Asn Ala Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 38
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 39
```

<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 39

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 40
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 40

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Phe Glu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 41
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys

```
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 42
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
```

115 120

<210> SEQ ID NO 43
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 43

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ala Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 44
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 45
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 46
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 46

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Thr Tyr Tyr Cys
                85                  90                  95
```

Ala Arg Ala Leu Tyr Asp Tyr Asp Gly Trp Phe Ala Tyr Trp Gly Gln
100 105 110

Gly Thr Leu Val Thr Val Ser Ser
115 120

<210> SEQ ID NO 47
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 47

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 48
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 48

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Phe Glu Gly Gly
225 230 235 240

Pro Ser Val Phe Leu Phe Pro Pro Lys Pro Lys Asp Thr Leu Met Ile

```
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 49
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 50
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Ala Ser Thr Ala Tyr
65                  70                  75                  80
```

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser
115 120

<210> SEQ ID NO 51
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 51

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ala Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 52
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 52

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ala Gln Lys Phe
50 55 60

Gln Gly Arg Val Thr Leu Thr Ala Asp Lys Ser Ala Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

-continued

```
Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 53
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Ala Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
```

130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 54
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 54

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe

```
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 55
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 56
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 57
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

```
Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 58
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30
```

```
Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 59
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 60
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 61
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 62
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 62

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 63
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 64
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 65
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 65

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
```

```
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 66
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120

<210> SEQ ID NO 67
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly

```
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 68
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Phe Glu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Ser Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 69
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 69

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

```
Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 70
<211> LENGTH: 120
<212> TYPE: PRT

<213> ORGANISM: Artificial Sequence
<220> FEATURE:
<223> OTHER INFORMATION: Engineered antibody from hybridoma

<400> SEQUENCE: 70

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Ser Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser
115 120

<210> SEQ ID NO 71
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 71

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Ser Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 72
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
```

```
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 73
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 73

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30
```

-continued

```
Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 74
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 74

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120
```

<210> SEQ ID NO 75
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 75

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 76
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 76

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Ser Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ala Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

```
Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 77
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 77

Gln Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
            85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430
```

```
His Asn His Tyr Thr Gln Lys Ser Leu Ser Leu Ser Leu Gly
        435                 440                 445


<210> SEQ ID NO 78
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 79
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 80
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80
```

```
Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 81
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg 405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 82
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 82

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Ser Gly Asn Ala Asn Tyr Ala Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser
115 120

<210> SEQ ID NO 83
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 83

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Ser Gly Asn Ala Asn Tyr Ala Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 84
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 84

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ala Gln Lys Phe
```

```
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 85
<211> LENGTH: 446

<212> TYPE: PRT
<213> ORGANISM: Artificial Sequence
<220> FEATURE:
<223> OTHER INFORMATION: Engineered antibody from hybridoma

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Asn Ala Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 86
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser
        115                 120


<210> SEQ ID NO 87
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 88
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 88

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

```
Trp Met Asn Trp Val Arg Gln Ala Pro Gly Gln Gly Leu Glu Trp Met
        35                  40                  45

Gly Trp Ile Tyr Pro Gly Asp Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 89
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 90
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 90

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Ser Ser
20 25 30

Trp Met Asn Trp Val Arg Gln Ala Pro Gly Gln Gly Leu Glu Trp Met
35 40 45

Gly Trp Ile Tyr Pro Gly Ser Gly Ser Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln
100 105 110

Gly Thr Leu Val Thr Val Ser Ser
115 120

<210> SEQ ID NO 91
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 91

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Ser Ser
20 25 30

Trp Met Asn Trp Val Arg Gln Ala Pro Gly Gln Gly Leu Glu Trp Met
35 40 45

Gly Trp Ile Tyr Pro Gly Ser Gly Ser Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Tyr Asp Tyr Asp Gly Trp Phe Ala Tyr Trp Gly Gln

```
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 92
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 92

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
        435                 440                 445

Gly

<210> SEQ ID NO 93
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Tyr Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro

```
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 94
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser
        115                 120


<210> SEQ ID NO 95
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Asn Ser
            20                  25                  30

Trp Met Asn Trp Val Arg Gln Ala Pro Gly Gln Gly Leu Glu Trp Met
        35                  40                  45

Gly Trp Ile Tyr Pro Gly Asp Gly Asn Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80
```

```
Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

```
<210> SEQ ID NO 96
<211> LENGTH: 449
<212> TYPE: PRT
<213> ORGANISM: Artificial Sequence
<220> FEATURE:
<223> OTHER INFORMATION: Engineered antibody from hybridoma
```

<400> SEQUENCE: 96

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Gln Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Phe Glu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Ser Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 97
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 97

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Gly Asn Ser
20 25 30

Trp Met Asn Trp Val Arg Gln Ala Pro Gly Gln Gly Leu Glu Trp Met
35 40 45

Gly Trp Ile Tyr Pro Gly Asp Gly Asn Ala Asn Tyr Ser Gln Lys Phe
50 55 60

Gln Gly Arg Val Thr Leu Thr Ala Asp Lys Ser Thr Ser Thr Ala Tyr
65 70 75 80

Met Glu Leu Ser Ser Leu Arg Ser Glu Asp Thr Ala Thr Tyr Tyr Cys
85 90 95

Ala Arg Ala Leu Gln Asp Tyr Asp Gly Trp Phe Ala Tyr Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 98
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser
        115                 120


<210> SEQ ID NO 99
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60
```

```
Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 100
<211> LENGTH: 449
<212> TYPE: PRT

<213> ORGANISM: Artificial Sequence
<220> FEATURE:
<223> OTHER INFORMATION: Engineered antibody from hybridoma

<400> SEQUENCE: 100

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 101
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Gly Ser Ser
            20                  25                  30

Trp Met Asn Trp Val Arg Gln Ala Pro Gly Gln Gly Leu Glu Trp Met
        35                  40                  45

Gly Trp Ile Tyr Pro Gly Ser Gly Ser Ala Asn Tyr Ser Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Ala Leu Gln Asp Tyr Asp Gly Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 102
<211> LENGTH: 113
<212> TYPE: PRT
<213> ORGANISM: Artificial Sequence
<220> FEATURE:
<223> OTHER INFORMATION: Engineered antibody from hybridoma

<400> SEQUENCE: 102

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Leu Tyr Phe Ala Ser Thr Arg Glu Ser Gly Val
    50                  55                  60

Pro Asp Arg Phe Ile Gly Ser Gly Ser Gly Thr Asp Phe Thr Leu Ser
65                  70                  75                  80

Ile Ser Ser Val Gln Ala Glu Asp Leu Ala Asp Tyr Phe Cys Gln Gln
                85                  90                  95

His Tyr Ser Thr Pro Phe Thr Phe Gly Ser Gly Thr Lys Leu Glu Ile
            100                 105                 110

Lys


<210> SEQ ID NO 103
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 103

Lys Ser Ser Gln Ser Leu Leu Asn Ser Ser Asn Gln Lys Asn Tyr Leu
1               5                   10                  15

Ala


<210> SEQ ID NO 104
<211> LENGTH: 7
```

<212> TYPE: PRT
<213> ORGANISM: Artificial Sequence
<220> FEATURE:
<223> OTHER INFORMATION: Engineered antibody from hybridoma

<400> SEQUENCE: 104

Phe Ala Ser Thr Arg Glu Ser
1               5

<210> SEQ ID NO 105
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 105

Gln Gln His Tyr Ser Thr Pro Phe Thr
1               5

<210> SEQ ID NO 106
<211> LENGTH: 220
<212> TYPE: PRT
<213> ORGANISM: Artificial Sequence
<220> FEATURE:
<223> OTHER INFORMATION: Engineered antibody from hybridoma

<400> SEQUENCE: 106

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Leu Tyr Phe Ala Ser Thr Arg Glu Ser Gly Val
    50                  55                  60

Pro Asp Arg Phe Ile Gly Ser Gly Ser Gly Thr Asp Phe Thr Leu Ser
65                  70                  75                  80

Ile Ser Ser Val Gln Ala Glu Asp Leu Ala Asp Tyr Phe Cys Gln Gln
                85                  90                  95

His Tyr Ser Thr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 107
<211> LENGTH: 118
<212> TYPE: PRT

<213> ORGANISM: Artificial Sequence
<220> FEATURE:
<223> OTHER INFORMATION: Engineered antibody from hybridoma

<400> SEQUENCE: 107

Glu Ile Gln Leu Gln Gln Ser Gly Ala Glu Leu Val Lys Pro Gly Ala
1               5                   10                  15

Ser Val Lys Ile Ser Cys Lys Ala Ser Gly His Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Thr Gln Lys Phe
    50                  55                  60

Lys Gly Lys Ala Thr Leu Thr Val Asp Lys Ser Ser Thr Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Tyr Asp Asp Tyr Phe Asp Tyr Trp Gly Gln Gly Thr
            100                 105                 110

Thr Leu Thr Val Ser Ser
        115

<210> SEQ ID NO 108
<211> LENGTH: 5
<212> TYPE: PRT
<213> ORGANISM: Artificial Sequence
<220> FEATURE:
<223> OTHER INFORMATION: Engineered antibody from hybridoma

<400> SEQUENCE: 108

Gly Tyr Asn Met Asn
1               5

<210> SEQ ID NO 109
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 109

Asn Ile Asn Pro Tyr Tyr Gly Ser Thr Ser Tyr Thr Gln Lys Phe Lys
1               5                   10                  15

Gly

<210> SEQ ID NO 110
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 110

Gly Gly Tyr Asp Asp Tyr Phe Asp Tyr
1               5

<210> SEQ ID NO 111
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 111

Glu Ile Gln Leu Gln Gln Ser Gly Ala Glu Leu Val Lys Pro Gly Ala
1               5                   10                  15

Ser Val Lys Ile Ser Cys Lys Ala Ser Gly His Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Thr Gln Lys Phe
    50                  55                  60

Lys Gly Lys Ala Thr Leu Thr Val Asp Lys Ser Ser Thr Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Tyr Asp Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 112
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 112

Glu Ile Gln Leu Gln Gln Ser Gly Ala Glu Leu Val Lys Pro Gly Ala
1 5 10 15

Ser Val Lys Ile Ser Cys Lys Ala Ser Gly His Ser Phe Thr Gly Tyr
20 25 30

Asn Met Asn Trp Val Lys Gln Ser His Gly Lys Ser Leu Glu Trp Ile
35 40 45

Gly Asn Ile Asn Pro Tyr Tyr Gly Ser Thr Ser Tyr Thr Gln Lys Phe
50 55 60

Lys Gly Lys Ala Thr Leu Thr Val Asp Lys Ser Ser Thr Thr Ala Tyr
65 70 75 80

Met Gln Leu Asn Ser Leu Thr Ser Glu Asp Ser Ala Val Tyr Tyr Cys
85 90 95

Ala Arg Gly Gly Tyr Asp Asp Tyr Phe Asp Tyr Trp Gly Gln Gly Thr
100 105 110

Thr Leu Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Phe Glu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Ser Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 113
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 113

Glu Ile Gln Leu Gln Gln Ser Gly Ala Glu Leu Val Lys Pro Gly Ala
1 5 10 15

Ser Val Lys Ile Ser Cys Lys Ala Ser Gly His Ser Phe Thr Gly Tyr
20 25 30

Asn Met Asn Trp Val Lys Gln Ser His Gly Lys Ser Leu Glu Trp Ile
35 40 45

Gly Asn Ile Asn Pro Tyr Tyr Gly Ser Thr Ser Tyr Thr Gln Lys Phe
50 55 60

Lys Gly Lys Ala Thr Leu Thr Val Asp Lys Ser Ser Thr Thr Ala Tyr
65 70 75 80

Met Gln Leu Asn Ser Leu Thr Ser Glu Asp Ser Ala Val Tyr Tyr Cys
85 90 95

Ala Arg Gly Gly Tyr Asp Asp Tyr Phe Asp Tyr Trp Gly Gln Gly Thr
100 105 110

Thr Leu Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys
210 215 220

Pro Pro Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly
435 440

<210> SEQ ID NO 114
<211> LENGTH: 106
<212> TYPE: PRT
<213> ORGANISM: Artificial Sequence
<220> FEATURE:
<223> OTHER INFORMATION: Engineered antibody from hybridoma

<400> SEQUENCE: 114

Asp Ile Val Met Thr Gln Ser His Lys Phe Met Ser Thr Ser Val Gly
1 5 10 15

Asp Arg Val Thr Ile Thr Cys Lys Ala Ser Gln Asp Val Gly Thr Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln Gln Tyr Ser Ser Tyr Pro Thr
85 90 95

Phe Gly Gly Gly Thr Lys Leu Glu Ile Lys
100 105

<210> SEQ ID NO 115
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 115

Lys Ala Ser Gln Asp Val Gly Thr Ala Val Ala 1 5 10

<210> SEQ ID NO 116
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 116

Trp Ala Ser Thr Arg His Thr
1 5

<210> SEQ ID NO 117
<211> LENGTH: 8
<212> TYPE: PRT
<213> ORGANISM: Artificial Sequence
<220> FEATURE:
<223> OTHER INFORMATION: Engineered antibody from hybridoma

<400> SEQUENCE: 117

Gln Gln Tyr Ser Ser Tyr Pro Thr
1 5

<210> SEQ ID NO 118
<211> LENGTH: 213
<212> TYPE: PRT
<213> ORGANISM: Artificial Sequence
<220> FEATURE:
<223> OTHER INFORMATION: Engineered antibody from hybridoma

<400> SEQUENCE: 118

Asp Ile Val Met Thr Gln Ser His Lys Phe Met Ser Thr Ser Val Gly
1 5 10 15

Asp Arg Val Thr Ile Thr Cys Lys Ala Ser Gln Asp Val Gly Thr Ala
20 25 30

Val Ala Trp Tyr Gln Gln Lys Pro Gly Gln Ser Pro Lys Leu Leu Ile
35 40 45

Tyr Trp Ala Ser Thr Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln Gln Tyr Ser Ser Tyr Pro Thr
85 90 95

Phe Gly Gly Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 119
<211> LENGTH: 115
<212> TYPE: PRT
<213> ORGANISM: Artificial Sequence
<220> FEATURE:
<223> OTHER INFORMATION: Engineered antibody from hybridoma

<400> SEQUENCE: 119

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Arg Val Asn Pro Ser Asn Gly Val Thr Ser Tyr Asn Gln Lys Phe
50 55 60

Lys Gly Lys Ala Ala Leu Thr Val Asp Lys Ser Leu Ser Thr Ala Tyr
65 70 75 80

Met Gln Leu Asn Ser Leu Thr Ser Glu Asp Ser Ala Val Tyr Tyr Cys
85 90 95

Ala Arg Asp Phe Leu Met Asp Tyr Trp Gly Gln Gly Thr Ser Val Thr
100 105 110

Val Ser Ser
115

<210> SEQ ID NO 120
<211> LENGTH: 5
<212> TYPE: PRT
<213> ORGANISM: Artificial Sequence
<220> FEATURE:
<223> OTHER INFORMATION: Engineered antibody from hybridoma

<400> SEQUENCE: 120

Asp Tyr Tyr Met Asn
1 5

<210> SEQ ID NO 121
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 121

Arg Val Asn Pro Ser Asn Gly Val Thr Ser Tyr Asn Gln Lys Phe Lys
1 5 10 15

Gly

<210> SEQ ID NO 122
<211> LENGTH: 6
<212> TYPE: PRT
<213> ORGANISM: Artificial Sequence
<220> FEATURE:
<223> OTHER INFORMATION: Engineered antibody from hybridoma

<400> SEQUENCE: 122

Asp Phe Leu Met Asp Tyr
1 5

<210> SEQ ID NO 123
<211> LENGTH: 444

<212> TYPE: PRT
<213> ORGANISM: Artificial Sequence
<220> FEATURE:
<223> OTHER INFORMATION: Engineered antibody from hybridoma

<400> SEQUENCE: 123

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Val Thr Ser Tyr Asn Gln Lys Phe
    50                  55                  60

Lys Gly Lys Ala Ala Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 124
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 124

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Val Thr Ser Tyr Asn Gln Lys Phe
    50                  55                  60

Lys Gly Lys Ala Ala Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Ala Leu Pro Ala Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440


<210> SEQ ID NO 125
<211> LENGTH: 441
<212> TYPE: PRT
<213> ORGANISM: Artificial Sequence
<220> FEATURE:
<223> OTHER INFORMATION: Engineered antibody from hybridoma

<400> SEQUENCE: 125

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Val Thr Ser Tyr Asn Gln Lys Phe
    50                  55                  60

Lys Gly Lys Ala Ala Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220
```

```
Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440
```

<210> SEQ ID NO 126
<211> LENGTH: 106
<212> TYPE: PRT
<213> ORGANISM: Artificial Sequence
<220> FEATURE:
<223> OTHER INFORMATION: Engineered antibody from hybridoma

<400> SEQUENCE: 126

```
Asp Ile Val Met Thr Gln Ser His Lys Phe Met Ser Thr Ser Ile Gly
1               5                   10                  15

Asp Arg Val Asn Ile Thr Cys Lys Ala Ser Gln Asp Val Gly Thr Ala
            20                  25                  30

Val Ala Trp Phe Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Thr
                85                  90                  95

Phe Gly Ala Gly Thr Thr Leu Glu Leu Lys
            100                 105
```

<210> SEQ ID NO 127
<211> LENGTH: 213
<212> TYPE: PRT
<213> ORGANISM: Artificial Sequence
<220> FEATURE:

<223> OTHER INFORMATION: Engineered antibody from hybridoma

<400> SEQUENCE: 127

```
Asp Ile Val Met Thr Gln Ser His Lys Phe Met Ser Thr Ser Ile Gly
1               5                   10                  15

Asp Arg Val Asn Ile Thr Cys Lys Ala Ser Gln Asp Val Gly Thr Ala
            20                  25                  30

Val Ala Trp Phe Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Thr
                85                  90                  95

Phe Gly Ala Gly Thr Thr Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 128
<211> LENGTH: 115
<212> TYPE: PRT
<213> ORGANISM: Artificial Sequence
<220> FEATURE:
<223> OTHER INFORMATION: Engineered antibody from hybridoma

<400> SEQUENCE: 128

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Tyr Pro Ser Asn Ser Gly Ala Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Ser Tyr Tyr Phe Asp Tyr Trp Gly Gln Gly Thr Thr Leu Thr
            100                 105                 110

Val Ser Ser
        115
```

<210> SEQ ID NO 129
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 129

```
Arg Val Tyr Pro Ser Asn Ser Gly Ala Ser Tyr Asn Gln Lys Phe Lys
1               5                   10                  15

Gly
```

<210> SEQ ID NO 130
<211> LENGTH: 5
<212> TYPE: PRT
<213> ORGANISM: Artificial Sequence
<220> FEATURE:
<223> OTHER INFORMATION: Engineered antibody from hybridoma

<400> SEQUENCE: 130

```
Tyr Tyr Phe Asp Tyr
1               5
```

<210> SEQ ID NO 131
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 131

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Tyr Pro Ser Asn Ser Gly Ala Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Ser Tyr Tyr Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
```

```
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440


<210> SEQ ID NO 132
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 132

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Tyr Pro Ser Asn Ser Gly Ala Ser Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Ser Tyr Tyr Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
```

```
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 133
<211> LENGTH: 441
<212> TYPE: PRT
<213> ORGANISM: Artificial Sequence
<220> FEATURE:
<223> OTHER INFORMATION: Engineered antibody from hybridoma

<400> SEQUENCE: 133

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Tyr Pro Ser Asn Ser Gly Ala Ser Tyr Asn Gln Lys Phe
```

```
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Ser Tyr Tyr Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440
```

<210> SEQ ID NO 134
<211> LENGTH: 113
<212> TYPE: PRT
<213> ORGANISM: Artificial Sequence
<220> FEATURE:
<223> OTHER INFORMATION: Engineered antibody from hybridoma

<400> SEQUENCE: 134

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Phe Thr Phe Gly Ser Gly Thr Lys Leu Glu Ile
            100                 105                 110

Lys
```

<210> SEQ ID NO 135
<211> LENGTH: 220
<212> TYPE: PRT
<213> ORGANISM: Artificial Sequence
<220> FEATURE:
<223> OTHER INFORMATION: Engineered antibody from hybridoma

<400> SEQUENCE: 135

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 136
<211> LENGTH: 118
<212> TYPE: PRT
<213> ORGANISM: Artificial Sequence
<220> FEATURE:
<223> OTHER INFORMATION: Engineered antibody from hybridoma

<400> SEQUENCE: 136

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Tyr Asp Asp Tyr Phe Asp Tyr Trp Gly Gln Gly Thr
            100                 105                 110

Thr Leu Thr Val Ser Ser
        115
```

<210> SEQ ID NO 137
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 137

```
Asn Ile Asn Pro Tyr Tyr Gly Ser Thr Ser Tyr Asn Gln Lys Phe Lys
1               5                   10                  15

Gly
```

<210> SEQ ID NO 138
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 138

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Tyr Asp Asp Tyr Phe Asp Tyr Trp Gly Gln Gly Thr
```

```
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 139
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 139

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
```

```
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Tyr Asp Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 140
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 140

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asn Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Ser Gly Gly Tyr Asp Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440


<210> SEQ ID NO 141
<211> LENGTH: 113
<212> TYPE: PRT
<213> ORGANISM: Artificial Sequence
<220> FEATURE:
<223> OTHER INFORMATION: Engineered antibody from hybridoma

<400> SEQUENCE: 141

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Phe Thr Phe Gly Ser Gly Thr Lys Leu Glu Ile
            100                 105                 110

Lys


<210> SEQ ID NO 142
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 142

Gln Gln His Tyr Ser Ile Pro Phe Thr
1               5


<210> SEQ ID NO 143
<211> LENGTH: 220
<212> TYPE: PRT
<213> ORGANISM: Artificial Sequence
<220> FEATURE:
<223> OTHER INFORMATION: Engineered antibody from hybridoma

<400> SEQUENCE: 143

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
```

```
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 144
<211> LENGTH: 121
<212> TYPE: PRT
<213> ORGANISM: Artificial Sequence
<220> FEATURE:
<223> OTHER INFORMATION: Engineered antibody from hybridoma

<400> SEQUENCE: 144

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Gly Tyr Gly Tyr Asp Asp Trp Tyr Phe Asp Val Trp Gly
            100                 105                 110

Ala Gly Thr Thr Val Thr Val Ser Ser
        115                 120
```

<210> SEQ ID NO 145
<211> LENGTH: 12
<212> TYPE: PRT
<213> ORGANISM: Artificial Sequence
<220> FEATURE:
<223> OTHER INFORMATION: Engineered antibody from hybridoma

<400> SEQUENCE: 145

Trp Gly Tyr Gly Tyr Asp Asp Trp Tyr Phe Asp Val
1 5 10

<210> SEQ ID NO 146
<211> LENGTH: 450
<212> TYPE: PRT
<213> ORGANISM: Artificial Sequence
<220> FEATURE:
<223> OTHER INFORMATION: Engineered antibody from hybridoma

<400> SEQUENCE: 146

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Asn Pro Tyr Tyr Gly Ser Thr Ser Tyr Asn Gln Lys Phe
50 55 60

Lys Gly Lys Ala Thr Leu Thr Val Asp Lys Ser Ser Asn Thr Ala Tyr
65 70 75 80

Met Gln Leu Asn Ser Leu Thr Ser Glu Asp Ser Ala Val Tyr Tyr Cys
85 90 95

Ala Arg Trp Gly Tyr Gly Tyr Asp Asp Trp Tyr Phe Asp Val Trp Gly
100 105 110

Ala Gly Thr Thr Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

```
Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 147
<211> LENGTH: 450
<212> TYPE: PRT
<213> ORGANISM: Artificial Sequence
<220> FEATURE:
<223> OTHER INFORMATION: Engineered antibody from hybridoma

<400> SEQUENCE: 147

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Gly Tyr Gly Tyr Asp Asp Trp Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 148
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 148

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Gly Tyr Gly Tyr Asp Asp Trp Tyr Phe Asp Val Trp Gly
            100                 105                 110

Ala Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Lys Thr Tyr Thr Cys Asn Val Asp His
195 200 205

Lys Pro Ser Asn Thr Lys Val Asp Lys Arg Val Glu Ser Lys Tyr Gly
210 215 220

Pro Pro Cys Pro Pro Cys Pro Ala Pro Glu Phe Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser Gln Glu Asp Pro
260 265 270

Glu Val Gln Phe Asn Trp Tyr Val Asp Gly Val Glu Val His Asn Ala
275 280 285

Lys Thr Lys Pro Arg Glu Glu Gln Phe Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Gly Leu Pro Ser Ser Ile Glu Lys Thr
325 330 335

Ile Ser Lys Ala Lys Gly Gln Pro Arg Glu Pro Gln Val Tyr Thr Leu
340 345 350

Pro Pro Ser Gln Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Arg Leu Thr Val Asp Lys Ser
405 410 415

Arg Trp Gln Glu Gly Asn Val Phe Ser Cys Ser Val Met His Glu Ala
420 425 430

Leu His Asn His Tyr Thr Gln Lys Ser Leu Ser Leu Ser Leu Gly
435 440 445

<210> SEQ ID NO 149
<211> LENGTH: 118
<212> TYPE: PRT
<213> ORGANISM: Artificial Sequence
<220> FEATURE:
<223> OTHER INFORMATION: Engineered antibody from hybridoma

<400> SEQUENCE: 149

Glu Ile Gln Leu Gln Gln Ser Gly Ala Glu Met Val Lys Pro Gly Ala
1 5 10 15

Ser Val Lys Ile Ser Cys Lys Ala Ser Gly His Ser Phe Thr Gly Tyr
20 25 30

Asn Met Asn Trp Val Lys Gln Ser His Glu Lys Ser Leu Glu Trp Ile
35 40 45

Gly Asn Ile Asn Pro Tyr Tyr Gly Ser Thr Ser Tyr Asn Gln Lys Phe
50 55 60

Lys Gly Lys Ala Thr Leu Thr Val Asp Lys Ser Ser Ser Thr Ala Tyr
65 70 75 80

```
Met Gln Leu Asn Ser Leu Thr Ser Glu Asp Ser Ala Val Tyr Tyr Cys
                85                  90                  95

Ala Arg Gly Gly Tyr Asp Asp Tyr Phe Asp Tyr Trp Gly Gln Gly Thr
            100                 105                 110

Thr Leu Thr Val Ser Ser
        115


<210> SEQ ID NO 150
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 150

Glu Ile Gln Leu Gln Gln Ser Gly Ala Glu Met Val Lys Pro Gly Ala
1               5                   10                  15

Ser Val Lys Ile Ser Cys Lys Ala Ser Gly His Ser Phe Thr Gly Tyr
            20                  25                  30

Asn Met Asn Trp Val Lys Gln Ser His Glu Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Tyr Asp Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 151
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 151

Glu Ile Gln Leu Gln Gln Ser Gly Ala Glu Met Val Lys Pro Gly Ala
1 5 10 15

Ser Val Lys Ile Ser Cys Lys Ala Ser Gly His Ser Phe Thr Gly Tyr
20 25 30

Asn Met Asn Trp Val Lys Gln Ser His Glu Lys Ser Leu Glu Trp Ile
35 40 45

Gly Asn Ile Asn Pro Tyr Tyr Gly Ser Thr Ser Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Ser Glu Asp Ser Ala Val Tyr Tyr Cys
85 90 95

Ala Arg Gly Gly Tyr Asp Asp Tyr Phe Asp Tyr Trp Gly Gln Gly Thr
100 105 110

Thr Leu Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Phe Glu Gly Gly Pro Ser
225 230 235 240

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 152
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 152

Glu Ile Gln Leu Gln Gln Ser Gly Ala Glu Met Val Lys Pro Gly Ala
1               5                   10                  15

Ser Val Lys Ile Ser Cys Lys Ala Ser Gly His Ser Phe Thr Gly Tyr
            20                  25                  30

Asn Met Asn Trp Val Lys Gln Ser His Glu Lys Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Tyr Asp Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 153
<211> LENGTH: 106
<212> TYPE: PRT
<213> ORGANISM: Artificial Sequence
<220> FEATURE:
<223> OTHER INFORMATION: Engineered antibody from hybridoma

<400> SEQUENCE: 153

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Thr Trp Tyr Gln Gln Lys Pro Gly Leu Ser Pro Lys Leu Leu Phe
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

Glu Asp Leu Ala Asp Tyr Phe Cys His Gln Tyr Ser Asn Tyr Pro Thr
85 90 95

Phe Gly Gly Gly Thr Lys Leu Glu Ile Lys
100 105

<210> SEQ ID NO 154
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 154

Lys Ala Ser Gln Asp Val Gly Thr Ala Val Thr
1 5 10

<210> SEQ ID NO 155
<211> LENGTH: 8
<212> TYPE: PRT
<213> ORGANISM: Artificial Sequence
<220> FEATURE:
<223> OTHER INFORMATION: Engineered antibody from hybridoma

<400> SEQUENCE: 155

His Gln Tyr Ser Asn Tyr Pro Thr
1 5

<210> SEQ ID NO 156
<211> LENGTH: 213
<212> TYPE: PRT
<213> ORGANISM: Artificial Sequence
<220> FEATURE:
<223> OTHER INFORMATION: Engineered antibody from hybridoma

<400> SEQUENCE: 156

Asp Ile Val Met Thr Gln Ser His Lys Phe Met Ser Thr Ser Val Gly
1 5 10 15

Asp Arg Val Ser Ile Thr Cys Lys Ala Ser Gln Asp Val Gly Thr Ala
20 25 30

Val Thr Trp Tyr Gln Gln Lys Pro Gly Leu Ser Pro Lys Leu Leu Phe
35 40 45

Tyr Trp Ala Ser Thr Arg His Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys His Gln Tyr Ser Asn Tyr Pro Thr
85 90 95

Phe Gly Gly Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe

```
        195                 200                 205

Asn Arg Gly Glu Cys
    210


<210> SEQ ID NO 157
<211> LENGTH: 115
<212> TYPE: PRT
<213> ORGANISM: Artificial Sequence
<220> FEATURE:
<223> OTHER INFORMATION: Engineered antibody from hybridoma

<400> SEQUENCE: 157

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Thr Tyr Asn Gln Arg Phe
    50                  55                  60

Lys Gly Lys Ala Thr Leu Thr Val Asp Glu Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser
        115


<210> SEQ ID NO 158
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 158

Arg Val Asn Pro Ser Asn Gly Gly Thr Thr Tyr Asn Gln Arg Phe Lys
1               5                   10                  15

Gly


<210> SEQ ID NO 159
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 159

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Thr Tyr Asn Gln Arg Phe
    50                  55                  60

Lys Gly Lys Ala Thr Leu Thr Val Asp Glu Ser Leu Ser Thr Ala Tyr
65                  70                  75                  80
```

```
Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 160
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 160

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Thr Tyr Asn Gln Arg Phe
    50                  55                  60

Lys Gly Lys Ala Thr Leu Thr Val Asp Glu Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
```

```
            420                 425                 430

His Tyr Thr Gln Lys Ser Leu Ser Leu Ser Pro Gly
        435                 440


<210> SEQ ID NO 161
<211> LENGTH: 441
<212> TYPE: PRT
<213> ORGANISM: Artificial Sequence
<220> FEATURE:
<223> OTHER INFORMATION: Engineered antibody from hybridoma

<400> SEQUENCE: 161

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Thr Tyr Asn Gln Arg Phe
    50                  55                  60

Lys Gly Lys Ala Thr Leu Thr Val Asp Glu Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
```

```
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440


<210> SEQ ID NO 162
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 162

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Lys Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105


<210> SEQ ID NO 163
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 163

Ile Thr Ser Thr Asp Ile Asp Asp Asp Met Asn
1               5                   10


<210> SEQ ID NO 164
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 164

Glu Gly Asn Thr Leu Arg Pro
1               5


<210> SEQ ID NO 165
```

<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 165

Leu Gln Ser Asp Asn Leu Pro Tyr Thr
1 5

<210> SEQ ID NO 166
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 166

Glu Thr Thr Val Thr Gln Ser Pro Ala Ser Leu Ser Met Ala Ile Gly
1 5 10 15

Glu Lys Val Thr Ile Arg Cys Ile Thr Ser Thr Asp Ile Asp Asp Asp
20 25 30

Met Asn Trp Tyr Gln Gln Lys Pro Gly Lys Pro Pro Lys Leu Leu Ile
35 40 45

Ser Glu Gly Asn Thr Leu Arg Pro Gly Val Pro Ser Arg Phe Ser Ser
50 55 60

Ser Gly Tyr Gly Thr Asp Phe Val Phe Thr Ile Glu Asn Met Leu Ser
65 70 75 80

Glu Asp Val Ala Asp Tyr Tyr Cys Leu Gln Ser Asp Asn Leu Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 167
<211> LENGTH: 120
<212> TYPE: PRT
<213> ORGANISM: Artificial Sequence
<220> FEATURE:
<223> OTHER INFORMATION: Engineered antibody from hybridoma

<400> SEQUENCE: 167

Glu Ile Gln Leu Gln Gln Ser Gly Thr Glu Leu Val Lys Pro Gly Ala
1 5 10 15

Ser Val Lys Ile Ser Cys Lys Ala Ser Gly Tyr Ser Phe Thr Gly Tyr
20 25 30

```
Asn Met Asn Trp Met Lys Gln Ser His Gly Met Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Arg Lys Asn Trp Glu Tyr Phe Phe Asp Tyr Trp Gly Gln
            100                 105                 110

Gly Thr Thr Leu Thr Val Ser Ser
        115                 120
```

<210> SEQ ID NO 168
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 168

```
Asp Arg Lys Asn Trp Glu Tyr Phe Phe Asp Tyr
1               5                   10
```

<210> SEQ ID NO 169
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 169

```
Glu Ile Gln Leu Gln Gln Ser Gly Thr Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Met Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Arg Lys Asn Trp Glu Tyr Phe Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 170
<211> LENGTH: 449
<212> TYPE: PRT
<213> ORGANISM: Artificial Sequence
<220> FEATURE:
<223> OTHER INFORMATION: Engineered antibody from hybridoma

<400> SEQUENCE: 170

Glu Ile Gln Leu Gln Gln Ser Gly Thr Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Met Lys Gln Ser His Gly Met Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Arg Lys Asn Trp Glu Tyr Phe Phe Asp Tyr Trp Gly Gln
            100                 105                 110

```
Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Phe Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

<210> SEQ ID NO 171
<211> LENGTH: 446
<212> TYPE: PRT
<213> ORGANISM: Artificial Sequence
<220> FEATURE:
<223> OTHER INFORMATION: Engineered antibody from hybridoma

<400> SEQUENCE: 171

```
Glu Ile Gln Leu Gln Gln Ser Gly Thr Glu Leu Val Lys Pro Gly Ala
1               5                   10                  15

Ser Val Lys Ile Ser Cys Lys Ala Ser Gly Tyr Ser Phe Thr Gly Tyr
```

```
            20                  25                  30

Asn Met Asn Trp Met Lys Gln Ser His Gly Met Ser Leu Glu Trp Ile
        35                  40                  45

Gly Asn Ile Asn Pro Tyr Tyr Gly Ser Thr Ser Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Arg Lys Asn Trp Glu Tyr Phe Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445
```

<210> SEQ ID NO 172
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 172

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Leu Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Leu
                85                  90                  95

Thr Phe Gly Ala Gly Thr Lys Leu Glu Leu Lys
            100                 105
```

<210> SEQ ID NO 173
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 173

```
Lys Ala Ser Gln Asp Leu Ser Thr Ala Val Ala
1               5                   10
```

<210> SEQ ID NO 174
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 174

```
Ser Ala Ser Tyr Arg Tyr Thr
1               5
```

<210> SEQ ID NO 175
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 175

```
Gln Gln His Tyr Ser Thr Pro Leu Thr
1               5
```

<210> SEQ ID NO 176
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 176

Asp Ile Val Met Thr Gln Ser His Lys Phe Met Ser Thr Ser Val Gly
1 5 10 15

Asp Arg Val Ser Ile Thr Cys Lys Ala Ser Gln Asp Leu Ser Thr Ala
20 25 30

Val Ala Trp Tyr Gln Gln Lys Pro Gly Gln Ser Pro Lys Leu Leu Ile
35 40 45

Tyr Ser Ala Ser Tyr Arg Tyr Thr Gly Val Pro Asp Arg Phe Thr Gly
50 55 60

Ser Gly Ser Gly Thr Asp Phe Thr Phe Thr Ile Ser Ser Val Gln Ala
65 70 75 80

Glu Asp Leu Ala Val Tyr Tyr Cys Gln Gln His Tyr Ser Thr Pro Leu
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 177
<211> LENGTH: 121
<212> TYPE: PRT
<213> ORGANISM: Artificial Sequence
<220> FEATURE:
<223> OTHER INFORMATION: Engineered antibody from hybridoma

<400> SEQUENCE: 177

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Thr Pro Tyr Tyr Gly Ser Ala Ser Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Ser Glu Asp Ser Ala Val Tyr Tyr Cys
85 90 95

Ala Arg Arg Ser Tyr Asp Tyr Asp Glu Asn Ala Met Asp Tyr Trp Gly
100 105 110

Gln Gly Thr Ser Val Thr Val Ser Ser
115 120

<210> SEQ ID NO 178
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 178

```
Asn Ile Thr Pro Tyr Tyr Gly Ser Ala Ser Tyr Asn Gln Lys Phe Lys
1               5                   10                  15

Gly
```

<210> SEQ ID NO 179
<211> LENGTH: 12
<212> TYPE: PRT
<213> ORGANISM: Artificial Sequence
<220> FEATURE:
<223> OTHER INFORMATION: Engineered antibody from hybridoma

<400> SEQUENCE: 179

```
Arg Ser Tyr Asp Tyr Asp Glu Asn Ala Met Asp Tyr
1               5                   10
```

<210> SEQ ID NO 180
<211> LENGTH: 450
<212> TYPE: PRT
<213> ORGANISM: Artificial Sequence
<220> FEATURE:
<223> OTHER INFORMATION: Engineered antibody from hybridoma

<400> SEQUENCE: 180

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Thr Pro Tyr Tyr Gly Ser Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ser Tyr Asp Tyr Asp Glu Asn Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 181
<211> LENGTH: 450
<212> TYPE: PRT
<213> ORGANISM: Artificial Sequence
<220> FEATURE:
<223> OTHER INFORMATION: Engineered antibody from hybridoma

<400> SEQUENCE: 181

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Thr Pro Tyr Tyr Gly Ser Ala Ser Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Ser Glu Asp Ser Ala Val Tyr Tyr Cys
85 90 95

Ala Arg Arg Ser Tyr Asp Tyr Asp Glu Asn Ala Met Asp Tyr Trp Gly
100 105 110

Gln Gly Thr Ser Val Thr Val Ser Ser Ala Ser Thr Lys Gly Pro Ser
115 120 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 182
<211> LENGTH: 447
<212> TYPE: PRT
<213> ORGANISM: Artificial Sequence
<220> FEATURE:
<223> OTHER INFORMATION: Engineered antibody from hybridoma

<400> SEQUENCE: 182

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

```
Asn Met Asn Trp Val Lys Gln Ser His Gly Lys Ser Leu Glu Trp Ile
        35                  40                  45

Gly Asn Ile Thr Pro Tyr Tyr Gly Ser Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Ser Tyr Asp Tyr Asp Glu Asn Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445
```

<210> SEQ ID NO 183
<211> LENGTH: 106
<212> TYPE: PRT
<213> ORGANISM: Artificial Sequence
<220> FEATURE:
<223> OTHER INFORMATION: Engineered antibody from hybridoma

<400> SEQUENCE: 183

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys
            100                 105

<210> SEQ ID NO 184
<211> LENGTH: 10
<212> TYPE: PRT
<213> ORGANISM: Artificial Sequence
<220> FEATURE:
<223> OTHER INFORMATION: Engineered antibody from hybridoma

<400> SEQUENCE: 184

Ser Ala Ser Ser Ser Val Ser Tyr Met His
1               5                   10

<210> SEQ ID NO 185
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 185

Asp Thr Ser Lys Leu Ala Ser
1               5

<210> SEQ ID NO 186
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 186

Gln Gln Trp Ser Gly Asn Pro Tyr Thr
1               5

<210> SEQ ID NO 187
<211> LENGTH: 213
<212> TYPE: PRT
<213> ORGANISM: Artificial Sequence
<220> FEATURE:
<223> OTHER INFORMATION: Engineered antibody from hybridoma

<400> SEQUENCE: 187

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Val Ser Tyr Met
20 25 30

His Trp Tyr Gln Gln Lys Ser Gly Thr Ser Pro Lys Arg Trp Ile Tyr
35 40 45

Asp Thr Ser Lys Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Ser Gly Asn Pro Tyr Thr
85 90 95

Phe Gly Gly Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 188
<211> LENGTH: 122
<212> TYPE: PRT
<213> ORGANISM: Artificial Sequence
<220> FEATURE:
<223> OTHER INFORMATION: Engineered antibody from hybridoma

<400> SEQUENCE: 188

Glu Val Lys Leu Glu Glu Ser Gly Gly Gly Leu Val Gln Pro Gly Gly
1 5 10 15

Ser Met Lys Leu Ser Cys Val Val Ser Gly Phe Thr Phe Ser Asn Tyr
20 25 30

Trp Met Asn Trp Val Arg Gln Ser Pro Glu Lys Gly Leu Glu Trp Val
35 40 45

Ala Gln Ile Arg Leu Lys Ser Asp Asn Tyr Ala Thr His Tyr Ala Glu
50 55 60

Ser Val Lys Gly Arg Phe Thr Ile Ser Arg Asp Asp Ser Lys Ser Ser
65 70 75 80

Val Tyr Leu Gln Met Asn Asn Leu Arg Ala Glu Asp Thr Gly Ile Tyr
85 90 95

Tyr Cys Thr Gly Glu Ser Asn Ile Tyr Tyr Gly Tyr Phe Asp Tyr Trp
100 105 110

Gly Gln Gly Thr Thr Leu Thr Val Ser Ser
115 120

<210> SEQ ID NO 189
<211> LENGTH: 5

<212> TYPE: PRT
<213> ORGANISM: Artificial Sequence
<220> FEATURE:
<223> OTHER INFORMATION: Engineered antibody from hybridoma

<400> SEQUENCE: 189

Asn Tyr Trp Met Asn
1               5

<210> SEQ ID NO 190
<211> LENGTH: 19
<212> TYPE: PRT
<213> ORGANISM: Artificial Sequence
<220> FEATURE:
<223> OTHER INFORMATION: Engineered antibody from hybridoma

<400> SEQUENCE: 190

Gln Ile Arg Leu Lys Ser Asp Asn Tyr Ala Thr His Tyr Ala Glu Ser
1               5                   10                  15

Val Lys Gly

<210> SEQ ID NO 191
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 191

Glu Ser Asn Ile Tyr Tyr Gly Tyr Phe Asp Tyr
1               5                   10

<210> SEQ ID NO 192
<211> LENGTH: 451
<212> TYPE: PRT
<213> ORGANISM: Artificial Sequence
<220> FEATURE:
<223> OTHER INFORMATION: Engineered antibody from hybridoma

<400> SEQUENCE: 192

Glu Val Lys Leu Glu Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Ser Asn Ile Tyr Tyr Gly Tyr Phe Asp Tyr Trp
            100                 105                 110

Gly Gln Gly Thr Thr Leu Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro 165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Asp Glu Leu Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly
450

<210> SEQ ID NO 193
<211> LENGTH: 451
<212> TYPE: PRT
<213> ORGANISM: Artificial Sequence
<220> FEATURE:
<223> OTHER INFORMATION: Engineered antibody from hybridoma

<400> SEQUENCE: 193

Glu Val Lys Leu Glu Glu Ser Gly Gly Gly Leu Val Gln Pro Gly Gly
1 5 10 15

Ser Met Lys Leu Ser Cys Val Val Ser Gly Phe Thr Phe Ser Asn Tyr
20 25 30

Trp Met Asn Trp Val Arg Gln Ser Pro Glu Lys Gly Leu Glu Trp Val
35 40 45

Ala Gln Ile Arg Leu Lys Ser Asp Asn Tyr Ala Thr His Tyr Ala Glu
50 55 60

Ser Val Lys Gly Arg Phe Thr Ile Ser Arg Asp Asp Ser Lys Ser Ser

```
65                  70                  75                  80

Val Tyr Leu Gln Met Asn Asn Leu Arg Ala Glu Asp Thr Gly Ile Tyr
                85                  90                  95

Tyr Cys Thr Gly Glu Ser Asn Ile Tyr Tyr Gly Tyr Phe Asp Tyr Trp
            100                 105                 110

Gly Gln Gly Thr Thr Leu Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450
```

<210> SEQ ID NO 194
<211> LENGTH: 448
<212> TYPE: PRT
<213> ORGANISM: Artificial Sequence
<220> FEATURE:
<223> OTHER INFORMATION: Engineered antibody from hybridoma

<400> SEQUENCE: 194

```
Glu Val Lys Leu Glu Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Ser Asn Ile Tyr Tyr Gly Tyr Phe Asp Tyr Trp
            100                 105                 110

Gly Gln Gly Thr Thr Leu Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Arg Leu Thr Val Asp Lys
405 410 415

Ser Arg Trp Gln Glu Gly Asn Val Phe Ser Cys Ser Val Met His Glu
420 425 430

Ala Leu His Asn His Tyr Thr Gln Lys Ser Leu Ser Leu Ser Leu Gly
435 440 445

<210> SEQ ID NO 195
<211> LENGTH: 107
<212> TYPE: PRT
<213> ORGANISM: Artificial Sequence
<220> FEATURE:
<223> OTHER INFORMATION: Engineered antibody from hybridoma

<400> SEQUENCE: 195

Asp Ile Gln Met Thr Gln Ser Pro Ala Ser Gln Ser Ala Ser Leu Gly
1 5 10 15

Glu Ser Val Thr Ile Thr Cys Leu Ala Ser Gln Thr Ile Gly Thr Trp
20 25 30

Leu Ala Trp Tyr Gln Gln Lys Pro Gly Lys Ser Pro Gln Leu Leu Ile
35 40 45

Tyr Ala Ala Thr Ser Leu Ala Asp Gly Val Pro Ser Arg Phe Ser Gly
50 55 60

Ser Gly Ser Gly Thr Lys Phe Ser Phe Lys Ile Ser Ser Leu Gln Ala
65 70 75 80

Glu Asp Phe Val Ser Tyr Tyr Cys Gln Gln Leu Tyr Ser Asn Pro Tyr
85 90 95

Thr Phe Gly Gly Gly Thr Lys Leu Glu Ile Lys
100 105

<210> SEQ ID NO 196
<211> LENGTH: 11
<212> TYPE: PRT
<213> ORGANISM: Artificial Sequence
<220> FEATURE:
<223> OTHER INFORMATION: Engineered antibody from hybridoma

<400> SEQUENCE: 196

Leu Ala Ser Gln Thr Ile Gly Thr Trp Leu Ala
1 5 10

<210> SEQ ID NO 197
<211> LENGTH: 7
<212> TYPE: PRT
<213> ORGANISM: Artificial Sequence
<220> FEATURE:
<223> OTHER INFORMATION: Engineered antibody from hybridoma

<400> SEQUENCE: 197

Ala Ala Thr Ser Leu Ala Asp
1 5

<210> SEQ ID NO 198
<211> LENGTH: 9
<212> TYPE: PRT
<213> ORGANISM: Artificial Sequence
<220> FEATURE:
<223> OTHER INFORMATION: Engineered antibody from hybridoma

<400> SEQUENCE: 198

Gln Gln Leu Tyr Ser Asn Pro Tyr Thr
1 5

<210> SEQ ID NO 199
<211> LENGTH: 214
<212> TYPE: PRT
<213> ORGANISM: Artificial Sequence
<220> FEATURE:
<223> OTHER INFORMATION: Engineered antibody from hybridoma

<400> SEQUENCE: 199

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Asn Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 200
<211> LENGTH: 124
<212> TYPE: PRT
<213> ORGANISM: Artificial Sequence
<220> FEATURE:
<223> OTHER INFORMATION: Engineered antibody from hybridoma

<400> SEQUENCE: 200

```
Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Thr Pro Tyr Tyr Gly Ser Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
```

```
                85                  90                  95

Ala Arg Arg Asp Tyr Tyr Gly Ser Ser Tyr Gly Ser Ser Tyr Phe Asp
            100                 105                 110

Tyr Trp Gly Gln Gly Thr Thr Leu Thr Val Ser Ser
        115                 120


<210> SEQ ID NO 201
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 201

Asn Ile Thr Pro Tyr Tyr Gly Ser Thr Phe Tyr Asn Gln Lys Phe Lys
1               5                   10                  15

Gly


<210> SEQ ID NO 202
<211> LENGTH: 15
<212> TYPE: PRT
<213> ORGANISM: Artificial Sequence
<220> FEATURE:
<223> OTHER INFORMATION: Engineered antibody from hybridoma

<400> SEQUENCE: 202

Arg Asp Tyr Tyr Gly Ser Ser Tyr Gly Ser Ser Tyr Phe Asp Tyr
1               5                   10                  15


<210> SEQ ID NO 203
<211> LENGTH: 453
<212> TYPE: PRT
<213> ORGANISM: Artificial Sequence
<220> FEATURE:
<223> OTHER INFORMATION: Engineered antibody from hybridoma

<400> SEQUENCE: 203

Glu Ile Gln Leu Gln Gln Ser Gly Ala Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser His Gly Lys Ser Leu Glu Trp Ile
        35                  40                  45

Gly Asn Ile Thr Pro Tyr Tyr Gly Ser Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asp Tyr Tyr Gly Ser Ser Tyr Gly Ser Ser Tyr Phe Asp
            100                 105                 110

Tyr Trp Gly Gln Gly Thr Thr Leu Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Asp Glu Leu Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly
450

<210> SEQ ID NO 204
<211> LENGTH: 453
<212> TYPE: PRT
<213> ORGANISM: Artificial Sequence
<220> FEATURE:
<223> OTHER INFORMATION: Engineered antibody from hybridoma

<400> SEQUENCE: 204

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Thr Pro Tyr Tyr Gly Ser Thr Phe Tyr Asn Gln Lys Phe
50 55 60

Lys Gly Lys Ala Thr Leu Thr Val Asp Lys Ser Ser Ser Thr Ala Tyr
65 70 75 80

```
Met Gln Leu Asn Ser Leu Thr Ser Glu Asp Ser Ala Val Tyr Tyr Cys
                85                  90                  95

Ala Arg Arg Asp Tyr Tyr Gly Ser Ser Tyr Gly Ser Ser Tyr Phe Asp
            100                 105                 110

Tyr Trp Gly Gln Gly Thr Thr Leu Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Ser Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 205
<211> LENGTH: 450
<212> TYPE: PRT
<213> ORGANISM: Artificial Sequence
<220> FEATURE:
<223> OTHER INFORMATION: Engineered antibody from hybridoma

<400> SEQUENCE: 205

Glu Ile Gln Leu Gln Gln Ser Gly Ala Glu Leu Val Lys Pro Gly Ala
1 5 10 15

Ser Val Lys Ile Ser Cys Lys Ala Ser Gly Tyr Ser Phe Thr Gly Tyr
20 25 30

Asn Met Asn Trp Val Lys Gln Ser His Gly Lys Ser Leu Glu Trp Ile
35 40 45

Gly Asn Ile Thr Pro Tyr Tyr Gly Ser Thr Phe Tyr Asn Gln Lys Phe
50 55 60

Lys Gly Lys Ala Thr Leu Thr Val Asp Lys Ser Ser Ser Thr Ala Tyr
65 70 75 80

Met Gln Leu Asn Ser Leu Thr Ser Glu Asp Ser Ala Val Tyr Tyr Cys
85 90 95

Ala Arg Arg Asp Tyr Tyr Gly Ser Ser Tyr Gly Ser Ser Tyr Phe Asp
100 105 110

Tyr Trp Gly Gln Gly Thr Thr Leu Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Lys Thr Tyr Thr Cys Asn
195 200 205

Val Asp His Lys Pro Ser Asn Thr Lys Val Asp Lys Arg Val Glu Ser
210 215 220

Lys Tyr Gly Pro Pro Cys Pro Pro Cys Pro Ala Pro Glu Phe Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser Gln
260 265 270

Glu Asp Pro Glu Val Gln Phe Asn Trp Tyr Val Asp Gly Val Glu Val
275 280 285

His Asn Ala Lys Thr Lys Pro Arg Glu Glu Gln Phe Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Gly Leu Pro Ser Ser Ile
325 330 335

Glu Lys Thr Ile Ser Lys Ala Lys Gly Gln Pro Arg Glu Pro Gln Val
340 345 350

Tyr Thr Leu Pro Pro Ser Gln Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Arg Leu Thr Val

```
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly
    450


<210> SEQ ID NO 206
<211> LENGTH: 106
<212> TYPE: PRT
<213> ORGANISM: Artificial Sequence
<220> FEATURE:
<223> OTHER INFORMATION: Engineered antibody from hybridoma

<400> SEQUENCE: 206

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Ala Leu Thr Ile Ser Asn Val Gln Ser
65                  70                  75                  80

Ala Asp Leu Ala Tyr Tyr Phe Cys Gln Gln Tyr Ser Asn Tyr Pro Thr
                85                  90                  95

Phe Gly Gly Gly Thr Lys Leu Glu Ile Lys
            100                 105


<210> SEQ ID NO 207
<211> LENGTH: 8
<212> TYPE: PRT
<213> ORGANISM: Artificial Sequence
<220> FEATURE:
<223> OTHER INFORMATION: Engineered antibody from hybridoma

<400> SEQUENCE: 207

Gln Gln Tyr Ser Asn Tyr Pro Thr
1               5


<210> SEQ ID NO 208
<211> LENGTH: 213
<212> TYPE: PRT
<213> ORGANISM: Artificial Sequence
<220> FEATURE:
<223> OTHER INFORMATION: Engineered antibody from hybridoma

<400> SEQUENCE: 208

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Ala Leu Thr Ile Ser Asn Val Gln Ser
65                  70                  75                  80
```

Ala Asp Leu Ala Tyr Tyr Phe Cys Gln Gln Tyr Ser Asn Tyr Pro Thr
85 90 95

Phe Gly Gly Gly Thr Lys Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 209
<211> LENGTH: 115
<212> TYPE: PRT
<213> ORGANISM: Artificial Sequence
<220> FEATURE:
<223> OTHER INFORMATION: Engineered antibody from hybridoma

<400> SEQUENCE: 209

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Arg Val Asn Pro Ser Asn Gly Gly Thr Thr Tyr Asn Gln Lys Phe
50 55 60

Lys Gly Lys Ala Thr Leu Thr Val Asp Lys Ser Leu Ser Thr Ala Tyr
65 70 75 80

Met Gln Leu Asn Ser Leu Thr Ser Glu Asp Ser Ala Val Tyr Tyr Cys
85 90 95

Ala Arg Asn Phe Leu Met Asp Tyr Trp Gly Gln Gly Thr Ser Val Thr
100 105 110

Val Ser Ser
115

<210> SEQ ID NO 210
<211> LENGTH: 17
<212> TYPE: PRT
<213> ORGANISM: Artificial Sequence
<220> FEATURE:
<223> OTHER INFORMATION: Engineered antibody from hybridoma

<400> SEQUENCE: 210

Arg Val Asn Pro Ser Asn Gly Gly Thr Thr Tyr Asn Gln Lys Phe Lys
1 5 10 15

Gly

<210> SEQ ID NO 211

<211> LENGTH: 6
<212> TYPE: PRT
<213> ORGANISM: Artificial Sequence
<220> FEATURE:
<223> OTHER INFORMATION: Engineered antibody from hybridoma

<400> SEQUENCE: 211

Asn Phe Leu Met Asp Tyr
1 5

<210> SEQ ID NO 212
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 212

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Arg Val Asn Pro Ser Asn Gly Gly Thr Thr Tyr Asn Gln Lys Phe
50 55 60

Lys Gly Lys Ala Thr Leu Thr Val Asp Lys Ser Leu Ser Thr Ala Tyr
65 70 75 80

Met Gln Leu Asn Ser Leu Thr Ser Glu Asp Ser Ala Val Tyr Tyr Cys
85 90 95

Ala Arg Asn Phe Leu Met Asp Tyr Trp Gly Gln Gly Thr Ser Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys 305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Asp Glu Leu Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly
435 440

<210> SEQ ID NO 213
<211> LENGTH: 444
<212> TYPE: PRT
<213> ORGANISM: Artificial Sequence
<220> FEATURE:
<223> OTHER INFORMATION: Engineered antibody from hybridoma

<400> SEQUENCE: 213

Glu Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Asp Tyr
20 25 30

Tyr Met Asn Trp Val Lys Gln Ser His Gly Lys Ser Leu Glu Trp Ile
35 40 45

Gly Arg Val Asn Pro Ser Asn Gly Gly Thr Thr Tyr Asn Gln Lys Phe
50 55 60

Lys Gly Lys Ala Thr Leu Thr Val Asp Lys Ser Leu Ser Thr Ala Tyr
65 70 75 80

Met Gln Leu Asn Ser Leu Thr Ser Glu Asp Ser Ala Val Tyr Tyr Cys
85 90 95

Ala Arg Asn Phe Leu Met Asp Tyr Trp Gly Gln Gly Thr Ser Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Phe Glu Gly Gly Pro Ser Val Phe Leu

```
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 214
<211> LENGTH: 441
<212> TYPE: PRT
<213> ORGANISM: Artificial Sequence
<220> FEATURE:
<223> OTHER INFORMATION: Engineered antibody from hybridoma

<400> SEQUENCE: 214

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Thr Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asn Phe Leu Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
```

```
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440


<210> SEQ ID NO 215
<211> LENGTH: 760
<212> TYPE: PRT
<213> ORGANISM: Artificial Sequence
<220> FEATURE:
<223> OTHER INFORMATION: Engineered antibody from hybridoma

<400> SEQUENCE: 215

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
```

```
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495
```

```
Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Leu Val Pro Arg Gly Ser Asp Lys Thr His Thr Cys Pro Pro Cys Pro
    530                 535                 540

Ala Pro Glu Leu Leu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
        595                 600                 605

Gln Tyr Asn Ser Thr Tyr Arg Val Val Ser Val Leu Thr Val Leu His
    610                 615                 620

Gln Asp Trp Leu Asn Gly Lys Glu Tyr Lys Cys Lys Val Ser Asn Lys
625                 630                 635                 640

Ala Leu Pro Ala Pro Ile Glu Lys Thr Ile Ser Lys Ala Lys Gly Gln
                645                 650                 655

Pro Arg Glu Pro Gln Val Tyr Thr Leu Pro Pro Ser Arg Asp Glu Leu
            660                 665                 670

Thr Lys Asn Gln Val Ser Leu Thr Cys Leu Val Lys Gly Phe Tyr Pro
        675                 680                 685

Ser Asp Ile Ala Val Glu Trp Glu Ser Asn Gly Gln Pro Glu Asn Asn
    690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly
        755                 760
```

```
<210> SEQ ID NO 216
<211> LENGTH: 760
<212> TYPE: PRT
<213> ORGANISM: Artificial Sequence
<220> FEATURE:
<223> OTHER INFORMATION: Engineered antibody from hybridoma

<400> SEQUENCE: 216
```

```
Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95
```

```
Glu Phe Pro Thr Asn Leu Pro Lys Tyr Val Lys Glu Leu His Leu Gln
            100                 105                 110

Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510
```

```
Leu Asn Arg Glu Gln Glu Lys Glu Pro Tyr Lys Asn Pro Asn Leu Pro
        515                 520                 525

Leu Val Pro Arg Gly Ser Asp Lys Thr His Thr Cys Pro Pro Cys Pro
    530                 535                 540

Ala Pro Glu Phe Glu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
        595                 600                 605

Gln Tyr Asn Ser Thr Tyr Arg Val Val Ser Val Leu Thr Val Leu His
    610                 615                 620

Gln Asp Trp Leu Asn Gly Lys Glu Tyr Lys Cys Lys Val Ser Asn Lys
625                 630                 635                 640

Ala Leu Pro Ala Ser Ile Glu Lys Thr Ile Ser Lys Ala Lys Gly Gln
                645                 650                 655

Pro Arg Glu Pro Gln Val Tyr Thr Leu Pro Pro Ser Arg Asp Glu Leu
            660                 665                 670

Thr Lys Asn Gln Val Ser Leu Thr Cys Leu Val Lys Gly Phe Tyr Pro
        675                 680                 685

Ser Asp Ile Ala Val Glu Trp Glu Ser Asn Gly Gln Pro Glu Asn Asn
    690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly
        755                 760


<210> SEQ ID NO 217
<211> LENGTH: 756
<212> TYPE: PRT
<213> ORGANISM: Artificial Sequence
<220> FEATURE:
<223> OTHER INFORMATION: Engineered antibody from hybridoma

<400> SEQUENCE: 217

Met Ile Ser Ala Ala Trp Ser Ile Phe Leu Ile Gly Thr Lys Ile Gly
1               5                   10                  15

Leu Phe Leu Gln Val Ala Pro Leu Ser Val Met Ala Lys Ser Cys Pro
            20                  25                  30

Ser Val Cys Arg Cys Asp Ala Gly Phe Ile Tyr Cys Asn Asp Arg Phe
        35                  40                  45

Leu Thr Ser Ile Pro Thr Gly Ile Pro Glu Asp Ala Thr Thr Leu Tyr
    50                  55                  60

Leu Gln Asn Asn Gln Ile Asn Asn Ala Gly Ile Pro Ser Asp Leu Lys
65                  70                  75                  80

Asn Leu Leu Lys Val Glu Arg Ile Tyr Leu Tyr His Asn Ser Leu Asp
                85                  90                  95

Glu Phe Pro Thr Asn Leu Pro Lys Tyr Val Lys Glu Leu His Leu Gln
            100                 105                 110
```

```
Glu Asn Asn Ile Arg Thr Ile Thr Tyr Asp Ser Leu Ser Lys Ile Pro
        115                 120                 125

Tyr Leu Glu Glu Leu His Leu Asp Asp Asn Ser Val Ser Ala Val Ser
    130                 135                 140

Ile Glu Glu Gly Ala Phe Arg Asp Ser Asn Tyr Leu Arg Leu Leu Phe
145                 150                 155                 160

Leu Ser Arg Asn His Leu Ser Thr Ile Pro Trp Gly Leu Pro Arg Thr
                165                 170                 175

Ile Glu Glu Leu Arg Leu Asp Asp Asn Arg Ile Ser Thr Ile Ser Ser
            180                 185                 190

Pro Ser Leu Gln Gly Leu Thr Ser Leu Lys Arg Leu Val Leu Asp Gly
        195                 200                 205

Asn Leu Leu Asn Asn His Gly Leu Gly Asp Lys Val Phe Phe Asn Leu
    210                 215                 220

Val Asn Leu Thr Glu Leu Ser Leu Val Arg Asn Ser Leu Thr Ala Ala
225                 230                 235                 240

Pro Val Asn Leu Pro Gly Thr Asn Leu Arg Lys Leu Tyr Leu Gln Asp
                245                 250                 255

Asn His Ile Asn Arg Val Pro Pro Asn Ala Phe Ser Tyr Leu Arg Gln
            260                 265                 270

Leu Tyr Arg Leu Asp Met Ser Asn Asn Asn Leu Ser Asn Leu Pro Gln
        275                 280                 285

Gly Ile Phe Asp Asp Leu Asp Asn Ile Thr Gln Leu Ile Leu Arg Asn
    290                 295                 300

Asn Pro Trp Tyr Cys Gly Cys Lys Met Lys Trp Val Arg Asp Trp Leu
305                 310                 315                 320

Gln Ser Leu Pro Val Lys Val Asn Val Arg Gly Leu Met Cys Gln Ala
                325                 330                 335

Pro Glu Lys Val Arg Gly Met Ala Ile Lys Asp Leu Asn Ala Glu Leu
            340                 345                 350

Phe Asp Cys Lys Asp Ser Gly Ile Val Ser Thr Ile Gln Ile Thr Thr
        355                 360                 365

Ala Ile Pro Asn Thr Val Tyr Pro Ala Gln Gly Gln Trp Pro Ala Pro
    370                 375                 380

Val Thr Lys Gln Pro Asp Ile Lys Asn Pro Lys Leu Thr Lys Asp His
385                 390                 395                 400

Gln Thr Thr Gly Ser Pro Ser Arg Lys Thr Ile Thr Ile Thr Val Lys
                405                 410                 415

Ser Val Thr Ser Asp Thr Ile His Ile Ser Trp Lys Leu Ala Leu Pro
            420                 425                 430

Met Thr Ala Leu Arg Leu Ser Trp Leu Lys Leu Gly His Ser Pro Ala
        435                 440                 445

Phe Gly Ser Ile Thr Glu Thr Ile Val Thr Gly Glu Arg Ser Glu Tyr
    450                 455                 460

Leu Val Thr Ala Leu Glu Pro Asp Ser Pro Tyr Lys Val Cys Met Val
465                 470                 475                 480

Pro Met Glu Thr Ser Asn Leu Tyr Leu Phe Asp Glu Thr Pro Val Cys
                485                 490                 495

Ile Glu Thr Glu Thr Ala Pro Leu Arg Met Tyr Asn Pro Thr Thr Thr
            500                 505                 510

Leu Asn Arg Glu Gln Glu Lys Glu Pro Tyr Lys Asn Pro Asn Leu Pro
        515                 520                 525

Glu Ser Lys Tyr Gly Pro Pro Cys Pro Pro Cys Pro Ala Pro Glu Phe
```

-continued

```
        530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser Gln Glu Asp Pro Glu Val Gln Phe Asn Trp Tyr Val Asp Gly Val
            580                 585                 590

Glu Val His Asn Ala Lys Thr Lys Pro Arg Glu Glu Gln Phe Asn Ser
        595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Gly Leu Pro Ser
625                 630                 635                 640

Ser Ile Glu Lys Thr Ile Ser Lys Ala Lys Gly Gln Pro Arg Glu Pro
                645                 650                 655

Gln Val Tyr Thr Leu Pro Pro Ser Gln Glu Glu Met Thr Lys Asn Gln
            660                 665                 670

Val Ser Leu Thr Cys Leu Val Lys Gly Phe Tyr Pro Ser Asp Ile Ala
        675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Tyr Ser Arg Leu
705                 710                 715                 720

Thr Val Asp Lys Ser Arg Trp Gln Glu Gly Asn Val Phe Ser Cys Ser
                725                 730                 735

Val Met His Glu Ala Leu His Asn His Tyr Thr Gln Lys Ser Leu Ser
            740                 745                 750

Leu Ser Leu Gly
        755
```